US008158389B2

(12) United States Patent
Anderson et al.

(10) Patent No.: US 8,158,389 B2
(45) Date of Patent: Apr. 17, 2012

(54) PRODUCTS AND METHODS FOR IN VIVO SECRETION OF MONATIN

(75) Inventors: James C. Anderson, Eden Prairie, MN (US); Mervyn L. DeSouza, Plymouth, MN (US); Paula M. Hicks, Eden Prairie, MN (US); Sherry R. Kollmann, Maple Grove, MN (US)

(73) Assignee: Cargill, Incorporated, Wayzata, MN (US)

( * ) Notice: Subject to any disclaimer, the term of this patent is extended or adjusted under 35 U.S.C. 154(b) by 0 days.

(21) Appl. No.: 11/545,024

(22) Filed: Oct. 10, 2006

(65) Prior Publication Data

US 2007/0099277 A1 May 3, 2007

Related U.S. Application Data

(63) Continuation-in-part of application No. 11/379,528, filed on Apr. 20, 2006.

(60) Provisional application No. 60/673,262, filed on Apr. 20, 2005.

(51) Int. Cl.
*C12P 13/22* (2006.01)
*C12N 1/21* (2006.01)

(52) U.S. Cl. ...................... 435/108; 435/193; 435/252.3

(58) Field of Classification Search .................. 435/108, 435/193, 252.3
See application file for complete search history.

(56) References Cited

U.S. PATENT DOCUMENTS

| | | | |
|---|---|---|---|
| 3,002,889 A | 10/1961 | Kinoshita et al. | |
| 3,128,237 A | 4/1964 | Motozaki et al. | |
| 3,399,114 A | 8/1968 | Ohsawa et al. | |
| 3,751,458 A | 8/1973 | Wiley | |
| 4,371,614 A | 2/1983 | Anderson et al. | |
| 4,975,298 A | 12/1990 | Van Wyk et al. | |
| 5,128,164 A | 7/1992 | Van Wyk et al. | |
| 5,128,482 A | 7/1992 | Olivier et al. | |
| 5,300,437 A | 4/1994 | Stirling et al. | |
| 5,728,555 A | 3/1998 | Fotheringham et al. | |
| 5,985,617 A | 11/1999 | Liao | |
| 5,994,559 A | 11/1999 | Abushanab et al. | |
| 6,207,427 B1 | 3/2001 | Hashimoto et al. | |
| 6,264,999 B1 | 7/2001 | Yatka et al. | |
| 6,489,100 B1 | 12/2002 | Liao | |
| 7,064,219 B2 | 6/2006 | Kawahara et al. | |
| 7,396,941 B2 | 7/2008 | Mori et al. | |
| 7,534,898 B2 | 5/2009 | Amino et al. | |
| 7,670,822 B2 | 3/2010 | Smirnov et al. | |
| 7,781,005 B2 | 8/2010 | Mori | |
| 7,888,081 B2 | 2/2011 | Khare et al. | |
| 8,003,361 B2 | 8/2011 | Brady et al. | |
| 2003/0228403 A1 | 12/2003 | Amino et al. | |
| 2004/0063175 A1 | 4/2004 | Abraham et al. | |
| 2005/0004394 A1 | 1/2005 | Kawahara et al. | |
| 2005/0009153 A1 | 1/2005 | Sugiyama et al. | |
| 2005/0020508 A1 | 1/2005 | Amino et al. | |
| 2005/0095670 A1 | 5/2005 | Ikeda et al. | |
| 2005/0106305 A1 | 5/2005 | Abraham et al. | |
| 2005/0112260 A1 | 5/2005 | Abraham et al. | |
| 2005/0118317 A1 | 6/2005 | Amino et al. | |
| 2005/0137246 A1 | 6/2005 | Amino et al. | |
| 2005/0153405 A1 | 7/2005 | Sugiyama et al. | |
| 2005/0170041 A1 | 8/2005 | Abraham et al. | |
| 2005/0221453 A1 | 10/2005 | Takagi et al. | |
| 2005/0221455 A1 | 10/2005 | McFarlan et al. | |
| 2005/0244937 A1 | 11/2005 | Abraham et al. | |
| 2005/0244939 A1 | 11/2005 | Sugiyama et al. | |
| 2005/0272939 A1 | 12/2005 | Amino et al. | |
| 2005/0282260 A1 | 12/2005 | Hicks et al. | |
| 2006/0003411 A1 | 1/2006 | Sugiyama et al. | |
| 2006/0003426 A1 | 1/2006 | Sugiyama et al. | |
| 2006/0009394 A1 | 1/2006 | Amino | |
| 2006/0014819 A1 | 1/2006 | Mori et al. | |
| 2006/0074249 A1 | 4/2006 | Kawahara et al. | |
| 2006/0083695 A1 | 4/2006 | Mori | |
| 2006/0154343 A1 | 7/2006 | Mori et al. | |
| 2006/0172396 A1 | 8/2006 | Sugiyama et al. | |
| 2006/0252135 A1 | 11/2006 | Brazeau et al. | |
| 2007/0105938 A1 | 5/2007 | Anderson et al. | |
| 2008/0020434 A1 | 1/2008 | Brazeau et al. | |
| 2008/0020435 A1 | 1/2008 | Burke et al. | |
| 2008/0193984 A1 | 8/2008 | Sugiyama et al. | |
| 2008/0274518 A1 | 11/2008 | Hicks et al. | |
| 2009/0087888 A1 | 4/2009 | Buddoo et al. | |
| 2009/0088577 A1 | 4/2009 | Buddoo et al. | |
| 2009/0117625 A1 | 5/2009 | Abraham et al. | |
| 2009/0130285 A1 | 5/2009 | Abraham et al. | |
| 2009/0198072 A1 | 8/2009 | Khare et al. | |
| 2010/0095390 A1 | 4/2010 | Weiner et al. | |

(Continued)

FOREIGN PATENT DOCUMENTS

EP  0 438 314 A1  7/1991

(Continued)

OTHER PUBLICATIONS

Aono et al., "Involvement of outer membrane protein To1C, a possible member of the mar-sox regulon, in maintenance and improvement of organic solvent tolerance of *Escherichia coli* K-12," *J. Bacteriol.*, 1998, 180(4):938-944.

Azuma et al., "Hyper-production of L-tryptophan via fermentation with crystallization," *Appl. Microbiol. Biotechnol.*, 1993, 39:471-476.

Baranova and Nikaido, "The baeSR two-component regulatory system activates transcription of the yegMNOB (mdtABCD) transporter gene cluster in *Escherichia coli* and increases its resistance to novobiocin and deoxycholate," *J. Bacteriol.*, 2002, 184:4168-4176.

Barbosa and Levy, "Activation of the *Escherichia coli* nfnB gene by MarA through a highly divergent marbox in a class II promoter," *Mol. Microbiol.*, 2002, 45:191-202.

(Continued)

*Primary Examiner* — Tekchand Saidha

(57) ABSTRACT

Products and methods for the in vivo production of monatin sweetener are provided. The products include microorganisms that are genetically modified to secrete or to improve secretion of monatin; microorganisms that are genetically modified to produce monatin; and microorganisms that are genetically modified to both secrete or improve secretion of monatin and produce monatin. The methods include producing monatin in such genetically engineered microorganisms.

12 Claims, 4 Drawing Sheets

U.S. PATENT DOCUMENTS

| | | | |
|---|---|---|---|
| 2011/0020882 | A1 | 1/2011 | de Souza et al. |
| 2011/0045547 | A1 | 2/2011 | de Souza et al. |

FOREIGN PATENT DOCUMENTS

| | | | |
|---|---|---|---|
| EP | 1 045 029 | A2 | 10/2000 |
| EP | 1 445 323 | A1 | 8/2004 |
| EP | 1 449 832 | | 8/2004 |
| EP | 1 533 376 | | 5/2005 |
| EP | 1 580 268 | | 9/2005 |
| EP | 1 605 041 | | 12/2005 |
| EP | 1 350 791 | | 9/2006 |
| EP | 1 719 758 | A1 | 11/2006 |
| JP | 2002/060382 | | 2/2002 |
| JP | 2003/171365 | | 6/2003 |
| JP | 2004/222657 | | 8/2004 |
| JP | 2004/331644 | | 11/2004 |
| JP | 2004/331650 | | 11/2004 |
| WO | WO 87/01130 | A1 | 2/1987 |
| WO | WO 89/11212 | | 11/1989 |
| WO | WO 99/55877 | A1 | 11/1999 |
| WO | WO 03/000913 | A2 | 1/2003 |
| WO | WO 03/045914 | | 6/2003 |
| WO | WO 03/056026 | | 7/2003 |
| WO | WO 03/056026 | A1 | 7/2003 |
| WO | WO 03/059865 | A1 | 7/2003 |
| WO | WO 03/091396 | A2 | 11/2003 |
| WO | WO 2004/018672 | A1 | 3/2004 |
| WO | WO 2004/053125 | A1 | 6/2004 |
| WO | WO 2004/085624 | | 10/2004 |
| WO | WO 2005/001105 | | 1/2005 |
| WO | WO 2005/014839 | A2 | 2/2005 |
| WO | WO 2005/016022 | A1 | 2/2005 |
| WO | WO 2005/020721 | A1 | 3/2005 |
| WO | WO 2005/042756 | A2 | 5/2005 |
| WO | WO 2005/082850 | A1 | 9/2005 |
| WO | WO 2006/011613 | A1 | 2/2006 |
| WO | WO 2006/058893 | A2 | 6/2006 |
| WO | WO 2006/093322 | | 9/2006 |
| WO | WO 2006/116487 | | 11/2006 |
| WO | WO 2007/103389 | | 9/2007 |
| WO | WO 2007/133183 | | 11/2007 |
| WO | WO 2007/133184 | | 11/2007 |
| WO | WO 2010/105014 | | 9/2010 |
| WO | WO 2010/138513 | | 12/2010 |
| WO | WO 2011/082351 | | 7/2011 |
| WO | WO 2011/082353 | | 7/2011 |
| WO | WO 2011/082363 | | 7/2011 |
| WO | WO 2011/082365 | | 7/2011 |

OTHER PUBLICATIONS

Barbosa and Levy, "Differential expression of over 60 chromosomal genes in *Escherichia coli* by constitutive expression of MarA," *J. Bacteriol.*, 2000, 182:3467-3474.

Barany, "The Ligase Chain Reaction in a PCR World," *PCR Methods and Applications*, 1991, 1:5-16.

Bassoli et al., "General Pseudoreceptor Model for Sweet Compounds: A Semiquantitative Prediction of Binding Affinity for Sweet-Tasting Molecules," *J. Med. Chem.*, 2002, 45:4402-4409.

Bassoli et al., "Monatin and Its Stereoisomers: Chemoenzymatic Synthesis and Taste Properties," *Eur. J. Org. Chem.*, 2005, 8:1652-1658.

Bhatnagar et al., "The Broad-specificity, Membrane-bound Lactate Dehydrogenase of *Neisseria gonorrhoeae*: Ties to Aromatic Metabolism," *J. Gen. Microbiol.*, 1989, 135:353-360.

Bommarius et al., "Some new developments in reductive amination with cofactor regeneration," *Biocatalysis*, 1994, 10:37-47.

Brandl and Lindow, "Cloning and characterization of a locus encoding an indolepyruvate decarboxylase involved in indole-3-acetic acid synthesis in *Erwinia herbicola*," *Appl. Environ. Microbiol.*, 1996, 62:4121-4128.

Camargo (Ediclea Cristina Fregonese Camargo), "Preparation of amino acids not proteinogênicos, structurally related to adoçante natural Monatina" [translated by Google], Jan. 2003, *Universidade Estadual de Campinas Instituto de Quimica, Dissertation of Masters*.

Chollet et al., "RamA is an alternate activator of the multidrug resistance cascade in *Enterobacter aerogenes*," *Antimicrob. Agents Chemother.*, 2004, 48:2518-2523.

Cohen et al., "Salicylate induction of the antibiotic resistance in *Escherichia coli*: activation of the mar operon and mar-independent pathway," *J. Bacteriol.*, 1993, 175:7856-7862.

Eggeling and Sahm, "Amino-acid production: principles of metabolic engineering," *Metabolic Engineering*, 1999, Lee & Papoutsakis eds., Marcel Dekker, Inc., New York.

Eggeling and Sahm, "The Cell Wall Barrier of *Corynebacterium glutamicum* and Amino Acid Efflux," *J. BioSci. BioEng.*, 2001, 92:201-213.

Eikmanns et al., "Cloning, sequence analysis, and inactivation of the *Corynebacterium glutamicum* icd gene encoding isocitrate dehydrogenase and biochemical characterization of the enzyme," *J. Bacteriol.*, 1995, 177:774-782.

El-Abyad and Farid, "Optimization of culture conditions for indole-3-pyruvic acid production by *Streptomyces griseoflavus*," *Can. J. Microbiol.*, 1994, 40:754-760.

Fotheringham et al., "The cloning and sequence analysis of the aspC and tyrB genes from *Escherichia coli* K12," *Biochem. J.*, 1986, 234:593-604.

Fralick, "Evidence that TolC is required for functioning of the Mar/AcrAB efflux pump of *E. coli*," *J. Bacteriol.*, 1996, 178:5803-5805.

Furuya et al., "A Novel Enzyme, L-Tryptophan Oxidase, from a Basidiomycete, *Coprinus* sp. SF-1: Purification and Characterization," *Biosci. Biotechnol. Biochem.*, 2000, 64(7):1486-1493.

Hoischen and Kraemer, "Evidence for an efflux carrier system involved in the secretion of glutamate by *Corynebacterium glutamicum*," *Arch. Microbiol.*, 1989, 151:342-347.

Jetten et al., "Metabolic Engineering of *Corynebacterium glutamicum*," *Ann. N.Y. Acad. Sci.*, 1994, 721:12-29.

Jetten et al., "Recent advances in the physiology and genetics of amino acid-producing bacteria," *Crit. Rev. Biotechnol.*, 1995, 15:73-103.

Kawasaki et al., "L-Tryptophan Production by Pyruvic Acid-Producing *Escherichia coli* Strain Carrying the Enterobacter aerogenes Tryptophanase Gene," *Journal of Fermentation and Bioengineering*, 1996, 82(6):604-606.

Koffas et al., "Engineering metabolism and product formation in *Corynebacterium glutamicum* by coordinated gene overexpression," *Metabolic Engineering*, 2003, 5:32-41.

Koga et al., "Involvement of L-tryptophan aminotransferase in indole-3-acetic acid biosynthesis in *Enterobacter cloacae*," *Biochim. Biophys. Acta*, 1994, 1209:241-247.

Koronakis, "TolC—the bacterial exit duct for proteins and drugs," *FEBS Lett.*, 2003, 555:66-71.

Koronakis et al., "Structure and function of TolC: the bacterial exit duct for proteins and drugs," *Annu. Rev. Biochem.*, 2004, 73:467-489.

Labrou et al., "Oxaloacetate Decarboxylase from *Pseudomonas stutzeri*: Purification and Characterization," *Arch. Biochem. Biophys.*, 1999, 365(1):17-24.

Nagakubo et al., "The putative response regulator BaeR stimulates multidrug resistance of *Escherichia coli* via a novel multidrug exporter system, MdtABC," *J. Bacteriol.*, 2002, 184:4161-4167.

Nishino et al., "Genome-wide analyses of *Escherichia coli* gene expression responsive to the BaeSR two-component regulatory system," *J. Bacteriol.*, 2005, 187:1763-1772.

Nishino et al., "Roles of TolC-dependent multidrug transporters of *Escherichia coli* in resistance of beta-lactams," *Antimicrob. Agents Chemother.*, 2003, 47:3030-3033.

Patnaik et al., "Engineering of *Escherichia coli* Central Metabolism for Aromatic Metabolite Production with Near Theoretical Yield," *Applied and Environmental Microbiology*, 1994, 60(11):3903-3908.

Randall and Woodward, "The multiple antibiotic resistance (mar) locus and its significance," *Res. Vet. Sci.*, 2002, 72:87-93.

Rijnen et al., "Genetic Characterization of the Major Lactococcal Aromatic Aminotransferase and Its Involvement in Conversion of Amino Acids to Aroma Compounds," *Applied Environmental Biology*, 1999, 65(11):4873-488.

Sharff et al., "The role of the TolC family in protein transport and multidrug efflux: From stereochemical certainty to mechanistic hypothesis," *Eur. J. Biochem.*, 2001, 268:5011-5026.

Tamura et al., "Stereoselective Synthesis of 4-Hydroxy 4-Substituted Glutamic Acids," *J. Org. Chem.*, 2005, 70(12):4569-4577.

Werner et al., "Assembly of TolC, a structurally unique and multifunctional outer membrane protein of *Escherichia coli* K-12," *J. Bacteriol.*, 2003, 185:6540-6547.

Wolf et al., "A Biocatalytic Route to Enantiomerically Pure Unsaturated -H—Amino Acids," *Adv. Synth. & Catalysis*, 2001, 343:662-674.

Yonaha et al., "D-Amino Acid Aminotransferase of *Bacillus sphaericus*," *J. Biol. Chem.*, 1975, 250(17):6983-6989.

Abraham et al., "Beverage compositions comprising monatin and methods of making same," *Business News for the Food Industry*, Nov. 11, 2006.

Barany, "The Ligase Chain Reaction in a PCR World," *PCR Methods and Applications*, 1991, 1:5-16

Dixon and Chopra, "Leakage of periplasmic proteins from *Escherichia coli* mediated by polymyxin B nonapeptide," *Antimicrobial Agents and Chemotherapy*, 1986, 29:781-788.

Guo et al., "Protein tolerance to random amino acid change," *Proc. Natl. Acad. Sci.*, 2004, 101(25):9205-10.

Seffernick et al., "Melamine Deaminase and Atrazine Chlorohydrolase: 98 Percent Identical but Functionally Different," *J. Bacteriology*, 2001, 183(80):2405-2410.

Seo Jeong-Sun et al., "The genome sequence of the ethanologenic bacterium *Zymomonas mobilis* ZM4," *Nature Biotechnology*, 2005, 23(1):63-68.

Whisstock and Lesk, "Prediction of protein function from protein sequence and structure," *Q. Rev. Biophys.*, 2003, 36(3):307-340.

Witkowski et al., "Conversion of beta-Ketoacyl Synthase to a Malonyl Decarboxylase by Replacement of the Active-Site Cysteine with Glutamine," *Biochemistry*, 1999, 38:11643-11650.

Ackerman, L.G., "Structure Elucidation of and Synthetic Approaches to Monatin, a Metabolite from *Schlerochiton illicifolius*," Ph.D. Dissertation, University of Stellenbosch 175 pages (1990).

Ager, D.J., et al., "Commercial, Synthetic Nonnutritive Sweeteners," *Angew. Chem. Int. Ed.* 37:1802-1817, Verlag Chemie (1998).

Ager, D.J., et al., "Novel biosynthetic routes to non-proteinogenic amino acids as chiral pharmaceutical intermediates," *J. Mol. Catal., B: Enzym.* 11:199-205, Elsevier Science (2001).

Bae, H., at al., "Production of aromatic D-amino acids from α-keto acids and ammonia by coupling of four enzyme reactions," *J. Mol. Catal., B: Enzym.* 6:241-247, Elsevier Science (1999).

Bassoli, A., et al., "Design and Synthesis of New Monatin Derivatives," *Abstracts presented at the 13th International Symposium on Olfaction and Taste and 14th European Chemoreception Research Organisation Congress*, Brighton, UK, Jul. 20-24, 2000.

Bassoli A., "'Chemistry-Nature,' still an open match for the discovery of new intensive sweeteners," *European Journal of Nutraceuticals & Functional Foods* 15:27-29, Tekno Scienze (Jul./Aug. 2004).

Bongaerts, J., et al., "Metabolic Engineering for Microbial Production of Aromatic Amino Acids and Derived Compounds," *Metab. Eng.* 3:289-300, Academic Press (Oct. 2001).

Buldain, G., et al., "Carbon-13 Nuclear Magnetic Resonance Spectra of the Hydrate, Keto and Enol forms of Oxalacetic Acid," *Magnetic Resonance in Chemistry* 23:478-481, Wiley Heden Ltd. (1985).

DeLuna, A., et al., "NADP-Glutamate Dehydrogenase Isoenzymes of *Saccharomyces cerevisiae*," *J. Biol. Chem.* 276:43775-43783, The American Society for Biochemistry and Molecular Biology, Inc. (2001).

Flores, N., et al., "Pathway engineering for the production of aromatic compounds in *Escherichia coli*," *Nat. Biotechnol.* 14:620-623, Nature America Publishing (1996).

Floyd, N. C., et al., "A Simple Strategy for obtaining both Enantiomers from an Aldolase Reaction: Preparation of L- and D-4-Hydroxy-2-ketogluterate," *J. Chem. Soc. Perkin Trans. 1* 9:1085-1086, Chemical Society (1992).

Galkin, A., et al., "Synthesis of Optically Active Amino Acids from α-Keto Acids with *Escherichia coli* Cells Expressing Heterologous Genes," *Appl. Environ. Microbiol.* 63: 4651-4656, American Society for Microbiology (1997).

Gosset, G., et al., "A direct comparison of approaches for increasing carbon flow to aromatic biosynthesis in *Escherichia coli*," *J. Ind. Microbial.* 17:47-52, Stockton Press on behalf of the Society for Industrial Microbiology (1996).

Hayashi, H., et al., "*Escherichia coli* Aromatic Amino Acid Aminotransferase: Characterization and Comparison with Aspartate Aminotransferase," *Biochemistry* 32:12229-12239, American Chemical Society (1993).

Hibino, S. and Choshi, T., "Simple indole alkaloids and those with a nonrearranged monoterpenoid unit," *Nat. Prod. Rep.* 19:148-180, Royal Society of Chemistry (Apr. 2002).

Holzapfel, C. and Olivier, J., "The Synthesis of a γ-Keto-α-Amino Acid, a Key Intermediate in the Sythesis of Monatin, a New Natural Sweetener," *Synthetic Communications* 23:2511-2526, Marcel Dekker (1993).

Holzapfel, C., et al., "A Simple Cycloaddition Approach to a Racemate of the Natural Sweetener Monatin," *Synthetic Communications* 24:3197-3211, Marcel Dekker (1994).

Izumi, Y., *Amino-san Kogyo—Gosei to Riyo*, Kaneko, T., et al., eds., Kodansha Ltd., pp. 8-9 (1973).

Izumi, Y., *Synthetic production and utilization of amino acids*, Kaneko, T., et al., eds., Kodansha Ltd., pp. 3-16 (1974) (republished English translation that includes NPL18).

Juhl, K., et al., "Catalytic asymmetric homo-aldol reaction of pyruvate-a chiral Lewis acid catalyst that mimics aldolase enzymes," *Chem. Commun.*, No. 22, pp. 2211-2212, Royal Society of Chemistry (2000).

Katsumata, R. and Ikeda, M., "Hyperproduction of Tryptophan in *Corynebacterium glutamicum* by Pathway Engineering," *Bio/Technology* 11:921-925, Nature Publishing Co. (1993).

Koeller, K.M. And Wong, C.-H., "Enzymes for chemical synthesis," *Nature* 409:232-240, Nature Publishing Group (2001).

Kogiso, K., et al., "Control of Lactamization during the Synthesis of the Monatin Analogue," *Peptide Science 2003*, The Proceedings of the 40th Symposium on Japanese Peptide Symposium, pp. 195-198, The Japanese Peptide Society (2004).

Koshiba, T. and Mito, N., "Partial Purification and some Properties of L- and D-Tryptophan Aminotransferases form Maize Coleoptiles," Proceedings of the 8*th* International Symposium on Vitamin $B_6$ and Carbonyl Catalysis, Osaka, Japan, pp. 245-247, Pergamon Press, Oct. 15-19, 1990.

Li, T., et al., "Nonproteinogenic α-Amino Acid Preparation Using Equilibrium Shifted Transamination," *Organic Process Research & Development* 6:533-538, American Chemical Society (2002).

Liao, J.C., et al., "Pathway Analysis, Engineering, and Physiological Considerations for Redirecting Central Metabolism," *Biotechnol. Bioeng.* 52:129-140, John Wiley & Sons, Inc. (1996).

Nakamura, K., et al., "Total Synthesis of Monatin," *Org. Lett.* 2:2967-2970, American Chemical Society (2000).

Nakamura, K., et al., "Total Synthesis of Monatin and the Taste Expression," *Peptide Science 2003*, The Proceedings of the 40th Symposium on Japanese Peptide Symposium, pp. 61-64, The Japanese Peptide Society (2004).

Oliveira, D. and Coelho, F., "Highly Diastereoselective Alkylation of a Pyroglutamate Derivative with an Electrophile Obained from Indole. Synthesis of a Potential Intermediate for the Preparation of the Natural Sweetener (-)-Monatin," *Synthetic Communications* 30:2143-2159, Marcel Dekker (2000).

Oliveira, D. and Coelho, F., "Diastereoselective formation of a quanternary center in a pyroglutamate derivative. Formal synthesis of Monatin," *Tetrahedron Lett.* 42:6793-6796, Elsevier Science Ltd. (2001).

Passerat, N. and Bolte, J., "Large-Scale Enzymatic Synthesis of Diastereoisomeric γ-Hydroxy L-Glutamic Acids," *Tetrahedron Lett.* 28:1277-1280, Elsevier (1987).

Patil, R. and Dekker, E., "Cloning Nucleotide Sequence, Overexpression, and Inactivation of the *Escherichia coli* 2-Keto-4-Hydroxyglutarate Aldolase Gene," *J. Bacteriol.* 174:102-107, American Society for Microbiology (1992).

Patrick, W.M., et al., "Site-Directed Mutagenesis of Tyr354 in *Geobacillus stearothermophilus* Alanine Racemase Identifies a Role in Controling Substrate Specificity and a Possible Role in the Evolution of Antibiotic Resistance," *Chembiochem* 3:789-792, Wiley-VCH-Verlag GmbH (2002).

Shelton, M.C., et al., "2-Keto3-deoxy6-phosphogluconate Aldolases as Catalysts for Stereocontrolled Carbon—Carbon Bond Formation," *J. Am. Chem. Soc.* 118:2117-2125, American Chemical Society (1996).

Tamura, O., et al., "Highly stereoselective synthesis of (−)-monatin, a high-intensity sweetener, using chelation-controlled nitrone cycloaddition," *Chem. Commun. (Camb.)* 21:2678-2679, The Royal Society of Chemistry (2003).

Vleggaar, R., et al., "Structure Elucidation of Monatin, a High-intensity Sweetener Isolated from the Plant *Schlerochiton ilicifolius*," *J. Chem. Soc. Perkin Trans.* 122:3095-3098, Royal Society of Chemistry (1992).

Zeman, R., et al., "Enzyme Synthesis of L-Tryptophan," *Folia Microbiol.* 35:200-204, Slovak Academy of Sciences (1990).

"Bacteria: *Corynebacterium glutamicum*," ATCC No. 13058, available online @ www.atcc.org/SearchCatalogs/longview.cfm?atccsearch=yes (accessed on Mar. 11, 2005).

Dialog File 351, Accession No. 12442290, Derwent WPI English language abstract for JP 2002/060382 (2002).

Dialog File 351, Accession No. 13542893, Derwent WPI English language abstract for WO 03/056026 A1 (2003).

Dialog File 351, Accession No. 13655060, Derwent WPI English language abstract for JP 2003/171365.

Dialog File 351, Accession No. 14386782, Derwent WPI English language abstract for JP 2004/222657.

Dialog File 351, Accession No. 14644791, Derwent WPI English language abstract for JP 2004/331644.

Dialog File 351, Accession No. 14655288, Derwent WPI English language abstract for JP 2004/331650.

Dialog File 351, Accession No. 15288756, Derwent WPI English language abstract for WO 2005/082850 A1 (2005).

Dialog File 351, Accession No. 15581479, Derwent WPI English language abstract for WO 2006/011613 A1 (2006).

ISTA's Paterra™, unverified English language translation of JP 2002-60382 A, 36 pages (2002).

Broun et al. "Catalytic plasticity of fatty acid modification enzymes underlying chemical diversity of plant lipids" Science 1998, 282:1315-1317.

Chica et al., "Semi-rational approaches to engineering enzyme activity: combining the benefits of directed evolution and rational design", Curr Opin Biotechnol., Aug. 16, 2005 pp. 378-384.

Delepelaire., "Type 1 secretion in gram-negative bacteria," Biochimica et Biophysica Acta. 2004, vol. 1694; 149-161.

Devos et al. "Practical limits of function prediction: Proteins, Structure, Function and Genetics" 41: 98-107 (2000).

Kishimoto et al., Mutation of Arginine 98, which serves as a substrate-recognition site of D-AminoAcid Aminotransferase, can be partly compensated for by mutation of tyrosine Journal of Biochemistry 122 1182-89 (1997).

Moriya et al., "A facile synthesis of 6-chloro-D-tryptophan", Bulletin of the Chemical Society of Japan, 1975, vol. 48,: 2217-2218.

Office Action issued in U.S. Appl. No. 10/979,821, filed Nov. 3, 2004, on Jun. 15, 2007.

Office Action issued in U.S. Appl. No. 10/979,821, filed Nov. 3, 2004, on Aug. 24, 2007.

Office Action issued in U.S. Appl. No. 10/903,582, filed Aug. 2, 2004, on Jun. 27, 2007.

```
AtPGP1              ------------------------------------------------MDNDGGA
BrABB97035          --------------MQGLELLPE--------PSSNSNSNSRNPETELQEHPPEMGNGGGT
StAAD10836          --------------MQGVELVVS--------EDKNSN----TPTTTTTTNSHQFQETRME
ZmPGP1_AAR00316     MSSSDPEEIRARVVVLGSPHAD--GGDEWARPELEAFHLPSPAHQPPGFLAG---QPEAA
SbAAR10387          MSTNDPDEIRARVVVLGAPHADDDAGDEWARPELEAFHLPSPAHQPPGFHLAAGHQPEAA
OsXP_483819         ----MEEEIKGRVVVLGADAAAD--------PELEAFHLPSADQPPHSHLLHHHHSPQSH
OS_CAD59580         ----MPPPTRSSRPSISP-PPTS--------PRTRTSSTTTILHNPILNLMHQQQQRHRH
AtPGP19             ------------------------------------------------MSETNTT
Consensus/100%      ............................................................

AtPGP1              PPPPPTLVVEEPKK----------------------------------------------
BrABB97035          PPPPPPATVEEPKK----------------------------------------------
StAAD10836          VKKEEGGDVEKPS-----------------------------------------------
ZmPGP1_AAR00316     EQPTLPAPAGRSSS(5)TTSAGGGAAPPPPSSPPPPPASLETEQPPNARPAS---AGAND
SbAAR10387          AEQPTTLPAARRTS---DTSTAAGAAPPSPS-PPPPPAPLEMDQPPNAKPAS(5)AGAND
OsXP_483819         PQPDAPAAAAPPPP-------APLTPPPPKSPPPPPHIQTTDLPPP--------------
OS_CAD59580         LLPLLLLLLSRRRR-------LPTSKPP------------TFHRP---------------
AtPGP19             DAKTVPAEAEKKKE----------------------------------------------
Consensus/100%      ............................................................

AtPGP1              --AEIRGVAFKELFRFADGLDYVLMGIGSVGAFVHGCSLPLFLRFFADLVNSFGSNSNNV
BrABB97035          --AEIRGVAFKELFRFADGLDYVLMTIGSVGAFVHGCSLPLFLRFFADLVNSFGSNANNV
StAAD10836          --SPPPAVGFGELFRFADGLDCVLMIIGSLGAFVHGCSLPLFLRFFADLVNSFGSYANDV
ZmPGP1_AAR00316     SKKPTPPAALRDLFRFADGLDCALMLVGTLGALVHGCSLPVFLRFFADLVDSFGSHADDP
SbAAR10387          NKKPTPPAALRDLFRFADGLDCALMLVGTLGALVHGCSLPVFLRFFADLVDSFGSHANDP
OsXP_483819         --KPLPPAPLRQLFSFADGLDYVLMTLGTLGALVHGCSLPVFLRFFADLVDSFGSHAAHP
OS_CAD59580         --RPLPPAPFRQLFSFGDGLDYVLMTLGTLGALVHGCSLTVFLRFFADLVDSFGSHAAHP
AtPGP19             -----QSLPFFKLFSFADKFDYLLMFVGSLGAIVHGSSMPVFFLLFGQMVNGFGKNQMDL
Consensus/100%      ............LF.F.D..D..LM..G..GA.VHG.S...F...F...V..FG......

AtPGP1              EKMMEEVLKYALYFLVVGAAIWASSWAEISCWMWSGERQTTKMRIKYLEAALNQDIQFFD
BrABB97035          DKMMQEVLKYALYFLVVGAAIWASSWAEISCWMWTGERQTTKMRIKYLEAALNQDIQFFD
StAAD10836          DKMTQEVLKYAFYFLVVGAAIWASSWAEISCWMWTGERQTTKMRIKYLEAALNQDIQYFD
ZmPGP1_AAR00316     DTMVRLVVKYAFYFLVVGAAIWASSWAEISCWMWTGERQSTRMRIRYLDAALRQDVSFFD
SbAAR10387          DTMVRLVVKYAFYFLVVGAAIWASSWAEISCWMWTGERQSTRMRIRYLDAALRQDVSFFD
OsXP_483819         DTMLRLVVKYAFYFLVVGAAIWASSWAEISCWMWTGERQSTRMRIRYLHAALHQDVSFFD
OS_CAD59580         DTMLRLVVKYAFYFLVVGAAIWASSWAEISCWMWTGERQSTRMRIRYLHAALHQDVSFFD
AtPGP19             HQMVHEVSRYSLYFVYLGLVVCFSSYAEIACWMYSGERQVAALRKKYLEAVLKQDVGFFD
Consensus/100%      ..M...V..Y..YF...G.....SS.AEI.CWM..GERQ....R..YL.A.L.QD...FD AtPGP1              TEVRTSDVVFAINTDAVMVQDAISEKLGNFIHYMATFVSGFIVGFTAVWQLALVTLAVVP
BrABB97035          TEVRTSDVVSAINTDAVMVQDAISEKLGNFIHYMA---------------LVTIAVVP
StAAD10836          TEVRTSDVVSAINTDAVVVQDAISEKLGNFIHYMATFLSGFVVGFTAVWQLALVTLAVVP
ZmPGP1_AAR00316     TDVRASDVIYAINADAVVVQDAISQKLGNLIHYMATFVAGFVVGFTAAWQLALVTLAVVP
SbAAR10387          TDVRTSDVIYAINADAVVVQDAISEKLGNLIHYMATFVAGFVVGFTAAWQLALVTLAVVP
OsXP_483819         TDVRTSDVIHAINADAVVVQDAISEKLGNLIHYLATFVSGFVVGFTAAWQLALVTLAVVP
OS_CAD59580         TDVRTSDVIHAINADAVVVQDAISEKLGNLIHYLATFVSGFVVGFTAAWQLALVTLAVVP
AtPGP19             TDARTGDIVFSVSTDTLLVQDAISEKVGNFIHYLSTFLAGLVVGFVSAWKLALLSVAVIP
Consensus/100%      T..R..D.......D...VQDAIS.K.GN.IHY..............L...AV.P AtPGP1              LIAVIGGIHTTTLSKLSNKSQESLSQAGNIVEQTVVQIRVVMAFVGESRASQAYSSALKI
BrABB97035          LIAVIGGIHTTTLSKLSNKSQESLSQAGNIVEQTVVQIRVVMAFVGESRASQAYSSALKT
StAAD10836          LIAVIGAIYTVTSAKLSSQSQEALSKAGNIVEQTVVQIRTVLVFVGEAKALQAYTAALRV
ZmPGP1_AAR00316     LIAVIGGLSAAALAKLSSRQDALSGASGIAEQALAQIRIVQAFVGEEREMRAYSAALAV
SbAAR10387          LIAVIGGLSAAALAKLSSRQDALSGASGIAEQALAQIRIVQAFVGEEREMRAYSAALAV
OsXP_483819         LIAVIGGLSAAALAKLSSRQDALSDASGIAEQALAQIRIVQSFVGEERVMRAYSAALAV
OS_CAD59580         LIAVIGGLSAAALAKLSSRQDALSDASGIAEQALAQIRIVQSFVGEERVMRAYSAALAV
AtPGP19             GIAFAGGLYAYTLTGITSKSRESYANAGVIAEQAIAQVRTVYSYVGESKALNAYSDAIQY
Consensus/100%      .IA..G............S......A..I.EQ...Q.R.V...VGE.....AY..A...
```

FIG. 1A

```
AtPGP1            AQKLGYKTGLAKGMGLGATYFVVFCCYALLLWYGGYLVRHHLTNGGLAIATMFAVMIGGL
BrABB97035        AQKLGYKTGFAKGMGLGATYFVVFCCYALLLWYGGYLVRHHLTNGGLAIATMFAVMIGGL
StAAD10836        SQKIGYKSGFSKGLGLGATYFTVFCCYALLLWYGGYLVRHHFTNGGLAIATMFAVMIGGL
ZmPGP1_AAR00316   AQRIGYRSGFAKGLGLGGTYFTVFCCYGLLLWYGGHLVRAQHTNGGLAIATMFSVMIGGL
SbAAR10387        AQKIGYRSGFAKGLGLGGTYFTVFCCYGLLLWYGGHLVRGHHTNGGLAIATMFSVMIGGL
OsXP_483819       AQRIGYRSGFAKGIGLGGTYFTVFCCYALLLWYGGHLVRRAHTNGGLAIATMFSVMIGGL
OS_CAD59580       AQRIGYRSGFAKGIGLGGTYFTVFCCYALLLWYGGHLVRRAHTNGGLAIATMFSVMIGGL
AtPGP19           TLKLGYKAGMAKGLGLGCTYGIACMSWALVFWYAGVFIRNGQTDGGKAFTAIFSAIVGGM
Consensus/100%    ....GY..G..KG.GLG.TY........L..WY.G...R...T.GG.A....F....GG.

AtPGP1            ALGQSAPSMAAFAKAKVAAAKIFRIIDHKPTIERNSES---GVELDSVTGLVELKNVDFS
BrABB97035        GLGQSVPSMAAFAKAKVAAAKIFRIIDHKPTIERNSES---GVELESVTGLVELKNVDFS
StAAD10836        ALGQSAPSMTAFAKARVAAAKIFRIIDHKPSVDRNAKT---GLELDTVSGQLELKNVEFS
ZmPGP1_AAR00316   PR-QSAPSMAAFAKARVAAAKIFRIIDHRPGISSRDG-----AEPESVTGRVEMRGVDFA
SbAAR10387        ALGQSAPSMAAFAKARVAAAKIFRIIDHRPGISSRDGEDGGGVELESVTGRVEMRGVDFA
OsXP_483819       ALGQSAPSMAAFAKARVAAAKIFRMMEHKPSMEREGG-----VELEAVTGRVELRDVEFS
OS_CAD59580       ALGQSAPSMAAFAKARVAAAKIFRMMEHKPSMEREGG-----VELEAVTGRVELRDVEFS
AtPGP19           SLGQSFSNLGAFSKGKAAGYKLMEIINQRPTIIQDPLDG---KCLDQVHGNIEFKDVTFS
Consensus/100%    ...QS.....AF.K...A..K........P..............V.G..E...V.F.

AtPGP1            YPSRPDVKILNNFCLSVPAGKTIALVGSSGSGKSTVVSLIERFYDPNSGQVLLDGQDLKT
BrABB97035        YPSRPDVKILNDFTLSVPAGKTIALVGSSGSGKSTVVSLIERFYDPTSGQVLLDGHDLKT
StAAD10836        YPSRPEIKILNNFNLVVPAGKTIALVGSSGSGKSTVVSLIERFYDPTSGQLMLDGNDIKT
ZmPGP1_AAR00316   YPSRPDVPILRGFSLSVPAGKTIALVGSSGSGKSTVVSLIERFYDPSAGQILLDGHDLRS
SbAAR10387        YPSRPDVPILRGFSLSVPAGKTIALVGSSGSGKSTVVSLLERFYDPSAGQILLDGHDLKS
OsXP_483819       YPSRPDVGILRGLSLSVPAGKTIALVGSSGSGKSTVVSLIERFYEPNAGTILLDGHDLRD
OS_CAD59580       YPSRPDVGILRGLSLSVPAGKTIALVGSSGSGKSTVVSLIERFYEPNAGTILLDGHDLRD
AtPGP19           YPSRPDVMIFRNFNIFFPSGKTVAVVGGSGSGKSTVVSLIERFYDPNSGQILLDGVEIKT
Consensus/100%    YPSRP...I........P.GKT.A.VG.SGSGKSTVVSL.ERFY.P..G...LDG.....

AtPGP1            LKLRWLRQQIGLVSQEPALFATSIKENILLGRPD--ADQVEIEEAARVANAHSFIIKLPD
BrABB97035        LKLKWLRQQIGLVSQEPALFATSIKENILLGRPD--ADQVEEEAARVANAHSFIIKLPD
StAAD10836        LKLKWLRQQIGLVSQEPALFATSIKENILLGRPD--ATQIEIEEAARVANAHSFVIKLPD
ZmPGP1_AAR00316   LELRWLRRQIGLVSQEPALFATSIRENLLLGRDSQSATLAEMEEAARVANAHSFIIKLPD
SbAAR10387        LKLRWLRQQIGLVSQEPTLFATSIKENLLLGRDSQSATQAEMEEAARVANAHSFIVKLPD
OsXP_483819       LNLRWLRRQIGLVSQEPALFATTIRENLLLGRDG--ATQEELEEAARVANAHSFIVKLPD
OS_CAD59580       LNLRWLRRQIGLVSQEPALFATTIRENLLLGRDG--ATQEELEEAARVANAHSFIVKLPD
AtPGP19           LQLKFLREQIGLVNQEPALFATTILENILYGKPD--ATMVEVEAAASAANAHSFITLLPK
Consensus/100%    L.L..LR.QIGLV.QEP.LFAT.I.EN.L.G.....A...E.E.AA..ANAHSF...LP.

AtPGP1            GFDT----QVGERGLQLSGGQKQRIAIARAMLKNPAILLLDEATSALDSESEKLVQEALD
BrABB97035        GFDT----QVGERGLQLSGGQKQRIAIARAMLKNPAILLLDEATSALDSESEKLVQEALD
StAAD10836        GFDT----QVGERGLQLSGGQKQRIAIARAMLKNPAILLLDEATSALDSESEKLVQEALD
ZmPGP1_AAR00316   GYDT----QVGERGLQLSGGQKQRIAIARAMLKNPAILLLDEATSALDSESEKLVQEALD
SbAAR10387        GYDT----QVGERGLQLSGGQKQRIAIARAMLKNPAILLLDEATSALDSESEKLVQEALD
OsXP_483819       AYNT----QVGERGLQLSGGQKQRIAIARAMLRNPAILLLDEATSALDSESEKLVQEALD
OS_CAD59580       AYNT(19)QVGERGLQLSGGQKQRIAIARAMLRNPAILLLDEATSALDSESEKLVQEALD
AtPGP19           GYDT----QVGERGVQLSGGQKQRIAIARAMLKDPKILLLDEATSALDASSESIVQEALD
Consensus/100%    ...T....QVGERG.QLSGGQKQRIAIARAML..P.ILLLDEATSALD..SE..VQEALD AtPGP1            RFMIGRTTL-IIAHRLSTIRKADLVAVLQQGSVSEIGTHDELFSKGENGVYAKLIKMQEA
BrABB97035        RFMIGRTTL-IIAHRLSTIRKADLVAVLQQGSVSEIGTHDELFAKGENGIYSKLIKMQEA
StAAD10836        RFMIGRTTL-VIAHRLSTIRKADLVAVLQQGSVSEIGSHDELMSKGENGMYAKLIKMQEA
ZmPGP1_AAR00316   RFMMGRTTLGDRATGCPPSAKADVVAVLQGGAVSEMSAHDELMAKGENGTYAKLIRMQEQ
SbAAR10387        RFMIGRTTL-VIAHRMSTIRKADVVAVLQGGPVSEMGAHDELMAKGENGTYAKFIRMQEQ
OsXP_483819       RFMIGRTTL-VIAHRLSTIRKADLVAVLQGGAISEVGTHDELMARGD-GTYARLIRMQEQ
OS_CAD59580       RFMIGRTTL-VIAHRLSTIRKADLVAVLQGGAISEVGTHDELMARGD-GTYARLIRMQEQ
AtPGP19           RVMVGRTTV-VVAHRLCTIRNVDSIAVIQQGQVVETGTHEELIAKSG--AYASLIRFQEM
Consensus/100%    R.M.GRTT....A.........D..AV.Q.G...E...H.EL........Y...I..QE.
```

FIG. 1B

```
AtPGP1          AHETAMSNARKSSARPSSARNSVSSPIMTRNSSYGRSPYSRRLSDFS-TSDFSLSIDASS
BrABB97035      AHETAMNNARKSSARPSSARNSVSSPIIARNSSYGRSPYSRRLSDFS-TTDFSLSVEASS
StAAD10836      AHETALSNARKSSARPSSARNSVSSPIITRNSSYGRSPYSRRLSDFS-TSDFSLSLDAA-
ZmPGP1_AAR00316 AHEAALVNARRSSARPSSARNSVSSPIMTRNSSYGRSPYSRRLSDFS-TSDFTLSIHDPH
SbAAR10387      AHEAAFVNARRSSARPSSARNSVSSPIMTRNSSYGRSPYSRRLSDFS-TSDFTLSIHDPH
OsXP_483819     AHEAALVAARRSSARPSSARNSVSSPIITRNSSYGRSPYSRRLSDADFITGLGLGVDSKQ
OS_CAD59580     AHEAALVAARRSSARPSSARNSVSSPIITRNSSYGRSPYSRRLSDADFITGLGLGVDSKQ
AtPGP19         VGTRDFSNPSTRRTRSTRLSHSLSTKSLSLRSGSLRNLSYSYSTGADGRIEMISNAETDR
Consensus/100%  ..............R......S.S.......S...R........................

AtPGP1          YPNYR--NEKLAFKDQANSFWRLAKMNSPEWKYALLGSVGSVICGSLSAFFAYVLSAVLS
BrABB97035      YPNYR--HDKLPFKDQANSFWRLAKMNSPEWKYALVGSVGSVICGSLSAFFAYVLSAVLS
StAAD10836      YSNYR--NEKLAFKDQASSFGRLAKMNSPEWTYALIGSIGSVICGSLSAFFAYVLSAVLS
ZmPGP1_AAR00316 HHHRTMADKQLAFRAGASSFLRLARMNSPEWAYALAGSIGSMVCGSFSAIFAYILSAVLS
SbAAR10387      HHHRTMADKQLAFRAGASSFLRLARMNSPEWAYALVGSLGSMVCGSFSAIFAYILSAVLS
OsXP_483819     QQQ------QHYFRVQASSFWRLAKMNSPEWGYALVASLGSMVCGSFSAIFAYVLSAVLS
OS_CAD59580     QQQ------QHYFRVQASSFWRLAKMNSPEWGYALVASLGSMVCGSFSAIFAYVLSAVLS
AtPGP19         KTR----------APENYFYRLLKLNSPEWPYSIMGAVGSILSGFIGPTFAIVMSNMIE
Consensus/100%  ....................F.RL...NSPEW.Y......GS...G.....FA...S....

AtPGP1          VYYNPDHEYMIKQIDKYCYLLIGLSSAALVFNTLQHSFWDIVGENLTKRVREKMLSAVLK
BrABB97035      IYYNPDHNYMIKQIDKYCYLLIGLSSAALIFNTLQHSFWDIVGENLTKRVREKMLTAVLK
StAAD10836      VYYNPDHAYMSEQIAKYCYLLIGVSSAALIFNTLQHYFWDVVGENLTKRVREKMLAAVLK
ZmPGP1_AAR00316 VYYAPDPRYMKREIAKYCYLLIGMSSAALLFNTVQHVFWDTVGENLTKRVREKMFAAVFR
SbAAR10387      VYYAPDPRYMKREIAKYCYLLIGMSSAALLFNTVQHVFWDTVGENLTKRVREKMFAAVLR
OsXP_483819     VYYAPDAAYMDRQIAKYCYLLIGMSSAALLFNTVQHLFWDTVGENLTKRVRERMLAAVLR
OS_CAD59580     VYYAPDAAYMDRQIAKYCYLLIGMSSAALLFNTVQHLFWDTVGENLTKRVRERMLAAVLR
AtPGP19         VFYYTDYDSMERKTKEYVFIYIGAGLYAVGAYLIQHYFFSIMGENLTTRVRRMMLSAILR
Consensus/100%  ..Y..D...M......Y....IG....A......QH......GENLT.RVR..M..A...

AtPGP1          NEMAWFDQEENESARIAARLALDANNVRSAIGDRISVIVQNTALMLVACTAGFVLQWRLA
BrABB97035      NEMAWFDQEENESARISARLALDANNVRSAIGDRISVIVQNTALMLVACTAGFVLQWRLA
StAAD10836      MEMAWFDQEENDSSRIAARLSLDANNVRSAIGDRISVIMQNSALMLVACTAGFVLQWRLA
ZmPGP1_AAR00316 NEIAWFDADENASARVTARLALDAQNVRSAIGDRISVIVQNSALMLVACTAGFVLQWRLA
SbAAR10387      NEIAWFDADENASARVAARLALDAQNVRSAIGDRISVIVQNSALMLVACTAGFVLQWRLA
OsXP_483819     NEIAWFDMEDNSSARIAARLALDAQNVRSAIGDRISIIVQNSALMLVACTAGFVLQWRLA
OS_CAD59580     NEIAWFDMEDNSSARIAARLALDAQNVRSAIGDRISIIVQNSALMLVACTAGFVLQWRLA
AtPGP19         NEVGWFDEDEHNSSLIAARLATDAADVKSAIAERISVILQNMTSLLTSFIVAFIVEWRVS
Consensus/100%  .E..WFD.....S....ARL..DA..V.SAI..RIS.I.QN....L......F...WR..

AtPGP1          LVLVAVFPVVVAATVLQKMFMTGFSGDLEAAHAKGTQLAGEAIANVRTVAAFNSEAKIVR
BrABB97035      LVLVAVFPVVVAATVLQKMFMTGFSGDLEAAHAKATQLAGEAIANVRTVAAFNSETKIVN
StAAD10836      LVLIGVFPVVVAATVLQKMFMKGFSGDLEAAHAKATQLAGEAVANVRTVAAFNSETKIVN
ZmPGP1_AAR00316 LVLLAVFPLVVGATVLQKMFMKGFSGDLEAAHARATQIAGEAVANLRTVAAFNAERKITG
SbAAR10387      LVLLAVFPLVVAATVLQKMFMKGFSGDLEAAHARATQIAGEAVANLRTVAAFNAERKITG
OsXP_483819     LVLLAVFPLVVAATVLQKMFLKGFSGDLERAHARATQIAGEAVANVRTVAAFGSEAKIVG
OS_CAD59580     LVLLAVFPLVVAATVLQKMFLKGFSGDLERAHARATQIAGEAVANVRTVAAFGSEAKIVG
AtPGP19         LLILGTFPLLVLANFAQQLSLKGFAGDTAKAHAKTSMIAGEGVSNIRTVAAFNAQSKILS
Consensus/100%  L.....FP..V.A...Q.....GF.GD...AHA.....AGE...N.RTVAAF....KI..

AtPGP1          LYTANLEPPLKRCFWKGQIAGSGYGVAQFCLYASYALGLWYASWLVKHGISDFSKTIRVF
BrABB97035      LYTANLEPPLKRCFWKGQIAGSGYGVAQFCLYASYALGLWYASWLVKHGISDFSKTIRVF
StAAD10836      LFDSSLQTPLRRCFWKGQIAGSGYGIAQFLLYSSYALGLWYASWLVKHGISDFSKTIRVF
ZmPGP1_AAR00316 LFEANLRGPLRRCFWKGQIAGSGYGVAQFLLYASYALGLWYAAWLVKHGVSDFSRTIRVF
SbAAR10387      LFEANLRGPLRRCFWKGQIAGSGYGVAQFLLYASYALGLWYAAWLVKHGVSDFSRTIRVF
OsXP_483819     LFEANLAGPLRRCFWKGQIAGSGYGVAQFLLYASYALGLWYAAWLVKHGVSDFSKTIRVF
OS_CAD59580     LFEANLAGPLRRCFWKGQIAGSGYGVAQFLLYASYALGLWYAAWLVKHGVSDFSKTIRVF
AtPGP19         LFCHELRVPQKRSLYRSQTSGFLFGLSQLALYGSEALILWYGAHLVSKGVSTFSKVIKVF
Consensus/100%  L....L..P..R.....Q..G...G..Q..LY.S.AL.LWY...LV..G.S.FS..I.VF
```

FIG. 1C

```
AtPGP1          MVLMVSANGAAETLTLAPDFIKGGQAMRSVFELLDRKTEIEPDDPDTTPVPDRLRGEVEL
BrABB97035      MVLMVSANGAAETLTLAPDFIKGGQAMRSVFELLDRKTEIEPDDLDTTPVPDRLRGEVEL
StAAD10836      MVLMVSANGAAETLTLAPDFIKGGRAMRSVFELLDRKTEVEPDDPDATAVPDRLRGEVEF
ZmPGP1_AAR00316 MVLMVSANGAAETLTLAPDFIKGGRAMRSVFETIDRKTEVEPHDVDAAPVPDGPGAKVEL
SbAAR10387      MVLMVSANGAAETLTLAPDFVKGGRAMRSVFETIDRKTEVEPDDVDAAPVPERPKGEVEL
OsXP_483819     MVLMVSANGAAETLTLAPDFVKGGRAMQAVFEAMDRRTEIEPDDVDAAAVPERPRGEVEL
OS_CAD59580     MVLMVSANGAAETLTLAPDFVKGGRAMQAVFEAMDRRTEIEPDDVDAAAVPERPRGEVEL
AtPGP19         VVLVITANSVAETVSLAPEIIRGGEAVGSVFSVLDRQTRIDPDDADADPV-ETIRGDIEF
Consensus/100%  .VL...AN..AET..LAP....GG.A...VF...DR.T...P.D.D...V........E.

AtPGP1          KHIDFSYPSRPDIQIFRDLSLRARAGKTLALVGPSGCGKSSVISLIQRFYEPSSGRVMID
BrABB97035      KHIDFSYPSRPDIQVFRDLSLRARAGKTLALVGPSGCGKSSVISLIQRFYEPSSGRVLID
StAAD10836      KHVDFSYPTRPDVSIFRDLNLRARAGKTLALVGPSGCGKSSVISLIERFYEPSSGRVIID
ZmPGP1_AAR00316 KHVDFLYPSRPDIQVFRDLSLRARAGKTLALVGPSGSGKSSVLALVQRFYKPTSGRVLLD
SbAAR10387      KHVDFSYPSRPDIQVFRDLSLRARAGKTLALVGPSGCGKSSVLALVQRFYEPTSGRVLLD
OsXP_483819     KHVDFAYPSRPEVQVFRDLSLRARAGRTLALVGASGCGKSSVLALVQRFYEPNSGRVLLD
OS_CAD59580     KHVDFAYPSRPEVQVFRDLSLRARAGRTLALVGASGCGKSSVLALVQRFYEPNSGRVLLD
AtPGP19         RHVDFAYPSRPDVMVFRDFNLRIRAGHSQALVGASGSGKSSVIAMIERFYDPLAGKVMID
Consensus/100%  .H.DF.YP.RP....FRD..LR.RAG...ALVG.SG.GKSSV.....RFY.P..G.V..D AtPGP1          GKDIRKYNLKAIRKHIAIVPQEPCLFGTTIYENIAYGHECATEAEIIQAATLASAHKFIS
BrABB97035      GKDIRKYNLKAIRKHIAIVPQEPCLFGTTIYENIAYGHECATEAEIIQAATLASAHKFIS
StAAD10836      GKDIRKYNLKSLRRHIAVVPQEPCLFATTIYENIAYGHESATEAEITEAATLANAHKFIS
ZmPGP1_AAR00316 GKDVRKYNLRALRRVVAVVPQEPFLAASIHENIAYGREGATEAEVVEAAAQANAHRFIA
SbAAR10387      GKDVRKYNLRALRRVVAVAPQEPFLAASIHDNIAYGREGATEAEVVEAATQANAHRFIA
OsXP_483819     GRDLRKFNLRSLRRAMALVPQEPFLAATIHDNIAYGREGATEAEVVEAATAANAHKFIS
OS_CAD59580     GRDLRKFNLRSLRRAMALVPQEPFLAATIHDNIAYGREGATEAEVVEAATAANAHKFIS
AtPGP19         GKDIRRLNLKSLRLKIGLVQQEPALFAATIFDNIAYGKDGATESEVIDAARAANAHGFIS
Consensus/100%  G.D.R..NL...R.......QEP.LF...I..NIAYG...ATE.E...AA..A.AH.FI.

AtPGP1          ALPEGYKTYVGERGVQLSGGQKQRIAIARALVRKAEIMLLDEATSALDAESERSVQEALD
BrABB97035      ALPDGYKTYVGERGVQLSGGQKQRIAIARALVRKAEIMLLDEATSALDAESERSVQEALD
StAAD10836      ALPDGYKTFVGERGVQLSGGQKQRIAIARAFLRKAELMLLDEATSALDAESERCVQEALD
ZmPGP1_AAR00316 ALPEGYRTQVGERGVQLSGGQRQRIAIARALVKQAAIVLLDEATSALDAESERCVQEALE
SbAAR10387      ALPEGYGTQVGERGVQLSGGQRQRIAIARALVKQAAIVLLDEATSALDAESERCVQEALE
OsXP_483819     ALPEGYGTLVGERGVQLSGGQRQRIAIARALVKQAPILLLDEATSALDAESERSVQEALA
OS_CAD59580     ALPEGYGTLVGERGVQLSGGQRQRIAIARALVKQAPILLLDEATSALDAESERSVQEALA
AtPGP19         GLPEGYKTPVGERGVQLSGGQKQRIAIARAVLKNPTVLLLDEATSALDAESECVLQEALE
Consensus/100%  .LP.GY.T.VGERGVQLSGGQ.QRIAIARA........LLDEATSALDAESE...QEAL.

AtPGP1          Q-ACSGRTSIVVAHRLSTIRNAHVIAVIDDGKVAEQGSHSHLLKNHPDGIYARMIQLQRF
BrABB97035      Q-ACSGRTSIVVAHRLSTIRNAHVIAVIDDGKVVEQGSHSHLLKNYPDGIYARMIQLQRF
StAAD10836      R-ACAGKTTIVVAHRLSTIRNAHVIAVIDDGKVAEQGSHSHLLKNYSDGIYARMIQLQRF
ZmPGP1_AAR00316 R-AGSGRTTIVVAHRLATVRGAHTIAVIDDGKVAEQGSHSHLLKHHPDGCYARMLQLAAA
SbAAR10387      R-AGSGRTTIVVAHRLATVRGAHTIAVIDDGKVAEQGSHSHLLKHHPDGCYARMLQLRL
OsXP_483819     SSSGSGRTTIVVAHRLATVRNAHTIAVIDDGKVAEQGSHSHLLNHHPDGCYARMLQLRL
OS_CAD59580     SSSGSGRTTIVVAHRLATVRNAHTIAVIDDGKVAEQGSHSHLLNHHPDGCYARMLQLRL
AtPGP19         R-LMRGRTTVVVAHRLSTIRGVDCIGVIQDGRIVEQGSHSELVS-RPEGAYSRLLQLQTH
Consensus/100% .....G.T..VVAHRL.T.R....I.VI.DG...EQGSHS.L......G.Y.R..QL...

AtPGP1          THTQVIGMTSG--SSSRVKEDDA-----------
BrABB97035      THTQVIGMTSG--SSSRVKEDDA-----------
StAAD10836      THGEAVNMATGSTSSSRPKEDQD-----------
ZmPGP1_AAR00316 DGRGGR-ARAVVLVQRGRVGRNGWMDGFGSSRD-
SbAAR10387      TGGCRA-RAAAVVVQRGR--RVGWMDGSWMSLVP
OsXP_483819     SHSHVAPGPSSSTTTHGT----------------
OS_CAD59580     SHSHVAPGPSSSTTTHGT----------------
AtPGP19         RI--------------------------------
Consensus/100%  ..................................
```

FIG. 1D

SEQUENCE LISTING

```
<160> NUMBER OF SEQ ID NOS: 54

<210> SEQ ID NO 1
<211> LENGTH: 38
<212> TYPE: PRT
<213> ORGANISM: Artificial Sequence
<220> FEATURE:
<223> OTHER INFORMATION: Auxin transporter homolog
<220> FEATURE:
<221> NAME/KEY: MISC_FEATURE
<222> LOCATION: (2)..(2)
<223> OTHER INFORMATION: Ala or Ser
<220> FEATURE:
<221> NAME/KEY: MISC_FEATURE
<222> LOCATION: (6)..(6)
<223> OTHER INFORMATION: Ile or Val
<220> FEATURE:
<221> NAME/KEY: MISC_FEATURE
<222> LOCATION: (8)..(8)
<223> OTHER INFORMATION: Leu or Val
<220> FEATURE:
<221> NAME/KEY: MISC_FEATURE
<222> LOCATION: (11)..(11)
```

```
<223> OTHER INFORMATION: Ser or Gly
<220> FEATURE:
<221> NAME/KEY: MISC_FEATURE
<222> LOCATION: (23)..(23)
<223> OTHER INFORMATION: Ile or Leu
<220> FEATURE:
<221> NAME/KEY: MISC_FEATURE
<222> LOCATION: (28)..(28)
<223> OTHER INFORMATION: Asp or Glu
<220> FEATURE:
<221> NAME/KEY: MISC_FEATURE
<222> LOCATION: (30)..(30)
<223> OTHER INFORMATION: Asn, Thr, or Ser
<220> FEATURE:
<221> NAME/KEY: MISC_FEATURE
<222> LOCATION: (31)..(31)
<223> OTHER INFORMATION: Ser or Ala
<220> FEATURE:
<221> NAME/KEY: MISC_FEATURE
<222> LOCATION: (33)..(33)
<223> OTHER INFORMATION: Gln or Thr
<220> FEATURE:
<221> NAME/KEY: MISC_FEATURE
<222> LOCATION: (34)..(34)
<223> OTHER INFORMATION: Val, Leu, or Ile
<220> FEATURE:
<221> NAME/KEY: MISC_FEATURE
<222> LOCATION: (35)..(35)
<223> OTHER INFORMATION: Leu or Met

<400> SEQUENCE: 1

Pro Xaa Gly Lys Thr Xaa Ala Xaa Val Gly Xaa Ser Gly Ser Gly Lys
1               5                   10                  15

Ser Thr Val Val Ser Leu Xaa Glu Arg Phe Tyr Xaa Pro Xaa Xaa Gly
            20                  25                  30

Xaa Xaa Xaa Leu Asp Gly
        35

<210> SEQ ID NO 2
<211> LENGTH: 31
<212> TYPE: PRT
<213> ORGANISM: Artificial Sequence
<220> FEATURE:
<223> OTHER INFORMATION: Auxin transporter homolog
<220> FEATURE:
<221> NAME/KEY: MISC_FEATURE
<222> LOCATION: (2)..(2)
<223> OTHER INFORMATION: Lys, Glu, Asn, or Gln
<220> FEATURE:
<221> NAME/KEY: MISC_FEATURE
<222> LOCATION: (4)..(4)
<223> OTHER INFORMATION: Arg or Lys
<220> FEATURE:
<221> NAME/KEY: MISC_FEATURE
<222> LOCATION: (5)..(5)
<223> OTHER INFORMATION: Trp or Phe
<220> FEATURE:
<221> NAME/KEY: MISC_FEATURE
<222> LOCATION: (8)..(8)
<223> OTHER INFORMATION: Gln, Arg, or Glu
<220> FEATURE:
<221> NAME/KEY: MISC_FEATURE
<222> LOCATION: (14)..(14)
<223> OTHER INFORMATION: Ser or Asn
<220> FEATURE:
<221> NAME/KEY: MISC_FEATURE
<222> LOCATION: (18)..(18)
<223> OTHER INFORMATION: Ala or Thr
<220> FEATURE:
<221> NAME/KEY: MISC_FEATURE
<222> LOCATION: (23)..(23)
<223> OTHER INFORMATION: Ser or Thr
<220> FEATURE:
<221> NAME/KEY: MISC_FEATURE
<222> LOCATION: (25)..(25)
<223> OTHER INFORMATION: Lys, Arg, or Leu
```

```
<220> FEATURE:
<221> NAME/KEY: MISC_FEATURE
<222> LOCATION: (28)..(28)
<223> OTHER INFORMATION: Ile or Leu
<220> FEATURE:
<221> NAME/KEY: MISC_FEATURE
<222> LOCATION: (30)..(30)
<223> OTHER INFORMATION: Leu or Tyr

<400> SEQUENCE: 2

Leu Xaa Leu Xaa Xaa Leu Arg Xaa Gln Ile Gly Leu Val Xaa Gln Glu
1               5                   10                  15

Pro Xaa Leu Phe Ala Thr Xaa Ile Xaa Glu Asn Xaa Leu Xaa Gly
            20                  25                  30

<210> SEQ ID NO 3
<211> LENGTH: 40
<212> TYPE: PRT
<213> ORGANISM: Artificial Sequence
<220> FEATURE:
<223> OTHER INFORMATION: Auxin transporter homolog
<220> FEATURE:
<221> NAME/KEY: MISC_FEATURE
<222> LOCATION: (7)..(7)
<223> OTHER INFORMATION: Leu or Val
<220> FEATURE:
<221> NAME/KEY: MISC_FEATURE
<222> LOCATION: (25)..(25)
<223> OTHER INFORMATION: Lys or Arg
<220> FEATURE:
<221> NAME/KEY: MISC_FEATURE
<222> LOCATION: (26)..(26)
<223> OTHER INFORMATION: Asn or Asp
<220> FEATURE:
<221> NAME/KEY: MISC_FEATURE
<222> LOCATION: (28)..(28)
<223> OTHER INFORMATION: Ala or Lys

<400> SEQUENCE: 3

Gln Val Gly Glu Arg Gly Xaa Gln Leu Ser Gly Gly Gln Lys Gln Arg
1               5                   10                  15

Ile Ala Ile Ala Arg Ala Met Leu Xaa Xaa Pro Xaa Ile Leu Leu Leu
            20                  25                  30

Asp Glu Ala Thr Ser Ala Leu Asp
            35                  40

<210> SEQ ID NO 4
<211> LENGTH: 29
<212> TYPE: PRT
<213> ORGANISM: Artificial Sequence
<220> FEATURE:
<223> OTHER INFORMATION: Auxin transporter homolog
<220> FEATURE:
<221> NAME/KEY: MISC_FEATURE
<222> LOCATION: (3)..(3)
<223> OTHER INFORMATION: Glu or Asp
<220> FEATURE:
<221> NAME/KEY: MISC_FEATURE
<222> LOCATION: (6)..(6)
<223> OTHER INFORMATION: Lys, Gly, or Arg
<220> FEATURE:
<221> NAME/KEY: MISC_FEATURE
<222> LOCATION: (8)..(8)
<223> OTHER INFORMATION: Tyr, Phe, Gln, Leu, or Pro
<220> FEATURE:
<221> NAME/KEY: MISC_FEATURE
<222> LOCATION: (21)..(21)
<223> OTHER INFORMATION: Lys or Arg

<400> SEQUENCE: 4

Leu Pro Xaa Gly Tyr Xaa Thr Xaa Val Gly Glu Arg Gly Val Gln Leu
1               5                   10                  15
```

```
Ser Gly Gly Gln Xaa Gln Arg Ile Ala Ile Ala Arg Ala
            20                  25

<210> SEQ ID NO 5
<211> LENGTH: 21
<212> TYPE: PRT
<213> ORGANISM: Artificial Sequence
<220> FEATURE:
<223> OTHER INFORMATION: Auxin transporter homolog
<220> FEATURE:
<221> NAME/KEY: MISC_FEATURE
<222> LOCATION: (15)..(15)
<223> OTHER INFORMATION: Arg or Cys
<220> FEATURE:
<221> NAME/KEY: MISC_FEATURE
<222> LOCATION: (16)..(16)
<223> OTHER INFORMATION: Ser, Cys, or Val
<220> FEATURE:
<221> NAME/KEY: MISC_FEATURE
<222> LOCATION: (17)..(17)
<223> OTHER INFORMATION: Val or Leu

<400> SEQUENCE: 5

Leu Leu Asp Glu Ala Thr Ser Ala Leu Asp Ala Glu Ser Glu Xaa Xaa
1               5                   10                  15

Xaa Gln Glu Ala Leu
            20

<210> SEQ ID NO 6
<211> LENGTH: 56
<212> TYPE: DNA
<213> ORGANISM: Artificial Sequence
<220> FEATURE:
<223> OTHER INFORMATION: emrB knockout primer

<400> SEQUENCE: 6
aagctaacgc tggctaatcc agaggtgcgt gtgatggtgt aggctggagc tgcttc         56

<210> SEQ ID NO 7
<211> LENGTH: 55
<212> TYPE: DNA
<213> ORGANISM: Artificial Sequence
<220> FEATURE:
<223> OTHER INFORMATION: emrB knockout primer

<400> SEQUENCE: 7
aaagccagtt caaatgaact ggcttagttg tacttacata tgaatatcct cctta          55

<210> SEQ ID NO 8
<211> LENGTH: 58
<212> TYPE: DNA
<213> ORGANISM: Artificial Sequence
<220> FEATURE:
<223> OTHER INFORMATION: acrAB knockout primer

<400> SEQUENCE: 8
gaccaatttg aaatcggaca ctcgaggttt acatatgagt gtaggctgga gctgcttc       58

<210> SEQ ID NO 9
<211> LENGTH: 58
<212> TYPE: DNA
<213> ORGANISM: Artificial Sequence
<220> FEATURE:
<223> OTHER INFORMATION: acrAB knockout primer

<400> SEQUENCE: 9
cttacgcggc cttagtgatt acacgttgta tcaatgatgc atatgaatat cctcctta       58
```

```
<210> SEQ ID NO 10
<211> LENGTH: 20
<212> TYPE: DNA
<213> ORGANISM: Artificial Sequence
<220> FEATURE:
<223> OTHER INFORMATION: emrB upstream forward primer

<400> SEQUENCE: 10
gtatcggtca gccggtcact                                                      20

<210> SEQ ID NO 11
<211> LENGTH: 20
<212> TYPE: DNA
<213> ORGANISM: Artificial Sequence
<220> FEATURE:
<223> OTHER INFORMATION: emrB upstream reverse primer

<400> SEQUENCE: 11
tgttcgatct gcgcttctgc                                                      20

<210> SEQ ID NO 12
<211> LENGTH: 20
<212> TYPE: DNA
<213> ORGANISM: Artificial Sequence
<220> FEATURE:
<223> OTHER INFORMATION: acrA upstream forward primer

<400> SEQUENCE: 12
taatcgacgc cgttcttctg                                                      20

<210> SEQ ID NO 13
<211> LENGTH: 20
<212> TYPE: DNA
<213> ORGANISM: Artificial Sequence
<220> FEATURE:
<223> OTHER INFORMATION: acrB downstream reverse primer

<400> SEQUENCE: 13
gcggttgaac taacggacac                                                      20

<210> SEQ ID NO 14
<211> LENGTH: 34
<212> TYPE: DNA
<213> ORGANISM: Artificial Sequence
<220> FEATURE:
<223> OTHER INFORMATION: PCR primer

<400> SEQUENCE: 14
ggccttggcc atggaaatga agaaattgct cccc                                      34

<210> SEQ ID NO 15
<211> LENGTH: 32
<212> TYPE: DNA
<213> ORGANISM: Artificial Sequence
<220> FEATURE:
<223> OTHER INFORMATION: PCR primer

<400> SEQUENCE: 15
ccggccaagc tttcagttac ggaaagggtt at                                        32

<210> SEQ ID NO 16
<211> LENGTH: 32
<212> TYPE: DNA
<213> ORGANISM: Artificial Sequence
<220> FEATURE:
<223> OTHER INFORMATION: Mutagenic oligonucleotide
<220> FEATURE:
```

```
<221> NAME/KEY: misc_feature
<222> LOCATION: (14)..(19)
<223> OTHER INFORMATION: NdeI site

<400> SEQUENCE: 16
gaggagaaag gtacatatgg gtgaacagaa ac                                    32

<210> SEQ ID NO 17
<211> LENGTH: 32
<212> TYPE: DNA
<213> ORGANISM: Artificial Sequence
<220> FEATURE:
<223> OTHER INFORMATION: Mutagenic oligonucleotide
<220> FEATURE:
<221> NAME/KEY: misc_feature
<222> LOCATION: (16)..(21)
<223> OTHER INFORMATION: NdeI site

<400> SEQUENCE: 17
cagtttctgt tcacccatat gtacctttct cc                                    32

<210> SEQ ID NO 18
<211> LENGTH: 32
<212> TYPE: DNA
<213> ORGANISM: Artificial Sequence
<220> FEATURE:
<223> OTHER INFORMATION: Mutagenic primer

<400> SEQUENCE: 18
acgtctgtgt ggaattctcg gacaccgagg ag                                    32

<210> SEQ ID NO 19
<211> LENGTH: 32
<212> TYPE: DNA
<213> ORGANISM: Artificial Sequence
<220> FEATURE:
<223> OTHER INFORMATION: Mutagenic primer

<400> SEQUENCE: 19
ctcctcggtg tccgagaatt ccacacagac gt                                    32

<210> SEQ ID NO 20
<211> LENGTH: 34
<212> TYPE: DNA
<213> ORGANISM: Artificial Sequence
<220> FEATURE:
<223> OTHER INFORMATION: PCR primer

<400> SEQUENCE: 20
ttaaggccgt cgacatggat caggccggca ttat                                  34

<210> SEQ ID NO 21
<211> LENGTH: 34
<212> TYPE: DNA
<213> ORGANISM: Artificial Sequence
<220> FEATURE:
<223> OTHER INFORMATION: PCR primer

<400> SEQUENCE: 21
ttccaaggtt ggatccctaa acgatgcggc aggc                                  34

<210> SEQ ID NO 22
<211> LENGTH: 35
<212> TYPE: DNA
<213> ORGANISM: Artificial Sequence
<220> FEATURE:
<223> OTHER INFORMATION: PCR primer
```

-continued

<400> SEQUENCE: 22
ggccggttaa gtcgacatga atatatccgc tcagg                                35

<210> SEQ ID NO 23
<211> LENGTH: 31
<212> TYPE: DNA
<213> ORGANISM: Artificial Sequence
<220> FEATURE:
<223> OTHER INFORMATION: PCR primer

<400> SEQUENCE: 23
ttaaccttgg atcctcagtg cgcgcggctg t                                    31

<210> SEQ ID NO 24
<211> LENGTH: 36
<212> TYPE: DNA
<213> ORGANISM: Artificial Sequence
<220> FEATURE:
<223> OTHER INFORMATION: E. coli MarASalIF primer

<400> SEQUENCE: 24
ttaaggccgt cgacatgacg atgtccagac gcaata                               36

<210> SEQ ID NO 25
<211> LENGTH: 34
<212> TYPE: DNA
<213> ORGANISM: Artificial Sequence
<220> FEATURE:
<223> OTHER INFORMATION: E. coli MarABamHIR primer

<400> SEQUENCE: 25
gcagtgccgg atccctagct gttgtaatga ttta                                 34

<210> SEQ ID NO 26
<211> LENGTH: 32
<212> TYPE: DNA
<213> ORGANISM: Artificial Sequence
<220> FEATURE:
<223> OTHER INFORMATION: PCR primer

<400> SEQUENCE: 26
ggccttccgt cgacatgacc gagttaccaa tc                                   32

<210> SEQ ID NO 27
<211> LENGTH: 34
<212> TYPE: DNA
<213> ORGANISM: Artificial Sequence
<220> FEATURE:
<223> OTHER INFORMATION: PCR primer

<400> SEQUENCE: 27
ttccaaggtt ggatccctaa acgatgcggc aggc                                 34

<210> SEQ ID NO 28
<211> LENGTH: 71
<212> TYPE: DNA
<213> ORGANISM: Artificial Sequence
<220> FEATURE:
<223> OTHER INFORMATION: cysH knockout forward primer

<400> SEQUENCE: 28
cgcgtgagcg tcgcatcagg caaggcaaac agtgaggaat ctatgtccaa agtgtaggct     60
ggagctgctt c                                                          71

<210> SEQ ID NO 29

```
<211> LENGTH: 75
<212> TYPE: DNA
<213> ORGANISM: Artificial Sequence
<220> FEATURE:
<223> OTHER INFORMATION: cysH knockout reverse primer

<400> SEQUENCE: 29
cgcccccatc atttctgaca gaggcgttta atttgtccgg caatatttac ccttccatat    60
gaatatcctc cttag                                                    75

<210> SEQ ID NO 30
<211> LENGTH: 62
<212> TYPE: DNA
<213> ORGANISM: Artificial Sequence
<220> FEATURE:
<223> OTHER INFORMATION: ENVR1 primer

<400> SEQUENCE: 30
cactctgtgt cgaatatatt tatttcctga ataattaatc tggtgtaggc tggagctgct    60
tc                                                                  62

<210> SEQ ID NO 31
<211> LENGTH: 59
<212> TYPE: DNA
<213> ORGANISM: Artificial Sequence
<220> FEATURE:
<223> OTHER INFORMATION: ENVR2 primer

<400> SEQUENCE: 31
actgtgacga actgaattt caggacagaa tgtgaattta catatgaata tcctccttag    59

<210> SEQ ID NO 32
<211> LENGTH: 41
<212> TYPE: DNA
<213> ORGANISM: Artificial Sequence
<220> FEATURE:
<223> OTHER INFORMATION: ENVR3 primer

<400> SEQUENCE: 32
cctctcgtat aaatacacat taggtgatag attaaccttc g                       41

<210> SEQ ID NO 33
<211> LENGTH: 30
<212> TYPE: DNA
<213> ORGANISM: Artificial Sequence
<220> FEATURE:
<223> OTHER INFORMATION: ENVR4 primer

<400> SEQUENCE: 33
gcaacagaaa cagacaaatg ccgcaatatg                                    30

<210> SEQ ID NO 34
<211> LENGTH: 35
<212> TYPE: DNA
<213> ORGANISM: Artificial Sequence
<220> FEATURE:
<223> OTHER INFORMATION: PGP1 primer

<400> SEQUENCE: 34
catatgatgg ataatgacgg tggtgctcct cctcc                              35

<210> SEQ ID NO 35
<211> LENGTH: 31
<212> TYPE: DNA
<213> ORGANISM: Artificial Sequence
<220> FEATURE:
```

```
<223> OTHER INFORMATION: PGP2 primer

<400> SEQUENCE: 35
catttgcgac tcgagcagcc tcctctatct c                                31

<210> SEQ ID NO 36
<211> LENGTH: 31
<212> TYPE: DNA
<213> ORGANISM: Artificial Sequence
<220> FEATURE:
<223> OTHER INFORMATION: PGP3 primer

<400> SEQUENCE: 36
gagatagagg aggctgctcg agtcgcaaat g                                31

<210> SEQ ID NO 37
<211> LENGTH: 39
<212> TYPE: DNA
<213> ORGANISM: Artificial Sequence
<220> FEATURE:
<223> OTHER INFORMATION: PGP4 primer

<400> SEQUENCE: 37
gagagcataa gatgcataaa gacagaactg agctacacc                        39

<210> SEQ ID NO 38
<211> LENGTH: 48
<212> TYPE: DNA
<213> ORGANISM: Artificial Sequence
<220> FEATURE:
<223> OTHER INFORMATION: PGP5 primer

<400> SEQUENCE: 38
gcggccgcct aagcatcatc ttccttaacc ctagaacttg aacctgac              48

<210> SEQ ID NO 39
<211> LENGTH: 39
<212> TYPE: DNA
<213> ORGANISM: Artificial Sequence
<220> FEATURE:
<223> OTHER INFORMATION: PGP6 primer

<400> SEQUENCE: 39
ggtgtagctc agttctgtct ttatgcatct tatgctctc                        39

<210> SEQ ID NO 40
<211> LENGTH: 852
<212> TYPE: DNA
<213> ORGANISM: Artificial Sequence
<220> FEATURE:
<223> OTHER INFORMATION: ATCC 4978 D-aminotransferase
<220> FEATURE:
<221> NAME/KEY: CDS
<222> LOCATION: (1)..(852)

<400> SEQUENCE: 40 atg agt tat agc tta tgg aat gac caa att gtg aat gat gaa gaa gta    48
Met Ser Tyr Ser Leu Trp Asn Asp Gln Ile Val Asn Asp Glu Glu Val
1               5                   10                  15 gta gtt gat aag gag gac cgt ggc tat caa ttt ggc gat ggt gtt tat    96
Val Val Asp Lys Glu Asp Arg Gly Tyr Gln Phe Gly Asp Gly Val Tyr
            20                  25                  30 gaa gtt gta aaa gta tat aac ggt gaa tta ttt aca gcg gag gag cat   144
Glu Val Val Lys Val Tyr Asn Gly Glu Leu Phe Thr Ala Glu Glu His
        35                  40                  45 gtc gat cgt ttt tac gcg agt gct gaa aaa att cgc gtt acg atc cct   192
```

```
                Val Asp Arg Phe Tyr Ala Ser Ala Glu Lys Ile Arg Val Thr Ile Pro
                 50                  55                  60 tat aca aaa gac aaa ttg cat caa tta ttg cat cag tta gtt gaa atg        240
Tyr Thr Lys Asp Lys Leu His Gln Leu Leu His Gln Leu Val Glu Met
 65                  70                  75                  80 aat aaa gtt caa aca gga cat att tat ttc caa att acg cgt ggt gca        288
Asn Lys Val Gln Thr Gly His Ile Tyr Phe Gln Ile Thr Arg Gly Ala
                 85                  90                  95 ggc cct cgt aat cat att ttc cct ggt gat gaa gtg aag cca gta tta        336
Gly Pro Arg Asn His Ile Phe Pro Gly Asp Glu Val Lys Pro Val Leu
            100                 105                 110 aca ggt aat acc aag gaa aat cca cgt ccc gta gca aac ttt gaa aaa        384
Thr Gly Asn Thr Lys Glu Asn Pro Arg Pro Val Ala Asn Phe Glu Lys
        115                 120                 125 ggt gtg aaa gca aca ttt gta gaa gac att cgt tgg tta cgc tgt gac        432
Gly Val Lys Ala Thr Phe Val Glu Asp Ile Arg Trp Leu Arg Cys Asp
    130                 135                 140 att aaa tca tta aat tta ctt ggt gcg gta ctt gct aaa caa gaa gca        480
Ile Lys Ser Leu Asn Leu Leu Gly Ala Val Leu Ala Lys Gln Glu Ala
145                 150                 155                 160 cat gaa aaa gga tgc tat gaa gcg gtt tta cat cgt gat gaa atc gta        528
His Glu Lys Gly Cys Tyr Glu Ala Val Leu His Arg Asp Glu Ile Val
                165                 170                 175 aca gaa ggc tct tct tca aat att tat gga att aaa gat ggc gta tta        576
Thr Glu Gly Ser Ser Ser Asn Ile Tyr Gly Ile Lys Asp Gly Val Leu
            180                 185                 190 tac aca cat cca gcg aat aac ttc atc tta aat ggt att aca cgt caa        624
Tyr Thr His Pro Ala Asn Asn Phe Ile Leu Asn Gly Ile Thr Arg Gln
        195                 200                 205 gta atc att aaa tgt gct gct gaa att ggc tta cca gtg aag gaa gaa        672
Val Ile Ile Lys Cys Ala Ala Glu Ile Gly Leu Pro Val Lys Glu Glu
    210                 215                 220 gca atg aca aaa act cag ctt ctt gca atg gat gaa gtg att gtt tca        720
Ala Met Thr Lys Thr Gln Leu Leu Ala Met Asp Glu Val Ile Val Ser
225                 230                 235                 240 tca acg act tca gaa gta acg cca att atc gac ata gat gga aca gta        768
Ser Thr Thr Ser Glu Val Thr Pro Ile Ile Asp Ile Asp Gly Thr Val
                245                 250                 255 att ggt gcg ggt aaa ccg ggt gac tgg aca cgt aaa tta caa gca caa        816
Ile Gly Ala Gly Lys Pro Gly Asp Trp Thr Arg Lys Leu Gln Ala Gln
            260                 265                 270 ttt gat acg aaa atc cca aaa ggt att cgc gca taa                        852
Phe Asp Thr Lys Ile Pro Lys Gly Ile Arg Ala
        275                 280

<210> SEQ ID NO 41
<211> LENGTH: 283
<212> TYPE: PRT
<213> ORGANISM: Artificial Sequence
<220> FEATURE:
<223> OTHER INFORMATION: Synthetic Construct

<400> SEQUENCE: 41

Met Ser Tyr Ser Leu Trp Asn Asp Gln Ile Val Asn Asp Glu Glu Val
 1               5                  10                  15

Val Val Asp Lys Glu Asp Arg Gly Tyr Gln Phe Gly Asp Gly Val Tyr
                20                  25                  30

Glu Val Val Lys Val Tyr Asn Gly Glu Leu Phe Thr Ala Glu Glu His
            35                  40                  45

Val Asp Arg Phe Tyr Ala Ser Ala Glu Lys Ile Arg Val Thr Ile Pro
     50                  55                  60
```

```
Tyr Thr Lys Asp Lys Leu His Gln Leu Leu His Gln Leu Val Glu Met
 65                  70                  75                  80

Asn Lys Val Gln Thr Gly His Ile Tyr Phe Gln Ile Thr Arg Gly Ala
                 85                  90                  95

Gly Pro Arg Asn His Ile Phe Pro Gly Asp Glu Val Lys Pro Val Leu
            100                 105                 110

Thr Gly Asn Thr Lys Glu Asn Pro Arg Pro Val Ala Asn Phe Glu Lys
        115                 120                 125

Gly Val Lys Ala Thr Phe Val Glu Asp Ile Arg Trp Leu Arg Cys Asp
    130                 135                 140

Ile Lys Ser Leu Asn Leu Leu Gly Ala Val Leu Ala Lys Gln Glu Ala
145                 150                 155                 160

His Glu Lys Gly Cys Tyr Glu Ala Val Leu His Arg Asp Glu Ile Val
                165                 170                 175

Thr Glu Gly Ser Ser Ser Asn Ile Tyr Gly Ile Lys Asp Gly Val Leu
            180                 185                 190

Tyr Thr His Pro Ala Asn Asn Phe Ile Leu Asn Gly Ile Thr Arg Gln
        195                 200                 205

Val Ile Ile Lys Cys Ala Ala Glu Ile Gly Leu Pro Val Lys Glu Glu
    210                 215                 220

Ala Met Thr Lys Thr Gln Leu Leu Ala Met Asp Glu Val Ile Val Ser
225                 230                 235                 240

Ser Thr Thr Ser Glu Val Thr Pro Ile Ile Asp Ile Asp Gly Thr Val
                245                 250                 255

Ile Gly Ala Gly Lys Pro Gly Asp Trp Thr Arg Lys Leu Gln Ala Gln
            260                 265                 270

Phe Asp Thr Lys Ile Pro Lys Gly Ile Arg Ala
        275                 280

<210> SEQ ID NO 42
<211> LENGTH: 675
<212> TYPE: DNA
<213> ORGANISM: Artificial Sequence
<220> FEATURE:
<223> OTHER INFORMATION: R-specific aldolase
<220> FEATURE:
<221> NAME/KEY: CDS
<222> LOCATION: (1)..(675)
<220> FEATURE:
<221> NAME/KEY: misc_feature
<222> LOCATION: (61)..(519)
<223> OTHER INFORMATION: Demethylmenaquinone methyltransferase domain

<400> SEQUENCE: 42 atg aag ccg gtg gtg gtg cag act atc gag cgg gcc gac cga gcg atc      48
Met Lys Pro Val Val Val Gln Thr Ile Glu Arg Ala Asp Arg Ala Ile
 1               5                  10                  15 atc gag ggt ctg gcc gcg tgt ggc gtt gcc acc gtc cat gag gcg cag      96
Ile Glu Gly Leu Ala Ala Cys Gly Val Ala Thr Val His Glu Ala Gln
             20                  25                  30 ggg cgc cgg ggg ctg ctt gcg tcc tac atg cgc ccg atc tat tcg ggc     144
Gly Arg Arg Gly Leu Leu Ala Ser Tyr Met Arg Pro Ile Tyr Ser Gly
         35                  40                  45 gct gcg gtt gcg gcc tcg gcc gtc acc atc ctc tct cca ccc tgc gac     192
Ala Ala Val Ala Ala Ser Ala Val Thr Ile Leu Ser Pro Pro Cys Asp
     50                  55                  60 aac tgg atg ctg cac gtc gcc atc gag cag atc cag ccg ggc gac att     240
Asn Trp Met Leu His Val Ala Ile Glu Gln Ile Gln Pro Gly Asp Ile
 65                  70                  75                  80
```

```
ctc gtt ctc ggc acg acc tct ccg tcc gat gcc ggt tat ttc ggt gat       288
Leu Val Leu Gly Thr Thr Ser Pro Ser Asp Ala Gly Tyr Phe Gly Asp
                85                  90                  95 ctg ctg gcg act tcg gcc aag gcg cgc ggt tgc gtc ggg ttg gtc atc       336
Leu Leu Ala Thr Ser Ala Lys Ala Arg Gly Cys Val Gly Leu Val Ile
            100                 105                 110 gat gcc ggc gta cgc gat atc cgc gac ctg aca gcg atg cag ttt ccg       384
Asp Ala Gly Val Arg Asp Ile Arg Asp Leu Thr Ala Met Gln Phe Pro
        115                 120                 125 gtc tgg tcc aag gcc gtt tcg gcc cag ggc acg atc aag gag acg ctg       432
Val Trp Ser Lys Ala Val Ser Ala Gln Gly Thr Ile Lys Glu Thr Leu
130                 135                 140 ggt tcg gtc aac gtc ccc gtc gtc tgc gcc ggt gct ctg gtc aat ccc       480
Gly Ser Val Asn Val Pro Val Val Cys Ala Gly Ala Leu Val Asn Pro
145                 150                 155                 160 ggc gac gtc gtc gtg gcc gat gac gac ggt gtc tgc gtg gtg cgc cgc       528
Gly Asp Val Val Val Ala Asp Asp Asp Gly Val Cys Val Val Arg Arg
                165                 170                 175 gag gaa gcc gcg gaa acg ctg gaa aag gcc cgg gcg cgg atc gcc aat       576
Glu Glu Ala Ala Glu Thr Leu Glu Lys Ala Arg Ala Arg Ile Ala Asn
            180                 185                 190 gag gag gaa aag cgc cag cgc ttt gcc gct ggc gaa ctc ggg ctc gac       624
Glu Glu Glu Lys Arg Gln Arg Phe Ala Ala Gly Glu Leu Gly Leu Asp
        195                 200                 205 atc tac aag atg cgc gaa cgc ctc gct gcc ctg ggg ctc acc tat gtc       672
Ile Tyr Lys Met Arg Glu Arg Leu Ala Ala Leu Gly Leu Thr Tyr Val
210                 215                 220 tga                                                                   675

<210> SEQ ID NO 43
<211> LENGTH: 224
<212> TYPE: PRT
<213> ORGANISM: Artificial Sequence
<220> FEATURE:
<223> OTHER INFORMATION: Synthetic Construct

<400> SEQUENCE: 43

Met Lys Pro Val Val Gln Thr Ile Glu Arg Ala Asp Arg Ala Ile
1               5                   10                  15

Ile Glu Gly Leu Ala Ala Cys Gly Val Ala Thr Val His Glu Ala Gln
            20                  25                  30

Gly Arg Arg Gly Leu Leu Ala Ser Tyr Met Arg Pro Ile Tyr Ser Gly
        35                  40                  45

Ala Ala Val Ala Ala Ser Ala Val Thr Ile Leu Ser Pro Pro Cys Asp
    50                  55                  60

Asn Trp Met Leu His Val Ala Ile Glu Gln Ile Gln Pro Gly Asp Ile
65                  70                  75                  80

Leu Val Leu Gly Thr Thr Ser Pro Ser Asp Ala Gly Tyr Phe Gly Asp
                85                  90                  95

Leu Leu Ala Thr Ser Ala Lys Ala Arg Gly Cys Val Gly Leu Val Ile
            100                 105                 110

Asp Ala Gly Val Arg Asp Ile Arg Asp Leu Thr Ala Met Gln Phe Pro
        115                 120                 125

Val Trp Ser Lys Ala Val Ser Ala Gln Gly Thr Ile Lys Glu Thr Leu
130                 135                 140

Gly Ser Val Asn Val Pro Val Val Cys Ala Gly Ala Leu Val Asn Pro
145                 150                 155                 160

Gly Asp Val Val Val Ala Asp Asp Asp Gly Val Cys Val Val Arg Arg
                165                 170                 175
```

```
Glu Glu Ala Ala Glu Thr Leu Glu Lys Ala Arg Ala Arg Ile Ala Asn
            180                 185                 190

Glu Glu Glu Lys Arg Gln Arg Phe Ala Ala Gly Glu Leu Gly Leu Asp
        195                 200                 205

Ile Tyr Lys Met Arg Glu Arg Leu Ala Ala Leu Gly Leu Thr Tyr Val
    210                 215                 220

<210> SEQ ID NO 44
<211> LENGTH: 48
<212> TYPE: DNA
<213> ORGANISM: Artificial Sequence
<220> FEATURE:
<223> OTHER INFORMATION: AldolaseFpstIrbs primer

<400> SEQUENCE: 44
ggccggaact gcagaagaag gagatatata atgaagccgg tggtggtg            48

<210> SEQ ID NO 45
<211> LENGTH: 32
<212> TYPE: DNA
<213> ORGANISM: Artificial Sequence
<220> FEATURE:
<223> OTHER INFORMATION: AldolaseRxbaI primer

<400> SEQUENCE: 45
ggccaaggtc tagattagac ataggtgagc cc                             32

<210> SEQ ID NO 46
<211> LENGTH: 1286
<212> TYPE: PRT
<213> ORGANISM: Arabidopsis thaliana

<400> SEQUENCE: 46

Met Asp Asn Asp Gly Gly Ala Pro Pro Pro Pro Thr Leu Val Val
1               5                   10                  15

Glu Glu Pro Lys Lys Ala Glu Ile Arg Gly Val Ala Phe Lys Glu Leu
            20                  25                  30

Phe Arg Phe Ala Asp Gly Leu Asp Tyr Val Leu Met Gly Ile Gly Ser
        35                  40                  45

Val Gly Ala Phe Val His Gly Cys Ser Leu Pro Leu Phe Leu Arg Phe
    50                  55                  60

Phe Ala Asp Leu Val Asn Ser Phe Gly Ser Asn Ser Asn Asn Val Glu
65                  70                  75                  80

Lys Met Met Glu Glu Val Leu Lys Tyr Ala Leu Tyr Phe Leu Val Val
                85                  90                  95

Gly Ala Ala Ile Trp Ala Ser Ser Trp Ala Glu Ile Ser Cys Trp Met
            100                 105                 110

Trp Ser Gly Glu Arg Gln Thr Thr Lys Met Arg Ile Lys Tyr Leu Glu
        115                 120                 125

Ala Ala Leu Asn Gln Asp Ile Gln Phe Phe Asp Thr Glu Val Arg Thr
    130                 135                 140

Ser Asp Val Val Phe Ala Ile Asn Thr Asp Ala Val Met Val Gln Asp
145                 150                 155                 160

Ala Ile Ser Glu Lys Leu Gly Asn Phe Ile His Tyr Met Ala Thr Phe
                165                 170                 175

Val Ser Gly Phe Ile Val Gly Phe Thr Ala Val Trp Gln Leu Ala Leu
            180                 185                 190

Val Thr Leu Ala Val Val Pro Leu Ile Ala Val Ile Gly Gly Ile His
        195                 200                 205
```

```
Thr Thr Thr Leu Ser Lys Leu Ser Asn Lys Ser Gln Glu Ser Leu Ser
    210                 215                 220

Gln Ala Gly Asn Ile Val Glu Gln Thr Val Val Gln Ile Arg Val Val
225                 230                 235                 240

Met Ala Phe Val Gly Glu Ser Arg Ala Ser Gln Ala Tyr Ser Ser Ala
                    245                 250                 255

Leu Lys Ile Ala Gln Lys Leu Gly Tyr Lys Thr Gly Leu Ala Lys Gly
                260                 265                 270

Met Gly Leu Gly Ala Thr Tyr Phe Val Phe Cys Cys Tyr Ala Leu
            275                 280                 285

Leu Leu Trp Tyr Gly Gly Tyr Leu Val Arg His His Leu Thr Asn Gly
        290                 295                 300

Gly Leu Ala Ile Ala Thr Met Phe Ala Val Met Ile Gly Gly Leu Ala
305                 310                 315                 320

Leu Gly Gln Ser Ala Pro Ser Met Ala Ala Phe Ala Lys Ala Lys Val
                325                 330                 335

Ala Ala Ala Lys Ile Phe Arg Ile Ile Asp His Lys Pro Thr Ile Glu
            340                 345                 350

Arg Asn Ser Glu Ser Gly Val Glu Leu Asp Ser Val Thr Gly Leu Val
        355                 360                 365

Glu Leu Lys Asn Val Asp Phe Ser Tyr Pro Ser Arg Pro Asp Val Lys
370                 375                 380

Ile Leu Asn Asn Phe Cys Leu Ser Val Pro Ala Gly Lys Thr Ile Ala
385                 390                 395                 400

Leu Val Gly Ser Ser Gly Ser Gly Lys Ser Thr Val Val Ser Leu Ile
                405                 410                 415

Glu Arg Phe Tyr Asp Pro Asn Ser Gly Gln Val Leu Leu Asp Gly Gln
            420                 425                 430

Asp Leu Lys Thr Leu Lys Leu Arg Trp Leu Arg Gln Gln Ile Gly Leu
        435                 440                 445

Val Ser Gln Glu Pro Ala Leu Phe Ala Thr Ser Ile Lys Glu Asn Ile
450                 455                 460

Leu Leu Gly Arg Pro Asp Ala Asp Gln Val Glu Ile Glu Glu Ala Ala
465                 470                 475                 480

Arg Val Ala Asn Ala His Ser Phe Ile Ile Lys Leu Pro Asp Gly Phe
                485                 490                 495

Asp Thr Gln Val Gly Glu Arg Gly Leu Gln Leu Ser Gly Gly Gln Lys
            500                 505                 510

Gln Arg Ile Ala Ile Ala Arg Ala Met Leu Lys Asn Pro Ala Ile Leu
        515                 520                 525

Leu Leu Asp Glu Ala Thr Ser Ala Leu Asp Ser Glu Ser Glu Lys Leu
530                 535                 540

Val Gln Glu Ala Leu Asp Arg Phe Met Ile Gly Arg Thr Thr Leu Ile
545                 550                 555                 560

Ile Ala His Arg Leu Ser Thr Ile Arg Lys Ala Asp Leu Val Ala Val
                565                 570                 575

Leu Gln Gln Gly Ser Val Ser Glu Ile Gly Thr His Asp Glu Leu Phe
            580                 585                 590

Ser Lys Gly Glu Asn Gly Val Tyr Ala Lys Leu Ile Lys Met Gln Glu
        595                 600                 605

Ala Ala His Glu Thr Ala Met Ser Asn Ala Arg Lys Ser Ser Ala Arg
610                 615                 620

Pro Ser Ser Ala Arg Asn Ser Val Ser Ser Pro Ile Met Thr Arg Asn
```

```
                625                 630                 635                 640
Ser Ser Tyr Gly Arg Ser Pro Tyr Ser Arg Arg Leu Ser Asp Phe Ser
                    645                 650                 655

Thr Ser Asp Phe Ser Leu Ser Ile Asp Ala Ser Ser Tyr Pro Asn Tyr
                    660                 665                 670

Arg Asn Glu Lys Leu Ala Phe Lys Asp Gln Ala Asn Ser Phe Trp Arg
                    675                 680                 685

Leu Ala Lys Met Asn Ser Pro Glu Trp Lys Tyr Ala Leu Leu Gly Ser
                    690                 695                 700

Val Gly Ser Val Ile Cys Gly Ser Leu Ser Ala Phe Phe Ala Tyr Val
705                 710                 715                 720

Leu Ser Ala Val Leu Ser Val Tyr Tyr Asn Pro Asp His Glu Tyr Met
                    725                 730                 735

Ile Lys Gln Ile Asp Lys Tyr Cys Tyr Leu Leu Ile Gly Leu Ser Ser
                    740                 745                 750

Ala Ala Leu Val Phe Asn Thr Leu Gln His Ser Phe Trp Asp Ile Val
                    755                 760                 765

Gly Glu Asn Leu Thr Lys Arg Val Arg Glu Lys Met Leu Ser Ala Val
                    770                 775                 780

Leu Lys Asn Glu Met Ala Trp Phe Asp Gln Glu Asn Glu Ser Ala
785                 790                 795                 800

Arg Ile Ala Ala Arg Leu Ala Leu Asp Ala Asn Asn Val Arg Ser Ala
                    805                 810                 815

Ile Gly Asp Arg Ile Ser Val Ile Val Gln Asn Thr Ala Leu Met Leu
                    820                 825                 830

Val Ala Cys Thr Ala Gly Phe Val Leu Gln Trp Arg Leu Ala Leu Val
                    835                 840                 845

Leu Val Ala Val Phe Pro Val Val Ala Ala Thr Val Leu Gln Lys
                    850                 855                 860

Met Phe Met Thr Gly Phe Ser Gly Asp Leu Glu Ala Ala His Ala Lys
865                 870                 875                 880

Gly Thr Gln Leu Ala Gly Glu Ala Ile Ala Asn Val Arg Thr Val Ala
                    885                 890                 895

Ala Phe Asn Ser Glu Ala Lys Ile Val Arg Leu Tyr Thr Ala Asn Leu
                    900                 905                 910

Glu Pro Pro Leu Lys Arg Cys Phe Trp Lys Gly Gln Ile Ala Gly Ser
                    915                 920                 925

Gly Tyr Gly Val Ala Gln Phe Cys Leu Tyr Ala Ser Tyr Ala Leu Gly
                    930                 935                 940

Leu Trp Tyr Ala Ser Trp Leu Val Lys His Gly Ile Ser Asp Phe Ser
945                 950                 955                 960

Lys Thr Ile Arg Val Phe Met Val Leu Met Val Ser Ala Asn Gly Ala
                    965                 970                 975

Ala Glu Thr Leu Thr Leu Ala Pro Asp Phe Ile Lys Gly Gly Gln Ala
                    980                 985                 990

Met Arg Ser Val Phe Glu Leu Leu Asp Arg Lys Thr Glu Ile Glu Pro
                    995                1000                1005

Asp Asp Pro Asp Thr Thr Pro Val Pro Asp Arg Leu Arg Gly Glu
                    1010                1015                1020

Val Glu Leu Lys His Ile Asp Phe Ser Tyr Pro Ser Arg Pro Asp
                    1025                1030                1035

Ile Gln Ile Phe Arg Asp Leu Ser Leu Arg Ala Arg Ala Gly Lys
                    1040                1045                1050
```

```
Thr Leu Ala Leu Val Gly Pro Ser Gly Cys Gly Lys Ser Ser Val
    1055                1060                1065

Ile Ser Leu Ile Gln Arg Phe Tyr Glu Pro Ser Ser Gly Arg Val
    1070                1075                1080

Met Ile Asp Gly Lys Asp Ile Arg Lys Tyr Asn Leu Lys Ala Ile
    1085                1090                1095

Arg Lys His Ile Ala Ile Val Pro Gln Glu Pro Cys Leu Phe Gly
    1100                1105                1110

Thr Thr Ile Tyr Glu Asn Ile Ala Tyr Gly His Glu Cys Ala Thr
    1115                1120                1125

Glu Ala Glu Ile Ile Gln Ala Ala Thr Leu Ala Ser Ala His Lys
    1130                1135                1140

Phe Ile Ser Ala Leu Pro Glu Gly Tyr Lys Thr Tyr Val Gly Glu
    1145                1150                1155

Arg Gly Val Gln Leu Ser Gly Gly Gln Lys Gln Arg Ile Ala Ile
    1160                1165                1170

Ala Arg Ala Leu Val Arg Lys Ala Glu Ile Met Leu Leu Asp Glu
    1175                1180                1185

Ala Thr Ser Ala Leu Asp Ala Glu Ser Glu Arg Ser Val Gln Glu
    1190                1195                1200

Ala Leu Asp Gln Ala Cys Ser Gly Arg Thr Ser Ile Val Val Ala
    1205                1210                1215

His Arg Leu Ser Thr Ile Arg Asn Ala His Val Ile Ala Val Ile
    1220                1225                1230

Asp Asp Gly Lys Val Ala Glu Gln Gly Ser His Ser His Leu Leu
    1235                1240                1245

Lys Asn His Pro Asp Gly Ile Tyr Ala Arg Met Ile Gln Leu Gln
    1250                1255                1260

Arg Phe Thr His Thr Gln Val Ile Gly Met Thr Ser Gly Ser Ser
    1265                1270                1275

Ser Arg Val Lys Glu Asp Asp Ala
    1280                1285

<210> SEQ ID NO 47
<211> LENGTH: 1300
<212> TYPE: PRT
<213> ORGANISM: Brassica rapa

<400> SEQUENCE: 47

Met Gln Gly Leu Glu Leu Leu Pro Glu Pro Ser Ser Asn Ser Asn Ser
1               5                   10                  15

Asn Ser Arg Asn Pro Glu Thr Glu Leu Gln Glu His Pro Pro Glu Met
            20                  25                  30

Gly Asn Gly Gly Gly Thr Pro Pro Pro Pro Pro Ala Thr Val Glu
        35                  40                  45

Glu Pro Lys Lys Ala Glu Ile Arg Gly Val Ala Phe Lys Glu Leu Phe
    50                  55                  60

Arg Phe Ala Asp Gly Leu Asp Tyr Val Leu Met Thr Ile Gly Ser Val
65                  70                  75                  80

Gly Ala Phe Val His Gly Cys Ser Leu Pro Leu Phe Leu Arg Phe Phe
                85                  90                  95

Ala Asp Leu Val Asn Ser Phe Gly Ser Asn Ala Asn Asn Val Asp Lys
                100                 105                 110

Met Met Gln Glu Val Leu Lys Tyr Ala Leu Tyr Phe Leu Val Val Gly
            115                 120                 125
```

-continued

```
Ala Ala Ile Trp Ala Ser Ser Trp Ala Glu Ile Ser Cys Trp Met Trp
    130                 135                 140
Thr Gly Glu Arg Gln Thr Thr Lys Met Arg Ile Lys Tyr Leu Glu Ala
145                 150                 155                 160
Ala Leu Asn Gln Asp Ile Gln Phe Phe Asp Thr Glu Val Arg Thr Ser
                165                 170                 175
Asp Val Val Ser Ala Ile Asn Thr Asp Ala Val Met Val Gln Asp Ala
                180                 185                 190
Ile Ser Glu Lys Leu Gly Asn Phe Ile His Tyr Met Ala Leu Val Thr
                195                 200                 205
Ile Ala Val Val Pro Leu Ile Ala Val Ile Gly Gly Ile His Thr Thr
    210                 215                 220
Thr Leu Ser Lys Leu Ser Asn Lys Ser Gln Glu Ser Leu Ser Gln Ala
225                 230                 235                 240
Gly Asn Ile Val Glu Gln Thr Val Val Gln Ile Arg Val Val Met Ala
                245                 250                 255
Phe Val Gly Glu Ser Arg Ala Ser Gln Ala Tyr Ser Ser Ala Leu Lys
                260                 265                 270
Thr Ala Gln Lys Leu Gly Tyr Lys Thr Gly Phe Ala Lys Gly Met Gly
                275                 280                 285
Leu Gly Ala Thr Tyr Phe Val Val Phe Cys Cys Tyr Ala Leu Leu Leu
    290                 295                 300
Trp Tyr Gly Gly Tyr Leu Val Arg His His Leu Thr Asn Gly Gly Leu
305                 310                 315                 320
Ala Ile Ala Thr Met Phe Ala Val Met Ile Gly Gly Leu Gly Leu Gly
                325                 330                 335
Gln Ser Val Pro Ser Met Ala Ala Phe Ala Lys Ala Lys Val Ala Ala
                340                 345                 350
Ala Lys Ile Phe Arg Ile Ile Asp His Lys Pro Thr Ile Glu Arg Asn
                355                 360                 365
Ser Glu Ser Gly Val Glu Leu Glu Ser Val Thr Gly Leu Val Glu Leu
    370                 375                 380
Lys Asn Val Asp Phe Ser Tyr Pro Ser Arg Pro Asp Val Lys Ile Leu
385                 390                 395                 400
Asn Asp Phe Thr Leu Ser Val Pro Ala Gly Lys Thr Ile Ala Leu Val
                405                 410                 415
Gly Ser Ser Gly Ser Gly Lys Ser Thr Val Val Ser Leu Ile Glu Arg
                420                 425                 430
Phe Tyr Asp Pro Thr Ser Gly Gln Val Leu Leu Asp Gly His Asp Leu
                435                 440                 445
Lys Thr Leu Lys Leu Lys Trp Leu Arg Gln Gln Ile Gly Leu Val Ser
    450                 455                 460
Gln Glu Pro Ala Leu Phe Ala Thr Ser Ile Lys Glu Asn Ile Leu Leu
465                 470                 475                 480
Gly Arg Pro Asp Ala Asp Gln Val Glu Val Glu Ala Ala Arg Val
                485                 490                 495
Ala Asn Ala His Ser Phe Ile Ile Lys Leu Pro Asp Gly Phe Asp Thr
                500                 505                 510
Gln Val Gly Glu Arg Gly Leu Gln Leu Ser Gly Gly Gln Lys Gln Arg
                515                 520                 525
Ile Ala Ile Ala Arg Ala Met Leu Lys Asn Pro Ala Ile Leu Leu Leu
    530                 535                 540
Asp Glu Ala Thr Ser Ala Leu Asp Ser Glu Ser Glu Lys Leu Val Gln
545                 550                 555                 560
```

```
Glu Ala Leu Asp Arg Phe Met Ile Gly Arg Thr Thr Leu Ile Ile Ala
                565                 570                 575
His Arg Leu Ser Thr Ile Arg Lys Ala Asp Leu Val Ala Val Leu Gln
            580                 585                 590
Gln Gly Ser Val Ser Glu Ile Gly Thr His Asp Glu Leu Phe Ala Lys
        595                 600                 605
Gly Glu Asn Gly Ile Tyr Ser Lys Leu Ile Lys Met Gln Glu Ala Ala
    610                 615                 620
His Glu Thr Ala Met Asn Asn Ala Arg Lys Ser Ser Ala Arg Pro Ser
625                 630                 635                 640
Ser Ala Arg Asn Ser Val Ser Ser Pro Ile Ile Ala Arg Asn Ser Ser
                645                 650                 655
Tyr Gly Arg Ser Pro Tyr Ser Arg Arg Leu Ser Asp Phe Ser Thr Thr
            660                 665                 670
Asp Phe Ser Leu Ser Val Glu Ala Ser Ser Tyr Pro Asn Tyr Arg His
        675                 680                 685
Asp Lys Leu Pro Phe Lys Asp Gln Ala Asn Ser Phe Trp Arg Leu Ala
    690                 695                 700
Lys Met Asn Ser Pro Glu Trp Lys Tyr Ala Leu Val Gly Ser Val Gly
705                 710                 715                 720
Ser Val Ile Cys Gly Ser Leu Ser Ala Phe Phe Ala Tyr Val Leu Ser
                725                 730                 735
Ala Val Leu Ser Ile Tyr Tyr Asn Pro Asp His Asn Tyr Met Ile Lys
            740                 745                 750
Gln Ile Asp Lys Tyr Cys Tyr Leu Leu Ile Gly Leu Ser Ser Ala Ala
        755                 760                 765
Leu Ile Phe Asn Thr Leu Gln His Ser Phe Trp Asp Ile Val Gly Glu
    770                 775                 780
Asn Leu Thr Lys Arg Val Arg Glu Lys Met Leu Thr Ala Val Leu Lys
785                 790                 795                 800
Asn Glu Met Ala Trp Phe Asp Gln Glu Glu Asn Glu Ser Ala Arg Ile
                805                 810                 815
Ser Ala Arg Leu Ala Leu Asp Ala Asn Asn Val Arg Ser Ala Ile Gly
            820                 825                 830
Asp Arg Ile Ser Val Ile Val Gln Asn Thr Ala Leu Met Leu Val Ala
        835                 840                 845
Cys Thr Ala Gly Phe Val Leu Gln Trp Arg Leu Ala Leu Val Leu Val
    850                 855                 860
Ala Val Phe Pro Val Val Val Ala Ala Thr Val Leu Gln Lys Met Phe
865                 870                 875                 880
Met Thr Gly Phe Ser Gly Asp Leu Glu Ala Ala His Ala Lys Gly Thr
                885                 890                 895
Gln Leu Ala Gly Glu Ala Ile Ala Asn Val Arg Thr Val Ala Ala Phe
            900                 905                 910
Asn Ser Glu Ala Lys Ile Val Arg Leu Tyr Thr Ala Asn Leu Glu Pro
        915                 920                 925
Pro Leu Lys Arg Cys Phe Trp Lys Gly Gln Ile Ala Gly Ser Gly Tyr
    930                 935                 940
Gly Val Ala Gln Phe Cys Leu Tyr Ala Ser Tyr Ala Leu Gly Leu Trp
945                 950                 955                 960
Tyr Ala Ser Trp Leu Val Lys His Gly Ile Ser Asp Phe Ser Lys Thr
                965                 970                 975
Ile Arg Val Phe Met Val Leu Met Val Ser Ala Asn Gly Ala Ala Glu
```

```
                     980             985              990
Thr Leu Thr Leu Ala Pro Asp Phe Ile Lys Gly Gly Gln Ala Met Arg
            995             1000            1005

Ser Val Phe Glu Leu Leu Asp Arg Lys Thr Glu Ile Glu Pro Asp
        1010            1015            1020

Asp Leu Asp Thr Thr Pro Val Pro Asp Arg Leu Arg Gly Glu Val
    1025            1030            1035

Glu Leu Lys His Ile Asp Phe Ser Tyr Pro Ser Arg Pro Asp Ile
    1040            1045            1050

Gln Val Phe Arg Asp Leu Ser Leu Arg Ala Arg Ala Gly Lys Thr
    1055            1060            1065

Leu Ala Leu Val Gly Pro Ser Gly Cys Gly Lys Ser Ser Val Ile
    1070            1075            1080

Ser Leu Ile Gln Arg Phe Tyr Glu Pro Ser Ser Gly Arg Val Leu
    1085            1090            1095

Ile Asp Gly Lys Asp Ile Arg Lys Tyr Asn Leu Lys Ala Ile Arg
    1100            1105            1110

Lys His Ile Ala Ile Val Pro Gln Glu Pro Cys Leu Phe Gly Thr
    1115            1120            1125

Thr Ile Tyr Glu Asn Ile Ala Tyr Gly His Glu Cys Ala Thr Glu
    1130            1135            1140

Ala Glu Ile Ile Gln Ala Ala Thr Leu Ala Ser Ala His Lys Phe
    1145            1150            1155

Ile Ser Ala Leu Pro Asp Gly Tyr Lys Thr Tyr Val Gly Glu Arg
    1160            1165            1170

Gly Val Gln Leu Ser Gly Gly Gln Lys Gln Arg Ile Ala Ile Ala
    1175            1180            1185

Arg Ala Leu Val Arg Lys Ala Glu Ile Met Leu Leu Asp Glu Ala
    1190            1195            1200

Thr Ser Ala Leu Asp Ala Glu Ser Glu Arg Ser Val Gln Glu Ala
    1205            1210            1215

Leu Asp Gln Ala Cys Ser Gly Arg Thr Ser Ile Val Val Ala His
    1220            1225            1230

Arg Leu Ser Thr Ile Arg Asn Ala His Val Ile Ala Val Ile Asp
    1235            1240            1245

Asp Gly Lys Val Val Glu Gln Gly Ser His Ser His Leu Leu Lys
    1250            1255            1260

Asn Tyr Pro Asp Gly Ile Tyr Ala Arg Met Ile Gln Leu Gln Arg
    1265            1270            1275

Phe Thr His Thr Gln Val Ile Gly Met Thr Ser Gly Ser Ser Ser
    1280            1285            1290

Arg Val Lys Glu Asp Asp Ala
    1295            1300

<210> SEQ ID NO 48
<211> LENGTH: 1313
<212> TYPE: PRT
<213> ORGANISM: Solanum tuberosum

<400> SEQUENCE: 48

Met Gln Gly Val Glu Leu Val Val Ser Glu Asp Lys Asn Ser Asn Thr
1               5                   10                  15

Pro Thr Thr Thr Thr Thr Thr Asn Ser His Gln Phe Gln Glu Thr Arg
            20                  25                  30

Met Glu Val Lys Lys Glu Glu Gly Gly Asp Val Glu Lys Pro Ser Ser
```

-continued

```
                35                  40                  45
Pro Pro Pro Ala Val Gly Phe Gly Glu Leu Phe Arg Phe Ala Asp Gly
    50                  55                  60

Leu Asp Cys Val Leu Met Ile Ile Gly Ser Leu Gly Ala Phe Val His
65                  70                  75                  80

Gly Cys Ser Leu Pro Leu Phe Leu Arg Phe Phe Ala Asp Leu Val Asn
                85                  90                  95

Ser Phe Gly Ser Tyr Ala Asn Asp Val Asp Lys Met Thr Gln Glu Val
            100                 105                 110

Leu Lys Tyr Ala Phe Tyr Phe Leu Val Val Gly Ala Ala Ile Trp Ala
            115                 120                 125

Ser Ser Trp Ala Glu Ile Ser Cys Trp Met Trp Thr Gly Glu Arg Gln
        130                 135                 140

Thr Thr Lys Met Arg Ile Lys Tyr Leu Glu Ala Ala Leu Asn Gln Asp
145                 150                 155                 160

Ile Gln Tyr Phe Asp Thr Glu Val Arg Thr Ser Asp Val Val Ser Ala
                165                 170                 175

Ile Asn Thr Asp Ala Val Val Val Gln Asp Ala Ile Ser Glu Lys Leu
            180                 185                 190

Gly Asn Phe Ile His Tyr Met Ala Thr Phe Leu Ser Gly Phe Val Val
        195                 200                 205

Gly Phe Thr Ala Val Trp Gln Leu Ala Leu Val Thr Leu Ala Val Val
    210                 215                 220

Pro Leu Ile Ala Val Ile Gly Ala Ile Tyr Thr Val Thr Ser Ala Lys
225                 230                 235                 240

Leu Ser Ser Gln Ser Gln Glu Ala Leu Ser Lys Ala Gly Asn Ile Val
                245                 250                 255

Glu Gln Thr Val Val Gln Ile Arg Thr Val Leu Val Phe Val Gly Glu
            260                 265                 270

Ala Lys Ala Leu Gln Ala Tyr Thr Ala Ala Leu Arg Val Ser Gln Lys
        275                 280                 285

Ile Gly Tyr Lys Ser Gly Phe Ser Lys Gly Leu Gly Leu Gly Ala Thr
    290                 295                 300

Tyr Phe Thr Val Phe Cys Cys Tyr Ala Leu Leu Leu Trp Tyr Gly Gly
305                 310                 315                 320

Tyr Leu Val Arg His His Phe Thr Asn Gly Gly Leu Ala Ile Ala Thr
                325                 330                 335

Met Phe Ala Val Met Ile Gly Gly Leu Ala Leu Gly Gln Ser Ala Pro
            340                 345                 350

Ser Met Thr Ala Phe Ala Lys Ala Arg Val Ala Ala Ala Lys Ile Phe
        355                 360                 365

Arg Ile Ile Asp His Lys Pro Ser Val Asp Arg Asn Ala Lys Thr Gly
    370                 375                 380

Leu Glu Leu Asp Thr Val Ser Gly Gln Leu Glu Leu Lys Asn Val Glu
385                 390                 395                 400

Phe Ser Tyr Pro Ser Arg Pro Glu Ile Lys Ile Leu Asn Asn Phe Asn
                405                 410                 415

Leu Val Val Pro Ala Gly Lys Thr Ile Ala Leu Val Gly Ser Ser Gly
            420                 425                 430

Ser Gly Lys Ser Thr Val Val Ser Leu Ile Glu Arg Phe Tyr Asp Pro
        435                 440                 445

Thr Ser Gly Gln Leu Met Leu Asp Gly Asn Asp Ile Lys Thr Leu Lys
    450                 455                 460
```

-continued

```
Leu Lys Trp Leu Arg Gln Gln Ile Gly Leu Val Ser Gln Glu Pro Ala
465                 470                 475                 480

Leu Phe Ala Thr Ser Ile Lys Glu Asn Ile Leu Leu Gly Arg Pro Asp
                485                 490                 495

Ala Thr Gln Ile Glu Ile Glu Glu Ala Ala Arg Val Ala Asn Ala His
            500                 505                 510

Ser Phe Val Ile Lys Leu Pro Asp Gly Phe Asp Thr Gln Val Gly Glu
        515                 520                 525

Arg Gly Leu Gln Leu Ser Gly Gly Gln Lys Gln Arg Ile Ala Ile Ala
530                 535                 540

Arg Ala Met Leu Lys Asn Pro Ala Ile Leu Leu Leu Asp Glu Ala Thr
545                 550                 555                 560

Ser Ala Leu Asp Ser Glu Ser Glu Lys Leu Val Gln Glu Ala Leu Asp
                565                 570                 575

Arg Phe Met Ile Gly Arg Thr Thr Leu Val Ile Ala His Arg Leu Ser
                580                 585                 590

Thr Ile Arg Lys Ala Asp Leu Val Ala Val Leu Gln Gln Gly Ser Val
            595                 600                 605

Ser Glu Ile Gly Ser His Asp Glu Leu Met Ser Lys Gly Glu Asn Gly
610                 615                 620

Met Tyr Ala Lys Leu Ile Lys Met Gln Glu Ala Ala His Glu Thr Ala
625                 630                 635                 640

Leu Ser Asn Ala Arg Lys Ser Ala Arg Pro Ser Ser Ala Arg Asn
                645                 650                 655

Ser Val Ser Ser Pro Ile Ile Thr Arg Asn Ser Ser Tyr Gly Arg Ser
                660                 665                 670

Pro Tyr Ser Arg Arg Leu Ser Asp Phe Ser Thr Ser Asp Phe Ser Leu
                675                 680                 685

Ser Leu Asp Ala Ala Tyr Ser Asn Tyr Arg Asn Glu Lys Leu Ala Phe
            690                 695                 700

Lys Asp Gln Ala Ser Ser Phe Gly Arg Leu Ala Lys Met Asn Ser Pro
705                 710                 715                 720

Glu Trp Thr Tyr Ala Leu Ile Gly Ser Ile Gly Ser Val Ile Cys Gly
                725                 730                 735

Ser Leu Ser Ala Phe Phe Ala Tyr Val Leu Ser Ala Val Leu Ser Val
                740                 745                 750

Tyr Tyr Asn Pro Asp His Ala Tyr Met Ser Glu Gln Ile Ala Lys Tyr
            755                 760                 765

Cys Tyr Leu Leu Ile Gly Val Ser Ser Ala Ala Leu Ile Phe Asn Thr
770                 775                 780

Leu Gln His Tyr Tyr Trp Asp Val Val Gly Glu Asn Leu Thr Lys Arg
785                 790                 795                 800

Val Arg Glu Lys Met Leu Ala Ala Val Leu Lys Met Glu Met Ala Trp
                805                 810                 815

Phe Asp Gln Glu Glu Asn Asp Ser Ser Arg Ile Ala Ala Arg Leu Ser
                820                 825                 830

Leu Asp Ala Asn Asn Val Arg Ser Ala Ile Gly Asp Arg Ile Ser Val
            835                 840                 845

Ile Met Gln Asn Ser Ala Leu Met Leu Val Ala Cys Thr Ala Gly Phe
850                 855                 860

Val Leu Gln Trp Arg Leu Ala Leu Val Leu Ile Gly Val Phe Pro Val
865                 870                 875                 880

Val Val Ala Ala Thr Val Leu Gln Lys Met Phe Met Lys Gly Phe Ser
                885                 890                 895
```

```
Gly Asp Leu Glu Ala Ala His Ala Lys Ala Thr Gln Leu Ala Gly Glu
            900                 905                 910
Ala Val Ala Asn Val Arg Thr Val Ala Ala Phe Asn Ser Glu Thr Lys
            915                 920                 925
Ile Val Asn Leu Phe Asp Ser Ser Leu Gln Thr Pro Leu Arg Arg Cys
            930                 935                 940
Phe Trp Lys Gly Gln Ile Ala Gly Ser Gly Tyr Gly Ile Ala Gln Phe
945                 950                 955                 960
Leu Leu Tyr Ser Ser Tyr Ala Leu Gly Leu Trp Tyr Ala Ser Trp Leu
            965                 970                 975
Val Lys His Gly Ile Ser Asp Phe Ser Lys Thr Ile Arg Val Phe Met
            980                 985                 990
Val Leu Met Val Ser Ala Asn Gly Ala Ala Glu Thr Leu Thr Leu Ala
            995                 1000                1005
Pro Asp Phe Ile Lys Gly Gly Arg Ala Met Arg Ser Val Phe Glu
    1010                1015                1020
Leu Leu Asp Arg Lys Thr Glu Val Glu Pro Asp Pro Asp Ala
    1025                1030                1035
Thr Ala Val Pro Asp Arg Leu Arg Gly Glu Val Glu Phe Lys His
    1040                1045                1050
Val Asp Phe Ser Tyr Pro Thr Arg Pro Asp Val Ser Ile Phe Arg
    1055                1060                1065
Asp Leu Asn Leu Arg Ala Arg Ala Gly Lys Thr Leu Ala Leu Val
    1070                1075                1080
Gly Pro Ser Gly Cys Gly Lys Ser Ser Val Ile Ser Leu Ile Glu
    1085                1090                1095
Arg Phe Tyr Glu Pro Ser Ser Gly Arg Val Ile Ile Asp Gly Lys
    1100                1105                1110
Asp Ile Arg Lys Tyr Asn Leu Lys Ser Leu Arg Arg His Ile Ala
    1115                1120                1125
Val Val Pro Gln Glu Pro Cys Leu Phe Ala Thr Thr Ile Tyr Glu
    1130                1135                1140
Asn Ile Ala Tyr Gly His Glu Ser Ala Thr Glu Ala Glu Ile Thr
    1145                1150                1155
Glu Ala Ala Thr Leu Ala Asn Ala His Lys Phe Ile Ser Ala Leu
    1160                1165                1170
Pro Asp Gly Tyr Lys Thr Phe Val Gly Glu Arg Gly Val Gln Leu
    1175                1180                1185
Ser Gly Gly Gln Lys Gln Arg Ile Ala Ile Ala Arg Ala Phe Leu
    1190                1195                1200
Arg Lys Ala Glu Leu Met Leu Leu Asp Glu Ala Thr Ser Ala Leu
    1205                1210                1215
Asp Ala Glu Ser Glu Arg Cys Val Gln Glu Ala Leu Asp Arg Ala
    1220                1225                1230
Cys Ala Gly Lys Thr Thr Ile Val Val Ala His Arg Leu Ser Thr
    1235                1240                1245
Ile Arg Asn Ala His Val Ile Ala Val Ile Asp Asp Gly Lys Val
    1250                1255                1260
Ala Glu Gln Gly Ser His Ser His Leu Leu Lys Asn Tyr Ser Asp
    1265                1270                1275
Gly Ile Tyr Ala Arg Met Ile Gln Leu Gln Arg Phe Thr His Gly
    1280                1285                1290
Glu Ala Val Asn Met Ala Thr Gly Ser Thr Ser Ser Ser Arg Pro
```

```
                        1295                1300                1305
Lys Glu  Asp Gln Asp
        1310

<210> SEQ ID NO 49
<211> LENGTH: 1394
<212> TYPE: PRT
<213> ORGANISM: Zea mays

<400> SEQUENCE: 49

Met Ser Ser Ser Asp Pro Glu Glu Ile Arg Ala Arg Val Val Val Leu
1               5                   10                  15

Gly Ser Pro His Ala Asp Gly Gly Asp Glu Trp Ala Arg Pro Glu Leu
            20                  25                  30

Glu Ala Phe His Leu Pro Ser Pro Ala His Gln Pro Pro Gly Phe Leu
        35                  40                  45

Ala Gly Gln Pro Glu Ala Ala Glu Gln Pro Thr Leu Pro Ala Pro Ala
    50                  55                  60

Gly Arg Ser Ser Ser Ser Asn Thr Pro Thr Thr Ser Ala Gly Gly
65                  70                  75                  80

Gly Ala Ala Pro Pro Pro Ser Ser Pro Pro Pro Pro Ala Ser
                85                  90                  95

Leu Glu Thr Glu Gln Pro Pro Asn Ala Arg Pro Ala Ser Ala Gly Ala
            100                 105                 110

Asn Asp Ser Lys Lys Pro Thr Pro Pro Ala Ala Leu Arg Asp Leu Phe
        115                 120                 125

Arg Phe Ala Asp Gly Leu Asp Cys Ala Leu Met Leu Ile Gly Thr Leu
130                 135                 140

Gly Ala Leu Val His Gly Cys Ser Leu Pro Val Phe Leu Arg Phe Phe
145                 150                 155                 160

Ala Asp Leu Val Asp Ser Phe Gly Ser His Ala Asp Asp Pro Asp Thr
                165                 170                 175

Met Val Arg Leu Val Val Lys Tyr Ala Phe Tyr Phe Leu Val Val Gly
            180                 185                 190

Ala Ala Ile Trp Ala Ser Ser Trp Ala Glu Ile Ser Cys Trp Met Trp
        195                 200                 205

Thr Gly Glu Arg Gln Ser Thr Arg Met Arg Ile Arg Tyr Leu Asp Ala
    210                 215                 220

Ala Leu Arg Gln Asp Val Ser Phe Phe Asp Thr Asp Val Arg Ala Ser
225                 230                 235                 240

Asp Val Ile Tyr Ala Ile Asn Ala Asp Ala Val Val Gln Asp Ala
                245                 250                 255

Ile Ser Gln Lys Leu Gly Asn Leu Ile His Tyr Met Ala Thr Phe Val
            260                 265                 270

Ala Gly Phe Val Val Gly Phe Thr Ala Ala Trp Gln Leu Ala Leu Val
        275                 280                 285

Thr Leu Ala Val Val Pro Leu Ile Ala Val Ile Gly Gly Leu Ser Ala
    290                 295                 300

Ala Ala Leu Ala Lys Leu Ser Ser Arg Ser Gln Asp Ala Leu Ser Gly
305                 310                 315                 320

Ala Ser Gly Ile Ala Glu Gln Ala Leu Ala Gln Ile Arg Ile Val Gln
                325                 330                 335

Ala Phe Val Gly Glu Glu Arg Glu Met Arg Ala Tyr Ser Ala Ala Leu
            340                 345                 350

Ala Val Ala Gln Arg Ile Gly Tyr Arg Ser Gly Phe Ala Lys Gly Leu
```

```
                355                 360                 365
Gly Leu Gly Gly Thr Tyr Phe Thr Val Phe Cys Cys Tyr Gly Leu Leu
    370                 375                 380

Leu Trp Tyr Gly Gly His Leu Val Arg Ala Gln His Thr Asn Gly Gly
385                 390                 395                 400

Leu Ala Ile Ala Thr Met Phe Ser Val Met Ile Gly Gly Leu Pro Arg
                405                 410                 415

Gln Ser Ala Pro Ser Met Ala Ala Phe Ala Lys Ala Arg Val Ala Ala
            420                 425                 430

Ala Lys Ile Phe Arg Ile Ile Asp His Arg Pro Gly Ile Ser Ser Arg
        435                 440                 445

Asp Gly Ala Glu Pro Glu Ser Val Thr Gly Arg Val Glu Met Arg Gly
    450                 455                 460

Val Asp Phe Ala Tyr Pro Ser Arg Pro Asp Val Pro Ile Leu Arg Gly
465                 470                 475                 480

Phe Ser Leu Ser Val Pro Ala Gly Lys Thr Ile Ala Leu Val Gly Ser
                485                 490                 495

Ser Gly Ser Gly Lys Ser Thr Val Val Ser Leu Ile Glu Arg Phe Tyr
            500                 505                 510

Asp Pro Ser Ala Gly Gln Ile Leu Leu Asp Gly His Asp Leu Arg Ser
        515                 520                 525

Leu Glu Leu Arg Trp Leu Arg Arg Gln Ile Gly Leu Val Ser Gln Glu
    530                 535                 540

Pro Ala Leu Phe Ala Thr Ser Ile Arg Glu Asn Leu Leu Leu Gly Arg
545                 550                 555                 560

Asp Ser Gln Ser Ala Thr Leu Ala Glu Met Glu Glu Ala Ala Arg Val
                565                 570                 575

Ala Asn Ala His Ser Phe Ile Ile Lys Leu Pro Asp Gly Tyr Asp Thr
            580                 585                 590

Gln Val Gly Glu Arg Gly Leu Gln Leu Ser Gly Gly Gln Lys Gln Arg
        595                 600                 605

Ile Ala Ile Ala Arg Ala Met Leu Lys Asn Pro Ala Ile Leu Leu Leu
    610                 615                 620

Asp Glu Ala Thr Ser Ala Leu Asp Ser Glu Ser Glu Lys Leu Val Gln
625                 630                 635                 640

Glu Ala Leu Asp Arg Phe Met Met Gly Arg Thr Thr Leu Gly Asp Arg
                645                 650                 655

Ala Thr Gly Cys Pro Pro Ser Ala Lys Ala Asp Val Val Ala Val Leu
            660                 665                 670

Gln Gly Gly Ala Val Ser Glu Met Ser Ala His Asp Glu Leu Met Ala
        675                 680                 685

Lys Gly Glu Asn Gly Thr Tyr Ala Lys Leu Ile Arg Met Gln Glu Gln
    690                 695                 700

Ala His Glu Ala Ala Leu Val Asn Ala Arg Arg Ser Ser Ala Arg Pro
705                 710                 715                 720

Ser Ser Ala Arg Asn Ser Val Ser Ser Pro Ile Met Thr Arg Asn Ser
                725                 730                 735

Ser Tyr Gly Arg Ser Pro Tyr Ser Arg Arg Leu Ser Asp Phe Ser Thr
            740                 745                 750

Ser Asp Phe Thr Leu Ser Ile His Asp Pro His His His Arg Thr
        755                 760                 765

Met Ala Asp Lys Gln Leu Ala Phe Arg Ala Gly Ala Ser Ser Phe Leu
    770                 775                 780
```

```
Arg Leu Ala Arg Met Asn Ser Pro Glu Trp Ala Tyr Ala Leu Ala Gly
785                 790                 795                 800

Ser Ile Gly Ser Met Val Cys Gly Ser Phe Ser Ala Ile Phe Ala Tyr
            805                 810                 815

Ile Leu Ser Ala Val Leu Ser Val Tyr Tyr Ala Pro Asp Pro Arg Tyr
            820                 825                 830

Met Lys Arg Glu Ile Ala Lys Tyr Cys Tyr Leu Leu Ile Gly Met Ser
            835                 840                 845

Ser Ala Ala Leu Leu Phe Asn Thr Val Gln His Val Phe Trp Asp Thr
850                 855                 860

Val Gly Glu Asn Leu Thr Lys Arg Val Arg Glu Lys Met Phe Ala Ala
865                 870                 875                 880

Val Phe Arg Asn Glu Ile Ala Trp Phe Asp Ala Asp Glu Asn Ala Ser
                885                 890                 895

Ala Arg Val Thr Ala Arg Leu Ala Leu Asp Ala Gln Asn Val Arg Ser
                900                 905                 910

Ala Ile Gly Asp Arg Ile Ser Val Ile Val Gln Asn Ser Ala Leu Met
                915                 920                 925

Leu Val Ala Cys Thr Ala Gly Phe Val Leu Gln Trp Arg Leu Ala Leu
930                 935                 940

Val Leu Leu Ala Val Phe Pro Leu Val Val Gly Ala Thr Val Leu Gln
945                 950                 955                 960

Lys Met Phe Met Lys Gly Phe Ser Gly Asp Leu Glu Ala Ala His Ala
                965                 970                 975

Arg Ala Thr Gln Ile Ala Gly Glu Ala Val Ala Asn Leu Arg Thr Val
                980                 985                 990

Ala Ala Phe Asn Ala Glu Arg Lys Ile Thr Gly Leu Phe Glu Ala Asn
                995                 1000                1005

Leu Arg Gly Pro Leu Arg Arg Cys Phe Trp Lys Gly Gln Ile Ala
    1010                1015                1020

Gly Ser Gly Tyr Gly Val Ala Gln Phe Leu Leu Tyr Ala Ser Tyr
    1025                1030                1035

Ala Leu Gly Leu Trp Tyr Ala Ala Trp Leu Val Lys His Gly Val
    1040                1045                1050

Ser Asp Phe Ser Arg Thr Ile Arg Val Phe Met Val Leu Met Val
    1055                1060                1065

Ser Ala Asn Gly Ala Ala Glu Thr Leu Thr Leu Ala Pro Asp Phe
    1070                1075                1080

Ile Lys Gly Gly Arg Ala Met Arg Ser Val Phe Glu Thr Ile Asp
    1085                1090                1095

Arg Lys Thr Glu Val Glu Pro His Asp Val Asp Ala Ala Pro Val
    1100                1105                1110

Pro Asp Gly Pro Gly Ala Lys Val Glu Leu Lys His Val Asp Phe
    1115                1120                1125

Leu Tyr Pro Ser Arg Pro Asp Ile Gln Val Phe Arg Asp Leu Ser
    1130                1135                1140

Leu Arg Ala Arg Ala Gly Lys Thr Leu Ala Leu Val Gly Pro Ser
    1145                1150                1155

Gly Ser Gly Lys Ser Ser Val Leu Ala Leu Val Gln Arg Phe Tyr
    1160                1165                1170

Lys Pro Thr Ser Gly Arg Val Leu Leu Asp Gly Lys Asp Val Arg
    1175                1180                1185

Lys Tyr Asn Leu Arg Ala Leu Arg Arg Val Val Ala Val Val Pro
    1190                1195                1200
```

```
Gln Glu Pro Phe Leu Phe Ala Ala Ser Ile His Glu Asn Ile Ala
    1205                1210                1215

Tyr Gly Arg Glu Gly Ala Thr Glu Ala Glu Val Val Glu Ala Ala
    1220                1225                1230

Ala Gln Ala Asn Ala His Arg Phe Ile Ala Ala Leu Pro Glu Gly
    1235                1240                1245

Tyr Arg Thr Gln Val Gly Glu Arg Gly Val Gln Leu Ser Gly Gly
    1250                1255                1260

Gln Arg Gln Arg Ile Ala Ile Ala Arg Ala Leu Val Lys Gln Ala
    1265                1270                1275

Ala Ile Val Leu Leu Asp Glu Ala Thr Ser Ala Leu Asp Ala Glu
    1280                1285                1290

Ser Glu Arg Cys Val Gln Glu Ala Leu Glu Arg Ala Gly Ser Gly
    1295                1300                1305

Arg Thr Thr Ile Val Val Ala His Arg Leu Ala Thr Val Arg Gly
    1310                1315                1320

Ala His Thr Ile Ala Val Ile Asp Asp Gly Lys Val Ala Glu Gln
    1325                1330                1335

Gly Ser His Ser His Leu Leu Lys His His Pro Asp Gly Cys Tyr
    1340                1345                1350

Ala Arg Met Leu Gln Leu Ala Ala Ala Asp Gly Arg Gly Gly Arg
    1355                1360                1365

Ala Arg Ala Val Val Leu Val Gln Arg Gly Arg Val Gly Arg Asn
    1370                1375                1380

Gly Trp Met Asp Gly Phe Gly Ser Ser Arg Asp
    1385                1390

<210> SEQ ID NO 50
<211> LENGTH: 1402
<212> TYPE: PRT
<213> ORGANISM: Sorghum bicolor

<400> SEQUENCE: 50

Met Ser Thr Asn Asp Pro Asp Glu Ile Arg Ala Arg Val Val Leu
1               5                   10                  15

Gly Ala Pro His Ala Asp Asp Ala Gly Asp Glu Trp Ala Arg Pro
                20                  25                  30

Glu Leu Glu Ala Phe His Leu Pro Ser Pro Ala His Gln Pro Gly
            35                  40                  45

Phe His Leu Ala Ala Gly His Gln Pro Glu Ala Ala Glu Gln Pro
    50                  55                  60

Thr Thr Leu Pro Ala Ala Arg Arg Thr Ser Asp Thr Ser Thr Ala Ala
65                  70                  75                  80

Gly Ala Ala Pro Pro Ser Pro Ser Pro Pro Pro Ala Pro Leu
                85                  90                  95

Glu Met Asp Gln Pro Pro Asn Ala Lys Pro Ala Ser Ser Ala Ala
                100                 105                 110

Ala Ala Gly Ala Asn Asp Asn Lys Lys Pro Thr Pro Ala Ala Leu
            115                 120                 125

Arg Asp Leu Phe Arg Phe Ala Asp Gly Leu Asp Cys Ala Leu Met Leu
    130                 135                 140

Val Gly Thr Leu Gly Ala Leu Val His Gly Cys Ser Leu Pro Val Phe
145                 150                 155                 160

Leu Arg Phe Phe Ala Asp Leu Val Asp Ser Phe Gly Ser His Ala Asn
                165                 170                 175
```

```
Asp Pro Asp Thr Met Val Arg Leu Val Lys Tyr Ala Phe Tyr Phe
            180                 185                 190

Leu Val Val Gly Ala Ala Ile Trp Ala Ser Ser Trp Ala Glu Ile Ser
        195                 200                 205

Cys Trp Met Trp Thr Gly Glu Arg Gln Ser Thr Arg Met Arg Ile Arg
210                 215                 220

Tyr Leu Asp Ala Ala Leu Arg Gln Asp Val Ser Phe Phe Asp Thr Asp
225                 230                 235                 240

Val Arg Thr Ser Asp Val Ile Tyr Ala Ile Asn Ala Asp Ala Val Val
                245                 250                 255

Val Gln Asp Ala Ile Ser Glu Lys Leu Gly Asn Leu Ile His Tyr Met
            260                 265                 270

Ala Thr Phe Val Ala Gly Phe Val Gly Phe Thr Ala Ala Trp Gln
        275                 280                 285

Leu Ala Leu Val Thr Leu Ala Val Val Pro Leu Ile Ala Val Ile Gly
        290                 295                 300

Gly Leu Ser Ala Ala Ala Leu Ala Lys Leu Ser Ser Arg Ser Gln Asp
305                 310                 315                 320

Ala Leu Ser Gly Ala Ser Gly Ile Ala Glu Gln Ala Leu Ala Gln Ile
                325                 330                 335

Arg Ile Val Gln Ala Phe Val Gly Glu Glu Arg Glu Met Arg Ala Tyr
            340                 345                 350

Ser Ala Ala Leu Ala Val Ala Gln Lys Ile Gly Tyr Arg Ser Gly Phe
        355                 360                 365

Ala Lys Gly Leu Gly Leu Gly Gly Thr Tyr Phe Thr Val Phe Cys Cys
370                 375                 380

Tyr Gly Leu Leu Leu Trp Tyr Gly Gly His Leu Val Arg Gly His His
385                 390                 395                 400

Thr Asn Gly Gly Leu Ala Ile Ala Thr Met Phe Ser Val Met Ile Gly
                405                 410                 415

Gly Leu Ala Leu Gly Gln Ser Ala Pro Ser Met Ala Ala Phe Ala Lys
            420                 425                 430

Ala Arg Val Ala Ala Ala Lys Ile Phe Arg Ile Ile Asp His Arg Pro
        435                 440                 445

Gly Ile Ser Ser Arg Asp Gly Glu Asp Gly Gly Val Glu Leu Glu
        450                 455                 460

Ser Val Thr Gly Arg Val Glu Met Arg Gly Val Asp Phe Ala Tyr Pro
465                 470                 475                 480

Ser Arg Pro Asp Val Pro Ile Leu Arg Gly Phe Ser Leu Ser Val Pro
                485                 490                 495

Ala Gly Lys Thr Ile Ala Leu Val Gly Ser Ser Gly Ser Gly Lys Ser
            500                 505                 510

Thr Val Val Ser Leu Leu Glu Arg Phe Tyr Asp Pro Ser Ala Gly Gln
        515                 520                 525

Ile Leu Leu Asp Gly His Asp Leu Lys Ser Leu Lys Leu Arg Trp Leu
530                 535                 540

Arg Gln Gln Ile Gly Leu Val Ser Gln Glu Pro Thr Leu Phe Ala Thr
545                 550                 555                 560

Ser Ile Lys Glu Asn Leu Leu Leu Gly Arg Asp Ser Gln Ser Ala Thr
                565                 570                 575

Gln Ala Glu Met Glu Glu Ala Ala Arg Val Ala Asn Ala His Ser Phe
            580                 585                 590

Ile Val Lys Leu Pro Asp Gly Tyr Asp Thr Gln Val Gly Glu Arg Gly
```

-continued

```
            595                 600                 605
Leu Gln Leu Ser Gly Gly Gln Lys Gln Arg Ile Ala Ile Ala Arg Ala
            610                 615                 620
Met Leu Lys Asn Pro Ala Ile Leu Leu Leu Asp Glu Ala Thr Ser Ala
625                 630                 635                 640
Leu Asp Ser Glu Ser Glu Lys Leu Val Gln Glu Ala Leu Asp Arg Phe
                    645                 650                 655
Met Ile Gly Arg Thr Thr Leu Val Ile Ala His Arg Met Ser Thr Ile
                660                 665                 670
Arg Lys Ala Asp Val Val Ala Val Leu Gln Gly Gly Pro Val Ser Glu
            675                 680                 685
Met Gly Ala His Asp Glu Leu Met Ala Lys Gly Glu Asn Gly Thr Tyr
        690                 695                 700
Ala Lys Phe Ile Arg Met Gln Glu Gln Ala His Glu Ala Ala Phe Val
705                 710                 715                 720
Asn Ala Arg Arg Ser Ser Ala Arg Pro Ser Ser Ala Arg Asn Ser Val
                    725                 730                 735
Ser Ser Pro Ile Met Thr Arg Asn Ser Ser Tyr Gly Arg Ser Pro Tyr
                740                 745                 750
Ser Arg Arg Leu Ser Asp Phe Ser Thr Ser Asp Phe Thr Leu Ser Ile
            755                 760                 765
His Asp Pro His His His Arg Thr Met Ala Asp Lys Gln Leu Ala
        770                 775                 780
Phe Arg Ala Gly Ala Ser Ser Phe Leu Arg Leu Ala Arg Met Asn Ser
785                 790                 795                 800
Pro Glu Trp Ala Tyr Ala Leu Val Gly Ser Leu Gly Ser Met Val Cys
                    805                 810                 815
Gly Ser Phe Ser Ala Ile Phe Ala Tyr Ile Leu Ser Ala Val Leu Ser
                820                 825                 830
Val Tyr Tyr Ala Pro Asp Pro Arg Tyr Met Lys Arg Glu Ile Ala Lys
            835                 840                 845
Tyr Cys Tyr Leu Leu Ile Gly Met Ser Ser Ala Ala Leu Leu Phe Asn
        850                 855                 860
Thr Val Gln His Val Phe Trp Asp Thr Val Gly Glu Asn Leu Thr Lys
865                 870                 875                 880
Arg Val Arg Glu Lys Met Phe Ala Ala Val Leu Arg Asn Glu Ile Ala
                    885                 890                 895
Trp Phe Asp Ala Asp Glu Asn Ala Ser Ala Arg Val Ala Ala Arg Leu
                900                 905                 910
Ala Leu Asp Ala Gln Asn Val Arg Ser Ala Ile Gly Asp Arg Ile Ser
            915                 920                 925
Val Ile Val Gln Asn Ser Ala Leu Met Leu Val Ala Cys Thr Ala Gly
        930                 935                 940
Phe Val Leu Gln Trp Arg Leu Ala Leu Val Leu Leu Ala Val Phe Pro
945                 950                 955                 960
Leu Val Val Ala Ala Thr Val Leu Gln Lys Met Phe Met Lys Gly Phe
                    965                 970                 975
Ser Gly Asp Leu Glu Ala Ala His Ala Arg Ala Thr Gln Ile Ala Gly
                980                 985                 990
Glu Ala Val Ala Asn Leu Arg Thr Val Ala Ala Phe Asn Ala Glu Arg
            995                 1000                1005
Lys Ile Thr Gly Leu Phe Glu Ala Asn Leu Arg Gly Pro Leu Arg
        1010                1015                1020
```

```
Arg Cys Phe Trp Lys Gly Gln Ile Ala Gly Ser Gly Tyr Gly Val
1025                1030                1035

Ala Gln Phe Leu Leu Tyr Ala Ser Tyr Ala Leu Gly Leu Trp Tyr
1040                1045                1050

Ala Ala Trp Leu Val Lys His Gly Val Ser Asp Phe Ser Arg Thr
1055                1060                1065

Ile Arg Val Phe Met Val Leu Met Val Ser Ala Asn Gly Ala Ala
1070                1075                1080

Glu Thr Leu Thr Leu Ala Pro Asp Phe Val Lys Gly Gly Arg Ala
1085                1090                1095

Met Arg Ser Val Phe Glu Thr Ile Asp Arg Lys Thr Glu Val Glu
1100                1105                1110

Pro Asp Asp Val Asp Ala Ala Pro Val Pro Glu Arg Pro Lys Gly
1115                1120                1125

Glu Val Glu Leu Lys His Val Asp Phe Ser Tyr Pro Ser Arg Pro
1130                1135                1140

Asp Ile Gln Val Phe Arg Asp Leu Ser Leu Arg Ala Arg Ala Gly
1145                1150                1155

Lys Thr Leu Ala Leu Val Gly Pro Ser Gly Cys Gly Lys Ser Ser
1160                1165                1170

Val Leu Ala Leu Val Gln Arg Phe Tyr Glu Pro Thr Ser Gly Arg
1175                1180                1185

Val Leu Leu Asp Gly Lys Asp Val Arg Lys Tyr Asn Leu Arg Ala
1190                1195                1200

Leu Arg Arg Val Val Ala Val Ala Pro Gln Glu Pro Phe Leu Phe
1205                1210                1215

Ala Ala Ser Ile His Asp Asn Ile Ala Tyr Gly Arg Glu Gly Ala
1220                1225                1230

Thr Glu Ala Glu Val Val Glu Ala Ala Thr Gln Ala Asn Ala His
1235                1240                1245

Arg Phe Ile Ala Ala Leu Pro Glu Gly Tyr Gly Thr Gln Val Gly
1250                1255                1260

Glu Arg Gly Val Gln Leu Ser Gly Gly Gln Arg Gln Arg Ile Ala
1265                1270                1275

Ile Ala Arg Ala Leu Val Lys Gln Ala Ala Ile Val Leu Leu Asp
1280                1285                1290

Glu Ala Thr Ser Ala Leu Asp Ala Glu Ser Glu Arg Cys Val Gln
1295                1300                1305

Glu Ala Leu Glu Arg Ala Gly Ser Gly Arg Thr Thr Ile Val Val
1310                1315                1320

Ala His Arg Leu Ala Thr Val Arg Gly Ala His Thr Ile Ala Val
1325                1330                1335

Ile Asp Asp Gly Lys Val Ala Glu Gln Gly Ser His Ser His Leu
1340                1345                1350

Leu Lys His His Pro Asp Gly Cys Tyr Ala Arg Met Leu Gln Leu
1355                1360                1365

Gln Arg Leu Thr Gly Gly Cys Arg Ala Arg Ala Ala Ala Val Val
1370                1375                1380

Val Gln Arg Gly Arg Arg Val Gly Trp Met Asp Gly Ser Trp Met
1385                1390                1395

Ser Leu Val Pro
1400

<210> SEQ ID NO 51
```

<211> LENGTH: 1344
<212> TYPE: PRT
<213> ORGANISM: Oryza sativa

<400> SEQUENCE: 51

```
Met Glu Glu Ile Lys Gly Arg Val Val Leu Gly Ala Asp Ala
1               5                   10                  15

Ala Ala Asp Pro Glu Leu Glu Ala Phe His Leu Pro Ser Ala Asp Gln
            20                  25                  30

Pro Pro His Ser His Leu Leu His His His Ser Pro Gln Ser His
        35                  40                  45

Pro Gln Pro Asp Ala Pro Ala Ala Ala Pro Pro Pro Ala Pro
    50                  55                  60

Leu Thr Pro Pro Pro Lys Ser Pro Pro Pro Pro His Ile Gln
65                  70                  75                  80

Thr Thr Asp Leu Pro Pro Pro Lys Pro Leu Pro Pro Ala Pro Leu Arg
                85                  90                  95

Gln Leu Phe Ser Phe Ala Asp Gly Leu Asp Tyr Val Leu Met Thr Leu
                100                 105                 110

Gly Thr Leu Gly Ala Leu Val His Gly Cys Ser Leu Pro Val Phe Leu
                115                 120                 125

Arg Phe Phe Ala Asp Leu Val Asp Ser Phe Gly Ser His Ala Ala His
            130                 135                 140

Pro Asp Thr Met Leu Arg Leu Val Val Lys Tyr Ala Phe Tyr Phe Leu
145                 150                 155                 160

Val Val Gly Ala Ala Ile Trp Ala Ser Ser Trp Ala Glu Ile Ser Cys
                165                 170                 175

Trp Met Trp Thr Gly Glu Arg Gln Ser Thr Arg Met Arg Ile Arg Tyr
                180                 185                 190

Leu His Ala Ala Leu His Gln Asp Val Ser Phe Phe Asp Thr Asp Val
                195                 200                 205

Arg Thr Ser Asp Val Ile His Ala Ile Asn Ala Asp Ala Val Val Val
            210                 215                 220

Gln Asp Ala Ile Ser Glu Lys Leu Gly Asn Leu Ile His Tyr Leu Ala
225                 230                 235                 240

Thr Phe Val Ser Gly Phe Val Val Gly Phe Thr Ala Ala Trp Gln Leu
                245                 250                 255

Ala Leu Val Thr Leu Ala Val Val Pro Leu Ile Ala Val Ile Gly Gly
                260                 265                 270

Leu Ser Ala Ala Ala Leu Ala Lys Leu Ser Ser Arg Ser Gln Asp Ala
            275                 280                 285

Leu Ser Asp Ala Ser Gly Ile Ala Glu Gln Ala Leu Ala Gln Ile Arg
290                 295                 300

Ile Val Gln Ser Phe Val Gly Glu Glu Arg Val Met Arg Ala Tyr Ser
305                 310                 315                 320

Ala Ala Leu Ala Val Ala Gln Arg Ile Gly Tyr Arg Ser Gly Phe Ala
                325                 330                 335

Lys Gly Ile Gly Leu Gly Gly Thr Tyr Phe Thr Val Phe Cys Cys Tyr
                340                 345                 350

Ala Leu Leu Leu Trp Tyr Gly Gly His Leu Val Arg Arg Ala His Thr
            355                 360                 365

Asn Gly Gly Leu Ala Ile Ala Thr Met Phe Ser Val Met Ile Gly Gly
                370                 375                 380

Leu Ala Leu Gly Gln Ser Ala Pro Ser Met Ala Ala Phe Ala Lys Ala
385                 390                 395                 400
```

-continued

Arg Val Ala Ala Ala Lys Ile Phe Arg Met Met Glu His Lys Pro Ser
              405                 410                 415
Met Glu Arg Glu Gly Val Glu Leu Glu Ala Val Thr Gly Arg Val
              420                 425                 430
Glu Leu Arg Asp Val Glu Phe Ser Tyr Pro Ser Arg Pro Asp Val Gly
              435                 440                 445
Ile Leu Arg Gly Leu Ser Leu Ser Val Pro Ala Gly Lys Thr Ile Ala
              450                 455                 460
Leu Val Gly Ser Ser Gly Ser Gly Lys Ser Thr Val Val Ser Leu Ile
465                 470                 475                 480
Glu Arg Phe Tyr Glu Pro Asn Ala Gly Thr Ile Leu Leu Asp Gly His
                  485                 490                 495
Asp Leu Arg Asp Leu Asn Leu Arg Trp Leu Arg Arg Gln Ile Gly Leu
              500                 505                 510
Val Ser Gln Glu Pro Ala Leu Phe Ala Thr Thr Ile Arg Glu Asn Leu
              515                 520                 525
Leu Leu Gly Arg Asp Gly Ala Thr Gln Glu Glu Leu Glu Glu Ala Ala
              530                 535                 540
Arg Val Ala Asn Ala His Ser Phe Ile Val Lys Leu Pro Asp Ala Tyr
545                 550                 555                 560
Asn Thr Gln Val Gly Glu Arg Gly Leu Gln Leu Ser Gly Gly Gln Lys
                  565                 570                 575
Gln Arg Ile Ala Ile Ala Arg Ala Met Leu Arg Asn Pro Ala Ile Leu
              580                 585                 590
Leu Leu Asp Glu Ala Thr Ser Ala Leu Asp Ser Glu Ser Glu Lys Leu
              595                 600                 605
Val Gln Glu Ala Leu Asp Arg Phe Met Ile Gly Arg Thr Thr Leu Val
              610                 615                 620
Ile Ala His Arg Leu Ser Thr Ile Arg Lys Ala Asp Leu Val Ala Val
625                 630                 635                 640
Leu Gln Gly Gly Ala Ile Ser Glu Val Gly Thr His Asp Glu Leu Met
                  645                 650                 655
Ala Arg Gly Asp Gly Thr Tyr Ala Arg Leu Ile Arg Met Gln Glu Gln
                  660                 665                 670
Ala His Glu Ala Ala Leu Val Ala Ala Arg Arg Ser Ser Ala Arg Pro
              675                 680                 685
Ser Ser Ala Arg Asn Ser Val Ser Ser Pro Ile Ile Thr Arg Asn Ser
690                 695                 700
Ser Tyr Gly Arg Ser Pro Tyr Ser Arg Arg Leu Ser Asp Ala Asp Phe
705                 710                 715                 720
Ile Thr Gly Leu Gly Leu Gly Val Asp Ser Lys Gln Gln Gln Gln Gln
                  725                 730                 735
His Tyr Phe Arg Val Gln Ala Ser Ser Phe Trp Arg Leu Ala Lys Met
              740                 745                 750
Asn Ser Pro Glu Trp Gly Tyr Ala Leu Val Ala Ser Leu Gly Ser Met
              755                 760                 765
Val Cys Gly Ser Phe Ser Ala Ile Phe Ala Tyr Val Leu Ser Ala Val
              770                 775                 780
Leu Ser Val Tyr Tyr Ala Pro Asp Ala Ala Tyr Met Asp Arg Gln Ile
785                 790                 795                 800
Ala Lys Tyr Cys Tyr Leu Leu Ile Gly Met Ser Ser Ala Ala Leu Leu
              805                 810                 815
Phe Asn Thr Val Gln His Leu Phe Trp Asp Thr Val Gly Glu Asn Leu

```
                    820            825              830
Thr Lys Arg Val Arg Glu Arg Met Leu Ala Ala Val Leu Arg Asn Glu
            835                840                845
Ile Ala Trp Phe Asp Met Glu Asp Asn Ser Ser Ala Arg Ile Ala Ala
        850                855                860
Arg Leu Ala Leu Asp Ala Gln Asn Val Arg Ser Ala Ile Gly Asp Arg
865            870                875                880
Ile Ser Ile Ile Val Gln Asn Ser Ala Leu Met Leu Val Ala Cys Thr
                885                890                895
Ala Gly Phe Val Leu Gln Trp Arg Leu Ala Leu Val Leu Leu Ala Val
            900                905                910
Phe Pro Leu Val Val Ala Thr Val Leu Gln Lys Met Phe Leu Lys
            915                920                925
Gly Phe Ser Gly Asp Leu Glu Arg Ala His Ala Arg Ala Thr Gln Ile
            930                935                940
Ala Gly Glu Ala Val Ala Asn Val Arg Thr Val Ala Ala Phe Gly Ser
945                950                955                960
Glu Ala Lys Ile Val Gly Leu Phe Glu Ala Asn Leu Ala Gly Pro Leu
                965                970                975
Arg Arg Cys Phe Trp Lys Gly Gln Ile Ala Gly Ser Gly Tyr Gly Val
            980                985                990
Ala Gln Phe Leu Leu Tyr Ala Ser Tyr Ala Leu Gly Leu Trp Tyr Ala
                995                1000               1005
Ala Trp Leu Val Lys His Gly Val Ser Asp Phe Ser Lys Thr Ile
    1010               1015               1020
Arg Val Phe Met Val Leu Met Val Ser Ala Asn Gly Ala Ala Glu
    1025               1030               1035
Thr Leu Thr Leu Ala Pro Asp Phe Val Lys Gly Gly Arg Ala Met
    1040               1045               1050
Gln Ala Val Phe Glu Ala Met Asp Arg Arg Thr Glu Ile Glu Pro
    1055               1060               1065
Asp Asp Val Asp Ala Ala Ala Val Pro Glu Arg Pro Arg Gly Glu
    1070               1075               1080
Val Glu Leu Lys His Val Asp Phe Ala Tyr Pro Ser Arg Pro Glu
    1085               1090               1095
Val Gln Val Phe Arg Asp Leu Ser Leu Arg Ala Arg Ala Gly Arg
    1100               1105               1110
Thr Leu Ala Leu Val Gly Ala Ser Gly Cys Gly Lys Ser Ser Val
    1115               1120               1125
Leu Ala Leu Val Gln Arg Phe Tyr Glu Pro Asn Ser Gly Arg Val
    1130               1135               1140
Leu Leu Asp Gly Arg Asp Leu Arg Lys Phe Asn Leu Arg Ser Leu
    1145               1150               1155
Arg Arg Ala Met Ala Leu Val Pro Gln Glu Pro Phe Leu Phe Ala
    1160               1165               1170
Ala Thr Ile His Asp Asn Ile Ala Tyr Gly Arg Glu Gly Ala Thr
    1175               1180               1185
Glu Ala Glu Val Val Glu Ala Thr Ala Ala Asn Ala His Lys
    1190               1195               1200
Phe Ile Ser Ala Leu Pro Glu Gly Tyr Gly Thr Leu Val Gly Glu
    1205               1210               1215
Arg Gly Val Gln Leu Ser Gly Gly Gln Arg Gln Arg Ile Ala Ile
    1220               1225               1230
```

```
Ala Arg Ala Leu Val Lys Gln Ala Pro Ile Leu Leu Leu Asp Glu
    1235                1240                1245

Ala Thr Ser Ala Leu Asp Ala Glu Ser Glu Arg Ser Val Gln Glu
    1250                1255                1260

Ala Leu Ala Ser Ser Gly Ser Gly Arg Thr Thr Ile Val Val
    1265                1270                1275

Ala His Arg Leu Ala Thr Val Arg Asn Ala His Thr Ile Ala Val
    1280                1285                1290

Ile Asp Asp Gly Lys Val Ala Glu Gln Gly Ser His Ser His Leu
    1295                1300                1305

Leu Asn His His Pro Asp Gly Cys Tyr Ala Arg Met Leu Gln Leu
    1310                1315                1320

Gln Arg Leu Ser His Ser His Val Ala Pro Gly Pro Ser Ser Ser
    1325                1330                1335

Thr Thr Thr His Gly Thr
    1340

<210> SEQ ID NO 52
<211> LENGTH: 1349
<212> TYPE: PRT
<213> ORGANISM: Oryza sativa

<400> SEQUENCE: 52

Met Pro Pro Pro Thr Arg Ser Ser Arg Pro Ser Ile Ser Pro Pro
1               5                   10                  15

Thr Ser Pro Arg Thr Arg Thr Ser Ser Thr Thr Thr Ile Leu His Asn
                20                  25                  30

Pro Ile Leu Asn Leu Met His Gln Gln Gln Arg His Arg His Leu
            35                  40                  45

Leu Pro Leu Leu Leu Leu Leu Ser Arg Arg Arg Arg Leu Pro Thr
    50                  55                  60

Ser Lys Pro Pro Thr Phe His Arg Pro Arg Pro Leu Pro Pro Ala Pro
65                  70                  75                  80

Phe Arg Gln Leu Phe Ser Phe Gly Asp Gly Leu Asp Tyr Val Leu Met
                85                  90                  95

Thr Leu Gly Thr Leu Gly Ala Leu Val His Gly Cys Ser Leu Thr Val
                100                 105                 110

Phe Leu Arg Phe Phe Ala Asp Leu Val Asp Ser Phe Gly Ser His Ala
            115                 120                 125

Ala His Pro Asp Thr Met Leu Arg Leu Val Val Lys Tyr Ala Phe Tyr
    130                 135                 140

Phe Leu Val Val Gly Ala Ala Ile Trp Ala Ser Ser Trp Ala Glu Ile
145                 150                 155                 160

Ser Cys Trp Met Trp Thr Gly Glu Arg Gln Ser Thr Arg Met Arg Ile
                165                 170                 175

Arg Tyr Leu His Ala Ala Leu His Gln Asp Val Ser Phe Phe Asp Thr
            180                 185                 190

Asp Val Arg Thr Ser Asp Val Ile His Ala Ile Asn Ala Asp Ala Val
    195                 200                 205

Val Val Gln Asp Ala Ile Ser Glu Lys Leu Gly Asn Leu Ile His Tyr
210                 215                 220

Leu Ala Thr Phe Val Ser Gly Phe Val Val Gly Phe Thr Ala Ala Trp
225                 230                 235                 240

Gln Leu Ala Leu Val Thr Leu Ala Val Val Pro Leu Ile Ala Val Ile
                245                 250                 255
```

```
Gly Gly Leu Ser Ala Ala Ala Leu Ala Lys Leu Ser Ser Arg Ser Gln
            260                 265                 270

Asp Ala Leu Ser Asp Ala Ser Gly Ile Ala Glu Gln Ala Leu Ala Gln
        275                 280                 285

Ile Arg Ile Val Gln Ser Phe Val Gly Glu Arg Val Met Arg Ala
    290                 295                 300

Tyr Ser Ala Ala Leu Ala Val Ala Gln Arg Ile Gly Tyr Arg Ser Gly
305                 310                 315                 320

Phe Ala Lys Gly Ile Gly Leu Gly Gly Thr Tyr Phe Thr Val Phe Cys
                325                 330                 335

Cys Tyr Ala Leu Leu Leu Trp Tyr Gly His Leu Val Arg Arg Ala
            340                 345                 350

His Thr Asn Gly Gly Leu Ala Ile Ala Thr Met Phe Ser Val Met Ile
        355                 360                 365

Gly Gly Leu Ala Leu Gly Gln Ser Ala Pro Ser Met Ala Ala Phe Ala
    370                 375                 380

Lys Ala Arg Val Ala Ala Lys Ile Phe Arg Met Met Glu His Lys
385                 390                 395                 400

Pro Ser Met Glu Arg Glu Gly Val Glu Leu Glu Ala Val Thr Gly
                405                 410                 415

Arg Val Glu Leu Arg Asp Val Glu Phe Ser Tyr Pro Ser Arg Pro Asp
            420                 425                 430

Val Gly Ile Leu Arg Gly Leu Ser Leu Ser Val Pro Ala Gly Lys Thr
        435                 440                 445

Ile Ala Leu Val Gly Ser Ser Gly Ser Gly Lys Ser Thr Val Val Ser
    450                 455                 460

Leu Ile Glu Arg Phe Tyr Glu Pro Asn Ala Gly Thr Ile Leu Leu Asp
465                 470                 475                 480

Gly His Asp Leu Arg Asp Leu Asn Leu Arg Trp Leu Arg Arg Gln Ile
                485                 490                 495

Gly Leu Val Ser Gln Glu Pro Ala Leu Phe Ala Thr Thr Ile Arg Glu
            500                 505                 510

Asn Leu Leu Leu Gly Arg Asp Gly Ala Thr Gln Glu Glu Leu Glu Glu
        515                 520                 525

Ala Ala Arg Val Ala Asn Ala His Ser Phe Ile Val Lys Leu Pro Asp
    530                 535                 540

Ala Tyr Asn Thr Gln Ala Arg Pro Gly Gly Asn Gln Trp Val Ala Phe
545                 550                 555                 560

Glu Arg Cys Ser Glu Leu Val Gln Val Gly Glu Arg Gly Leu Gln Leu
                565                 570                 575

Ser Gly Gly Gln Lys Gln Arg Ile Ala Ile Ala Arg Ala Met Leu Arg
            580                 585                 590

Asn Pro Ala Ile Leu Leu Leu Asp Glu Ala Thr Ser Ala Leu Asp Ser
        595                 600                 605

Glu Ser Glu Lys Leu Val Gln Glu Ala Leu Asp Arg Phe Met Ile Gly
    610                 615                 620

Arg Thr Thr Leu Val Ile Ala His Arg Leu Ser Thr Ile Arg Lys Ala
625                 630                 635                 640

Asp Leu Val Ala Val Leu Gln Gly Gly Ala Ile Ser Glu Val Gly Thr
                645                 650                 655

His Asp Glu Leu Met Ala Arg Gly Asp Gly Thr Tyr Ala Arg Leu Ile
            660                 665                 670

Arg Met Gln Glu Gln Ala His Glu Ala Ala Leu Val Ala Ala Arg Arg
        675                 680                 685
```

```
Ser Ser Ala Arg Pro Ser Ser Ala Arg Asn Ser Val Ser Ser Pro Ile
    690                 695                 700
Ile Thr Arg Asn Ser Ser Tyr Gly Arg Ser Pro Tyr Ser Arg Arg Leu
705                 710                 715                 720
Ser Asp Ala Asp Phe Ile Thr Gly Leu Gly Leu Gly Val Asp Ser Lys
                725                 730                 735
Gln Gln Gln Gln Gln His Tyr Phe Arg Val Gln Ala Ser Ser Phe Trp
            740                 745                 750
Arg Leu Ala Lys Met Asn Ser Pro Glu Trp Gly Tyr Ala Leu Val Ala
        755                 760                 765
Ser Leu Gly Ser Met Val Cys Gly Ser Phe Ser Ala Ile Phe Ala Tyr
    770                 775                 780
Val Leu Ser Ala Val Leu Ser Val Tyr Tyr Ala Pro Asp Ala Ala Tyr
785                 790                 795                 800
Met Asp Arg Gln Ile Ala Lys Tyr Cys Tyr Leu Leu Ile Gly Met Ser
                805                 810                 815
Ser Ala Ala Leu Leu Phe Asn Thr Val Gln His Leu Phe Trp Asp Thr
            820                 825                 830
Val Gly Glu Asn Leu Thr Lys Arg Val Arg Glu Arg Met Leu Ala Ala
        835                 840                 845
Val Leu Arg Asn Glu Ile Ala Trp Phe Asp Met Glu Asp Asn Ser Ser
    850                 855                 860
Ala Arg Ile Ala Ala Arg Leu Ala Leu Asp Ala Gln Asn Val Arg Ser
865                 870                 875                 880
Ala Ile Gly Asp Arg Ile Ser Ile Ile Val Gln Asn Ser Ala Leu Met
                885                 890                 895
Leu Val Ala Cys Thr Ala Gly Phe Val Leu Gln Trp Arg Leu Ala Leu
            900                 905                 910
Val Leu Leu Ala Val Phe Pro Leu Val Ala Ala Thr Val Leu Gln
        915                 920                 925
Lys Met Phe Leu Lys Gly Phe Ser Gly Asp Leu Glu Arg Ala His Ala
    930                 935                 940
Arg Ala Thr Gln Ile Ala Gly Glu Ala Val Ala Asn Val Arg Thr Val
945                 950                 955                 960
Ala Ala Phe Gly Ser Glu Ala Lys Ile Val Gly Leu Phe Glu Ala Asn
                965                 970                 975
Leu Ala Gly Pro Leu Arg Arg Cys Phe Trp Lys Gly Gln Ile Ala Gly
            980                 985                 990
Ser Gly Tyr Gly Val Ala Gln Phe  Leu Leu Tyr Ala Ser  Tyr Ala Leu
        995                 1000                1005
Gly Leu Trp Tyr Ala Ala Trp  Leu Val Lys His Gly  Val Ser Asp
    1010                1015                1020
Phe Ser Lys Thr Ile Arg Val  Phe Met Val Leu Met  Val Ser Ala
    1025                1030                1035
Asn Gly Ala Ala Glu Thr Leu  Thr Leu Ala Pro Asp  Phe Val Lys
    1040                1045                1050
Gly Gly Arg Ala Met Gln Ala  Val Phe Glu Ala Met  Asp Arg Arg
    1055                1060                1065
Thr Glu Ile Glu Pro Asp Asp  Val Asp Ala Ala Ala  Val Pro Glu
    1070                1075                1080
Arg Pro Arg Gly Glu Val Glu  Leu Lys His Val Asp  Phe Ala Tyr
    1085                1090                1095
Pro Ser Arg Pro Glu Val Gln  Val Phe Arg Asp Leu  Ser Leu Arg
```

```
              1100                1105                1110

Ala Arg Ala Gly Arg Thr Leu Ala Leu Val Gly Ala Ser Gly Cys
    1115                1120                1125

Gly Lys Ser Ser Val Leu Ala Leu Val Gln Arg Phe Tyr Glu Pro
    1130                1135                1140

Asn Ser Gly Arg Val Leu Leu Asp Gly Arg Asp Leu Arg Lys Phe
    1145                1150                1155

Asn Leu Arg Ser Leu Arg Arg Ala Met Ala Leu Val Pro Gln Glu
    1160                1165                1170

Pro Phe Leu Phe Ala Ala Thr Ile His Asp Asn Ile Ala Tyr Gly
    1175                1180                1185

Arg Glu Gly Ala Thr Glu Ala Glu Val Val Glu Ala Ala Thr Ala
    1190                1195                1200

Ala Asn Ala His Lys Phe Ile Ser Ala Leu Pro Glu Gly Tyr Gly
    1205                1210                1215

Thr Leu Val Gly Glu Arg Gly Val Gln Leu Ser Gly Gly Gln Arg
    1220                1225                1230

Gln Arg Ile Ala Ile Ala Arg Ala Leu Val Lys Gln Ala Pro Ile
    1235                1240                1245

Leu Leu Leu Asp Glu Ala Thr Ser Ala Leu Asp Ala Glu Ser Glu
    1250                1255                1260

Arg Ser Val Gln Glu Ala Leu Ala Ser Ser Ser Gly Ser Gly Arg
    1265                1270                1275

Thr Thr Ile Val Val Ala His Arg Leu Ala Thr Val Arg Asn Ala
    1280                1285                1290

His Thr Ile Ala Val Ile Asp Asp Gly Lys Val Ala Glu Gln Gly
    1295                1300                1305

Ser His Ser His Leu Leu Asn His His Pro Asp Gly Cys Tyr Ala
    1310                1315                1320

Arg Met Leu Gln Leu Gln Arg Leu Ser His Ser His Val Ala Pro
    1325                1330                1335

Gly Pro Ser Ser Ser Thr Thr His Gly Thr
    1340                1345

<210> SEQ ID NO 53
<211> LENGTH: 1252
<212> TYPE: PRT
<213> ORGANISM: Arabidopsis thaliana

<400> SEQUENCE: 53

Met Ser Glu Thr Asn Thr Thr Asp Ala Lys Thr Val Pro Ala Glu Ala
1               5                   10                  15

Glu Lys Lys Lys Glu Gln Ser Leu Pro Phe Phe Lys Leu Phe Ser Phe
                20                  25                  30

Ala Asp Lys Phe Asp Tyr Leu Leu Met Phe Val Gly Ser Leu Gly Ala
            35                  40                  45

Ile Val His Gly Ser Ser Met Pro Val Phe Phe Leu Leu Phe Gly Gln
        50                  55                  60

Met Val Asn Gly Phe Gly Lys Asn Gln Met Asp Leu His Gln Met Val
65                  70                  75                  80

His Glu Val Ser Arg Tyr Ser Leu Tyr Phe Val Tyr Leu Gly Leu Val
                85                  90                  95

Val Cys Phe Ser Ser Tyr Ala Glu Ile Ala Cys Trp Met Tyr Ser Gly
                100                 105                 110

Glu Arg Gln Val Ala Ala Leu Arg Lys Lys Tyr Leu Glu Ala Val Leu
```

-continued

```
            115                 120                 125
Lys Gln Asp Val Gly Phe Phe Asp Thr Asp Ala Arg Thr Gly Asp Ile
            130                 135                 140
Val Phe Ser Val Ser Thr Asp Thr Leu Leu Val Gln Asp Ala Ile Ser
145                 150                 155                 160
Glu Lys Val Gly Asn Phe Ile His Tyr Leu Ser Thr Phe Leu Ala Gly
                    165                 170                 175
Leu Val Val Gly Phe Val Ser Ala Trp Lys Leu Ala Leu Leu Ser Val
                    180                 185                 190
Ala Val Ile Pro Gly Ile Ala Phe Ala Gly Gly Leu Tyr Ala Tyr Thr
                    195                 200                 205
Leu Thr Gly Ile Thr Ser Lys Ser Arg Glu Ser Tyr Ala Asn Ala Gly
210                 215                 220
Val Ile Ala Glu Gln Ala Ile Ala Gln Val Arg Thr Val Tyr Ser Tyr
225                 230                 235                 240
Val Gly Glu Ser Lys Ala Leu Asn Ala Tyr Ser Asp Ala Ile Gln Tyr
                    245                 250                 255
Thr Leu Lys Leu Gly Tyr Lys Ala Gly Met Ala Lys Gly Leu Gly Leu
            260                 265                 270
Gly Cys Thr Tyr Gly Ile Ala Cys Met Ser Trp Ala Leu Val Phe Trp
            275                 280                 285
Tyr Ala Gly Val Phe Ile Arg Asn Gly Gln Thr Asp Gly Gly Lys Ala
            290                 295                 300
Phe Thr Ala Ile Phe Ser Ala Ile Val Gly Gly Met Ser Leu Gly Gln
305                 310                 315                 320
Ser Phe Ser Asn Leu Gly Ala Phe Ser Lys Gly Lys Ala Ala Gly Tyr
                    325                 330                 335
Lys Leu Met Glu Ile Ile Asn Gln Arg Pro Thr Ile Ile Gln Asp Pro
            340                 345                 350
Leu Asp Gly Lys Cys Leu Asp Gln Val His Gly Asn Ile Glu Phe Lys
            355                 360                 365
Asp Val Thr Phe Ser Tyr Pro Ser Arg Pro Asp Val Met Ile Phe Arg
            370                 375                 380
Asn Phe Asn Ile Phe Phe Pro Ser Gly Lys Thr Val Ala Val Val Gly
385                 390                 395                 400
Gly Ser Gly Ser Gly Lys Ser Thr Val Val Ser Leu Ile Glu Arg Phe
                    405                 410                 415
Tyr Asp Pro Asn Ser Gly Gln Ile Leu Leu Asp Gly Val Glu Ile Lys
                    420                 425                 430
Thr Leu Gln Leu Lys Phe Leu Arg Glu Gln Ile Gly Leu Val Asn Gln
            435                 440                 445
Glu Pro Ala Leu Phe Ala Thr Thr Ile Leu Glu Asn Ile Leu Tyr Gly
            450                 455                 460
Lys Pro Asp Ala Thr Met Val Glu Val Glu Ala Ala Ser Ala Ala
465                 470                 475                 480
Asn Ala His Ser Phe Ile Thr Leu Leu Pro Lys Gly Tyr Asp Thr Gln
                    485                 490                 495
Val Gly Glu Arg Gly Val Gln Leu Ser Gly Gly Gln Lys Gln Arg Ile
                    500                 505                 510
Ala Ile Ala Arg Ala Met Leu Lys Asp Pro Lys Ile Leu Leu Leu Asp
            515                 520                 525
Glu Ala Thr Ser Ala Leu Asp Ala Ser Ser Glu Ser Ile Val Gln Glu
            530                 535                 540
```

```
Ala Leu Asp Arg Val Met Val Gly Arg Thr Thr Val Val Ala His
545                 550                 555                 560

Arg Leu Cys Thr Ile Arg Asn Val Asp Ser Ile Ala Val Ile Gln Gln
                565                 570                 575

Gly Gln Val Val Glu Thr Gly Thr His Glu Glu Leu Ile Ala Lys Ser
                580                 585                 590

Gly Ala Tyr Ala Ser Leu Ile Arg Phe Gln Glu Met Val Gly Thr Arg
                595                 600                 605

Asp Phe Ser Asn Pro Ser Thr Arg Arg Thr Arg Ser Thr Arg Leu Ser
610                 615                 620

His Ser Leu Ser Thr Lys Ser Leu Ser Leu Arg Ser Gly Ser Leu Arg
625                 630                 635                 640

Asn Leu Ser Tyr Ser Tyr Ser Thr Gly Ala Asp Gly Arg Ile Glu Met
                645                 650                 655

Ile Ser Asn Ala Glu Thr Asp Arg Lys Thr Arg Ala Pro Glu Asn Tyr
                660                 665                 670

Phe Tyr Arg Leu Leu Lys Leu Asn Ser Pro Glu Trp Pro Tyr Ser Ile
                675                 680                 685

Met Gly Ala Val Gly Ser Ile Leu Ser Gly Phe Ile Gly Pro Thr Phe
690                 695                 700

Ala Ile Val Met Ser Asn Met Ile Glu Val Phe Tyr Tyr Thr Asp Tyr
705                 710                 715                 720

Asp Ser Met Glu Arg Lys Thr Lys Glu Tyr Val Phe Ile Tyr Ile Gly
                725                 730                 735

Ala Gly Leu Tyr Ala Val Gly Ala Tyr Leu Ile Gln His Tyr Phe Phe
                740                 745                 750

Ser Ile Met Gly Glu Asn Leu Thr Thr Arg Val Arg Arg Met Met Leu
                755                 760                 765

Ser Ala Ile Leu Arg Asn Glu Val Gly Trp Phe Asp Glu Asp Glu His
770                 775                 780

Asn Ser Ser Leu Ile Ala Ala Arg Leu Ala Thr Asp Ala Ala Asp Val
785                 790                 795                 800

Lys Ser Ala Ile Ala Glu Arg Ile Ser Val Ile Leu Gln Asn Met Thr
                805                 810                 815

Ser Leu Leu Thr Ser Phe Ile Val Ala Phe Ile Val Glu Trp Arg Val
                820                 825                 830

Ser Leu Leu Ile Leu Gly Thr Phe Pro Leu Leu Val Leu Ala Asn Phe
                835                 840                 845

Ala Gln Gln Leu Ser Leu Lys Gly Phe Ala Gly Asp Thr Ala Lys Ala
850                 855                 860

His Ala Lys Thr Ser Met Ile Ala Gly Glu Gly Val Ser Asn Ile Arg
865                 870                 875                 880

Thr Val Ala Ala Phe Asn Ala Gln Ser Lys Ile Leu Ser Leu Phe Cys
                885                 890                 895

His Glu Leu Arg Val Pro Gln Lys Arg Ser Leu Tyr Arg Ser Gln Thr
                900                 905                 910

Ser Gly Phe Leu Phe Gly Leu Ser Gln Leu Ala Leu Tyr Gly Ser Glu
                915                 920                 925

Ala Leu Ile Leu Trp Tyr Gly Ala His Leu Val Ser Lys Gly Val Ser
930                 935                 940

Thr Phe Ser Lys Val Ile Lys Val Phe Val Val Leu Val Ile Thr Ala
945                 950                 955                 960

Asn Ser Val Ala Glu Thr Val Ser Leu Ala Pro Glu Ile Ile Arg Gly
                965                 970                 975
```

```
Gly Glu Ala Val Gly Ser Val Phe Ser Val Leu Asp Arg Gln Thr Arg
                980                 985                 990

Ile Asp Pro Asp Asp Ala Asp Ala  Asp Pro Val Glu Thr  Ile Arg Gly
        995                 1000                1005

Asp Ile Glu Phe Arg His Val  Asp Phe Ala Tyr Pro  Ser Arg Pro
        1010                1015                1020

Asp Val Met Val Phe Arg Asp  Phe Asn Leu Arg Ile  Arg Ala Gly
        1025                1030                1035

His Ser Gln Ala Leu Val Gly  Ala Ser Gly Ser Gly  Lys Ser Ser
        1040                1045                1050

Val Ile Ala Met Ile Glu Arg  Phe Tyr Asp Pro Leu  Ala Gly Lys
        1055                1060                1065

Val Met Ile Asp Gly Lys Asp  Ile Arg Arg Leu Asn  Leu Lys Ser
        1070                1075                1080

Leu Arg Leu Lys Ile Gly Leu  Val Gln Gln Glu Pro  Ala Leu Phe
        1085                1090                1095

Ala Ala Thr Ile Phe Asp Asn  Ile Ala Tyr Gly Lys  Asp Gly Ala
        1100                1105                1110

Thr Glu Ser Glu Val Ile Asp  Ala Ala Arg Ala Ala  Asn Ala His
        1115                1120                1125

Gly Phe Ile Ser Gly Leu Pro  Glu Gly Tyr Lys Thr  Pro Val Gly
        1130                1135                1140

Glu Arg Gly Val Gln Leu Ser  Gly Gly Gln Lys Gln  Arg Ile Ala
        1145                1150                1155

Ile Ala Arg Ala Val Leu Lys  Asn Pro Thr Val Leu  Leu Leu Asp
        1160                1165                1170

Glu Ala Thr Ser Ala Leu Asp  Ala Glu Ser Glu Cys  Val Leu Gln
        1175                1180                1185

Glu Ala Leu Glu Arg Leu Met  Arg Gly Arg Thr Thr  Val Val Val
        1190                1195                1200

Ala His Arg Leu Ser Thr Ile  Arg Gly Val Asp Cys  Ile Gly Val
        1205                1210                1215

Ile Gln Asp Gly Arg Ile Val  Glu Gln Gly Ser His  Ser Glu Leu
        1220                1225                1230

Val Ser Arg Pro Glu Gly Ala  Tyr Ser Arg Leu Leu  Gln Leu Gln
        1235                1240                1245

Thr His Arg Ile
        1250

<210> SEQ ID NO 54
<211> LENGTH: 517
<212> TYPE: PRT
<213> ORGANISM: Artificial Sequence
<220> FEATURE:
<223> OTHER INFORMATION: Auxin transporter consensus sequence

<400> SEQUENCE: 54

Leu Phe Phe Asp Asp Leu Met Gly Gly Ala Val His Gly Ser Phe Phe
1               5                   10                  15

Val Phe Gly Met Val Tyr Tyr Phe Gly Ser Ser Ala Glu Ile Cys Trp
            20                  25                  30

Met Gly Glu Arg Gln Arg Tyr Leu Ala Leu Gln Asp Phe Asp Thr Arg
        35                  40                  45

Asp Asp Val Gln Asp Ala Ile Ser Lys Gly Asn Ile His Tyr Leu Ala
    50                  55                  60
```

```
Val Pro Ile Ala Gly Ser Ala Ile Glu Gln Gln Arg Val Val Gly Glu
 65                  70                  75                  80

Ala Tyr Ala Gly Tyr Gly Lys Gly Gly Leu Gly Thr Tyr Leu Trp Tyr
                 85                  90                  95

Gly Arg Thr Gly Gly Ala Phe Gly Gly Gln Ser Ala Phe Lys Ala Lys
            100                 105                 110

Pro Val Gly Glu Val Phe Tyr Pro Ser Arg Pro Ile Pro Gly Lys Thr
        115                 120                 125

Ala Val Gly Ser Gly Ser Gly Lys Ser Thr Val Val Ser Leu Glu Arg
    130                 135                 140

Phe Tyr Pro Gly Leu Asp Gly Leu Leu Leu Arg Gln Ile Gly Leu Val
145                 150                 155                 160

Gln Glu Pro Leu Phe Ala Thr Ile Glu Asn Leu Gly Ala Glu Glu Ala
                165                 170                 175

Ala Ala Asn Ala His Ser Phe Leu Pro Thr Gln Val Gly Glu Arg Gly
            180                 185                 190

Gln Leu Ser Gly Gly Lys Gln Arg Ile Ala Ile Ala Arg Ala Met
        195                 200                 205

Leu Pro Ile Leu Leu Leu Asp Glu Ala Thr Ser Ala Leu Asp Ser Glu
210                 215                 220

Val Gln Glu Ala Leu Asp Arg Met Gly Arg Thr Thr Ala Asp Ala Val
225                 230                 235                 240

Gln Gly Glu His Glu Leu Tyr Ile Gln Glu Arg Ser Ser Ser Arg Phe
                245                 250                 255

Arg Leu Asn Ser Pro Glu Trp Tyr Gly Ser Gly Phe Ala Ser Tyr Asp
            260                 265                 270

Met Tyr Ile Gly Ala Gln His Gly Glu Asn Leu Thr Arg Val Arg Met
        275                 280                 285

Ala Glu Trp Phe Asp Ser Ala Arg Leu Asp Ala Val Ser Ala Ile Arg
    290                 295                 300

Ile Ser Ile Gln Asn Leu Phe Trp Arg Leu Phe Pro Val Ala Gln Gly
305                 310                 315                 320

Phe Gly Asp Ala His Ala Ala Gly Glu Asn Arg Thr Val Ala Ala Phe
                325                 330                 335

Lys Ile Leu Leu Pro Arg Gln Gly Gln Leu Tyr Ser Ala Leu Leu
            340                 345                 350

Trp Tyr Leu Val Gly Ser Phe Ser Ile Val Phe Val Leu Ala Asn Ala
        355                 360                 365

Glu Thr Leu Ala Pro Gly Gly Ala Val Phe Asp Arg Thr Pro Asp Asp
    370                 375                 380

Val Glu His Asp Phe Tyr Pro Arg Pro Phe Arg Asp Leu Arg Arg Ala
385                 390                 395                 400

Gly Ala Leu Val Gly Ser Gly Lys Ser Ser Val Arg Phe Tyr Pro
                405                 410                 415

Gly Val Asp Gly Asp Arg Asn Leu Arg Gln Glu Pro Leu Phe Ile Asn
            420                 425                 430

Ile Ala Tyr Gly Ala Thr Glu Glu Ala Ala Ala His Phe Ile Leu
        435                 440                 445

Pro Gly Tyr Thr Val Gly Glu Arg Gly Val Gln Leu Ser Gly Gly Gln
450                 455                 460
```

-continued

```
Gln Arg Ile Ala Ile Ala Arg Ala Leu Leu Asp Glu Ala Thr Ser Ala
465                 470                 475                 480

Leu Asp Ala Glu Ser Glu Gln Glu Ala Leu Gly Thr Val Val Ala His
                485                 490                 495

Arg Leu Thr Arg Ile Val Ile Asp Gly Glu Gln Gly Ser His Ser Leu
            500                 505                 510

Gly Tyr Arg Gln Leu
        515
```

PRODUCTS AND METHODS FOR IN VIVO SECRETION OF MONATIN

CROSS-REFERENCE TO RELATED APPLICATION

This application is a continuation-in-part of U.S. application Ser. No. 11/379,528, filed Apr. 20, 2006, which claims the benefit of U.S. provisional application Ser. No. 60/673,262, filed Apr. 20, 2005, each of which is herein incorporated by reference.

BACKGROUND OF THE INVENTION

1. Field of the Invention

The present invention relates generally to products and methods for the in vivo production of monatin sweetener. More specifically, the present invention relates to products and methods for the in vivo secretion of monatin sweetener.

2. Related Art

Monatin is a high-intensity sweetener having the chemical formula:

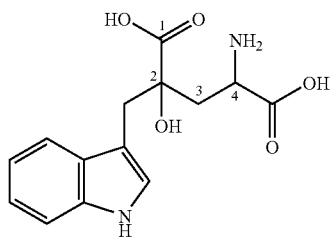

Monatin includes two chiral centers leading to four potential stereoisomeric configurations. The R,R configuration (the "R,R stereoisomer" or "R,R monatin"); the S,S configuration (the "S,S stereoisomer" or "S,S monatin"); the R,S configuration (the "R,S stereoisomer" or "R,S monatin"); and the S,R configuration (the "S,R stereoisomer" or "S,R monatin"). As used herein, unless stated otherwise, the term "monatin" is used to refer to compositions including all four stereoisomers of monatin, compositions including any combination of monatin stereoisomers, (e.g., a composition including only the R,R and S,S, stereoisomers of monatin), as well as a single isomeric form.

For purposes of this disclosure, the monatin carbon backbone will be numbered as illustrated above, with the carbon attached to the alcohol group being identified as the 2-position carbon and the carbon directly covalently attached to the amino group being identified as the 4-position carbon. Consequently, references herein to R,R monatin, S,S monatin, R,S monatin, and S,R monatin mean: 2R,4R monatin, 2S,4S monatin, 2R,4S monatin, and 2S,4R monatin, respectively, unless otherwise indicated.

It should be noted that in the literature, the monatin carbon backbone has also been numbered using an alternative convention, with the carbon attached to the alcohol group being the 4-position carbon, and the carbon attached to the amino group being the 2-position carbon. Accordingly, for example, references to 2S,4R monatin in this disclosure would be the same as references to 2R,4S monatin in literature using the alternative numbering convention.

Furthermore, because of various naming conventions, monatin is known by a number of alternative chemical names, including: 2-hydroxy-2-(indol-3-ylmethyl)-4-aminoglutaric acid; 4-amino-2-hydroxy-2-(1H-indol-3-ylmethyl)-pentanedioic acid; 4-hydroxy-4-(3-indolylmethyl)glutamic acid; and, 3-(1-amino-1,3-dicarboxy-3-hydroxy-but-4-yl)indole.

At least in part because of its sweetening characteristic, it would be desirable to have an economic source of monatin. Certain isomeric forms of monatin can be found in the bark of roots of the *Schlerochiton ilicifolius* plant located in the Transvaal Region of South Africa. However, the concentration of the monatin present in the dried bark, expressed as the indole in its acid form, has been found to be about 0.007% by mass. See U.S. Pat. No. 4,975,298. Further, the method by which monatin is produced in the plant is presently unknown. U.S. patent application Ser. No. 10/422,366 ("the '366 application"), on the other hand, which is hereby incorporated by reference, discloses, inter alia, polypeptides, pathways, and microorganisms for in vivo and in vitro production of monatin.

BRIEF SUMMARY OF THE INVENTION

The production of monatin is thought to be an equilibrium process. In order to increase production of monatin above the equilibrium amount, and potentially make production of monatin even more economical, it would be desirable to remove products or increase the amount of substrates involved in reactions for making monatin. With respect to in vivo production, it could therefore be desirable to secrete monatin from the cell as a means of removing product and pushing the equilibrium forward. For purposes of this specification, the terms "cell," "organism," and "microorganism" are used interchangeably, and include, without limitation, and unless otherwise stated, bacteria, fungi such as yeasts and molds, algae, protozoa, microbes, and viruses.

The inventors have developed a novel approach utilizing transporters—which were heretofore unknown to cooperate with monatin—for removing monatin from the cell, for example into the periplasmic space or into the surrounding medium. Transporters are cell membrane proteins, which catalyze the transfer of certain solutes across one or more cell membranes. For example, bacterial species that have developed clinical resistance to antibiotics use transporters to pump the drugs or other toxic agents across the cell membrane into the medium. These efflux pumps utilize energy either from ATP hydrolysis or the proton-motive force to promote the extrusion of toxic agents. No wild-type microorganisms are presently reported to produce monatin in nature, and so similarly there were heretofore no reported transporters for secreting monatin.

According to some embodiments, a method for producing monatin (i.e. all four stereoisomers of monatin or a subset thereof, including a single isomeric form) in vivo is provided that includes using one or more types of transporter systems to secrete monatin that is located inside a cell out into the periplasmic space or into a medium, such as a culture medium. Non-limiting examples of suitable transporter systems include the AcrAB system, the EmrAB system, and systems that include homologs of AcrAB or EmrAB. In one permutation, monatin is produced in and is at least partially secreted by a microorganism that is genetically modified to have the ability to produce monatin, and whose corresponding wild-type form includes one or more transporter systems capable of secreting monatin but itself does not produce monatin. In one permutation, monatin is produced in and is at least partially secreted by a microorganism naturally capable of producing monatin, but that is genetically modified to express or overexpress one or more transporter systems or one or more components of transporter systems capable of secreting monatin. In one permutation, monatin is produced and at least partially secreted by a microorganism that has been genetically modified to express transporters or components of transporter systems involved with secreting monatin. In one permutation, monatin is produced and at least partially secreted by a microorganism that has been genetically modified to express components of transporters capable of secreting monatin. For example, the microorganism may be genetically modified to overexpress the channel-forming protein component of the transporter system such as AcrAB and/or EmrAB. As another example, the microorganism may be genetically modified to express components of transporters that are heterologous to the microorganism, native to the microorganism, or a combination thereof.

According to some embodiments, microorganisms are provided that have been genetically modified to express or overexpress one or more transport systems that enable directed exchange of solutes between the microorganism and its environment. In some embodiments, the microorganisms are genetically engineered to express, or overexpress, transporters that selectively transport monatin, for example over intermediates in the monatin pathway.

According to some embodiments, monatin is produced in cells which exhibit increased transporter activity as compared to an appropriate control, e.g. as described in examples herein. In one permutation, monatin is produced in a microorganism that is genetically modified to overexpress one or more types of transporter systems capable of secreting monatin. In one permutation, monatin is produced in a microorganism genetically modified to overexpress one or more components of a transporter system. For example, monatin may be produced in a microorganism that is genetically modified to overexpress the channel-forming protein component (such as AcrAB or EmrAB) of a transporter system. As another example, monatin may be produced in a microorganism that in addition, or in the alternative, overexpresses the outer membrane factor component (e.g. TolC) of a transporter system. In one permutation, monatin is produced in a microorganism exposed to an inducing compound (i.e. a compound that triggers expression of a transporter system or component of a transporter system or that stimulates secretion activity). For example, monatin may be produced in a microorganism that is provided sodium decanoate, carbonyl cyanide 3-chlorophenylhydrazone ("CCCP"), or salicylate in its growth medium. "Growth medium," "culture medium," and "fermentation medium" are used herein interchangeably. In one permutation, the presence of inducing compounds results in monatin transport in microorganisms which do not appear to secrete monatin absent the inducing compounds. In one permutation, the presence of inducing compounds results in increased secretion of monatin by a microorganism relative to the amount secreted by an appropriate control.

According to some embodiments of the invention, methods for verifying transporter efficacy for secreting monatin are provided. In one permutation, the method includes transforming a plasmid containing the monatin operon genes into a host microorganism that has a deletion in the targeted transporter and screening for loss of monatin transport/secretion relative to wild-type controls. In one permutation, transporter genes are overexpressed by cloning them on a multi-copy plasmid, transforming a host engineered to produce monatin as described above, and screening is done for increase of monatin transport as compared to wild-type controls with no overexpression of the respective transporter genes. In one permutation, monatin secretion is evaluated by using an inducer to increase transporter activity and comparing monatin production and/or secretion to appropriate uninduced controls.

According to some embodiments, monatin is produced in a microorganism lacking one or more, transporters, for example, lacking four specific Putative Efflux Transporters identified as YhcP (AaeB), YccS, YjcQ and YhfK.

According to some embodiments, monatin is produced in a glutamate auxotroph. In one permutation, monatin is produced in a glutamate auxotroph genetically engineered to have the ability to produce monatin. In one permutation, monatin is produced in a glutamate auxotroph genetically engineered to overexpress one or more types of transporter systems capable of secreting monatin, or components of such transporter systems. In one permutation, monatin is produced in a glutamate auxotroph cultivated under fermentation conditions that increase amino acid transport.

According to some embodiments, monatin is produced in a microorganism containing a transporter system or systems capable of translocating glutamate or structurally similar molecules in exchange for malate. In one permutation, monatin is produced by a microorganism containing a transporter system or systems capable of translocating glutamate or structurally similar molecules in exchange for malate and that has been genetically modified to have the ability to produce monatin. In one permutation, monatin is produced in a microorganism containing a transporter system or systems capable of translocating glutamate or structurally similar molecules in exchange for malate and which has been genetically engineered to be a glutamate auxotroph.

It should be apparent to one of ordinary skill in the art from reading this disclosure that specific embodiments of the present invention may encompass one, some or all of the referenced permutations and embodiments, or alternatively or in addition encompass permutations or embodiments which are not explicitly identified, but may become apparent from the disclosure herein. For example, it would be considered within the scope of the invention to induce expression of transporters using compounds that are explicitly identified in the disclosure (e.g. sodium decanoate and/or CCCP and/or salicylate) and compounds that may not be identified in this disclosure.

Similarly, embodiments in accordance with the invention may encompass combinations of permutations/embodiments not explicitly identified. For example, it would be considered within the scope of the invention to simultaneously implement multiple treatments used to individually improve monatin excretion. For example, provision of ampicillin and/or Tween® 20 may be combined with provision of sodium decanoate. Example 7 provides another illustration of a suitable embodiment involving combining permutations/embodiments in accordance with the invention. In Example 7, monatin is produced in a microorganism that is both induced to express transporters by providing sodium decanoate to the growth medium and that is genetically engineered to overexpress TolC.

As should therefore be realized from the description herein the invention is capable of modifications in various aspects, all without departing from the spirit and scope of the present invention. The description, therefore, should be regarded as illustrative in nature and not restrictive and while multiple embodiments/permutations are disclosed, still other embodiments/permutations of the present invention should be apparent to those skilled in the art from the description herein, which shows and describes illustrative embodiments/permutations of the invention. Accordingly, unless otherwise indicated, all examples are non-limiting, whether or not explicitly identified as such.

BRIEF DESCRIPTION OF THE DRAWINGS/FIGURES

FIG. 1(A-D) is a sequence alignment showing the homology between the auxin transporter At PGP1 (SEQ ID NO:46) and 7 different proteins, a subset of the results of a BLAST analysis of the NCBI database. These proteins are designated as Br ABB97035 (SEQ ID NO:47), St AAD10836 (SEQ ID NO:48), Sb AAR 10387 (SEQ ID NO:50), Os XP_483819 (SEQ ID NO:51), Os_CAD59580 (SEQ ID NO:52), ZMPGP1_AAR00316 (SEQ ID NO:49), and AtPGP19 (SEQ ID NO:53). The consensus sequence is designated SEQ ID NO:54.

DETAILED DESCRIPTION OF THE INVENTION

According to some embodiments, the present disclosure provides methods and products for secreting monatin out of a microorganism, for example into the periplasmic space or into a medium, such as a culture medium. According to some embodiments, the present disclosure also provides for the development and use of transporters for secreting monatin outside a host microorganism into a desired environment, such as a medium, including a culture medium. Such transportation of monatin out of the microorganism may also increase the amount and/or rate of production of monatin relative to an appropriate control, e.g. as described in the examples herein.

As used herein, "including" means "comprising." In addition, the singular forms "a" or "an" or "the" include plural references unless the context clearly dictates otherwise. For example, reference to "comprising a protein" includes one or a plurality of such proteins, and reference to "comprising the cell" includes reference to one or more cells and equivalents thereof known to those skilled in the art, and so forth.

As used herein, the term "about" encompasses the range of experimental error that occurs in any measurement. Unless otherwise stated, all measurement numbers are presumed to have the word "about" in front of them even if the word "about" is not expressly used.

As used herein, the term "increased transporter activity" encompasses an observation that the amount and/or rate of monatin production or secretion is higher than the amount and/or rate of monatin production from the appropriate control.

As used herein, the terms "secreted" and "excreted" are used interchangeably and encompass cells that generate and separate a substance from those cells by moving that substance from within the cell into the periplasmic space or into the environment outside of the cell, such as into a surrounding medium.

As used herein, the terms "partially secreted" and "partially excreted" are used interchangeably and encompass cells that generate and separate some of a specific substance from the cell, but not all. In some aspects, the cells will maintain some of the substance within the cell.

As used herein, the terms "monatin operon gene" and "monatin operon genes" encompass gene(s) that encode one or more of the enzymes used in the synthesis of monatin.

As used herein, the terms "pump," "pumps," "pump system," "pump systems," "efflux system," and "efflux systems" are used interchangeably and encompass one or more transporters that are capable of moving a substance from the inside of a cell to a desired environment, for example, medium surrounding the cell and/or are capable of moving a substance from the area surrounding a cell to the inside of the cell.

As used herein, the term "heterologous" encompasses elements that are foreign or not native to the recited element. For example, heterologous components of a transport system encompass components that are not naturally components of that system.

As used herein, the terms "cooperate with" and "cooperates with" encompass molecule(s) that interact, covalently binds and/or regulates another molecule in a manner to achieve or enhance the functioning of that molecule. Additionally, the terms encompass molecule(s) that initiate a regulatory pathway leading to the down-stream activation or inhibition of another molecule.

As used herein, the terms "isolation," "isolating," and "isolate" encompass the process of removing a substance from its environment or host; the process does not have to yield a substance with a certain degree of purity unless otherwise indicated.

As used herein, the term "isolated" encompasses a substance that has been removed from its environment or host; the substance does not have to be pure.

As used herein, the phrase "one or more components of a transporter system" includes the complete transport system itself.

Production of Monatin in Microorganisms

As described, inter alia, in WO 03/091396 A2 (see, e.g., FIGS. 1-3 and 11-13), monatin can be produced from tryptophan through a multi-step pathway involving biological conversions (i.e. facilitating the reaction of a substrate to a product with a polypeptide). A pathway described involves biologically converting tryptophan to indole-3-pyruvate, biologically converting indole-3-pyruvate to 2-hydroxy 2-(indol-3-ylmethyl)-4-keto glutaric acid ("MP"), and biologically converting MP to monatin.

Enzymes useful for converting tryptophan to indole-3-pyruvate include members of enzyme classes ("EC") 2.6.1.27, 1.4.1.19, 1.4.99.1, 2.6.1.28, 1.4.3.2, 1.4.3.3, 2.6.1.5, 2.6.1.-, 2.6.1.1, 2.6.1.21 and 3.5.1.-. These classes include polypeptides such as: tryptophan aminotransferase, which converts L-tryptophan and α-KG (i.e., α-ketoglutarate, also called 2-oxoglutarate) to indole-3-pyruvate and L-glutamate; D-tryptophan aminotransferase, which converts D-tryptophan and a 2-oxo acid to indole-3-pyruvate and an amino acid; tryptophan dehydrogenase, which converts L-tryptophan and NAD(P) to indole-3-pyruvate and $NH_3$ and NAD(P)H; D-amino acid dehydrogenase, which converts D-amino acids and FAD to indole-3-pyruvate and $NH_3$ and $FADH_2$; tryptophan-phenylpyruvate transaminase, which converts L-tryptophan and phenylpyruvate to indole-3-pyruvate and L-phenylalanine; L-amino acid oxidase, which converts an L-amino acid and $H_2O$ and $O_2$ to a 2-oxo acid and $NH_3$ and $H_2O_2$; D-amino acid oxidase, which converts a D-amino acid and $H_2O$ and $O_2$ to a 2-oxo acid and $NH_3$ and $H_2O_2$; and tryptophan oxidase, which converts L-tryptophan and $H_2O$ and $O_2$ to indole-3-pyruvate and $NH_3$ and $H_2O_2$. These classes also contain tyrosine (aromatic) aminotransferase, aspartate aminotransferase, D-amino acid (or D-alanine) aminotransferase, and broad (multiple substrate) aminotransferase which have multiple aminotransferase activities, some of which can convert tryptophan and a 2-oxo acid to indole-3-pyruvate and an amino acid. In addition, these classes include phenylalanine deaminases, which can convert tryptophan to indole-3-pyruvate and ammonium in the presence of water.

Enzymes useful for converting indole-3-pyruvate to MP include members of enzyme classes 4.1.3.-, 4.1.3.16, 4.1.3.17, and 4.1.2.-. These classes include carbon-carbon synthases/lyases, such as aldolases that catalyze the condensation of two carboxylic acid substrates. Peptide class EC 4.1.3.- are synthases/lyases that form carbon-carbon bonds utilizing oxo-acid substrates (such as indole-3-pyruvate) as the electrophile, while EC 4.1.2.- are synthases/lyases that form carbon-carbon bonds utilizing aldehyde substrates (such as benzaldehyde) as the electrophile. For example, KHG aldolase (EC 4.1.3.16) and ProA aldolase (EC 4.1.3.17), are known to convert indole-3-pyruvate and pyruvate to MP. MP can also be generated using chemical reactions, such as the aldol condensations.

Enzymes useful for converting MP to monatin include members of enzyme classes: tryptophan aminotransferases (2.6.1.27), tryptophan dehydrogenases (1.4.1.19), D-amino acid dehydrogenases (1.4.99.1), glutamate dehydrogenases (1.4.1.2-4), phenylalanine dehydrogenase (EC 1.4.1.20), tryptophan-phenylpyruvate transaminases (2.6.1.28), or more generally members of the aminotransferase family (2.6.1.-) such as aspartate aminotransferase (EC 2.6.1.1), tyrosine (aromatic) aminotransferase (2.6.1.5), D-tryptophan aminotransferase, or D-alanine (2.6.1.21) aminotransferase (see FIG. 2 of WO 03/091396 A2). This reaction can also be performed using chemical reactions. Amination of the keto acid (MP) is performed by reductive amination using ammonia and sodium cyanoborohydride. FIGS. 11-13 of WO 03/091396 A2 show additional polypeptides that can be used to convert MP to monatin, as well as providing increased yields of monatin from indole-3-pyruvate or tryptophan.

As described herein, monatin can be produced in vivo using organisms genetically modified to have the ability to produce monatin, for example using the above-disclosed pathway, or by providing appropriate substrates under appropriate conditions to organisms that express the enzymes disclosed in the above-pathway. For example, monatin can be produced using an organism whose wild-type form produces tryptophan and expresses at least one of the enzymes disclosed in the pathway elucidated in WO 03/091396 and that is genetically modified to express other enzymes not present in the wild-type form but useful in the monatin production pathway.

In accordance with some embodiments of the present invention, monatin is produced in an organism (for example, a host cell) that expresses one or more transporter systems capable of secreting monatin. According to some embodiments, monatin is produced in an organism that expresses the transporter system(s) in its wild-type form. According to some embodiments, monatin is produced in an organism that is genetically modified to express one or more transporter system(s) that are heterologous to the microorganism. According to some embodiments, monatin is produced in an organism that is genetically modified to express one or more components of the transporter systems used to transport the monatin to the external medium.

Any nucleic acid encoding a polypeptide having transporter activity can be isolated from any organism and cloned into the host organism of choice. Examples of genes encoding a polypeptide having transporter activity include, without limitation, (1) AAp and Bra genes from *Rhizobium*, (2) *Arabidopsis* AUX1 gene or PIN1 polypeptide (permease, auxin secretion), (3) MadN of *Malonomonas rubra* (an acetate efflux pump), (4) *L. lactis* organic anion transporters which are similar to mammalian multidrug resistance polypeptides and yeast Pdr12, with a specificity for anions instead of cations or hydrophobic molecules, (5) multidrug resistance polypeptide Mrp2, which can secrete non-bile organic anions from the liver, and (6) aspartate/glutamate carrier (AGC) polypeptides. The AAp and Bra genes from *Rhizobium* are general amino acid transporters primarily involved in uptake of glutamate and aspartate in bacteroids. They, however, can efflux other amino acids when heterologous amino acids are present in high levels in the media. Example 25 indicates that overexpression of the *Arabidopsis* auxin transporter gene results in increased monatin production.

Additionally, expression or overexpression of homologs to auxin transporters would be expected to also yield increased monatin production. Examples of such homologs include those containing the conserved regions of the auxin transporters indicated in FIG. 1. For example, the homolog of the auxin transporter may comprise one or more amino acid sequences chosen from PXGKTXAXVGXSGSGKSTVVSLXER-FYXPXXGXXXLDG (SEQ ID NO. 1), LXLXXLRX-QIGLVXQEPXLFATXIXENXLXG (SEQ ID. NO. 2), and QVGERGXQLSGGQKQRIAIARAMLXXPX-ILLLDEATSALD (SEQ ID NO. 3), wherein X is an amino acid at the indicated position of any one of AtPGP1, BrABB97035, StAAD10836, ZmPGP1_AAR00316, SbAAR10387, OsXP_483819, OS_CAD59580, and AtPGP19 as aligned with the amino acid sequence of the homolog, as shown in FIG. 1B. Another suitable homolog of an auxin transporter may comprise one or more amino acid sequences chosen from LPXGYXTXVGERGVQLSGGQX-QRIAIARA (SEQ ID NO. 4) and LLDEATSALDAE-SEXXXQEAL (SEQ ID NO. 5), wherein X is an amino acid at the indicated position of any one of AtPGP1, BrABB97035, StAAD10836, ZmPGP1_AAR00316, SbAAR10387, OsXP_483819, OS_CAD59580, and AtPGP19 when aligned with the amino acid sequence of the homolog, as shown in FIG. 1D.

Non-limiting examples of transporters capable of secreting monatin include the AcrAB efflux system and the EmrAB efflux system. Example 1 demonstrates that the AcrAB pump is capable of secreting monatin. Example 2 demonstrates that the EmrAB pump is capable of secreting monatin. Example 3 also illustrates the capability of both the AcrAB and the EmrAB efflux systems for secreting monatin.

Based on the positive test results for AcrAB and EmrAB, it is expected that certain other transporters should be capable of secreting monatin. Generally, the AcrAB and EmrAB systems belong to a class of transporters known as multi-drug transporters. Multi-drug transporters are transporters thought to be capable of protecting cells against a wide variety of toxic molecules by active extrusion of those toxic molecules. Based on the broad overlap in the type of molecules effluxed by multi-drug transporters, and the AcrAB and the EmrAB transporter systems classification as multi-drug transporters, it is expected that other multi-drug transporters should be capable of secreting monatin. In particular, other transporters in the RND family (a subclass of the multi-drug transporters that includes AcrAB) and other transporters in the MF family (another subclass of the multi-drug transporters but which includes EmrAB) are expected to be capable of secreting monatin. Homologs of the tested transporter are also expected to secrete monatin. A BLAST search of a microbial database, ERGO, conducted using the AcrA, AcrB, EmrA, EmrB or TolC peptides as bait, resulted in the identification of 154, 213, 231, 236 and 115 homologs, respectively.

Even more specifically, AcrEF is an efflux pump highly homologous to AcrAB, and consequently the AcrEF system are expected to be capable of secreting monatin. Example 24 provides a mutant *E. coli* strain in which the gene that encodes the AcrEF transporter system has been knocked out.

Other non-limiting examples of transporters are expected to be useful for secreting monatin because of their homology to AcrAB include:

AcrA homologue MexA from *Pseudomonas aeruginosa*. Fernandez-Recio, J., et al, "A model of a transmembrane drug-efflux pump from Gram-negative bacteria," *FEBS Lett.* 578:5-9, (2004);

Multi-drug transporter systems derived from *Neisseria gonorrhoeae*, which contains genes mtrRCD whose products are related to AcrRAB. Pan, W., and Spratt, B. G., "Regulation of the permeability of the gonococcal envelope by the mtr system," *Mol. Microbiol.* 11:769-775, (1994);

The product of the gene ameB, which is homologous to members of the RND-type transporters. These include AcrB of *E. coli*, MexB, MexD and mexF of *Pseudomonas aeruginosa*, TtgB, TtgE and SrpB of *Pseudomonas putida;*

The AcrEF efflux pump implicated in multidrug resistance with a substrate range similar to that of AcrAB (also transports novobiocin). The AcrEF system plays a significant role in indole efflux. The AcrEF efflux pump is involved in solvent resistance in *E. coli* and utilizes TolC to improve solvent resistance.

The product of the yegMNOB operon which was renamed mdtABCD, where mdt stands for multidrug transporter. Baranova N., and Nikaido H., "The baeSR two-component regulatory system activates transcription of the yegMNOB (mdtABCD) transporter gene cluster in *Escherichia coli* and increases its resistance to novobiocin and deoxycholate," *J Bacteriol.* 184:4168-4176 (2002). Because AcrAB is a multidrug transporter as well and can also efflux novobiocin, the mdtABCD operon could also be a candidate for a monatin transporter.

The yhiU/V gene products. Ma, D., et al., "Genes acrA and acrB encode a stress-induced efflux of *Escherichia coli,*" *Mol. Microbiol.* 16:45-55, (1995); Ma, D., et al., "Efflux pumps and drug resistance in gram negative bacteria," *Trends Microbiol.* 2:489-493, (1994).

AcrB and AcrD belong to the resistance modulation division ("RND") superfamily and share a similar topology, which includes a pair of large periplasmic loops containing more than 300 amino acid residues each. The alterations in substrate range accompanying the exchange of loop regions is taken to imply that substrate recognition (and presumably binding) is determined largely by the two periplasmic loops. Elkins, C. A., and Nikaido, H., "Substrate specificity of the RND-type multidrug efflux pumps AcrB and AcrD of *Escherichia coli* is determined predominantly by two large periplasmic loops," *J Bacteriol.* 184:6490-6498, (2002). It is possible to make mutations in the two periplasmic loops that could have an impact on the specificity of substrates that are transported by the AcrAB transporter, to increase selectivity for monatin and decrease transport of monatin intermediates.

Non-limiting examples of transporters that also are expected to be capable of secreting monatin due to their homology with EmrAB include:

MdeA (multidrug efflux A) is a chromosomally encoded multidrug resistance efflux protein identified in *Staphylococcus aureus*. MdeA belongs to the major facilitator superfamily and is most closely related, among known efflux proteins to EmrB from *E. coli* and LmrB from *Bacillus subtilis*. Comparison of MdeA with protein sequence databases revealed significant residue identity to hypothetical and known MDR proteins. Among the top 100 hits in a standard BLASTP search (June 2002), there were only 5 experimentally proven efflux or MDR proteins:

LmrB of *B. subtilis* (O35018) 37% identity to MdeA (Kumano M., et al., "A 32 kb nucleotide sequence from the region of the lincomycin-resistance gene (22 degrees-25 degrees) of the *Bacillus subtilis* chromosome and identification of the site of the lin-2 mutation," *Microbiology* 143:2775-2782, (1997));

FarB of *Neisseria gonorrhoeae* (AAD54074) 24% identity to MdeA (Lee E. H., and Shafer W. M., "The farAB-encoded efflux pump mediates resistance of gonococci to long-chained antibacterial fatty acids," *Mol Microbiol.* 33:839-845 (1999));

TcmA of *Streptomyces glaucescens* (P39886) 24% identity to MdeA (Guilfoile P. G., and Hutchinson C. R., "The *Streptomyces glaucescens* TcmR protein represses transcription of the divergently oriented tcmR and tcmA genes by binding to an intergenic operator region," *J Bacteriol.* 174:3659-3666 (1992));

Pur8 of *Streptomyces anulatus* (P42670) 25% identity to MdeA (Tercero J. A., et al., "The pur8 gene from the pur cluster of *Streptomyces alboniger* encodes a highly hydrophobic polypeptide which confers resistance to puromycin," *Eur J Biochem.* 218:963-971 (1993)). The LmrB, TcmA, Pur8, and EmrB proteins mentioned above, confer resistance to hydrophobic compounds or antibiotics while the FarB protein confers resistance to antibacterial fatty acids;

The QacA protein of *S. aureus*, at 23% identity to MdeA, is the closest related, functionally characterized staphylococcal efflux protein. Mitchell B. A., et al., "QacA multidrug efflux pump from *Staphylococcus aureus*: comparative analysis of resistance to diamidines, biguanidines, and guanylhydrazones," *Antimicrob Agents Chemother.* 42:475-477, (1998). Multiple alignment of MdeA and these six known MDRs demonstrates conservation of many of the motifs identified in bacterial MDR proteins. Putman M., et al., "Molecular properties of bacterial multidrug transporters," *Microbiol Mol Biol Rev.* 64:672-693 (2000). MdeA was predicted to have 14 TMS, and the alignment of the MdeA and QacA sequences illustrated the coincidence of the predicted and experimentally demonstrated TMS regions, respectively. (Huang J., et al., "Novel chromosomally encoded multidrug efflux transporter MdeA in *Staphylococcus aureus,*" *Antimicrob Agents Chemother.* 48:909-917 (2004).

The methods in Example 4 can be used to verify the ability of a given transporter such as those identified above for secreting monatin. Moreover, the methods of Example 4 can be used to screen for additional transporters useful for secreting monatin. A strategy for identifying transporters capable of transporting monatin, would be to apply the screening methods of Example 4 to any organism that can transport glutamate, tryptophan, indole compounds, or that has other characteristics that may be consistent with an ability to secrete monatin. Such organisms include, but are not limited to, (1) organisms having a high number of predicted secondary transporters such as *E. coli, B. subtilis, Pantoea* and *Ricksettia*, (secondary active transporters use electrochemical gradients and typically have many (>7) transmembrane regions as well as regions located in the cytoplasm and extracellular space), (2) organisms that secrete glutamate such as Corynebacteria and Brevibacteria, (3) plants and legume containing plants such as soybean, peas, peanuts, and beans, (4) *Rhizobium* species, (5) organisms that have a high resistance to acids such as lactic acid bacteria, *Acetobacter* strains, *Kluyveromyces, Saccharomyces cerevisiae,* and *Aspergillus niger*, (6) organisms that secrete indole-pyruvic acid such as *Streptomyces griseoflavus* and *P. stewartii*, (7) organisms that are GRAS (generally recognized as safe), including, but not limited to, *Streptomyces natalensis, Streptomyces chattanoogensis, Saccharomyces cerevisiae, Saccharomyces fragilis, Candida utilis*, members of the Gigartinaceae and Soliericeae families, *Furcellaria fastigiata, Candida guilliermondii, Candida lipolytica*, and (8) organisms that are capable of synthesizing amino acids, including, but not limited to, *E. coli* and other Enterobacteriaceae (such as *Klebsiella, Panitoea*, and *Erwinia* strains), *Corynebacteriuin glutamicum, Brevibacterium* strains, *Bacillus* strains, and *Saccharomyces* strains. Organisms also can be screened for the ability to utilize glutamate rich synthetic or natural polypeptides (e.g., GLURP, the glutamate-rich polypeptide from *Plasmodium falciparum*) as sole nitrogen sources. Such organisms can have the ability to secrete glutamate, allowing them to survive in the presence of high levels of intracellular glutamate, which may be toxic or may adversely affect cellular osmotic potential. Example 15 indicates that *Pantoea*, specifically *Pantoea stewartii* is capable of monatin production and export.

Several types of transporter polypeptides can recognize monatin as a substrate such as general amino acid/polyamine exporter polypeptides, dicarboxylic acid exporter polypeptides, auxin secretory polypeptides, and multi-drug resistance polypeptides. In addition, several superfamilies contain transporter polypeptides that can perform monatin efflux. These include 2.A.1 (MFS), 2.A.6 (RND), 2.A.7 (SMR), 2.A.67 (MATE), CAAT (TC 2.A.78), and 2.A.69 (AEC). These superfamilies contain efflux transporter polypeptides that recognize substrates related to auxins (which are structurally similar to monatin derivatives), drugs, antimicrobials, and a wide variety of organic molecules. For instance, the AcrEF polypeptides in *E. coli* (and other RND members such as AcrAB and MexAB) are multiple efflux pumps that expel indoles and many other compounds with hydrophobic domains. In addition, five ABC exporter families contain polypeptides that function to secrete molecules such as polypeptides. These ABC family polypeptides can be used to transport monatin.

According to some embodiments of the present invention, monatin is produced in a microorganism that can exhibit increased transporter activity as compared to an appropriate control, e.g. as described in examples herein. "Increased transporter activity" is observed by an increase in the amount and/or rate of monatin production or secretion. Without being bound by theory, it is believed that overexpressing pump components, increases the availability of components, translating into an increased likelihood of formation and/or availability of functional transporters systems, and thus increased secretion corresponding to increased production of monatin.

According to some embodiments, increased transporter activity can be implemented by genetically modifying a microorganism to overexpress one or more types of transporter systems capable of secreting monatin, such as the AcrAB and/or the EmrAB systems.

According to some embodiments, increased activity can be implemented by genetically modifying a microorganism to overexpress one or more components of a transporter system capable of secreting monatin. For example, monatin can be produced in a microorganism that is genetically modified to overexpress a channel-forming protein component of a RND family multi-drug transporter, such as overexpressing a channel forming protein (e.g. AcrAB and/or EmrAB) or such as overexpressing individual components of the system, e.g. AcrA and AcrB.

Production or over-production, of transport systems may be accomplished by various methods. One general method that is known to those of ordinary skill in the art for increasing expression of a gene(s) involved with transport of monatin is to increase the number of gene copies. Increasing the number of gene copies may be achieved by transforming an appropriate host microorganism that is capable of monatin transport, with a vector/plasmid carrying the transporter gene(s) of interest, linked to regulatory elements on the vector. This vector with the transporter/transporter component gene could cause the host microorganism to overexpress the respective transporter(s) or components. Another method for increasing the transport system(s) within an organism is using regulatory molecules, such as inducers or repressors.

Production or over-production of the AcrAB transport system or components thereof may be accomplished by the following methods:

RamA is a 113-amino-acid regulatory protein belonging to the AraC-XylS transcriptional activator family, in the *Enterobacter aerogenes* ATCC 13048 type strain. Overexpression of RamA increases production of AcrA, a component of the AcrAB-TolC drug efflux pump. Example 17 indicates that overexpression of RamA results in an increase in monatin excretion.

RamA is also reported to be a transcriptional activator of the marRAB operon and MarA is an activator protein encoded by the marRAB operon. Chollet, R., et al., "RamA is an alternate activator of the multidrug resistance cascade in *Enterobacter aerogenes*," *Antimicrob Agents Chemother.* 48:2518-2523, (2004). The marRAB operon is reported to mediate resistance primarily by up-regulating efflux of toxic compounds via the AcrAB-TolC efflux pump.

It is reported that overexpression of some response regulators of two component signal transduction systems up regulate a number of drug transporter genes including acrD, emrKY, mdtABC, and mdtEF. Hirakawa, H., et al., "Indole induces the expression of multidrug transporter genes in *Escherichia coli*," *Molecular Microbiology*, 55:113-1126, (2005). These are all candidate transporter systems for monatin.

The baeSR two-component regulatory system activates transcription of the yegMNOB (mdtABCD) transporter gene cluster in *Escherichia coli* which is homologous to the AcrAB transport system. Baranova, N., and Nikaido, H., "The baeSR two-component regulatory system activates transcription of the yegMNOB (mdtABCD) transporter gene cluster in *Escherichia coli* and increases its resistance to novobiocin and deoxycholate," *J. Bacteriol.* 184:4168-4176, (2002).

The BaeSR two-component regulatory system also controls expression of exporter genes conferring drug resistance in *Escherichia coli*. Nagakubo, S. et al., *J. Bacteriol.* 184:4161-4167, (2002); Baranova, N., and Nikaido, H., *J. Bacteriol.* 184:4168-4176, (2002). BaeR overproduction in the absence of the *E. coli* multidrug exporter AcrB confers resistance against a number of toxic substrates including the antibiotic novobiocin. Because AcrAB can transport novobiocin and monatin, this indicates that there are additional transporter(s) activated by BaeR that can transport novobiocin and possibly monatin as well. Nishino K., et al., "Genome-wide analyses of *Escherichia coli* gene expression responsive to the BaeSR two-component regulatory system," *J.*

*Bacteriol.* 187:1763-1772, (March 2005). Example 19 indicates that overexpression of BaeR results in increased monatin excretion.

Mutations in marR result in increased expression of acrAB genes. (Ma, D., et al., "Genes acrA and acrB encode a stress-induced efflux system of *E. coli*," *Mol. Microbiol.* 16:45-55, (1995)) and in strains carrying multicopy plasmids expressing marA. Miller, P. F., and Sulavik, M. C, "Overlaps and parallels in the regulation of intrinsic multiple-antibiotic resistance in *Escherichia coli*," *Mol. Microbiol.* 21:441-448 (1996). Thus, overexpression of the marA gene or an inactive marR gene result in an increase in the AcrAB transport system.

MarA, SoxS, and SidA (members of the XylS/AraC family of transcriptional regulators) are global regulators and activate the expression of AcrAB transport system. AcrAB and three other *E. coli* genes involved with multi drug resistance (and also candidates for monatin transport) tolC, acrEF and acrD are also activated by SdiA. Baranova, N., and Nikaido, H., "The baeSR two-component regulatory system activates transcription of the yegMNOB (mdtABCD) transporter gene cluster in *Escherichia coli* and increases its resistance to novobiocin and deoxycholate," *J Bacteriol.* 184:4168-4176, (2002). Example 18 indicates that overexpression of MarA results in increased monatin excretion.

According to some embodiments, increased activity of AcrEF, a pump which is highly homologous to AcrAB and therefore is also expected to secrete monatin could be accomplished by the following modification:

The presence of insertion elements IS1 and IS 10 elements containing putative promoter sequences result in an 8- to 10-fold increase in expression of acrF expression in these insertional mutants, thus, increasing AcrEF activity and possibly monatin transport in a host that is capable of monatin production. Oliver A., et al., "Overexpression of the multidrug efflux operon acrEF by insertional activation with IS1 or IS10 elements in *Salmonella enterica* serovar *typhimurium* DT204 acrB mutants selected with fluoroquinolones," *Antimicrob Agents Chemother.* 49:289-301 (January 2005). In a different case an *E. coli* strain in which the acrEF operon had IS1 or IS2 integrated upstream produced high levels of AcrE and AcrF proteins. Kobayashi K., et al. "Suppression of hypersensitivity of *Escherichia coli* acrB mutant to organic solvents by integrational activation of the acrEF operon with the IS1 or IS2 element, *J Bacteriol.* 183:2646-2653 (2001). The examples listed above describe some ways to overexpress the AcrEF transport system which could transport monatin because it is highly homologous to the AcrAB transport system;

EnvR (formerly envCD) is a transcriptional repressor of the acrEF operon. Therefore a non-functional EnvR regulator might increase acrEF transcription. Increasing acrEF transcription results in overexpressing the AcrEF transport system which could transport monatin because it is highly homologous to the AcrAB transport system.

According to some embodiments, increased transporter activity can be implemented by: overexpressing an outer membrane factor component of a RND family multi-drug transporter, such as TolC; by overexpressing other transport system components which cooperate with TolC to form functional transporters in organisms whose wild-type form expresses TolC; or combinations thereof. The transport system components that cooperate with TolcC may be non-genetically engineered. Any method known in the art for screening microorganisms for the existence of functional TolC could be used. See, for example, Werner, J., et al., "Assembly of TolC, a structurally unique and multifunctional outer membrane protein of *Escherichia coli* K-12," *J. Bact.* 185:6540-6547 (2003). In addition, Example 5 describes methods that can be used to clone and overexpress TolC, however any method known in the art can be used. Example 6 demonstrates that overexpression of TolC increases secretion of monatin. Because TolC functions in conjunction with several different efflux pumps, overexpression of TolC could lead to even greater increased transporter activity than would occur by overexpressing other components of transporters which are more discriminating.

TolC-dependent machineries present ubiquitous exit routes for virulence proteins and antibacterial drugs. Koronakis, V., "TolC—the bacterial exit duct for proteins and drugs," *FEBS Lett.* 555:66-71, (2003). Based on the results from Example 6, any host strain capable of producing monatin and that L has efflux pumps/transport systems (for example AcrAB and EmrAB) that work in conjunction with TolC might show an increase in monatin transport due to an increase in TolC channel presence. Non-limiting examples of such other transporter systems include:

A four-component type I secretion system (TISS) encoded by rtxB, rtxD, rtxE, and tolC in *Vibrio cholerae*. Boardman, B. K., and Satchell, K. J., "*Vibrio cholerae* strains with mutations in an atypical type I secretion system accumulate RTX toxin intracellularly," *J Bacteriol.* 186: 8137-8143, (2004).

EmrKY and YhiUV are three component efflux pumps requiring TolC for their activity. Fralick, J. A., "Evidence that TolC is required for functioning of the Mar/AcrAB efflux pump of *E. coli.*," *J. Bact.* 178:5803-5805, (1996); Nishino, K. and Yamaguchi, A., "EvgA of the two-component signal transduction system modulates production of the YhiUV multidrug transport in *Escherichia coli*," *J. Bact.* 184:2319-2323, (2002)

Similarly, TolC homologs might also cooperate with the AcrAB system to provide improvements in the production rate or amount of monatin. Overall comparisons between the TolC family members demonstrate that the characteristic structural elements are conserved. This strongly indicates that all homologs fold similarly and have comparable properties. Conservation of the key structural amino acids among TolC homologs establishes a common mechanism for the export and efflux systems that involve the TolC family of proteins. It is reported that one can conclude that the core functions of the channel-tunnel are common throughout Gram-negative bacteria. Andersen, C., et al., "Chunnel vision. Export and efflux through bacterial channel-tunnels," *EMBO Rep.* 1:313-8, (2000). Non-limiting examples of homologs that may also have utility in the secretion of monatin include:

Nearly a hundred homologs identified in over 30 bacterial species consistent with reports that TolC family members are widespread among Gram-negative bacteria. Dinh, T., et al., "A family of extracytoplasmic proteins that allow transport of large molecules across the outer membranes of gram-negative bacteria," *J Bacteriol.* 176:3825-3831, (1994); Andersen, C., et al., "Chunnel vision. Export and efflux through bacterial channel-tunnels," *EMBO Rep.* 1:313-318, (2000).

The *E. coli* genome encodes three tolC homologs and approximately 30 inner membrane translocases of the ABC, MFS (EmrAB) and RND (AcrAB) families.

*Pseudomonas aeruginosa* has four major efflux (Mex) systems containing and RNA proton antiporter and one of three TolC homologs, OprM, OprJ and Opr N. These observations are consistent with the fact that bacteria are reported to have several TolC homologs acting in parallel with a number of efflux pumps with broad and sometimes overlapping specificities. Koronakis V., et al., "Structure and function of TolC: the bacterial exit duct for proteins and drugs," *Annu Rev Biochem.* 73:467-489, (2004).

Some TolC homologs involved in drug efflux (and that could be potentially involved in monatin efflux) are: FusA, OprA, OpcM, NodT3, NodT2, NodT1, SmeC, SrpC, TtgC, MtrE. Andersen C., et al., "Chunnel vision. Export and efflux through bacterial channel-tunnels," *EMBO Rep.* 1:313-318 (2000).

Activity of TolC may also be increased to achieve enhanced secretion of monatin. Non-limiting examples of potential methods of increasing TolC activity include:

TolC is upregulated by MarA. The multiple antibiotic resistance (mar) locus of *Escherichia coli* and *Salmonella* is perhaps the best described system involved in this type of resistance which is induced by MarA, the activator protein encoded by the marRAB locus. The mar locus is reported to mediate resistance primarily by up-regulating efflux of some antibiotics, disinfectants and organic solvents via the AcrAB-TolC efflux pump. Randall, L. P., and Woodward, M. J., "The multiple antibiotic resistance (mar) locus and its significance," *Res Vet Sci.* 72:87-93, (2002).

The TolC level is regulated positively by Rob, or SoxS, in addition to MarA. A possible mar-rob-sox box sequence is present upstream of the tolC gene. These findings suggest that tolC is a member of the mar-sox regulon responsive to stress conditions. *Escherichia coli* mutants with improved organic solvent tolerance levels showed high levels of outer membrane protein TolC and inner membrane protein AcrA. Aono, R., et al., "Involvement of outer membrane protein TolC, a possible member of the mar-sox regulon, in maintenance and improvement of organic solvent tolerance of *Escherichia coli* K-12," *J Bacteriol.* 180:938-944 (1998).

RamA is a regulatory protein that enhances marA transcription which in turn causes tolC overexpression. Chollet, R., et al., "RamA is an alternate activator of the multidrug resistance cascade in *Enterobacter aerogenes," Antimicrob Agents Chemother.* 48:2518-2523, (2004). Example 17 indicates that overexpression of RamA results in increased monatin excretion.

According to some embodiments, increased transporter activity is implemented by exposing a microorganism expressing a pump capable of secreting monatin to an inducing compound (i.e. a compound that triggers expression of a transporter system or component of a transporter system). For example, a microorganism expressing the AcrAB system can be exposed to sodium decanoate or salicylate. Example 1 demonstrates that sodium decanoate can be used to induce the AcrAB pump to secrete monatin. As another example, a microorganism expressing the EmrAB system may be exposed to carbonyl 2-chlorophenylhydrazone ("CCCP") in its growth medium. Example 2 demonstrates that CCCP can induce increased monatin transport. Example 14 demonstrates that salicylate can induce increased monatin transport.

Other potential inducers of AcrAB include, but are not limited to:

Phytoalexin is an inducer of the AcrAB transport system. Burse, A., et al., "The phytoalexin-inducible multidrug efflux pump AcrAB contributes to virulence in the fire blight pathogen, *Erwinia amylovora," Mol Plant Microbe Interact.* 17:43-54, (2004).

Limitation of nutrients such as glucose, iron or nitrogen act as inducing conditions for overexpression of AcrAB transport system. It is reported that acrAB is regulated as a function of the growth rate of *E. coli* during growth in batch and chemostat culture. In chemostat culture, expression of acrAB is inversely related to growth rate irrespective of the limiting nutrient. The level of expression of acrAB is greater under glucose limitation compared with either iron or nitrogen limitation. Slow growth rate regulation of acrAB transcription does not require the presence of the stationary-phase sigma factor. A putative gearbox consensus sequence was identified at the −10 region of the acrAB promoter. Rand, J. D., et al., "Increased expression of the multidrug efflux genes acrAB occurs during slow growth/stationary phase of *Escherichia coli," FEMS Microbiol Lett.* 207:91-95 (2002).

RobA is a member of the XylS/AraC subfamily of DNA binding proteins and activates the AcrAB transport system. When robA is overexpressed, it induces multiple antibiotic resistance in *Escherichia coli*. It is reported that the multiple antibiotic resistance induced by the overexpression of RobA largely depends on the activation of the AcrAB efflux, as well as the activation of micF. Tanaka, T., et al., "RobA-induced multiple antibiotic resistance largely depends on the activation of the AcrAB efflux," *Microbiol Immunol.* 41:697-702, (1997). Example 16 indicates that overexpression of RobA results in increased monatin excretion.

cysH, icdA (isocitrate dehydrogenase), metE, or purB (adenylosuccinate lyase) mutations cause an activation of the AcrAB transport system. While screening mutants of *E. coli* and other bacteria on nutrient plates with low levels of nalidixic acid, it is reported that resistance results from mutations at different genetic loci. About 10% of the nalidixic acid-resistant ($Nal^r$) mutants in a transposition-induced library exhibit a growth factor requirement as the result of cysH, icdA (isocitrate dehydrogenase), metE, orpurB (adenylosuccinate lyase) mutation. Resistance in all of these mutants requires a functional AcrAB-TolC efflux pump. Transcription of acrAB increases in each type of $Nal^r$) mutant. In the icdA and purB mutants, each of the known signaling pathways could be used to activate the AcrAB-TolC pump. The metabolites that accumulate upstream of the blocks caused by the mutations could increase the levels of the AcrAB-TolC pump, thereby removing nalidixic acid from the organism. Helling, et al., "Toxic waste disposal in *Escherichia coli," J Bacteriol.* 184:3699-3703, (2002). Each of the mutations above could be generated in a host strain capable of monatin production to increase the monatin transported via the AcrAB transporter. Example 23 illustrates deletion of the cysH gene results in increased monatin production.

Salicylate induces the AcrAB-TolC efflux pump by at least two mechanisms, one of which involves Mar. Cohen, S. P. et al., "Salicylate induction of the antibiotic resistance in *Escherichia coli*: activation of the mar operon and mar-independent pathway," *J Bacteriol.* 175:7856-7862, (1993).

Several global stress signals such as 4% ethanol, fatty acids like decanoate, or media of high osmolarity (0.4M NaCl) enhance the expression of AcrAB transport system. Thus one could use environmental conditions to indirectly affect expression of the AcrAB transport system. Ma D, et al. "Efflux pumps and drug resistance in gram-negative bacteria," *Trends Microbiol.* 2:489-493 (1994).

One general method that is known to those skilled in the art for increasing the expression of a gene(s) involved with transport of monatin is to increase the number of gene copies. This could be achieved by transformation of an appropriate host microorganism that is capable of monatin transport, with a vector/plasmid carrying the transporter gene(s) of interest, linked to regulatory elements on the vector. This vector with the transporter/transporter component gene could cause the host microorganism to overexpress the respective transporter(s) or components.

Another embodiment in accordance with the invention comprises producing monatin in a glutamate auxotroph, which is an organism that has lost the ability to synthesize glutamate as the result of mutational changes. Without being bound by theory, the inventors hypothesized that transporters useful for secreting glutamate may also secrete monatin. A glutamate auxotroph would likely still have the glutamate transporters, but because there would be more carbon available in the cell to make monatin (because it is not being consumed to make glutamate) and/or because there would not be competition for the glutamate transporters from glutamate, glutamate auxotrophs may be suitable for producing and secreting monatin.

One method for preparing a glutamate auxotroph is provided in Eikmanns, B. J., et al., "Cloning, sequence analysis, and inactivation of the *Corynebacterium glutamicum* icd gene encoding isocitrate dehydrogenase and biochemical characterization of the enzyme," *J Bacteriol.*, 177:774-782, (1995). However, any method known in the art can be used.

Example 8 provides an example of a host strain, *Corynebacterium glutamacium* ATCC strain 13032, which has been mutated to become a glutamate auxotroph, and demonstrates increased excretion of monatin in this strain. Example 9 provides an example of a strain, *E. coli* glutamate auxotroph (icdA deficient), which is expected to increase monatin excretion potential.

It is contemplated that a glutamate auxotroph adapted to produce monatin could be combined with one or more other methods to provide secretion of monatin to further increase monatin transport. Glutamate auxotrophs (with an inactivated icd gene) transformed with the genes required for monatin production, combined with other treatments and cell modifications predicted or shown to increase monatin production and/or transport could show further increases in monatin production/transport. For example, the glutamate auxotroph may be exposed to inducers for the AcrAB and/or the EmrAB transporters; or the glutamate auxotroph may be engineered to overexpress transporters or transporter components such as TolC; or the fermentation medium components could be modified to include detergents such as Tween® 20/40/60 and/or ampicillin (10 µg/mL); or combinations thereof.

Another embodiment in accordance with the invention for secreting monatin involves genetically modifying a microorganism capable of translocating glutamate or oxoglutarate in exchange for malate to have the ability to produce monatin. A related embodiment involves producing monatin in such an organism wherein that organism has also been genetically modified to be a glutamate auxotroph. Example 10 illustrates use of a microorganism capable of translocating glutamate for malate in the production of monatin.

Without being bound by theory, monatin has a glutamate backbone or can be considered to be a 4-substituted glutamate derivative. Monatin may therefore be transported out of a bacterial cell by transporters that translocate glutamate in exchange for substrates like malate. The glutamate/malate transporter in *Arabidopsis* plastids, encoded by the DiT2 gene, translocates glutamate and malate in antiport manner. Renne, P., et al., "The *Arabidopsis* mutant dct is deficient in the plastidic glutamate/malate translocator DiT2," *Plant J.* 35:316-331, (2003); Taniguchi, M., et al., "Identifying and Characterizing Plastidic 2-Oxoglutarate/Malate and Dicarboxylate Transporters in *Arabidopsis thaliana*," *Plant and Cell Physiology* 43:706-717, (2002). The glutamate/malate transporter family is homologous with the 2-oxoglutarate/malate transporter in spinach chloroplasts which is related to the CitT transporter in *E. coli* that is believed to be an antiporter for citrate and succinate. Pos, K. M., et al., "The *Escherichia coli* Citrate Carrier CitT: a Member of a Novel Eubacterial Transporter Family Related to the 2-Oxoglutarate/Malate Translocator from Spinach Chloroplasts," *Journal of Bacteriology* 180:4160-4165, (1998). There is a possibility that this transporter could permit a host to take up malate while excreting glutamate or monatin into the supernatant. Another possibility for malate functioning to increase monatin transport could be due to the role that malate might play as an alternative carbon source affecting growth rate and carbon distribution to metabolic pathways differently than with glucose. Malate can also be converted to pyruvate internally by malic enzymes encoded by 2 genes (Fischer, E., and Sauer, U., "Metabolic flux profiling of *Escherichia coli* mutants in central carbon metabolism using GC-MS," *Eur. J. Biochem.* 270:880-891, (2003)), and, because pyruvate is one of the precursors to monatin, a greater availability of pyruvate may result in increased monatin production and consequently increased monatin secretion (see other references to induction of transporters in microorganisms to get rid of accumulated metabolites). Growth of *E. coli* on malate as the primary carbon source resulted in increases in monatin excretion into the medium, such as the culture medium.

In another embodiment according to the invention, the amount of monatin produced may be affected by temperature and/or treatment with one or more additional compounds, such as those that perturb the cell membrane (ampicillin and Tween®). Additionally, the efflux of monatin from the microorganism may be increased by selecting an optimal temperature and/or by treating the microorganism with one or more additional compounds, such as those that perturb the cell membrane (ampicillin and Tween®). Examples of suitable compounds for these effects include ethambutol, ampicillin, Tween® and/or biotin. For example, Example 20 indicates that an increase in temperature, as well as an increase in the amount of sodium pyruvate provided to *Corneybacterium glutamicum* cells resulted in increased monatin efflux. Additionally, Example 21 indicates that treatment with ampicillin alone, or in combination with biotin, resulted in increased efflux of monatin. Further, Example 22 demonstrates that treatment with ethambutol, alone or in combination with Tween® and ampicillin, had a positive impact on monatin efflux in *Corynebacterium*.

Another embodiment according to the invention includes producing monatin in a microorganism which is selected because it does not express certain transporters, or is engineered so that it does not express certain transporters. Example 11 demonstrates that the absence of certain transporters—the four Putative Efflux Transporters identified as YhcP (AaeB), YccS, YjcQ and YhfK, lead to increased production of monatin. Without being bound by theory, it is believed that certain pumps may also transport intermediates formed along the pathway for production of monatin, and the excretion of these intermediates would result in slower or decreased production of monatin. Consequently, absence of these pumps could lead to faster or increased production of monatin.

Another embodiment according to the invention includes producing monatin in a microorganism which is engineered to have a modified cell envelope, for example a microorganism that is engineered to be deficient or depressed in mycoloic acids. Without being bound by theory, it is believed that such an approach may lead to increased monatin efflux due to a weakened outer permeability barrier. More specifically, mycolic acids, the major lipid constituents of the cell envelope of the *Corynebacterineae*, are found covalently linked to the cell-wall arabinogalactan or esterifying trehalose and glycerol. Mycolic-acid-containing components are believed to play a crucial role in the structure and function of this cell envelope, primarily because they are organized with other lipids to form an outer permeability barrier with an extremely low fluidity that confers an exceptionally low permeability upon these bacteria; this may explain the intrinsic resistance of mycobacteria to many antibiotics. Kacem, R., et al., "Importance of mycoloyltransferases on the physiology of *Corynebacterium glutamicum*," *Microbiology* 150:73-84, (2004).

The monatin produced by the microorganism may be collected from the medium after it has been secreted. Additionally, the monatin produced by the microorganism may be isolated from the medium after it has been secreted. Separation methods are known to those in the art for the isolation of organic acids from fermentation media, which typically rely on chromatography methods and/or extractions. Monatin is similar to glutamic acid. Many methods are known in the art for purification of glutamic acid from fermentation broths. A description of the isolation of monatin from a complex biological medium has been previously described (see WO03091396 Example 6). One example of a method that may be used to collect and/or isolate the monatin from the medium is to use strong cation exchange chromatography at a low pH, such as the AG50WX-8 resin (H form) from Bio-Rad. In this method, the amino group of the compound, monatin, is charged and is bound to the resin. Any contaminating organic acids are not bound to the resin and flow through the resin at low pH. The amino acids may then be separated from each other (such as separating tryptophan from alanine from monatin) using anion exchange chromatography, such as a DEAE resin, at a neutral pH.

The following Examples are intended to assist one of ordinary skill in making, using, and/or understanding the present invention. These Examples are not intended in any way to limit the scope of the disclosure. For example, the monatin used in most Examples is predominately S,S monatin. However, the specificity of the transporters in the Examples is not expected to be based on chirality of the transported molecules. Therefore, the systems demonstrated to transport S,S monatin should be effective in transporting all four stereoisomers of monatin. And, in fact, Example 26 illustrates transport of R,R monatin.

All patents and publications cited herein are fully incorporated by reference herein in their entirety.

EXAMPLES

Example 1

Induction of the AcrAB Efflux Pump Increased Monatin Transport

The AcrAB TolC system of *Escherichia coli* is a multidrug efflux pump composed of a cytoplasmic membrane component/proton antiporter AcrB and a periplasmic accessory protein AcrA. Accession numbers for AcrA and AcrB are AcrA (protein, NP_414996, DNA, NC_000913) and AcrB (protein, NP_414995, DNA, NC_000913). The cell uses this system to pump out a wide variety of antimicrobial compounds, including antibiotics, detergents, dyes, and organic solvents directly into the medium through TolC, an outer membrane channel. The AcrAB genes are inducible by addition of sodium decanoate. Zgurskaya, H. I., and Nikaido, H., *Proc Natl Acad Sci USA* 96:7190-7195, (1999).

A preliminary study with *E. coli* BL21 DE3 was done that determined that 2.5 mM sodium decanoate addition to the medium resulted in tolerance to 80-160 µg/ml novobiocin. This was taken as evidence that acrAB genes are induced with sodium decanoate addition and conferred resistance to novobiocin. Rosenberg, E. Y., et al., *Molecular Microbiol.* 48:1609-1619, (2003).

The microbial strain used for the experiment was *E. coli* BL21 (DE3)::aspC/proA/pET32 (WO 03091396). The symbol : :, as is known in the art, stands for "transformed." Example 12 provides a non-limiting exemplary method for transforming a microorganism. For an inoculum, the *E. coli* strains were grown overnight at 37° C. and 250 rpm in Luria-Bertani ("LB") medium with 100 µg/mL ampicillin. For the experimental treatments, Trp-1+ glucose medium, a minimal medium that has been used for increased production of tryptophan in *E. coli* cells (Zeman et al. *Folia Microbiol.* 35:200-204, (1990)), was prepared as follows. To 800 mL nanopure water the following reagents were added: 2 g $(NH_4)_2SO_4$ and 13.6 g $KH_2PO_4$. The pH was adjusted to 7.0, the volume was increased to 948 mL, and the medium was autoclaved. Following sterilization, 0.2 g $MgSO_4.7H_2O$, 0.01 g $CaCl_2.2H_2O$, and 0.5 mg $FeSO_4.7H_2O$ were added to the medium in a 1.8 mL volume followed by addition of 0.2 mL of Neidhardt's micronutrient solution. Neidhardt, F. C., et al., "Culture medium for Enterobacteria," *J. Bacteriol.* 119:736-746 (1974). Neidhardt's medium includes (per liter): 0.18 g $(NH_4)_6(MO_7)_{24}.4H_2O$, 1.24 g $H_3BO_3$, 0.36 g $CoCl_2.6H_2O$, 0.12 g $CuSO_4$ (anhydrous), 0.8 g $MnCl_2.4H_2O$, and 0.14 g $ZnSO_4.7H_2O$. A 50% glucose solution was prepared separately and sterile-filtered. Forty mL of glucose solution and 10 mL of 1 M 3-Morpholinopropanesulfonic acid ("MOPS") buffer were added to the base medium (950 mL) for a 1 L final volume. 2-5 v/v % of *E. coli* inoculum was added to 100 mL medium volume in 500 mL baffled shake flasks with 100 µg/mL ampicillin. Flasks were incubated at 37° C. with agitation at 250 rpm up to induction. At 0.6 $OD_{600\ nm}$, induction of the monatin operon genes (aspC and proA) on the pET32 vector was initiated using 0.5 mM IPTG. 0.5 mM pyridoxine hydrochloride, and 0.2 mL of Balch's vitamins (Balch, W. E., et al., "Methanogens: reevaluation of a unique biological group," *Microbiol. Rev.* 43:260-296, (1979)) were added at induction and the incubation temperature was lowered to 30° C. following induction. Additions of 1 g L-tryptophan, 5 g/L sodium pyruvate, 0.04 mM pyridoxal-5'-phosphate ("PLP") and 0.2% Tween® 20 (polyoxyethylene 20-sorbitan monolaurate) were made 3.5 hours following induction. Some treatments included 2.5 mM sodium decanoate addition at 3.5 hours following induction. Samples for monatin analysis and dry cell weight determination were taken at 24 and 30 hours. Monatin analysis was done as described in Example 13.

TABLE 1.1

Monatin per dry cell weight effluxed by *E. coli*

| Trtmt. no. | Treatment | Monatin/dcw. at run hour: 24 | 30 |
|---|---|---|---|
| 1 | 2.5 mM Na decanoate | 17.0 | 17.4 |
| 2 | no decanoate | 1.3 | 1.3 |
| 3 | 2.5 mM Na decanoate | 14.7 | 14.3 |
| 4 | no decanoate | 1.7 | 1.6 |
| 5 | 2.5 mM Na decanoate | 12.0 | 13.8 |
| 6 | no decanoate | 1.8 | 1.8 |

Monatin/dcw = mg monatin/g dcw

TABLE 1.2

Average monatin per dry cell weight effluxed by *E. coli*

| Treatment | Monatin/dcw. at run hour: 24 | 30 |
|---|---|---|
| 2.5 mM Na decanoate | 14.6 | 15.2 |
| no decanoate | 1.58 | 1.57 |

Monatin/dcw = mg monatin/g dcw
n = 3

Greater than nine fold increase in monatin secreted/dry cell weight ("dcw") (14.6 to 1.58 or 15.2 to 1.57 mg monatin/g dcw) was observed by treating *E. coli* BL21 (DE3) : : aspC/proA/pET32 with 2.5 mM sodium decanoate which induces the AcrAB efflux system. Monatin excretion can therefore be increased by turning on or up-regulating expression of the AcrAB efflux system. Transporter system homologs of the AcrAB transport system, when exposed to appropriate inducers, might also increase monatin transport.

Example 2

Induction of the EmrAB Efflux Pump Increased Monatin Transport

*E. coli* and *C. glutamicum*

A multidrug efflux pump is encoded by the emrB gene, the EmrB efflux pump (GenBank Accession Number NP_417171, DNA NC_000913). Lomovskaya, O., and Lewis, K, "emr, an *E. coli* locus for multidrug resistance," *Proc. Natl. Acad. Sci. USA* 89:8938-8942, (1992). The emrB gene can be upregulated by addition of the inducer carbonyl cyanide 3-chlorophenylhydrazone ("CCCP") to the growth/fermentation medium. Lomovskaya O., et al., "Differential regulation of the mcb and einr operons of *E. coli*: Role of mcb in multidrug resistance," *Antimicrob Agents Chemother.* 40:1050-1052, (1996). This example shows increased monatin efflux as a result of CCCP treatment.

The strains used for the experiment included *E. coli* MG1655 : : aspC/proA/pProNde and *E. coli* BL21 (DE3) : : aspC/proA/pET30. For inoculum, the *E. coli* strains were grown overnight at 37° C. and 250 rpm in Luria-Bertani ("LB") medium with 50 µg/mL kanamycin.

For the experimental treatments, Trp-1+ glucose medium, a minimal medium that has been used for increased production of tryptophan in *E. coli* cells (Zeman, et al. *Folia Microbiol.* 35:200-204, (1990)), was prepared as follows. To 800 mL nanopure water the following reagents were added: 2 g $(NH_4)_2SO_4$ and 13.6 g $KH_2PO_4$. The pH was adjusted to 7.0, the volume was increased to 948 mL, and the medium was autoclaved. Following sterilization, 0.2 g $MgSO_4.7H_2O$, 0.01 g $CaCl_2.2H_2O$, and 0.5 mg $FeSO_4.7H_2O$ were added to the medium in a 1.8 mL volume followed by addition of 0.2 mL of Neidhardt's micronutrient solution. Neidhardt, F. C., et al., "Culture medium for Enterobacteria," *J. Bacteriol.* 119:736-746 (1974). Neidhardt's medium includes (per liter): 0.18 g $(NH_4)_6(MO_7)_{24}.4H_2O$, 1.24 g $H_3BO_3$, 0.36 g $CoCl_2.6H_2O$, 0.12 g $CuSO_4$ (anhydrous), 0.8 g $MnCl_2.4H_2O$, and 0.14 g $ZnSO_4.7H_2O$. A 50% glucose solution was prepared separately and sterile-filtered. Forty mL of glucose solution and 10 mL of 1 M 3-Morpholinopropanesulfonic acid ("MOPS") buffer were added to the base medium (950 mL) for a 1 L final volume.

For treatments, 2-5 v/v % of inoculum was added to 100 mL medium volume in 500 mL baffled shake flasks with 50 µg/mL kanamycin. Conditions for the treatments included 250 rpm agitation throughout and 37° C. up to induction, then, 30° C. following induction. At 0.5-0.6 $OD_{600\,nm}$, induction of the plasmid genes was initiated. At induction, 0.5 mM IPTG, 0.5% arabinose, 0.5 mM pyridoxine hydrochloride, and 0.2 mL of Balch's vitamins were added. Additions of 1 g L-tryptophan, 5 g/L sodium pyruvate, 0.04 mM pyridoxal-5'-phosphate ("PLP"), 10 µg/ml ampicillin and 0.2% Tween® 20 (polyoxyethylene 20-sorbitan monolaurate) were made 3.5 hours following induction. Some treatments included 10 µM carbonyl cyanide 3-chlorophenylhydrazone ("CCCP") addition to initial medium. One treatment included an additional 10 µM CCCP dose at 3.5 hours following induction. CCCP induces the EmrB efflux system. Samples for monatin analysis and dry cell weight determination were taken at 10, 15.5, 25.6 and 31 hours. Monatin analysis was preformed as described in Example 13.

TABLE 2.1

Monatin per dry cell weight effluxed by *E. coli* MG1655 and *E. coli* BL21 (DE3)

| Strain | Treatment | *Monatin/dry cell weight at run hour: 10 | 15.5 | 25.6 | 31 |
|---|---|---|---|---|---|
| *E. coli* MG1655::aspCproA pProNde | control (no CCCP**) |  | 0.5 | 3.3 | 6.2 |
| *E. coli* MG1655::aspCproA pProNde | 10 µM CCCP |  | 0.7 | 6.7 | 12.4 |
| *E. coli* BL21 (DE3)::aspCproA pET30 | control (no CCCP) | 3.9 | 9.6 | 19.1 | 18.1 |
| *E. coli* BL21 (DE3)::aspCproA pET30 | 10 µM CCCP | 6.4 | 22.5 | 34.3 | 33.0 |
| *E. coli* BL21 (DE3)::aspCproA pET30 | 10 µM CCCP + 10 µM CCCP | 16.2 | 38.0 | 52.1 | 64.2 |

*Monatin/dcw is in mg/g
**CCCP is carbonyl cyanide 3-chlorophenylhydrazone

With the *E. coli* BL21 (DE3) :: aspC proA pET30 strain, an increase of greater than 1.8 or 3.5-fold monatin/dcw (33.0/18.1 or 64.2/18.1) was obtained at 31 hours by treating shake flasks with one (10 µM) or two additions (20 µM) of CCCP. With the *E. coli* MG1655 :: aspCproA pProNde strain, a 2-fold increase in monatin/dew was observed at 31 hours. Monatin efflux can therefore be increased at least two fold by turning on or upregulating expression of the EmrAB efflux pump. Monatin efflux can be further increased by combination with other treatments shown to increase monatin transport.

Example 3

Knockout of *E. coli* emrB and acrAB Genes to Test Impact on Monatin Transport by the EmrAB and AcrAB Transporters Respectively Primers were designed to create the desired knockout product by PCR from template pKD3 as described. Datsenko K. A., and Wanner, B. L., "One-step inactivation of chromosomal genes in *Escherichia coli* K-12 using PCR products," *Proceed. Natl. Acad. Sci. USA*, 97:6640-6645, (2000). emrB knockout primer sequences:

*E. coli* EmrBF
(SEQ ID NO. 6)
(5'AAGCTAACGCTGGCTAATCCAGAGGTGCGTGTGATGGTGTAGGCTGG

AGCTGCTTC-3');

*E. coli* EmrBR
(SEQ ID NO. 7)
(5'-AAAGCCAGTTCAAATGAACTGGCTTAGTTGTACTTACATATGAATA

TCCTCCTTA-3');

acrAB knockout primer sequences:

*E. coli* AcrAF
(SEQ ID NO. 8)
(5'-GACCAATTTGAAATCGGACACTCGAGGTTTACATATGAGTGTAGGC

TGGAGCTGCTTC-3');

*E. coli* AcrBR
(SEQ ID NO. 9)
(5'-CTTACGCGGCCTTAGTGATTACACGTTGTATCAATGATGCATATGA

ATATCCTCCTTA-3').

The PCR products for deletion of emrB and acrAB genes were amplified using the following PCR protocol. In a 100 µL reaction, 100 ng of template (pKD3) (Datsenko, K. A., and Wanner, B. L., "One-step inactivation of chromosomal genes in *Escherichia coli* K-12 using PCR products," *Proceed. Natl. Acad. Sci. USA* 97:6640-6645, (2000)), 0.4 µM of each primer, 0.4 mM each dNTP, 5.6 U Expand High Fidelity™ Polymerase (Roche, Indianapolis, Ind.), 1.0 U Pfu polymerase (Stratagene, La Jolla, Calif.) and 1× Expand™ buffer with Mg were used. The thermocycler program used included a hot start at 94° C. for 3 minutes, 8 repetitions of the following steps: 94° C. for 30 seconds, 50° C. for 30 seconds, and 72° C. for 1 minute 30 seconds, followed by 22 repetitions of the following steps: 94° C. for 30 seconds, 58° C. for 30 seconds, and 72° C. for 1 minute 30 seconds. After the 22 repetitions the sample was maintained at 72° C. for 7 minutes and then stored at 4° C. This PCR protocol produced a product of 1.1-Kb for both emrB and acrAB knockout primer pairs.

The PCR products were gel purified from 0.8% TAE-agarose gels using the Qiagen gel extraction kit (Valencia, Calif.). The PCR products were quantified using a SmartSpec 3000™ spectrophotometer.

The gel-purified PCR products were used to transform *E. coli* strain BW25113/pKD46. Datsenko K. A., and Wanner, B. L., "One-step inactivation of chromosomal genes in *Escherichia coli* K-12 using PCR products," *Proceed. Natl. Acad. Sci. USA*, 97:6640-6645, (2000). 1 µL of each product was added to 40 µL of cells, which were transformed by electroporation using the BioRad Gene Pulsar II under the following conditions: 2.5 kV, 25 µF, 200 ohm in a 0.2 cm cuvette. The cells were allowed to recover in 1 mL of SOC for 4 hours at 37° C. with shaking at 225 rpm, and then placed at room temperature (no shaking) overnight. Cells were plated on LB plates containing chloramphenicol (10 µg/mL) and incubated at 37° C. overnight. Choloramphenicol-resistant transformants were single-colony purified on non-selective LB medium (grown at 42° C.), and single colonies were tested for retention of chloramphenicol resistance and loss of ampicillin resistance (indicating curing of pKD46). Confirmation of the correct deletion of the enirB or acrAB genes was carried out by colony PCR using primers upstream and downstream of the deletion locus:

EmrBupstreamF:
(SEQ ID NO. 10)
5' - GTATCGGTCAGCCGGTCACT - 3'

EmrBdownstreamR:
(SEQ ID NO. 11)
5' - TGTTCGATCTGCGCTTCTGC - 3'

AcrAupstreamF:
(SEQ ID NO. 12)
5' - TAATCGACGCCGTTCTTCTG - 3'

AcrBdownstreamR:
(SEQ ID NO. 13)
5' - GCGGTTGAACTAACGGACAC - 3'

For deletion of emrB, a truncated 1.9 kb PCR product was observed as compared to the wild-type 2.4 kb product using primers EmrBupstream F and EmrBdownstreamR. For deletion of acrAB, a truncated 1.9 Kb product was observed as compared to the wild-type 5.679 kb product using primers AcrAupstreamF and AcrBdownstreamnR.

Lysate production: P1 phage lysates were made for the BW25113ΔEmrB and BW25113ΔAcrAB strains, to allow transfer of the knockouts into the *E. coli* BL21DE3 or *E. coli* MG1655 production hosts respectively. Donor strains were grown overnight in LB medium containing 10 µg/mL chloramphenicol. The cultures were used to inoculate fresh LB medium containing 5 mM $CaCl_2$ using a 1:10 dilution and were incubated for 70 minutes at 37° C. One mL of each culture was incubated with 3 µL or 5 µL of a phage stock (ATCC 25404-B1) at 37° C. for 20 minutes. The phage/culture was then mixed with 4 mL of soft agar containing 5 mM $CaCl_2$ and overlaid on LB medium. Control experiments were set up using no phage. Plates were incubated at 37° C., right-side up for 5 hours, after which confluent lysis was observed for all plates containing phage; control plates had cell lawns as expected. Plates were incubated overnight at 37° C., after which phage-resistant colonies were observed on experimental plates as expected. The soft agar from each plate was scraped into a centrifuge tube using a sterile disposable loop. Two mL of LB was used to rinse the plate, and the rinse was combined with the soft agar in the centrifuge tube. Five drops of chloroform were added to the tubes, which were gently mixed and incubated at room temperature for 20 minutes. The mixtures were centrifuged at 10,000 g for 10 minutes and the supernatants filtered with a 0.2 μm syringe filter to obtain phage lysates. All phage lysates were stored at 4° C.

Transduction into production hosts: The emrB knockout was transferred to strain E. coli BL21DE3 and the acrAB knockout was transferred to strain E. coli MG1655 by P1 transduction to generate strains BL21DE3ΔemrB and MG1655ΔacrAB respectively. BL21DE3ΔemrB and MG1655ΔacrAB were grown overnight in LB medium containing 10 μg/mL chloramphenicol. Cultures were used to inoculate 5 mL of fresh LB medium supplemented with 5 mM CaCl$_2$ using a 1:10 dilution. The subcultures were incubated for 60 minutes at 37° C. The cultures was centrifuged, resuspended in 500 μL of MC buffer (0.1 M MgSO$_4$, 5 mM CaCl$_2$), and incubated at room temperature for 20 minutes. Various dilutions of the donor lysate (1:100 to 1× in MC buffer) were added in equal volume to 100 μL of culture. The mixtures were incubated for 20 minutes at 37° C., after which 200 μL of citrate buffer (0.1 M citric acid and 220 mM NaOH adjusted to pH 5.5) and one mL of LB were added to each tube. The cultures were incubated at 37° C. for one hour with agitation at 200 rpm, followed by centrifugation to obtain a cell pellet. Cell pellets were resuspended in 100 μL of citrate buffer and plated on LB medium containing 10 μg/mL chloramphenicol.

Single chloramphenicol-resistant colonies were purified by restreaking on appropriate selective media and single colonies were tested by PCR as previously described for the BW25113 knockout strains, to verify the presence of the emrB and acrAB knockouts. The effects of the emrB and acrAB knockouts on the EmrAB and AcrAB transporter systems respectively were determined by assessing the phenotype of the transport mutants using appropriate antibiotics and comparison to wild type control microorganisms as shown in Table 3.1 and Table 3.2 below.

TABLE 3.1

| Strain | Strain type | Treatment CCCP* (μM) | Optical Density @ 600 nM 6 hours | 24 hours |
|---|---|---|---|---|
| E. coli BL21DE3ΔemrB::aspCproApET30 | emrB knockout mutant | 20 | 0.024 | 0.014 |
| E. coli BL21DE3::aspCproApet30 | wild type control | 20 | 0.034 | 1.113 |
| E. coli BL21DE3ΔemrB::aspCproApET30 | emrB knockout mutant | 0 | 0.787 | 1.452 |
| E. coli BL21DE3::aspCproApET30 | wild type control | 0 | 1.021 | 1.597 |

*Carbonyl cyanide 3-chlorophenylhydrazone

Thus it was confirmed that the EmrAB transporter system is responsible for the efflux of CCCP, based on the observations in Table 3.1. In the absence of CCCP (0 μM), similar growth is observed at 24 hours for both wild type and ΔemrB E. coli strains, transformed with the monatin operon (aspC, proa) on the pET30 vector. However upon the addition of 20 μM CCCP, the deletion strain, E. coli BL21DE3ΔemrB: : aspCproApET30, shows an eighty fold/ninety nine percent decrease in growth, presumably due to an inability to efflux the toxic molecule CCCP. These data confirm the major role of the EmrAB system in transporting CCCP.

TABLE 3.2

| AcrAB k.o. validation Strain | Treatment sodium decanoate (mM) | novobiocin (ppm) | OD 600 nm at 19 hours |
|---|---|---|---|
| E. coli MG1655 ΔAcrAB 6-16::aspCproAproNde | 0 | 0 | 1.436 |
| E. coli MG1655 ΔAcrAB 6-16::aspCproAproNde | 0 | 40 | 0.007 |
| E. coli MG1655 ΔAcrAB 6-16::aspCproAproNde | 0 | 80 | 0.006 |
| E. coli MG1655::aspCproApProNde (control) | 0 | 0 | 1.556 |
| E. coli MG1655::aspCproApProNde (control) | 0 | 40 | 1.407 |
| E. coli MG1655::aspCproApProNde (control) | 0 | 80 | 0.793 |
| E. coli MG1655 ΔAcrAB 6-16::aspCproAproNde | 2.5 | 0 | 0.885 |
| E. coli MG1655 ΔAcrAB 6-16::aspCproAproNde | 2.5 | 40 | 0.008 |
| E. coli MG1655 ΔAcrAB 6-16::aspCproAproNde | 2.5 | 80 | 0.008 |

TABLE 3.2-continued

| AcrAB k.o. validation Strain | Treatment | | OD 600 nm at 19 hours |
|---|---|---|---|
| | sodium decanoate (mM) | novobiocin (ppm) | |
| E. coli MG1655::aspCproApProNde (control) | 2.5 | 0 | 1.396 |
| E. coli MG1655::aspCproApProNde (control) | 2.5 | 40 | 1.395 |
| E. coli MG1655::aspCproApProNde (control) | 2.5 | 80 | 1.374 |

Thus, it was confirmed that the AcrAB transporter system is responsible for the efflux of novobiocin, and that this system is induced by sodium decanoate, based on the observations in Table 3.2. In the absence of novobiocin (0 μM), similar growth is observed at 24 hours for both wild type and ΔacrAB E. coli strains, transformed with the monatin operon (aspC, proA) on the pProNde vector. However in the presence of 40 or 80 ppm novobiocin, growth is completely inhibited for the ΔacrAB E. coli strain, while the corresponding control exhibited only slight inhibition of growth. In the presence of the AcrAB induced, sodium decanoate, the corresponding control strain grew to similar optical densities with 0 ppm, 40 ppm or 80 ppm novobiocin, while growth of the ΔacrAB E. coli strain was completely inhibited.

Example 4

Strategy to Identify Monatin Transporters from E. coli, Corynebacterium sp. or Other Microorganisms Data from other examples in this application showed that the AcrAB and EmrAB multidrug efflux pumps are capable of transporting monatin. Induction of the AcrAB transport system with decanoic acid, resulted in a further increase in monatin efflux. In addition to the acrAB and emrAB transport system genes, numerous transporter genes can be identified using putative membrane topology inference and bioinformatics approaches. It has been reported that the E. coli genome encodes at least twenty drug transport systems that can confer drug resistance when overexpressed.

It is possible that some of these transporters might not be expressed from their native promoters or their expression might be repressed by general or specific repressor molecules in their native hosts. Nishino, K., and Yamaguchi, A., "Analysis of a complete library of putative drug transporter genes in Escherichia coli," J. Bacteriol. 183:5803-5812, (2001). It is also reported that some of these transporters with the exception of acrAB are not optimally expressed under normal fermentation/cultivation conditions (Sulavik, M. C., et al., "Antibiotic susceptibility profiles of Escherichia coli strains lacking multidrug efflux pump genes," Antimicrob. Agents Chemother. 45:1126-1136, (2001)), and thus special methods would need to be employed to detect the activity of these transporters. Based on the information above, additional transporters in E. coli as well as other microorganisms might be capable of transporting monatin with varying degrees of efficiency and selectivity.

Bioinformatics approaches (look for specific transporter characteristics, trans-membrane domains etc), public domain literature searches etc. can be used to identify sources of transporter gene candidates and also provide information about inducers for transporters. Transporters can be grouped into previously identified classes (acknowledged by experts). One or two members from each class could be identified to determine their role in monatin transport. This strategy has the potential to permit extrapolation of observations from representatives tested, to the entire transporter class.

For example the monatin operon (aspC, proA) can be cloned into a vector and transformed into host microorganisms which are deficient in a specific transporter, or transporter system or individual transporter components. The specific transporter mutants with the capability to make monatin can be screened for loss of monatin transport compared to the appropriate wild-type controls. Transporter deletions that result in a decrease or loss of monatin transport indicate that the respective transporter might play a role in monatin efflux.

For example the monatin operon (aspC, proA) can be cloned into a vector and transformed into host microorganisms each of which is engineered to overexpress a specific transporter, or transporter system or individual transporter components. Microbial strains that show an increase in monatin transport compared to wild-type control with no overexpression of the transporter genes indicate that the respective transporter might play a role in monatin efflux.

Specific growth conditions or global inducers can increase the monatin efflux activity of transporter systems. Inducers can be transporter specific or general, and are beneficial because these inducers increase the activity of transporters making it easier to screen for activity with monatin transport. For example, indole increases the expression of a number of transporter genes including acrD, acrE, cusB, emrK, mdtA, mdtE, and yceL. Hirakawa, H. et al., "Indole induces the expression of multidrug transporter genes in Escherichia coli," Molecular Microbiology 55:113-1126, (2005). Comparison of monatin efflux in induced systems with corresponding uninduced controls permits the evaluation of transporter systems and inducers capable of monatin transport. See, for example, Examples 1, 2, and 14.

For example the monatin operon (aspC, proA) can be cloned into a vector and transformed into appropriate host microorganisms. Monatin producing strains can be treated with appropriate inducers and checked for increase in monatin efflux. Microarray analysis can be used to identify the transporter genes that are overexpressed under induction conditions that result in increased monatin efflux. These transporter gene candidates can be overexpressed to determine role in monatin efflux as described above.

For example the monatin operon (aspC, proA) can be cloned into a vector and transformed into host microorganisms deficient in one or more known transporters for monatin such as the AcrAB or the EmrAB systems. Induction of monatin transport in a host background that is lacking some of the major known transporters will permit the detection of additional monatin transporters in wild-type microorganism or in strains which are engineered to overexpress a specific transporter, or transporter system or individual transporter components. Microbial strains that show an increase in monatin transport compared to appropriate control strains under the same induction conditions indicate that the respective inducer/transporter might play a role in monatin efflux.

In addition to monatin efflux observed in the examples described in this application, we also observed red color formation in the culture medium, presumably due to reactions involving monatin intermediates such as indole-3-pyruvate ("I3P"), in the culture medium indicating that monatin intermediates are also being transported.

The indole-3-pyruvate efflux with resultant color formation (due to I3P complex formation) could be used as a screen for I3P transport. Given similarities in structure with monatin and monatin intermediates like indole-3-pyruvate, transport systems capable of I3P transport could be candidates for monatin transport (assumption that transporters may not discriminate between I3P and Monatin). For example, *Streptomyces griseoglavus* is an active producer of cellular and extracellular indole-3-pyruvate and would be a good candidate organism to screen for I3P and monatin transporters. El-Abyad, M. S., and Farid, M., "Optimization of culture conditions for indole-3-pyruvic acid production by *Streptomyces griseoflavus*," *Can. J Microbio.* 40:754-760, (1994). Increasing the efficiency of monatin efflux would require modification of candidate transporters to increase specificity for monatin transport by reducing transport of monatin intermediates/precursors like indole 3-pyruvate and monatin as well as initial substrates like tryptophan or pyruvate.

Example 5

Cloning and Overexpression of TolC

This example describes methods that were used to clone and overexpress *E. coli* to/C gene.

Polymerase Chain Reaction Protocol: Primers were designed with 5' restriction sites and overhangs for cloning into the pProNco vector (Clontech, Palo Alto, Calif.). primers: N term: 5'-GGCCTTGGCCATGGAAATGAAGAAAT-TGCTCCCC-3' (SEQ ID NO. 14) and C term: 5'-CCGGC-CAAGCTTTCAGTTACGGAAAGGGTTAT-3' (SEQ ID NO. 15). The tolC gene was amplified using the following PCR protocol. In a 50 µL reaction 0.150 µg template (*E. coli* MG1655), 1.6 µM of each primer, 0.4 mM each dNTP, 2.8 U Expand High Fidelity™ Polymerase (Roche, Indianapolis, Ind.), 0.5 U Pfu polymerase (Stratagene, La Jolla, Calif.), 1× Expand™ buffer with Mg, and 2.5 µL DMSO were used. The thermocycler program used included a hot start at 94° C. for 3 minutes, 8 repetitions of the following steps: 94° C. for 30 seconds, 52° C. for 45 seconds, and 72° C. for 2 minutes 30 seconds, followed by 18 repetitions of the following steps, 94° C. for 30 seconds, 59° C. for 45 seconds, and 72° C. for 2 minutes 30 seconds. After the 22 repetitions the sample was maintained at 72° C. for 7 minutes and then stored at 4° C. This PCR protocol produced a product of 1475 bp.

Cloning of tolC gene: The PCR product was gel purified from 0.8% TAE-agarose gel using the Qiagen gel extraction kit (Valencia, Calif.). The PCR product was quantified using a SmartSpec 3000™ spectrophotometer. The product was TOPO Blunt cloned following manufacturer's recommended protocols (Invitrogen, Carlsbad, Calif.). Transformants were PCR screened to confirm TolC insert using protocol described above. Verified TOPO clones were digested with restriction enzymes NcoI and HindIII following the manufacturer's recommended protocols (New England Biolabs, Beverly, Mass.); the 1.475 kb band was gel purified from 0.8% TAE-agarose gel using the Qiagen gel extraction kit. Vector pProNco was prepared by digestion with restriction enzymes NcoI and HindIII followed by treatment with shrimp alkaline phosphatase and purification from 0.8% TAE-agarose gel using the Qiagen gel extraction kit.

The digested vector and inserts were ligated using the Rapid™ DNA Ligation Kit (Roche, Indianapolis, Ind.). Approximately 50 ng of treated insert, 100 ng of treated vector (3 to 1 molar ratio of insert to vector), 5 U of T4 DNA ligase, and 1× ligation buffer were incubated for 5 minutes at room temperature. The ligation reactions were cleaned up using the High Pure PCR Product Purification Kit (Roche) and used to transform *E. coli* DH10B electrocompetent cells (Invitrogen, Carlsbad, Calif.). 10 µL of each ligation reaction was added to 40 µL of DH10B cells, which were transformed by electroporation using the BioRad Gene Pulsar II under the following conditions: 2.5 kV, 25 µF, 200 ohm in a 0.2 cm cuvette. The cells were allowed to recover in 1 mL of room temperature SOC for 1 hour at 37° C. with shaking at 225 rpm. Cells were plated on LB plates containing kanamycin (50 µg/mL); plates were incubated at 37° C. overnight.

Plasmid DNA was purified from the resulting transformants using the Qiagen spin miniprep kit and screened for the correct inserts by restriction digest with NcoI and HindIII. The sequences of plasmids appearing to have the correct insert were verified by dideoxy chain termination DNA sequencing.

tolC Gene Expression: Plasmid DNA, verified by sequence analysis, was subcloned into *E. coli* expression host BL21 (DE3) (Novagen, Madison, Wis.). The cultures were grown and the plasmids were isolated using Qiagen miniprep kit, and analyzed by restriction digest to confirm identity. Cultures were grown in 50 mL LB containing kanamycin (50 mg/L) at 30° C., 225 rpm to an $OD_{600}$ of 0.5-0.6 and induced with 100 mM IPTG (isopropyl thiogalacatoside) and 0.5% arabinose for overexpression of the tolC gene. The effect of overexpression of TolC on monatin transport is described in Examples 6 and 7 below.

Example 6

Excretion of Monatin Increased with tolC Overexpression in *E. coli*

In Gram-negative bacteria, drug resistance is due in part to the activity of transmembrane efflux-pumps, which are composed of three types of proteins. A representative pump from *Escherichia coli* is an assembly of the trimeric outer-membrane protein TolC, which is an allosteric channel, the trimeric inner-membrane proton-antiporter AcrB, and the periplasmic protein, AcrA. The pump transports substrates outside from the bacterium using proton electrochemical force. Fernandez-Recio, J., et al., "A model of a transmembrane drug-efflux pump from Gram-negative bacteria," *FEBS Lett.* 578:5-9, (2004).

The tolC gene in *E. coli* encodes an outer membrane protein that functions in conjunction with several different efflux pumps. TolC plays an active role in transport of various substrates from Gram-negative bacteria such as *E. coli* and *Pseudomonas aeruginosa*. TolC homologs are ubiquitous among Gram-negative bacteria and approximately a hundred TolC homologs have been identified. Dinh, T. et al., *J. Bacteriol.* 176:3825-3831, (1994); Johnson, J. and Church, M. J. *Mol. Biol.* 287:695-715, (1999); Anderson, C. et al., *EMBO Rep.* 1:313-318, (2000). The tolC gene was overexpressed in *E. coli* to determine if an increase in availability of the TolC channel would increase monatin transport.

*E. coli* strains BL21 (DE3) with the monatin operon (aspC, aspartate aminotransferase and proA, aldolase genes) and the pProNde plasmid (pProLAR from Clontech, modified as described in US20040235123) either with or without the tolC gene were tested for monatin transport.

Strains used for the experiment included E. coli BL21 (DE3) : : aspCproApET32 and tolC pProNde or pProNde without tolC. For inoculum, the E. coli strains were grown overnight at 37° C. and 250 rpm in Luria-Bertani ("LB") medium with 100 μg/mL ampicillin and 50 μg/mL kanamycin.

For the experimental treatments, Trp-1+glucose medium, a minimal medium that has been used for increased production of tryptophan in E. coli cells (Zeman, et al. Folia Microbiol. 35:200-204, (1990)), was prepared as follows. To 800 mL nanopure water the following reagents were added: 2 g $(NH_4)_2SO_4$ and 13.6 g $KE_2PO_4$. The pH was adjusted to 7.0, the volume was increased to 948 mL, and the medium was autoclaved. Following sterilization, 0.2 g $MgSO_4.7H_2O$, 0.01 g $CaCl_2.2H_2O$, and 0.5 mg $FeSO_4.7H_2O$ were added to the medium in a 1.8 mL volume followed by addition of 0.2 mL of Neidhardt's micronutrient solution. Neidhardt, F. C., et al., "Culture medium for Enterobacteria," J. Bacteriol. 119: 736-746, (1974). Neidhardt's medium includes (per liter): 0.18 g $(NH_4)_6(MO_7)_{24}$-$4H_2O$, 1.24 g $H_3BO_3$, 0.36 g $CoCl_2.6H_2O$, 0.12 g $CuSO_4$ (anhydrous), 0.8 g $MnCl_2.4H_2O$, and 0.14 g $ZnSO_4.7H_2O$. A 50% glucose solution was prepared separately and sterile-filtered. Forty mL of glucose solution and 10 mL of 1 M 3-Morpholinopropanesulfonic acid ("MOPS") buffer were added to the base medium (950 mL) for a 1 L final volume.

For treatments, 3-4 v/v % of inoculum was added to 100 mL medium volume in 500 mL baffled shake flasks with 100 μg/mL ampicillin and 50 μg/mL kanamycin. Conditions for the treatments included 30° C. throughout the experiment and 250 rpm agitation. At 0.4 $OD_{600\ nm}$, induction of the plasmid genes was initiated. At induction, 0.5 mM IPTG, 0.5% arabinose, 0.5 mM pyridoxine hydrochloride, and 0.2 mL of Balch's vitamins (Balch, W. E., et al., "Methanogens: reevaluation of a unique biological group," Microbiol. Rev. 43:260-296, (1979)) were added. Additions of 1 g L-tryptophan, 5 g/L sodium pyruvate, 0.04 mM pyridoxal-5'-phosphate ("PLP") and 0.2% Tween® 20 (polyoxyethylene 20-sorbitan monolaurate) were made 3 hours following induction. Some treatments included 2.5 mM sodium decanoate addition at 3 hours following induction. Samples for monatin and dry cell weight determination were taken at 6.5, 25 and 50 hours.

The amount of monatin excreted was determined using the method described in Example 13.

TABLE 6.1

Monatin per dry cell weight excreted by E. coli

| Strain | Monatin/dry cell weight (mg monatin/g dcw) | |
|---|---|---|
| | 25 hours | 50 hours |
| E. coli BL21 DE3 aspCproApET32 & pProNde w/o tolC (control) | nd | nd |
| E. coli BL21 DE3 aspCproApET32 & pProNde w/o tolC (control) | 0.11 | 0.09 |
| E. coli BL21 DE3 aspCproApET32 & tolCpProNde | 0.69 | 0.50 |
| E. coli BL21 DE3 aspCproApET32 & tolCpProNde | 1.18 | 0.86 | nd: not detected

TABLE 6.2

Average monatin per dry cell weight excreted by E. coli

| Strain | Monatin/dry cell weight (mg monatin/g dcw) | |
|---|---|---|
| | 25 hr average | 50 hr average |
| E. coli BL21 DE3 aspCproApET32 & pProNde w/o tolC (control) | 0.056 | 0.043 |
| E. coli BL21 DE3 aspCproApET32 & tolCpProNde | 0.939 | 0.679 |

As described above, the strain with TolC overexpression excreted 0.939 mg monatin per g dry cell weight versus 0.056 mg/g without tolC overexpression at the 25 hour sampling point. This is a 16.8 fold increase in monatin transporter in a strain that has increase availability of the TolC channel. A similar trend was obtained at the 50 hour sampling point with a 15.8 fold increase in monatin transported. These data show that more monatin is transported in E. coli strains that have tolC gene overexpressed.

Example 7

Excretion of Monatin Increased with to/C Overexpression in Combination with Induction of the AcrAB Efflux Pump in E. coli It was demonstrated above that the AcrAB multidrug efflux pump could be induced in E. coli by the addition of 2.5 mM sodium decanoate. In this example, the combination of induction of the AcrAB efflux pump with increased availability of the TolC channels was evaluated. E. coli strains overexpressing the tolC gene were additionally subjected to treatment with 2.5 mM sodium decanoate to simultaneously induce the AcrAB pumps.

The amount of monatin excreted was determined using the method described in Example 13.

TABLE 7.1

2.5 mM sodium decanoate treatment: Monatin per dry cell weight excreted by E. coli

| Strain | Monatin/dry cell weight (mg monatin/g dcw) | |
|---|---|---|
| | 25 hr | 50 hr |
| E. coli BL21 DE3 aspC proApET32 & pProNde w/o tolC (control) | 0.17 | 0.11 |
| E. coli BL21 DE3 aspC proApET32 & pProNde w/o tolC (control) | 0.19 | 0.09 |
| E. coli BL21 DE3 aspC proApET32 & tolCpProNde | 8.88 | 7.99 |
| E. coli BL21 DE3 aspCproApET32 & tolCpProNde | 12.19 | 10.23 |

TABLE 7.2

2.5 mM sodium decanoate treatment: Average monatin per dry cell weight excreted by *E. coli*

| Strain | Monatin/dry cell weight (mg monatin/g dcw) | |
|---|---|---|
| | 25 hr average | 50 hr average |
| *E. coli* BL21 DE3 aspCproApET32 & pProNde w/o tolC (control) | 0.18 | 0.10 |
| *E. coli* BL21 DE3 aspCproApET32 & tolCpProNde | 10.53 | 9.11 |

Average of n = 2 treatments

As shown in the tables above, in *E. coli* strains under conditions that have the AcrAB transport system induced by sodium decanoate treatment, combined with the overexpression of the tolC gene, there was a 58.5 and 91.1 fold increase in monatin transport, over the treatment without tolC overexpression at the 25 and 50 hour sample points, respectively. These data demonstrated the additional advantages of combining overexpression of the tolC gene with induction of the AcrAB transport system for increased monatin efflux.

Example 8

*Corynebacterium glutamicuni* Glutamate Auxotroph (Deficient) Strains have Increased Monatin Excretion and/or Production

*Corynebacterium glutamicum* ATCC strain 13032 is a glutamate-producing strain. The $NADP^+$-dependent isocitrate dehydrogenase gene (ICD; EC 1.1.1.42, Gen bank accession number X71489) is one of the key enzymes of the citric acid cycle and converts D-isocitrate to 2-oxoglutarate, $CO_2$ and NADPH. 2-oxoglutarate can be further reductively aminated to form glutamate. Inactivation of the icd gene resulted in glutamate auxotrophy. Eikmanns, B. J., et al., "Cloning, sequence analysis, and inactivation of the *Corynebacterium glutamicum* icd gene encoding isocitrate dehydrogenase and biochemical characterization of the enzyme," *J Bacteriol.*, 177: 774-782, (1995). Two icd mutants were obtained from Prof. Hermann Sahm (Institut fur Biotechnologie des Forschungszentrums Julich, Germany.). Glutamate auxotrophy was confirmed by the inability of the icd mutants to grow in minimal media without glutamate supplementation. The icd mutants were transformed with the monatin operon (aspC/proA) located on the pEKEX-2 vector (Eikmanns, et al., *Gene* 102: 93-98, (1991)) hereafter referred to as APpEKEX-2. Induction of the monatin operon resulted in monatin production and excretion outside the cell.

*C. glutamicum* 13032 strains (with or without the inactivated icd gene) transformed with APpEKEX-2 were grown overnight in LB medium supplemented with 5 μg/mL chloramphenicol at 30° C. and 250 rpm. For the experimental treatment flasks, 100 mL of Kraemer's (Krämer's) "A" medium was used in each shake flask. Hoischen, C. and Krämer, R., "Evidence for an efflux carrier system involved in the secretion of glutamate by *Corynebacterium glutamicum*," *Arch. Microbiol.* 151:342-347, (1989). Krämer's A medium contained (per liter): 5 g $(NH_4)_2SO_4$, 5 g urea, 2 g $KH_2PO_4$, 1.53 g $K_2HPO_4$, 0.249 g $MgSO_4.7H_2O$, 50 g glucose, 0.01 g $FeSO_4.7H_2O$, 0.01 g $MnSO_4.H_2O$, 0.01 g $CaCl_2.2H_2O$, 0.03 mg $ZnSO_4.7H_2O$, 0.1 mg $H_3BO_3$, 0.07 mg $CaCl_2.6H_2O$, 0.01 mg $NiCl_2.2H_2O$, 0.03 mg $CuCl_2.2H_2O$, 0.1 mg as $Mo^{+6}$ from $(NH_4)_6Mo_7O_{24}.4H_2O$ and 1 μg biotin. The pH was adjusted to 7.0. All flasks (with the glutamate auxotroph strain (icd2) as well as the wild-type control) were supplemented with 5 mM glutamate.

For treatments, 4-7 v/v % of inoculum was added to 100 mL medium volume in 500 mL baffled shake flasks. Conditions for the treatments included 30° C. throughout the experiment and 250 rpm agitation. At 0.4-0.7, $OD_{600\ nm}$ induction of the monatin operon genes was initiated. 0.5 mM IPTG was used for induction and 0.5 mM pyridoxine hydrochloride, and 0.04 mM pyridoxal-5'-phosphate ("PLP") were added at the time of induction. Additions of 1 g L-tryptophan, 5 g/L sodium pyruvate and 10 μg/mL ampicillin were made 3 hours following induction. Samples for monatin and dry cell weight determination were taken at about 24, and 48 hours after inoculation (run time).

TABLE 8.1

Monatin per unit biomass for glutamate auxotrophs and control

| Strain | Strain type | Run hour | |
|---|---|---|---|
| | | 24.5 | 48 |
| *C. glutamicum* 13032 icd2 no76:: APpEKEX2 | glutamate auxotroph | 4.01 | 15.97 |
| *C. glutamicum* 13032 control on APpEKEX2 (5 mM glutamate) | Wild-type control | 0.16 | 0.28 |

Results for monatin/dry cell weight in mg monatin/g dcw
n = 3 for both treatments at all sample times Because monatin has a glutamate backbone, one possible candidate for the transport of monatin outside the cell could be a glutamate efflux transporter. However, to date a glutamate transporter has not been identified in Corynebacteria. In the event that a glutamate transporter could transport monatin, without being bound by theory, one might expect that without the competition for glutamate transport in the case of a glutamate auxotroph, more monatin could be effluxed by the transporter. In addition, pyruvate is an intermediate for both glutamate and monatin production in *Corynebacterium glutamicum*. Because there is a high carbon flux to glutamate in the glutamate-producing bacterium, the use of *Corynebacterium* strains that are deficient in glutamate production could result in increased conversion of the pyruvate to monatin. ICD enzymes have roles in both energy production and intermediary metabolism (Eikmanns, B. J., et al., "Cloning, sequence analysis, and inactivation of the *Corynebacterium glutamicum* icd gene encoding isocitrate dehydrogenase and biochemical characterization of the enzyme," *J. Bacteriol.* 177: 774-782, (1995)) and thus there could be additional advantages for monatin production in a strain with an inactivated icd gene. One additional possibility is that the accumulation of intermediates from reactions upstream of ICD might activate the formation of an efflux pump that prevents the build up of these intermediates and that this efflux pump is capable of monatin transport.

The *C. glutamicum* 13032 icd2 glutamate auxotroph transformed with the monatin operon (aspCproApEKEX-2) produced an average of 15.97 mg monatin per gram of dry cell weight compared to 0.28 mg monatin per gram of dry cell weight for the wild type control with the monatin operon. These results showed that *C. glutamicum* 13032 glutamate auxotrophs with an inactive icd gene, transformed with the monatin operon excreted 57 fold more monatin than wild type strains with a functional icd gene.

Example 9

E. coli Glutamate Auxotroph (icdA Deficient) Strains should have Increased Monatin Excretion Potential While screening mutants of E. coli and other bacteria on nutrient plates with low levels of nalidixic acid, it was reported that resistance was found to result from mutations at different genetic loci. One such locus is the icdA gene encoding isocitrate dehydrogenase. A mutation in the icdA gene results in glutamate auxotrophy and accumulation of large amounts of citrate and isocitrate, the intermediates before the reaction catalyzed by IcdA. The association of intermediate accumulation and nalidixic acid resistance is predicted as follows: the metabolites/intermediates activate the formation of an efflux pump that removes nalidixic acid from the cell and thus prevents toxicity. It was reported that there was increased acrAB transcription in the icdA mutant and demonstrated that in an E. coli icdA mutant, the expression of nalidixic acid resistance required the AcrAB-TolC efflux pump. Helling, R. B., et al., "Toxic waste disposal in Escherichia coli," J Bacteriol. 184:3699-3703, (2002). Thus in an E. coli strain that had a mutation in icdA and transformed with the genes for monatin production, one would expect an increase in monatin transport due to an induction of the AcrAB-TolC transporter.

Example 10

Malate as the Carbon Substrate Increased Monatin Excretion/Efflux in E. coli Monatin has a glutamate backbone or can be considered to be a 4-substituted glutamate derivative. Monatin may therefore be transported out of a cell, for example, a bacterial cell, by transporters that translocate glutamate in exchange for substrates like malate. The glutamate/malate transporter in Arabidopsis plastids, encoded by the DiT2 gene, translocates glutamate and malate in antiport manner. Renne, P., et al., "The Arabidopsis mutant dct is deficient in the plastidic glutamate/malate translocator DiT2," Plant J. 35:316-331, (2003); Taniguchi, M., et al., "Identifying and Characterizing Plastidic 2-Oxoglutarate/Malate and Dicarboxylate Transporters in Arabidopsis thaliana," Plant and Cell Physiology, 2002, 43:706-717, (2002). The glutamate/malate transporter family is homologous with the 2-oxoglutarate/malate transporter in spinach chloroplasts which is related to the CitT transporter in E. coli that is believed to be an antiporter for citrate and succinate. Pos, K. M., "The Escherichia coli citrate carrier CitT: a member of a novel eubacterial transporter family related to the 2-oxoglutarate/malate translocator from spinach chloroplasts," J. Bacteriol. 180:4160-4165, (1998). It is reported that the E. coli CitT protein is a member of a novel family of eubacterial transporters involved in the transport of di- and tricarboxylic acids. Monatin is a dicarboxylic acid. There is a possibility that this transporter could permit a host to take up malate while excreting glutamate or monatin into the supernatant. Another possibility for malate functioning to increase monatin transport could be due to the role that malate might play as an alternative carbon source affecting growth rate and carbon distribution to metabolic pathways differently than with glucose. Malate can also be converted to pyruvate internally by malic enzymes encoded by 2 genes (Fischer, E., and Sauer, U., "Metabolic flux profiling of Escherichia coli mutants in central carbon metabolism using GC-MS," Eur J Biochem. 270:880-891, (2003)), and, because pyruvate is one of the precursors to monatin, a greater availability of pyruvate may result in increased monatin production and consequently increased monatin secretion. Growth of E. coli on malate as the primary carbon source resulted in increases in monatin excretion into the culture medium.

For inoculum, E. coli BL21 DE3 aspC/proA on pET30 was grown overnight in LB medium with 50 μg/mL kanamycin at 37° C. and 250 rpm. For the experimental treatments, Trp-1 medium, as described in Example 6 (Zeman, et al. Folia Microbiol. 35:200-204, (1990)), and 50 μg/mL kanamycin was used. Malate and glucose were 4 g/L initially for their respective treatments. For treatment flasks, 2.2 v/v % of inoculum was added to 50 mL medium volume in 250 mL baffled shake flasks. For glucose treatments, induction of the monatin operon was initiated at 0.8 $OD_{600\,nm}$. For malate treatments, induction was at 0.25 OD. At induction, 0.5 mM IPTG, 0.5 mM pyridoxine hydrochloride, and 0.2 mL of Balch's vitamins (Balch, W. E., et al., "Methanogens: reevaluation of a unique biological group," Microbiol. Rev. 43:260-296 (1979)) were added. Temperature was reduced to 30° C. at induction. Additions of 1 g L-tryptophan, 5 g/L sodium pyruvate, 0.04 mM pyridoxal-5'-phosphate ("PLP"), 10 μg/mL ampicillin, and 0.2% Tween® 20 (polyoxyethylene 20-sorbitan monolaurate) were made 3 hours following induction. Samples for monatin and dry cell weight determination were taken at 24 hours post induction.

TABLE 10.1

Summary table for E. coli with glucose or malate as carbon source

| | | Monatin/dcw (mg/g) | |
|---|---|---|---|
| Treatment no. | Carbon source | 24 hours | 24 hour average |
| 1 | glucose | 6.39 | |
| 2 | glucose | 6.17 | 6.28 |
| 3 | malate | 7.19 | |
| 4 | malate | 8.25 | 7.72 |

From the results shown above, the monatin transported per unit biomass was increased with the malate treatment when compared to the glucose treatment (7.72 to 6.28). Malate as the primary carbon source resulted in 23% higher monatin transported per unit biomass. Using malate as either a primary or supplementary carbon source in combination with the other conditions described that have been shown or expected to increase monatin efflux, could result in further increases in monatin production and excretion.

Example 11

Increased Monatin Excretion by Putative Efflux Transporter ("PET") Aae Transporter Deletion in E. coli A family of putative efflux transporters ("PET") has been reported in bacteria, yeast and plants. The PET family members with accession numbers, identified in E. coli include, YjcQ (P32715), YccS (P75870), YhfK (P45537) and YhcP (P46481). Only one of the members of the PET family, AaeAB/YhcP, has been functionally characterized to date. Van Dyk, T. K., et al., "Characterization of the Escherichia coli AaeAB efflux pump: a metabolic relief valve?," J Bacteriol. November 2004; 186:7196-7204, (2004) The bacterial and yeast proteins display a duplicated internal repeat element consisting of an N-terminal hydrophobic sequence of about 170 residues, exhibiting six putative alpha-helical transmembrane spanners (TMSs), followed by a large, C-terminal, hydrophilic, cytoplasmic domain. The plant proteins exhibit only one such unit, but they have a larger C-terminal cytoplasmic domain. *Arabidopsis thaliana* encodes at least seven paralogs of the PET family. The Gram-negative bacterial proteins are sometimes encoded by genes found in operons that also contain genes that encode membrane fusion proteins. This fact strongly suggests that PET family proteins are efflux pumps. Harley, K. T., and Saier, M. H. Jr., "A novel ubiquitous family of putative efflux transporters," *J Mol Microbiol Biotechnol.* 2:195-198, (2000).

The PET mutant strains used for the experiments were obtained from Prof. Milton Saier at the University of California at San Diego and included *E. coli* BW 25113 wild type and the four single knockout mutants *E. coli* BW 25113 ΔyhcP, *E. coli* BW 25113 ΔyccS, *E. coli* BW 25113 ΔyjcQ, *E. coli* BW 25113 ΔyhfK and the quad mutant *E. coli* BW 25113 ΔyhcP ΔyccS ΔyjcQ Δyhfk. All strains were transformed with the monatin operon genes aspC and proA on the pProNde vector as described in other examples in this application. The strains were grown overnight at 37° C. and 250 rpm in Luria-Bertani ("LB") medium with 50 µg/mL kanamycin.

For the experimental treatments, Trp-1+glucose medium, a minimal medium that has been used for increased production of tryptophan in *E. coli* cells (Zeman, et al. *Folia Microbiol.* 35:200-204, (1990)), was prepared as follows. To 800 mL nanopure water the following reagents were added: 2 g $(NH_4)_2SO_4$ and 13.6 g $KH_2PO_4$. The pH was adjusted to 7.0, the volume was increased to 948 mL, and the medium was autoclaved. Following sterilization, 0.2 g $MgSO_4.7H_2O$, 0.01 g $CaCl_2.2H_2O$, and 0.5 mg $FeSO_4.7H_2O$ were added to the medium in a 1.8 mL volume followed by addition of 0.2 mL of Neidhardt's micronutrient solution (Neidhardt, F. C., et al. "Culture medium for Enterobacteria," *J. Bacteriol.* 119: 736-746, (1974)). Neidhardt's medium includes (per liter): 0.18 g $(NH_4)_6(MO_7)_{24}.4H_2O$, 1.24 g $H_3BO_3$, 0.36 g $CoCl_2.6H_2O$, 0.12 g $CuSO_4$ (anhydrous), 0.8 g $MnCl_2.4H_2O$, and 0.14 g $ZnSO_4.7H_2O$. A 50% glucose solution was prepared separately and sterile-filtered. Forty mL of glucose solution and 10 mL of 1 M 3-Morpholinopropanesulfonic acid ("MOPS") buffer were added to the base medium (950 mL) for a 1 L final volume.

For monatin production shake flasks, 3-4% v/v of inoculum was added to 100 mL medium volume in 500 mL baffled shake flasks with 50 µg/mL kanamycin. Conditions for the treatments included 250 rpm agitation throughout and 37° C. up to induction, then, 30° C. following induction. At 0.6 $OD_{600\,nm}$, induction of the plasmid genes was initiated. At induction, 0.5 mM IPTG, 0.5% arabinose, 0.5 mM pyridoxine hydrochloride, and 0.2 mL of Balch's vitamins were added. Additions of 1 g L-tryptophan, 5 g/L sodium pyruvate, 0.04 mM pyridoxal-5'-phosphate ("PLP"), 10 µg/mL ampicillin and 0.2% Tween® 20 (polyoxyethylene 20-sorbitan monolaurate) were made 3.5 hours following induction. Samples for monatin and dry cell weight determination were taken at 24 and 30 or 31 hours. Monatin was measured by LC/MS/MS as described in Example 13. The results are shown below.

TABLE 11.1

Average monatin per dry cell weight for 30 hour samples

| Strain | 30 hour average monatin/dcw (mg/g) |
|---|---|
| *E. coli* BW 25113 wild type::aspCproApProNde | 1.81 |
| *E. coli* BW 25113 ΔyhcP::aspCproApProNde | 2.02 |
| *E. coli* BW 25113 ΔyccS::aspCproApProNde | 1.86 |
| *E. coli* BW 25113 ΔyjcQ::aspCproApProNde | 1.92 |
| *E. coli* BW 25113 ΔyhfK::aspCproApProNde | 1.60 |
| *E. coli* BW 25113 ΔyhcP ΔyccS ΔyjcQ ΔyhfK:: aspCproApProNde | 6.16 | n = 2 for all 6 strains

The quad PET mutant strain *E. coli* BW 25113 ΔyhcP (aaeB) ΔyccS ΔyjcQ ΔyhfK excreted significantly more monatin per dry cell weight, 6.16, than either the wild type or four single mutants which all averaged in the range of 1.6-2.02 mg monatin/g dry cell weight.

The YhcP efflux system has been reported to have a high degree of specificity to certain hydroxylated, aromatic carboxylic acids. The narrow specificity of the AaeAB (YhcP) efflux system is in distinct contrast to multidrug efflux systems such as AcrAB-TolC. Van Dyk, T. K., et al., "Characterization of the *Escherichia coli* AaeAB efflux pump: a metabolic relief valve?," *J. Bacteriol.* 186:7196-7204, (2004). It has been suggested that the role of the AaeAB efflux system is as a "metabolic relief valve" and it is expected that if a metabolic upset/internal stress were to occur (such as an accumulation of monatin or monatin intermediates) the expression of the efflux system would be activated.

The fact that an increase in monatin efflux is observed in a quad PET (Aae) transporter deletion background, indicates a putative role of one or more of the PET transporters in efflux of one or more monatin intermediates. Thus in the strain that is engineered to produce monatin but has a combined inactivation of these four PET/Aae transporters, there could be a reduction in loss of monatin intermediates and consequently more monatin being produced by the cell and transported by transporter systems such as AcrAB TolC/EmrAB TolC etc. Another possibility is that in a quad PET mutant background, there is greater accumulation of a metabolite that may or may not be related to monatin biosynthesis that then induces a monatin transporter, resulting in increased monatin efflux.

Various deletion combinations of the individual PET transporters could be as effective or more effective for monatin efflux than the quad PET transporter deletion strain. One could combine the quad PET mutant background with any of the other transporters or conditions shown to increase monatin transport to generate a strain with additional potential for monatin transport.

The results above demonstrated that either through a direct or indirect mechanism, an *E. coli* strain with combined deletions of the YhcP (AaeB), YccS, YjcQ and YhfK putative efflux transporters (PETs), excreted more monatin per dry cell weight than the corresponding wild-type control strain.

Example 12

Transformation of *Corynebacterium glutamicum*

Where the specification refers to transformation of *Corynebacterium glutamicum*, the following method was used.

Electrocompetent cells of *C. glutainicuni* were prepared by inoculating starter culture (grown overnight) into 200 ml MB medium (5 g/L yeast extract, 15 g/L tryptone, 5 g/L soytone, 5 g/L sodium chloride) to an initial $OD_{600\,nm}$ of 0.1. Cultures were incubated at 200 rpm to $OD_{600\,nm}$ of 0.7 and cells were collected by centrifugation at 4° C. The cell pellet was washed 3 times with 40 ml ice-cold buffer (20 mM HEPES, pH 7.2, containing 5% glycerol). The cell pellet is then washed 2 times with 20 ml ice-cold 10% v/v glycerol and the pellet is resuspended in 1 ml 10% v/v glycerol. The washed electrocompetent cells are divided into 150 µL aliquots and stored frozen at −80° C.

Before transformation of the electrocompetent *C. glutamicuin* cells, 150 µL electrocompetent cells were thawed on ice. 1 µg of the desired plasmid, was added to the cells and incubated on ice for 5 minutes, and then transferred to a chilled 0.2 cm cuvette. The cells were overlaid with 0.8 mL ice-cold 10% glycerol on top of cell suspension, being careful to avoid mixing of layers and electroporated at 200 ohms, 25 uFd, 12.5 kV/cm. The cell suspension was transferred to 4 mL of pre-warmed 46° C. MB medium and incubated at 46° C. for 6 minutes without shaking. Cell suspensions were incubated at 30° C., 200 rpm for 50 min before plating on MB plates containing appropriate selective antibiotic and incubation at 30° C. to allow the growth of transformed *C. glutamicum* strains.

Example 13

Method of Detecting Monatin and Monatin Stereoisomers

This example describes methods used to detect the presence of monatin, tryptophan and glutamic acid. It also describes a method for the separation and detection of the four stereoisomers of monatin.

LC/MS/MS Multiple Reaction Monitoring ("MRM") Analysis of Monatin and Tryptophan Analyses of mixtures for monatin and tryptophan derived from in vitro or in vivo biochemical reactions were performed using a Waters/Micromass liquid chromatography-tandem mass spectrometry ("LC/MS/MS") instrument including a Waters 2795 liquid chromatograph with a Waters 996 Photo-Diode Array (PDA) absorbance monitor placed in series between the chromatograph and a Micromass Quattro Ultima triple quadrupole mass spectrometer. LC separations were made using an Xterra MS $C_8$ reversed-phase chromatography column, 2.1 mm×250 mm at 40° C. The LC mobile phase consisted of A) water containing 0.05% (v/v) trifluoroacetic acid and B) methanol containing 0.05% (v/v) trifluoroacetic acid.

The gradient elution was linear from 5% B to 35% B, 0-4 min, linear from 35% B to 60% B, 4-6.5 min, linear from 60% B to 90% B, 6.5-7 min, isocratic at 90% B 7-11 min, linear from 90% B to 95% B, 11-12 min, linear from 95% B to 5% B, 12-13 min, with a 5 min re-equilibration period between runs. The flow rate was 0.25 mL/min, and PDA absorbance was monitored from 200 nm to 400 nm. All parameters of the ESI-MS were optimized and selected based on generation of protonated molecular ions ([M+H]$^+$) of the analytes of interest, and production of characteristic fragment ions. The following instrumental parameters were used for LC/MS/MS Multiple Reaction Monitoring ("MRM") analysis of monatin and tryptophan: Capillary: 3.5 kV; Cone: 40 V; Hex 1: 20 V; Aperture: 0 V; Hex 2: 0 V; Source temperature: 100° C.; Desolvation temperature: 350° C.; Desolvation gas: 500 L/h; Cone gas: 50 L/h; Low mass resolution (Q1): 12.0; High mass resolution (Q1): 12.0; Ion energy: 0.2; Entrance: −5 V; Collision Energy: 8; Exit: 1V; Low mass resolution (Q2): 15; High mass resolution (Q2): 15; Ion energy (Q2): 3.5; Multiplier: 650. Five monatin-specific parent-to daughter MRM transitions are used to specifically detect monatin in in vitro and in vivo reactions. The transitions monitored are 293.1 to 158.3, 293.1 to 168.2, 293.1 to 211.2, 293.1 to 230.2, and 293.1 to 257.2. Tryptophan is monitored with the MRM transition 204.7 to 146.4. For Internal standard quantification of monatin and tryptophan, four calibration standards containing four different ratios of each analyte to d5-tryptophan and d5-monatin, are analyzed. These data are subjected to a linear least squares analysis to form a calibration curve for monatin and tryptophan. To each sample is added a fixed amount of d5-tryptophan and d5-monatin, and the response ratios (monatin/d5-monatin; tryptophan/d5-tryptophan) used in conjunction with the calibration curves described above to calculate the amount of each analyte in the mixtures.

Chiral LC/MS/MS (MRM) Measurement of Monatin

Determination of the stereoisomer distribution of monatin in in vitro and in vivo reactions was accomplished by derivitization with 1-fluoro-2-4-dinitrophenyl-5-L-alanine amide ("FDAA"), followed by reversed-phase LC/MS/MS MRM measurement.

Derivitization of Monatin with FDAA

To 50 µL of sample or standard was added 200 µL of a 1% solution of FDAA in acetone. Forty µL of 1.0 M Sodium bicarbonate was added, and the mixture incubated for 1 h at 40° C. with occasional mixing. The sample was removed and cooled, and neutralized with 20 µL of 2.0 M HCl (more HCl may be required to effect neutralization of a buffered biological mixture). After degassing is complete, samples were ready for analysis by LC/MS/MS.

LC/MS/MS Multiple Reaction Monitoring for the Determination of the Stereoisomer Distribution of Monatin in in vitro and in vivo Reactions.

Analyses were performed using the LC/MS/MS instrumentation described in previous sections. LC separations capable of separating all four stereoisomers of monatin (specifically FDAA-monatin) were performed on a Phenomenex Luna 2.0×250 mm (3 µm) C18 reversed phase chromatography column at 40° C. The LC mobile phase consisted of A) water containing 0.05% (mass/volume) ammonium acetate and B) acetonitrile. The elution was isocratic at 13% B, 0-2 min, linear from 13% B to 30% B, 2-15 min, linear from 30% B to 80% B, 15-16 min, isocratic at 80% B 16-21 min, and linear from 80% B to 13% B, 21-22 min, with a 8 min re-equilibration period between runs. The flow rate was 0.23 mL/min, and PDA absorbance was monitored from 200 nm to 400 nmn. All parameters of the ESI-MS were optimized and selected based on generation of protonated molecular ions ([M−H]$^-$) of FDAA-monatin, and production of characteristic fragment ions.

The following instrumental parameters were used for LC/MS analysis of monatin in the negative ion ESI/MS mode: Capillary: 2.0 kV; Cone: 25 V; Hex 1: 10 V; Aperture: 0 V; Hex 2: 0 V; Source temperature: 100° C.; Desolvation temperature: 350° C.; Desolvation gas: 500 L/h; Cone gas: 50 L/h; Low mass resolution (Q1): 12.0; High mass resolution (Q1): 12.0; Ion energy: 0.2; Entrance: −5V; Collision Energy: 20; Exit: 1V; Low mass resolution (Q2): 12; High mass resolution (Q2): 12; Ion energy (Q2): 3.0; Multiplier: 650. Three FDAA-monatin-specific parent-to daughter transitions are used to specifically detect FDAA-monatin in in vitro and in vivo reactions. The transitions are 543.6 to 268.2, 543.6 to 499.2, and 543.6 to 525.2. Identification of FDAA-monatin stereoisomers is based on chromatographic retention time as compared to purified monatin stereoisomers, and mass spectral data.

Example 14

Induction with Salicylate Increased Monatin Transport

C. glutamicum ATCC 13032 strains transformed with aspCProApEKEX-2 were grown overnight in LB medium supplemented with 25 µg/mL kanamycin incubated at 37° C. and shaking at 250 rpm. For the experimental treatment flasks, 100 mL of Krämer's A medium was used in each shake flask. Hoischen, C. and Krämer, R., "Evidence for an efflux carrier system involved in the secretion of glutamate by *Corynebacterium glutamicum*," *Arch. Microbiol* 151:342-347, (1989). Krämer's A medium contained (per liter): 5 g $(NH_4)_2SO_4$, 5 g urea, 2 g $KH_2PO_4$, 1.53 g $K_2HPO_4$, 0.249 g $MgSO_4 \cdot 7H_2O$, 50 g glucose, 0.01 g $FeSO_4 \cdot 7H_2O$, 0.01 g $MnSO_4 \cdot H_2O$, 0.01 g $CaCl_2 \cdot 2H_2O$, 0.03 mg $ZnSO_4 \cdot 7H_2O$, 0.1 mg $H_3BO_3$, 0.07 mg $CaCl_2 \cdot 6H_2O$, 0.01 mg $NiCl_2 \cdot 2H_2O$, 0.03 mg $CuCl_2 \cdot 2H_2O$, 0.1 mg as $Mo^{+6}$ from $(NH_4)_6Mo_7O_{24} \cdot 4H_2O$ and 1 µg biotin. The pH was adjusted to 7.0.

For treatments, 4.2 v/v % of inoculum was added to 100 mL medium volume in 500 mL baffled shake flasks. Conditions for the treatments included 37° C. throughout the experiment and 250 rpm agitation. Sodium salicylate (0, 1 mM or 2 mM) was added 1 hour following inoculation. At 0.45-0.6 $OD_{600\ nm}$ induction of the monatin operon genes was initiated. IPTG at 0.5 mM was used for induction, and additions at the time of induction included 0.5 mM pyridoxine hydrochloride and 0.04 mM pyridoxal-5'-phosphate ("PLP"). Additions of 1 g L-tryptophan, 5 g/L sodium pyruvate and 10 µg/mL ampicillin were made 3 hours following induction. Samples for monatin and dry cell weight determination were taken at 23.5 and 48 hours.

TABLE 14.1

Salicylate induction increases monatin per dry cell weight

| sodium salicylate (mM) | Monatin/dcw (mg/g) | |
|---|---|---|
| | 23.5 hours | 48 hours |
| 0 | 4.34 | 9.30 |
| 1 | 7.41 | 9.94 |
| 2 | 7.54 | 9.82 |

MarA activates expression of the mar regulon, including acrAB, tolC, and marRAB, whereas MarR acts to downregulate this response by repressing the synthesis of MarA. The addition of some antibiotics, weak aromatic acids, such as salicylate, and a structurally diverse range of other compounds, such as the uncoupling agent carbonyl cyanide m-chlorophenylhydrazone ("CCCP") have all been shown to cause induction of mar regulon and thus AcrAB and TolC expression. Grkovic, S., et al., "Regulation of Bacterial Drug Export Systems," *Microbiology and Molecular Biology Reviews* 66:671-701, (2002).

In addition, the EmrAB multidrug pump of *E. coli* is induced in the presence of CCCP, the weak acid salicylate, and a number of other structurally unrelated drugs. The derepression is controlled by the EmrR, a MarR type of repressor protein. Cohen, S. P., et al., "Salicylate induction of antibiotic resistance in *Escherichia coli*: activation of the mar operon and a mar-independent pathway," *J. Bacteriol.* 175:7856-7862, (1993); Lomovskaya, O., et al., "EmrR is a negative regulator of the *Escherichia coli* multidrug resistance pump EmrAB," *J. Bacteriol.* 177:2328-2334, (1995). Thus salicylate addition increases AcrAB and EmrAB transporter system activity in *E. coli*. Salicylate addition to *Corynebacterium* could induce homologs of AcrAB/EmrAB or other transporters resulting in increased monatin transport.

Thus treatment of *Corynebacterium glutamicuin* with 1 mM or 2 mM sodium salicylate, resulted in an increase in the monatin transported. Monatin analysis was conducted as described in Example 13. A seven percent increase in monatin efflux was observed at 48 hours and a seventy percent increase in monatin transported at 23.5 hours.

Example 15

Demonstration of Monatin Production and Excretion in *Pantoea stewartii*

Electrocompetent *Pantoea stewartii* (ATCC 8200) were prepared by culturing a 1% inoculum of *P. stewartii* cells in Nutrient broth from an overnight culture. Cells were incubated at 26° C. and 250 rpm to an OD 600 of ~0.6. The bacteria were pelleted by centrifugation (10 minutes at 10,000×g) and washed in 50 ml of 10 mM HEPES (pH 7.0). The wash was repeated with 25 ml of 10 mM HEPES buffer (pH 7.0) followed by the same centrifugation protocol as above. The cells then were washed once in 25 ml of 10% glycerol. Following centrifugation, the cells were resuspended in 500 µL of 10% glycerol. Forty µL aliquots were frozen and kept at −80° C. until use.

pPROLarA.122 (ClonTech Laboratories, Inc.) was altered by site specific mutagenesis to introduce a Nde I restriction site at bp 132 (nucleotide numbering as described by ClonTech laboratories) and generated the vector pPRONde, by following the protocols as described in the Stratagene QuikChange site specific mutagenesis kit (Stratagene, Inc.) and using the mutagenic oligonucleotides (Nde I sites are underlined):

(SEQ ID NO. 16)
5'-GAGGAGAAAGGTA<u>CATATG</u>GGTGAACAGAAAC-3'

(SEQ ID NO. 17)
5'-CAGTTTCTGTTCACC<u>CATATG</u>TACCTTTCTCC-3'

Thermocycler protocol:
1) 96° C. for 5 minutes
2) 96° C. for 30 seconds
3) 55° C. for 45 seconds
4) 72° C. for 3 minutes
5) Repeat steps 2-4; 24 times
6) 72° C. for 10 minutes

| Recipe: | |
|---|---|
| 10x Expand Polymerase Buffer | 5 µL |
| dNTP's (10 mM each) | 1 µL |
| pPRONde (~50 ng/uL) | 0.1 µL |
| PCR primers (each) | 0.5 µL |
| Expand Polymerase | 0.5 µL |
| Water | 42.4 µL |
| Total | 50 µL |

The resulting PCR product was purified by PCR clean-up kit (Qiagen) and digested with Nde I restriction endonuclease. The digested DNA was then purified by gel purification on a 0.8% agarose gel and ligated together. Ligation mixtures were precipitated by ethanol precipitation and digested with KpnI restriction endonuclease in order to linearize any parental plasmid. The reaction mix was transformed into DH10B electrocompetent *E. coli*. Transformants were screened for removal of the KpnI site by digestion with KpnI restriction endonuclease.

A 29 bp section of the pPRONde vector was deleted using Quikchange site-directed mutagenesis (Strategene, La Jolla, Calif.), as the repetitiveness of this fragment within the vector had previously been shown to cause vector instability under stressful conditions. Primers for the mutagenesis were:

```
                                           (SEQ ID NO. 18)
5'-ACGTCTGTGTGGAATTCTCGGACACCGAGGAG-3'
and
                                           (SEQ ID NO. 19)
5'-CTCCTCGGTGTCCGAGAATTCCACACAGACGT-3'.
```

The mutagenesis was conducted as per manufacturer's protocol. Clones were screened by restriction digest with EcoRI, as a new EcoRI restriction site was created by deletion of the desired DNA fragment, and mutants were confirmed by sequencing. The resulting vector was named pPRONdeDel. The aspC gene was introduced into vector pPRONdeDel using restriction sites NdeI and BamHI. The proA gene was subsequently introduced a into vector pPRONdeDel using restriction sites BamHI and NotI, resulting in vector aspC/proA/pPRONdeDel (APpPRONdeDel).

Vector APpPRONdeDel was transformed into electrocompetent *Pantoea stewartii* using a 0.2 cm cuvette and a Bio-Rad Gene Pulser II system as described in the Bio-Rad electroporation manual. The cells were allowed to recover in 900 µL SOC medium for 1 hour at 26° C. at 250 rpm. Cells were plated on LB-agar plates containing kanamycin (25 µg/mL).

For inoculum, the *P. stewartii* was grown overnight at 30° C. and 250 rpm in Luria-Bertani ("LB") medium with 25 µg/mL kanamycin. For the experimental treatments, Trp-1+ glucose medium, (Zeman, et al. *Folia Microbiol.* 35:200-204, (1990)), was prepared as follows. To 800 mL nanopure water the following reagents were added: 2 g $(NH_4)_2SO_4$ and 13.6 g $KH_2PO_4$. The pH was adjusted to 7.0, the volume was increased to 948 mL, and the medium was autoclaved. Following sterilization, 0.2 g $MgSO_4.7H_2O$, 0.01 g $CaCl_2.2H_2O$, and 0.5 mg $FeSO_4.7H_2O$ were added to the medium in a 1.8 mL volume followed by addition of 0.2 mL of Neidhardt's micronutrient solution. Neidhardt F. C., et al., "Culture medium for Enterobacteria," *J. Bacteriol.* 119:736-746, (1974)). Neidhardt's medium includes (per liter): 0.18 g $(NH_4)_6(MO_7)_{24}.4H_2O$, 1.24 g $H_3BO_3$, 0.36 g $CoCl_2.6H_2O$, 0.12 g $CuSO_4$ (anhydrous), 0.8 g $MnCl_2.4H_2O$, and 0.14 g $ZnSO_4.7H_2O$. A 50% glucose solution was prepared separately and sterile-filtered. Forty mL of glucose solution and 10 mL of 1 M 3-Morpholinopropanesulfonic acid ("MOPS") buffer were added to the base medium (950 mL) for a 1 L final volume.

For treatments, 3.5-5.0 v/v % of inoculum was added to 100 mL medium volume in 500 mL baffled shake flasks with 25 µg/mL kanamycin. Conditions for the treatments included 250 rpm agitation throughout and 37° C. up to induction, then, 30° C. following induction. At 0.35-0.50 $OD_{600\,nm}$, induction of the plasmid genes was initiated. At induction, 1.0 mM IPTG, 0.5% L-arabinose, 0.5 mM pyridoxine hydrochloride, and 0.2 mLs of Balch's vitamins were added. Additions of 10 g/L L-tryptophan, 10 g/L sodium pyruvate, 0.04 mM pyridoxal-5'-phosphate ("PLP") and 0.2% Tweene® 20 (polyoxyethylene 20-sorbitan monolatrate) were made 3.0 hours following induction. Some treatments included 2.5 mM sodium decanoate and/or 10 µg/ml ampicillin addition at 3.0 hours following induction. Samples for monatin and dry cell weight determination were taken at 24, 30 and 48 hours.

TABLE 15.1

Monatin per dry cell weight excreted by *P. stewartii*

| Strain | Sodium decanoate (mM) | Tween ® 20/ ampicillin | Monatin/dcw (mg/g) | | |
|---|---|---|---|---|---|
| | | | 24 hours | 30 hours | 48 hours |
| *Pantoea stewartii*:: aspC/proA/pProNde del | 0 | no Tween ® 20/ ampicillin | 3.2 | 7.6 | 7.8 |
| *Pantoea stewartii*:: aspC/proA/pProNde del | 0 | +Tween ® 20/ ampicillin | 4.9 | 8.4 | 37.1 |

Overexpression of the monatin operon, aspC-aminotransferase and proA-aldolase, in *Pantoea stewartii* results in increased excretion of monatin (monatin per dry cell weight). There is a 4 to 5-fold increase by 48 hours in monatin excretion when Tween® 20 and ampicillin are added to the medium. Tween® and ampicillin have been reported to stress the cell by affecting the cell envelope and thus assist with transport of metabolites outside the cell.

This is the first evidence of monatin production and export in the genus *Pantoea* and species *Pantoea stewartii*.

Example 16

Increase of Monatin Excretion with Overexpression of the RobA Proteins

RobA is a member of the XylS/AraC subfamily of DNA binding proteins, and when overexpressed, has been shown to induce multiple antibiotic resistance in *Escherichia coli*. It has been reported that the multiple antibiotic resistance induced by the overexpression of RobA largely depends on the activation of the AcrAB efflux, as well as the activation of micF. Tanaka T., et al., "RobA-induced multiple antibiotic resistance largely depends on the activation of the AcrAB efflux," *Microbiol Immunol.* 41:697-702, (1997). The MicF small RNA is encoded divergently from the gene encoding the OmpC porin and represses the expression of OmpF, another porin. The exact role that MicF might play in monatin efflux remains to be determined.

The strains used for the experiment included *E. coli* MG1655 : : aspC/proA/pProNdeDel together with the robA gene from *E. coli* cloned into the pUC19 vector. The control strain was *E. coli* MG1655 : : aspC/proA/pProNde along with the pUC19 vector. The robA gene was amplified from *E. coli* W3110 using primers 5'TTAAGGCCGTCGACATGGAT-CAGGCCGGCATTAT3' (SEQ ID NO. 20) and 5'TTC-CAAGGTTGGATCCCTAAACGATGCGGCAGGC3' (SEQ ID NO. 21), which introduced SalI and BamHI sites at the end of the amplified fragment. The PCR fragment was cloned between the SalI and BamHI sites of the vector pUC19 (GenBank/EMBL accession number L09137). For inoculum, the *E. coli* strains were grown overnight at 37° C. and 250 rpm in Luria-Bertani ("LB") medium with 100 µg/mL ampicillin and 50 µg/mL kanamycin.

For the experimental treatments, Trp-1+glucose medium, a minimal medium that has been used for increased production of tryptophan in *E. coli* cells (Zeman et al. *Folia Microbiol.* 35:200-204, (1990)), was prepared as follows. To 800 mL nanopure water the following reagents were added: 2 g $(NH_4)_2SO_4$ and 13.6 g $KH_2PO_4$. The pH was adjusted to 7.0, the volume was increased to 948 mL, and the medium was autoclaved. Following sterilization, 0.2 g $MgSO_4.7H_2O$, 0.01 g $CaCl_2.2H_2O$, and 0.5 mg $FeSO_4.7H_2O$ were ad to the medium in a 1.8 mL volume followed by addition of 0.2 mL of Neidhardt's micronutrient solution. Neidhardt F. C., et al., "Culture medium for Enterobacteria," *J. Bacteriol.* 119:736-746, (1974). Neidhardt's medium includes (per liter): 0.18 g $(NH_4)_6(MO_7)_{24}$-$4H_2O$, 1.24 g $H_3BO_3$, 0.36 g $CoCl_2.6H_2O$, 0.12 g $CuSO_4$ (anhydrous), 0.8 g $MnCl_2.4H_2O$, and 0.14 g $ZnSO_4.7H_2O$. A 50% glucose solution was prepared separately and sterile-filtered. Forty mL of glucose solution and 10 mL of 1 M 3-Morpholinopropanesulfonic acid ("MOPS") buffer were added to the base medium (950 mL) for a 1 L final volume.

For treatments, 3.5-5.0 v/v % of inoculum was added to 100 mL medium volume in 500 mL baffled shake flasks with 100 μg/mL ampicillin and 50 μg/mL kanamycin. Conditions for the treatments included 250 rpm agitation throughout and 37° C. up to induction, then, 30° C. following induction. At 0.30-0.50 $OD_{600\,nm}$, induction of the plasmid genes was initiated. At induction, 1.0 mM IPTG, 0.5% L-arabinose, 0.5 mM pyridoxine hydrochloride, and 0.2 mLs of Balch's vitamins were added. Additions of 10 g/L L-tryptophan, 10 g/L sodium pyruvate, 0.04 mM pyridoxal-5'-phosphate ("PLP") and 0.2% Tween® 20 (polyoxyethylene 20-sorbitan monolaurate) were made 3 hours following induction. Some treatments included 2.5 mM sodium decanoate addition at 3 hours following induction. Samples for monatin and dry cell weight determination were taken at 24, 30 and 48 hours.

TABLE 16.1

Monatin per dry cell weight excreted by *E. coli*

| | Sodium decanoate (mM) | Monatin/dcw (mg/g) | |
|---|---|---|---|
| | | 30 hours | 48 hours |
| *E. coli* MG1655::aspC proA pProNdedel, pUC19 (control) | 0 | 2.59 | 2.94 |
| *E. coli* MG1655::aspC proA pProNdedel, robA pUC19 | 0 | 3.11 | 10.41 | n = 2 for all treatments

Overexpression of RobA without sodium decanoate treatment resulted in greater monatin excretion at 48 hours. Monatin per dry cell weight was 10.41 mg/g on average at 48 hours when RobA was overexpressed compared to 2.94 mg/g average with no RobA overexpression. RobA overexpression resulted in a 3.5-fold increase in monatin excretion. This is evidence that RobA overexpression had a positive impact on AcrAB expression or micF resulting in increased monatin excretion. The exact role that MicF might play in monatin efflux remains to be determined.

TABLE 16.2

Monatin per dry cell weight excreted by *E. coli*

| | Sodium decanoate (mM) | Monatin/dcw (mg/g) | |
|---|---|---|---|
| | | 30 hours | 48 hours |
| *E. coli* MG1655::aspC proA pProNdedel pUC19 (control) | 2.5 | 4.66 | 4.31 |
| *E. coli* MG1655::aspC proA pProNdedel, robA pUC19 | 2.5 | 6.91 | 25.62 | n = 2 for all treatments

Overexpression of RobA with 2.5 mM sodium decanoate treatment resulted in greater monatin excretion at 48 hours. Monatin per dry cell weight was 25.62 mg/g on average at 48 hours when RobA was overexpressed compared to 4.31 mg/g average with no RobA overexpression. RobA overexpression in the presence of sodium decanoate resulted in a greater than 5-fold increase in monatin excretion. This is evidence that RobA overexpression and decanoate addition had a positive and possibly synergistic impact on AcrAB expression or Micf resulting in increased monatin excretion. The exact role that MicF might play in monatin efflux remains to be determined.

TABLE 16.3

Monatin per dry cell weight excreted by *E. coli* ΔacrAB

| | Monatin/dcw (mg/g) | | |
|---|---|---|---|
| | 24 hours | 30 hours | 48 hours |
| *E. coli* MG1655 deltaAcrAB::aspC proA pProNdedel, pUC19 (control) | 10.7 | 29.7 | 39.3 |
| *E. coli* MG1655 deltaAcrAB::aspC proA pProNde del robA pUC19 | 45.7 | 58.6 | 81.7 | n = 2 for all treatments
2.5 mM sodium decanoate added to all treatments

Overexpression of RobA with 2.5 mM sodium decanoate addition in the *E. coli* MG1655 ΔAcrAB strain resulted in greater monatin excretion at 24, 30 and 48 hours. Monatin per dry cell weight was 81.7 mg/g on average at 48 hours when RobA was overexpressed in the ΔAcrAB strain compared to 39.3 mg/g average with no RobA overexpression in this strain. RobA overexpression in the ΔAcrAB strain with the presence of sodium decanoate resulted in a greater than 2-fold increase in monatin excretion. This is evidence that RobA overexpression and decanoate addition in the ΔAcrAB strain resulted in increased monatin excretion possibly due to action on the inicF gene or transporter system other than the AcrAB transport system.

Taken together the data above conclusively demonstrated that RobA has a positive impact on monatin efflux, which could be through the activation of the AcrAB or other transport systems.

Example 17

Increase of Monatin Excretion with Overexpression of the RamA Proteins

RamA, is a 113-amino-acid regulatory protein belonging to the AraC-XylS transcriptional activator family, in *Enterobacter aerogenes*. Overexpression of RamA was reported to induce an MDR phenotype in drug-susceptible *Escherichia coli* JM109 and *E. aerogenes* ATCC 13048, and resulted in an increased production of AcrA, a component of the AcrAB-TolC drug efflux pump. It was shown that RamA not only enhanced the transcription of the marRAB operon but was also able to induce a multi-drug resistance ("MDR") phenotype in a mar-deleted strain. Thus RamA is a transcriptional activator of the Mar regulon in addition to being a self-governing activator of the MDR cascade. Chollet R., et al., "RamA is an alternate activator of the multidrug resistance cascade in *Enterobacter aerogenes*," *Antimicrob Agents Chemother.* 48:2518-2523, (2004).

The strains used for the experiment included *E. coli* MG1655 : : aspC/proA/pProNdeDel together with the ramA gene from *Enterobacter aerogenes* cloned into the pUC19 vector (GenBank/EMBL accession number L09137). The control strain was *E. coli* MG1655 : : aspC/proA/pProNde along with the pUC19 vector. The ramA gene was amplified from *E. aerogenes* ATCC 13048 by using primers, 5'GGC-CGGTTAAGTCGACATGAATATATCCGCTCAGG3' (SEQ ID NO. 22) and 5'TTAACCTTGGATCCTCAGT-GCGCGCGGCTGT3' (SEQ ID NO. 23), which introduced Sal I and BamH I sites at the end of the amplified fragment. The PCR fragment was cloned between the Sal I and BamH I sites of the vector pUC19 (GenBank/EMBL accession number L09137). For inoculum, the *E. coli* strains were grown overnight at 37° C. and 250 rpm in Luria-Bertani ("LB") medium with 100 µg/mL ampicillin and 50 µg/mL kanamycin.

For the experimental treatments, Trp-1+glucose medium, a minimal medium that has been used for increased production of tryptophan in *E. coli* cells (Zeman et al. *Folia Microbiol.* 35:200-204, (1990)), was prepared as follows. To 800 mL nanopure water the following reagents were added: 2 g $(NH_4)_2SO_4$ and 13.6 g $KU_2PO_4$. The pH was adjusted to 7.0, the volume was increased to 948 mL, and the medium was autoclaved. Following sterilization, 0.2 g $MgSO_4.7H_2O$, 0.01 g $CaCl_2.2H_2O$, and 0.5 mg $FeSO_4.7H_2O$ were to the medium in a 1.8 mL volume followed by addition of 0.2 mL of Neidhardt's micronutrient solution. Neidhardt F. C., et al., "Culture medium for Enterobacteria," *J. Bacteriol.* 119:736-746, (1974). Neidhardt's medium includes (per liter): 0.18 g $(NH_4)_6(MO_7)_{24}.4H_2O$, 1.24 g $H_3BO_3$, 0.36 g $CoCl_2.6H_2O$, 0.12 g $CuSO_4$ (anhydrous), 0.8 g $MnCl_2.4H_2O$, and 0.14 g $ZnSO_4.7H_2O$. A 50% glucose solution was prepared separately and sterile-filtered. Forty mL of glucose solution and 10 mL of 1 M 3-morpholinopropanesulfonic acid ("MOPS") buffer were added to the base medium (950 mL) for a 1 L final volume.

For treatments, 3.5-5.0 v/v % of inoculum was added to 100 mL medium volume in 500 mL baffled shake flasks with 100 µg/mL ampicillin and 50 µg/mL kanamycin. Conditions for the treatments included 250 rpm agitation throughout and 37° C. up to induction, then, 30° C. following induction. At an $OD_{600\ nm}$ between 0.30-0.50, induction of the plasmid genes was initiated. At induction, 1.0 mM IPTG, 0.5% L-arabinose, 0.5 mM pyridoxine hydrochloride, and 0.2 mLs of Balch's vitamins were added. Additions of 10 g/L L-tryptophan, 10 g/L sodium pyruvate, 0.04 mM pyridoxal-5'-phosphate ("PLP") and 0.2% Tween® 20 (polyoxyethylene 20-sorbitan monolaurate) were made 3 hours following induction. Some treatments included 2.5 mM sodium decanoate addition at 3 hours following induction. Samples for monatin and dry cell weight determination were taken at 24, 30 and 48 hours.

TABLE 17.1

Monatin per dry cell weight excreted by *E. coli*

| | Sodium decanoate | Monatin/dcw (mg/g) | |
|---|---|---|---|
| | (mM) | 30 hours | 48 hours |
| *E. coli* MG1655::aspC proA pProNdedel, pUC19 (control) | 0 | 2.59 | 2.94 |
| *E. coli* MG1655::aspC proA pProNdedel, ramA pUC19 | 0 | 4.31 | 5.92 | n = 2 for all treatments

Overexpression of RamA without sodium decanoate treatment resulted in greater monatin excretion at both 30 and 48 hours. Monatin per dry cell weight was 5.92 mg/g on average at 48 hours when RamA was overexpressed compared to 2.94 mg/g average with no RamA overexpression. RamA overexpression resulted in a 2-fold increase in monatin excretion. This is evidence that RamA overexpression had a positive impact on the mar operon or multiple drug resistance transporter genes or both resulting in increased monatin excretion.

TABLE 17.2

Monatin per dry cell weight excreted by *E. coli*

| | Sodium decanoate | Monatin/dcw (mg/g) | |
|---|---|---|---|
| | (mM) | 30 hours | 48 hours |
| *E. coli* MG1655::aspC proA pProNdedel pUC19 (control) | 2.5 | 4.66 | 4.31 |
| *E. coli* MG1655::aspC proA pProNdedel, ramA pUC19 | 2.5 | 3.69 | 13.90 | n = 2 for all treatments

Overexpression of RamA with 2.5 mM sodium decanoate treatment resulted in greater monatin excretion at both 30 and 48 hours. Monatin per dry cell weight was 13.90 mg/g on average at 48 hours when RamA was overexpressed compared to 4.31 mg/g average with no RamA overexpression. RamA overexpression in the presence of sodium decanoate resulted in a 3.2-fold increase in monatin excretion. This is evidence that RamA overexpression acted on the mar operon or multiple drug resistance transporter genes or both to increase monatin excretion in the presence of sodium decanoate.

TABLE 17.3

Monatin per dry cell weight excreted by *E. coli* ΔacrAB

| | Monatin/dcw (mg/g) | | |
|---|---|---|---|
| | 24 hours | 30 hours | 48 hours |
| *E. coli* MG1655 ΔAcrAB:: aspC proA pProNde del, pUC19 (control) | 10.7 | 29.7 | 39.3 |
| *E. coli* MG1655 ΔAcrAB:: aspC proA pProNde del, ramA pUC19 | 32.3 | 41.7 | 61.1 | n = 2 for all treatments
2.5 mM sodium decanoate added to all treatments

Overexpression of RamA in the *E. coli* ΔAcrAB with the monatin operon resulted in greater monatin excretion than the same strain without overexpression of RamA. At 48 hours, overexpression of RamA resulted in 61.1 mg of monatin per gram of dry cell weight and 39.3 mg/g without overexpression of RamA. This represented a 1.5-fold increase in monatin efflux with RamA overexpression. These data are evidence that RamA overexpression increased monatin excretion without involvement of the AcrAB transporter. This positive impact on monatin efflux could be attributed to the activation of the mar operon or transporter genes/systems other than AcrAB.

Thus, we have demonstrated that overexpression of the ramA gene in E. coli resulted in an increase in monatin efflux. The increase in monatin efflux was also observed in a host background in which the AcrAB system was deleted. This was taken to be evidence that the positive impact of RamA on monatin efflux is also due to its impact on transport systems besides the AcrAB transport system.

Example 18

Increase of Monatin Excretion with Overexpression of the MarA Protein

Transcriptional activation of acrAB expression is the main cause of multidrug resistance in strains that overexpress MarA, a member of the AraC family of transcriptional activators. MarA, activates its own transcription and that of a large number of mar regulon genes by binding to DNA regions called marboxes that are located near the promoters for various target genes. The acrAB promoter is also adjacent to a marbox at which MarA has been demonstrated to bind and activate transcription. Alekshun, M. N., and Levy, S. B., "Regulation of chromosomally mediated multiple antibiotic resistance: the mar regulon," *Antimicrob. Agents Chemother.* 41:2067-2075, (1997).

In addition, overexpression of MarA has also been demonstrated to result in increased synthesis of the TolC component of the AcrAB-TolC pump complex, which, in combination with the identification of a putative mar/rob/sox-box upstream of the tolC gene, strongly suggests that tolC also belongs to the mar regulon. Aono, R. et al., "Involvement of outer membrane protein TolC, a possible member of the mar-sox regulon, in maintenance and improvement of organic solvent tolerance of *Escherichia coli* K-12," *J. Bacteriol.* 180:938-944, (1998).

The transcriptional activation functions of MarA are reported to be global in nature because MarA can promote the transcription of genes encoding proteins of diverse functions, both in vivo and in vitro. Gene array analysis of a strain constitutively expressing MarA has indicated that more than 60 *E. coli* genes are differentially regulated by this protein (Barbosa, T. M., and Levy, S. B., "Differential expression of over 60 chromosomal genes F in *Escherichia coli* by constitutive expression of MarA," *J. Bacteriol.* 182:3467-3474, (2000)), whereas a second study employing an inducible MarA expression system identified an additional 67 MarA-regulated genes. Pomposiello, P. J. et al., "Genome-wide transcriptional profiling of the *Escherichia coli* responses to superoxide stress and sodium salicylate," *J. Bacteriol.* 183: 3890-3902, (2001). It has been reported that MarA is also capable of activating a gene that possess a marbox which diverges substantially from the consensus sequence. Barbosa, T. M. and S. B. Levy, "Activation of the *Escherichia coli* nfnB gene by MarA through a highly divergent marbox in a class II promoter," *Mol. Microbiol.* 45:191-202, (2002).

Overall, MarA activates expression of the mar regulon, including acrAB, tolC, and marRAB, whereas MarR acts to downregulate this response by repressing the synthesis of MarA. Although overexpression of MarA from a plasmid is sufficient to activate the mar regulon genes, the addition of the antibiotics tetracycline and chloramphenicol, weak aromatic acids, such as salicylate, and a structurally diverse range of other compounds, such as the uncoupling agent carbonyl cyanide m-chlorophenylhydrazone and the redox-cycling compounds menadione and plumbagin, have all been shown to cause induction of mar regulon expression. Grkovic S et al., "Regulation of bacterial drug export systems," *Microbiol Mol Biol Rev.* 66:671-701, (2002).

The strain used for the experiment was E. coli MG1655: : aspC/proA/pProNde together with the marA gene from E. coli cloned into the pUC19 vector (GenBank/EMBL accession number L09137). The control strain was E. coli MG1655: : aspC/proA/pProNde along with the pUC19 vector. The marA gene was amplified from E. coli W3110 with PCR technology (known to one skilled in the art) using the primers E. coli MarASalIF-5'TTAAGGCCGTCGACAT-GACGATGTCCAGACGCAATA3' (SEQ ID NO. 24) and E. coli MarABamHIR-5'GCAGTGCCGGATCCCTAGCTGT-TGTAATGATTTA3' (SEQ ID NO. 25). For inoculum, the E. coli strains were grown overnight at 37° C. and 250 rpm in Luria-Bertani ("LB") medium with 100 μg/mL ampicillin and 50 μg/mL kanamycin.

For the experimental treatments, Trp-1+glucose medium, a minimal medium that has been used for increased production of tryptophan in E. coli cells (Zeman, et al. *Folia Microbiol.* 35:200-204, (1990)), was prepared as follows. To 800 mL nanopure water the following reagents were added: 2 g $(NH_4)_2SO_4$ and 13.6 g $KH_2PO_4$. The pH was adjusted to 7.0, the volume was increased to 948 mL, and the medium was autoclaved. Following sterilization, 0.2 g $MgSO_4.7H_2O$, 0.01 g $CaCl_2.2H_2O$, and 0.5 mg $FeSO_4.7H_2O$ were added to the medium in a 1.8 mL volume followed by addition of 0.2 mL of Neidhardt's micronutrient solution. Neidhardt F. C., et al., "Culture medium for Enterobacteria," *J. Bacteriol.* 119: 736-746, (1974). Neidhardt's medium includes (per liter): 0.18 g $(NH_4)_6(MO_7)_{24}.4H_2O$, 1.24 g $H_3BO_3$, 0.36 g $CoCl_2.6H_2O$, 0.12 g $CuSO_4$ (anhydrous), 0.8 g $MnCl_2.4H_2O$, and 0.14 g $ZnSO_4.7H_2O$. A 50% glucose solution was prepared separately and sterile-filtered. Forty mL of glucose solution and 10 mL of 1 M 3-Morpholinopropanesulfonic acid ("MOPS") buffer were added to the base medium (950 mL) for a 1 L final volume.

For treatments, 3.2-3.6 v/v % of inoculum was added to 100 mL medium volume in 500 mL baffled shake flasks with 100 μg/mL ampicillin and 50 μg/mL kanamycin. Conditions for the treatments included 250 rpm agitation throughout and 37° C. up to induction, then, 30° C. following induction. At an $OD_{600\,nm}$ between 0.35-0.50, induction of the plasmid genes was initiated. At induction, 1.0 mM IPTG, 0.5% L-arabinose, 0.5 mM pyridoxine hydrochloride, and 0.2 mLs of Balch's vitamins were added. Additions of 10 g/L L-tryptophan, 10 g/L sodium pyruvate, 0.04 mM pyridoxal-5'-phosphate ("PLP") and 0.2% Tween® 20 (polyoxyethylene 20-sorbitan monolaurate) were made 3.0 hours following induction. At 24 hours after inoculation, 10 g/L of sodium pyruvate was added to each flask again. Some treatments included 2.5 mM sodium decanoate addition at 3.0 hours following induction. Samples for monatin and dry cell weight determination were taken at 24, 30 and 72 hours.

TABLE 18.1

Monatin per dry cell weight excreted by E. coli

| Strain | Treatment (sodium decanoate addition in mM) | Mean monatin per dry cell weight (mg/g) | |
|---|---|---|---|
| | | 30 hours | 72 hours |
| E. coli MG1655 aspC proA pProNde del, pUC19 (control) | 0 | 2.2 | 2.3 |
| E. coli MG1655 aspC proA pProNde del, MarA pUC19 | 0 | 2.7 | 23.4 | n = 2 for all treatments

Overexpression of marA results in increased excretion of monatin (monatin per dry cell weight) in the absence of sodium decanoate addition as seen above. There is a 10 fold increase in mg monatin per g dry cell weight due to overexpression of the marA gene. This significant increase in monatin efflux can be explained by the impact of MarA on the AcrAB transport system, the increased transcription of the tolC gene, which interacts with multiple transport systems, and/or the possible upregulation of other transporters that could play a role in monatin efflux.

TABLE 18.2

Monatin per dry cell weight excreted by E. coli

| Strain | Treatment (sodium decanoate addition in mM) | Mean monatin per dry cell weight (mg/g) | |
|---|---|---|---|
| | | 30 hours | 72 hours |
| E. coli MG1655 aspC proA pProNde, del pUC19 (control) | 2.5 | 2.4 | 2.7 |
| E. coli MG1655 AspC ProA pProNde, del MarA pUC19 | 2.5 | 8.5 | 51.9 | n = 2 for all treatments

Overexpression of marA results in additional increased excretion of monatin (monatin per dry cell weight) in the presence of sodium decanoate addition as seen above. With 2.5 mM of sodium decanoate addition, the marA strain excreted 51.9 mg monatin per dry cell weight on average, and the control strain was only 2.7 mg/g at 72 hours, this represents a 19 fold increase in monatin efflux. This reveals the substantial effect that marA overexpression has on transporter(s) that excrete monatin. There appears to be a synergistic effect of sodium decanoate with marA overexpression.

TABLE 18.3

Monatin per dry cell weight excreted by E. coli ΔacrAB with the monatin operon

| Strain | Strain/insert | Mean monatin per dry cell weight (mg/g) | | |
|---|---|---|---|---|
| | | 24 | 30 | 72 |
| E. coli MG1655 ΔAcrAB AspC ProA pProNde del pUC19 (control) | ΔAcrAB | 22.2 | 20.6 | 62.6 |
| E. coli MG1655 ΔAcrAB AspC ProA pProNde del MarA pUC19 | ΔAcrAB with marA insert | 54.6 | 56.0 | 209.0 | n = 2 for all treatments
2.5 mM sodium decanoate addition for all treatments

The combination of marA overexpression with the acrAB knockout mutant resulted in an average of 209 mg of monatin per gram dry cell weight at 72 hours versus 62.6 for the acrAB knockout mutant without the marA plasmid. Even by 24 hours, the acrAB knockout/marA overexpression strain outperformed the control by over two-fold (54.6 to 22.2 mg monatin/g dcw). This is an example of the combination of a deletion of the AcrAB transporter and overexpression of a regulatory gene, for example marA, that has a synergistic effect on monatin excretion.

MarA is known to activate acrAB expression, but in the acrAB knockout, even more monatin was excreted than usual. It has been reported that MarA expression can increase the expression of a number of genes involved in transport, in addition to acrA such as mtr (tryptophan-specific transport protein), ompX (outer membrane protein X), and yadG (putative ATP binding component of a transport system). Thus, this effect may be attributed to the induction of a transporter other than AcrAB, involved in monatin excretion. It is also known that MarA activates the transcription of tolC, which is a component of multiple transporter systems. Thus an increase in monatin transport could be attributed to the action of multiple transporters requiring TolC.

These results demonstrate that MarA has a strong positive influence on monatin efflux in Escherichia coli.

Example 19

Increase of Monatin Excretion with Overexpression of the BaeR Protein

The BaeSR two-component regulatory system controls expression of exporter genes, conferring drug resistance in Escherichia coli. Nagakubo, S. et al., J. Bacteriol. 184:4161-4167, (2002); Baranova, N. and Nikaido, H., "The baeSR two-component regulatory system activates transcription of the yegMNOB (mdtABCD) transporter gene cluster in Escherichia coli and increases its resistance to novobiocin and deoxycholate," J. Bacteriol. 184:4168-4176, (2002). It has been reported that the BaeSR two-component system modulates the drug resistance of E. coli by regulating the expression of drug transporter genes. Baranova, N. and Nikaido, H., "The baeSR two-component regulatory system activates transcription of the yegMNOB (mdtABCD) transporter gene cluster in Escherichia coli and increases its resistance to novobiocin and deoxycholate," J. Bacteriol. 184: 4168-4176, (2002); Nagakubo, S. K., et al., "The putative response regulator BaeR stimulates multidrug resistance of Escherichia coli via a novel multidrug exporter system, MdtABC," J. Bacteriol. 184:4161-4167, (2002). The response regulator BaeR modulates the expression of mdtABC and acrD, which encode multidrug exporter systems. Hirakawa, H. K., et al. "Comprehensive studies on the drug resistance mediated by the overexpression of response regulators of two-component signal transduction systems in

*Escherichia coli*," *J Bacteriol.* 185:1851-1856, (2003); Hirakawa, H. K., et al., "β-Lactam resistance modulated by the overexpression of response regulators of two-component signal transduction systems in *Escherichia coli*," *J. Antimicrob. Chemother.* 52:576-582, (2003). Overproduction of BaeR, in the background of a deficiency of the *E. coli* major multidrug exporter AcrB, reportedly confers resistance against β-lactams, novobiocin, sodium dodecyl sulfate, and bile salts. It is also reported that BaeR increased the expression of the outer membrane channel tolC gene, which is required for the function of the MdtABC, AcrD and other transport systems. Nishino, K., et al., "Roles of TolC-dependent multidrug transporters of *Escherichia coli* in resistance to β-lactams," *Antimicrob. Agents Chemother.* 47:3030-3033, (2003); Nishino, K., and Yamaguchi, A., "Analysis of a complete library of putative drug transporter genes in *Escherichia coli*," *J. Bacteriol.* 183:5803-5812, (2001).

The strains used for the experiment were *E. coli*. MG1655 : : aspC/proA/pProNde in combination with either baeR or no insert in the pUC19 vector. The baeR gene was amplified from *E. coli* W3110 by using primers, *E. coli* baeR-SalIF 5'GGCCTTCCGTCGACATGACCGAGTTAC-CAATC3' (SEQ ID NO. 26) and *E. coli* baeRBamHIR 5'TTC-CAAGGTTGGATCCCTAAACGATGCGGCAGGC3' (SEQ ID NO. 27), which introduced SalI and BamHI sites at the end of the amplified fragment. The PCR fragment was cloned between the SalI and BamHI sites of the vector pUC19 (GenBank/EMBL accession number L09137). For inoculum, the *E. coli* strains were grown overnight at 37° C. and 250 rpm in Luria-Bertani ("LB") medium with 100 µg/mL ampicillin and 50 µg/mL kanamycin.

For the experimental treatments, Trp-1+glucose medium, a minimal medium that has been used for increased production of tryptophan in *E. coli* cells (Zeman et al. *Folia Microbiol.* 35:200-204, (1990)), was prepared as follows. To 800 mL nanopure water the following reagents were added: 2 g $(NE_4)_2SO_4$ and 13.6 g $KH_2PO_4$. The pH was adjusted to 7.0, the volume was increased to 948 mL, and the medium was autoclaved. Following sterilization, 0.2 g $MgSO_4.7H_2O$, 0.01 g $CaCl_2.2H_2O$, and 0.5 mg $FeSO_4.7H_2O$ were a to the medium in a 1.8 mL volume followed by addition of 0.2 mL of Neidhardt's micronutrient solution. Neidhardt F. C., et al., "Culture medium for Enterobacteria," *J. Bacteriol.* 119:736-746 (1974). Neidhardt's medium includes (per liter): 0.18 g $(NH_4)_6(MO_7)_{24}.4H_{2I\ O}$, 1.24 g $H_3BO_3$, 0.36 g $CoCl_2.6H_2O$, 0.12 g $CuSO_4$ (anhydrous), 0.8 g $MnCl_2.4H_2O$, and 0.14 g $ZnSO_4.7H_2O$. A 50% glucose solution was prepared separately and sterile-filtered. Forty mL of glucose solution and 10 mL of 1 M 3-Morpholinopropanesulfonic acid ("MOPS") buffer were added to the base medium (950 mL) for a 1 L final volume.

For treatments, 3.5-5.0 v/v % of inoculum was added to 100 mL medium volume in 500 mL baffled shake flasks with 100 µg/mL ampicillin and 50 µg/mL kanamycin. Conditions for the treatments included 250 rpm agitation throughout and 37° C. up to induction, then, 30° C. following induction. At 0.35-0.38 $OD_{600\ nm}$, induction of the plasmid genes was initiated. At induction, 1.0 mM IPTG, 0.5% L-arabinose, 0.5 mM pyridoxine hydrochloride, and 0.2 mLs of Balch's vitamins were added. Additions of 10 g/L L-tryptophan, 10 g/L sodium pyruvate, 0.04 mM pyridoxal-5'-phosphate ("PLP") and 0.2% Tween® 20 (polyoxyethylene 20-sorbitan monolaurate) were made 3.5 hours following induction. At 24 hours after inoculation, another 10 g/L increment of sodium pyruvate was added to each flask. Some treatments included 2.5 mM sodium decanoate addition at 3.5 hours following induction. Samples for monatin and dry cell weight determination were taken at 24, 30 and 72 hours.

TABLE 19.1

Monatin per dry cell weight excreted by *E. coli*

| Strain | Treatment (sodium decanoate addition in mM) | Mean monatin per dry cell weight (mg/g) | |
|---|---|---|---|
| | | 30 hours | 72 hours |
| *E. coli* MG1655 AspC ProA pProNde del pUC19 | 0 | 2.2 | 2.3 |
| *E. coli* MG1655 AspC ProA pProNde del BaeR pUC19 | 0 | 2.5 | 24.9 | n = 2 for all treatments

Overexpression of baeR resulted in greater monatin excretion with no sodium decanoate when compared to the control strain without baeR overexpression. At 72 hours, the baeR overexpression strain accumulated averages of 24.9 mg monatin per gram dry cell weight compared to 2.3 for the non-baeR control strain under similar conditions. This demonstrates that baeR overexpression without decanoate treatment results in approximately an 11-fold increase in monatin excretion. This effect could be due to activation of mdtABCD or acrD or both transport systems. The native AcrAB system might also play a role in monatin transport. In addition, it is known that BaeR can increase to/C gene expression which is required for the function of several export systems.

TABLE 19.2

Monatin per dry cell weight excreted by *E. coli*

| Strain | Treatment (sodium decanoate addition in mM) | Mean monatin per dry cell weight (mg/g) | |
|---|---|---|---|
| | | 30 hours | 72 hours |
| *E. coli* MG1655 AspC ProA pProNde del pUC19 | 2.5 | 2.4 | 2.7 |
| *E. coli* MG1655 AspC ProA pProNde del BaeR pUC19 | 2.5 | 16.2 | 66.8 | n = 2 for all treatments

Overexpression of baeR resulted in greater monatin excretion with 2.5 mM sodium decanoate when compared to the control strain without baeR overexpression. At 72 hours, the baeR overexpression strain accumulated averages of 66.8 mg monatin per gram dry cell weight compared to 2.7 for the non-baeR strain under similar conditions. This demonstrates that baeR overexpression in combination with decanoate treatment results in approximately 25-fold increased monatin excretion when compared to the treatment without decanoate. It is known that sodium decanoate can activate the AcrAB transport system. In addition, it is known that BaeR can increase tolC gene expression which is required for the function of several export systems. This enhanced monatin efflux may be due to activation of mdtABCD and/or acrD in addition to the AcrAB transport system activation due to decanoate addition.

TABLE 19.3

Monatin per dry cell weight excreted by *E. coli*

| Strain | Mean monatin per dry cell weight (mg/g) | | |
|---|---|---|---|
| | 24 hours | 30 hours | 48 hours |
| *E. coli* MG1655 ΔacrAB AspC ProA pProNde del pUC19 (control) | 10.7 | 29.7 | 39.3 |
| *E. coli* MG1655 ΔacrAB AspC ProA pProNde del BaeR pUC19 | 34.4 | 85.0 | 137.3 | n = 2 for all treatments
2.5 mM sodium decanoate addition for all treatments

It has been reported that the native multi-drug exporter AcrB can mask the effect of baeR overexpression. In order to determine the role of baeR overexpression in the absence of the AcrAB transport system, a host strain with a deletion of the acrAB genes was used. In a ΔacrAB host strain, overexpression of the baeR gene resulted in a 3.5-fold increase in monatin excretion (137.3 to 39.3 mg monatin per g dcw) over the control ΔacrAB strain. This is clear evidence that transporters in addition to AcrAB were involved in monatin transport. In addition, it is known that BaeR can increase tolC gene expression which is required for the function of several export systems in addition to the MdtABCD or AcrD multidrug transport systems. Nishino, K., et al., "Genome-wide analysis of *Escherichia coli* gene expression responsive to the BaeSR two-component regulatory system," *J Bacteriol.* 187:1763-1772, (March 2005). Thus, either MdtABCD or AcrD or both transporter systems were involved in monatin excretion in the acrAB knockout strain.

Thus, we have conclusively demonstrated the positive impact that BaeR has on monatin efflux. It has been reported that indole induces mdtABCD and acrD gene expression via the BaeSR two-component signal transduction system. Nishino, K., et al., "Genome-wide analysis of *Escherichia coli* gene expression responsive to the BaeSR two-component regulatory system," *J Bacteriol.* 187:1763-1772, (March 2005). It is reasonable to expect that indole treatment should also have a positive impact on monatin efflux. The quorum sensing regulator SdiA is reported to control the expression of acrAB and acrD. Wei, Y., et al., "Global impact of sdiA amplification revealed by comprehensive gene expression profiling of *Escherichia coli*," *J. Bacteriol.* 183:2265-2272, (2001). It is also reasonable then to expect that SdiA could have a positive impact on monatin efflux.

Example 20

Increase of Monatin Excretion in *Corynebacterium glutamicum* with Increased Temperature and Sodium Pyruvate Treatments

*C. glutamicum* 13032 strains transformed with aspCProA pEKEX-2 were grown overnight in LB medium supplemented with 25 μg/mL kanamycin incubated at 30° C. and shaking at 250 rpm. For the experimental treatment flasks, 100 mL of Krämer's A medium was used in each shake flask. Hoischen, C. and Krämer, R., "Evidence for an efflux carrier system involved in the secretion of glutamate by *Corynebacterium glutamicum*," *Arch. Microbiol* 151:342-347, (1989). Krämer's A medium contained (per liter): 5 g $(NH_4)_2SO_4$, 5 g urea, 2 g $KH_2PO_4$, 1.53 g $K_2HPO_4$, 0.249 g $MgSO_4.7H_2O$, 50 g glucose, 0.01 g $FeSO_4.7H_2O$, 0.01 g $MnSO_4.H_2O$, 0.01 g $CaCl_2.2H_2O$, 0.03 mg $ZnSO_4.7H_2O$, 0.1 mg $H_3BO_3$, 0.07 mg $CaCl_2.6H_2O$, 0.01 mg $NiCl_2.2H_2O$, 0.03 mg $CuCl_2.2H_2O$, 0.1 mg as $Mo^{+6}$ from $(NH_4)_6Mo_7O_{24}.4H_2O$ and 1 μg biotin. The pH was adjusted to 7.0.

For treatments, 3.5-5.0 v/v % of inoculum was added to 100 mL medium volume in 500 mL baffled shake flasks. Conditions for treatments included 30° or 35° C. throughout the experiment and 250 rpm agitation. At an $OD_{600\ nm}$, between 0.45-0.51, induction of the monatin operon genes was initiated. IPTG at 1.0 mM was used for induction, and additions at the time of induction included 0.2 mLs of Balch's 1000× vitamin stock and 0.5 mM pyridoxine hydrochloride. Additions of 1.0 g L-tryptophan, 10 or 15 g/L sodium pyruvate, 0.04 mM pyridoxal-5'-phosphate ("PLP"), were made 3 hours and also at 24 hours following induction. A total of 20 or 30 g/L sodium pyruvate was added to each flask by adding 10 or 15 g/l at each of the two feeding times. Samples for monatin and dry cell weight determination were taken at 24, 30 and 48 hours.

TABLE 20.1

Increasing temperature and pyruvate resulted in increased monatin efflux per dry cell weight

| Treatment | Monatin/dry cell weight (mg/g) | | | |
|---|---|---|---|---|
| | 24 hours | 31 hours | 48 hours | 54 hours |
| 30° C., 20 g/L pyruvate | 0.2 | 2.1 | 2.7 | 2.7 |
| 30° C., 30 g/L pyruvate | 0.3 | 1.8 | 4.3 | 4.7 |
| 35° C., 20 g/L pyruvate | 5.4 | 14.7 | 23.5 | 23.8 |
| 35° C., 30 g/L pyruvate | 5.8 | 18.1 | 29.4 | 35.2 |

At 30° C., increased levels of sodium pyruvate resulted in increased monatin per dry cell weight (4.7 mg/g vs. 2.7 at 54 hours). At 35° C., additional pyruvate increased the monatin per dry cell weight even further from 23.8 to 35.2 mg/g. An increase of 5° C. resulted in a 7 to 9 fold increase in monatin per dry cell weight. Increased temperature from 30 to 35° C. also reduced dry cell weight from 7.48 g/L to 2.50 g/L. Both temperature and sodium pyruvate were highly statistically significant factors for monatin per dry cell weight in the factorial design experiment with 16 total treatments. The increased yield of monatin with a reduction in biomass suggests that a change in carbon flux distribution occurred. Ohnishi, J., et al., *Appl Microbiol Biotechnol* 62:69-75, (2003).

Thus we have demonstrated that through manipulation of the amount of sodium pyruvate added and the incubation temperature of the organism, monatin efflux can be increased. Presumably this increased efflux in monatin is accompanied by an increased in monatin production, but the impact of factors on monatin efflux itself cannot be ruled out. The continued use of statistical design of experiments, known in the art, to vary growth media composition and growth conditions, can be used to increase the amount of monatin produced and effluxed out of the cell. Further benefits in monatin efflux may be obtained through the use of ethambutol in combination with, but not limited to, one or more of the following reagents that are known to affect the mycolic acid layer of *Coryenbacterium*, including Tween®, biotin, and/or ampicillin.

Example 21

Increase of Monatin Excretion in *Corynebacterium glutarnicum* with Biotin and Ampicillin Treatments

*C. glutamicum* ATCC 13032 strains transformed with aspCProA pEKEX-2 were grown overnight in LB medium supplemented with 50 μg/mL kanamycin incubated at 30° C. and shaking at 250 rpm. For the experimental treatment flasks, 100 mL of Krämer's A medium was used in each shake flask. Hoischen, C. and Krämer, R., "Evidence for an efflux carrier system involved in the secretion of glutamate by *Corynebacterium glutamicum,*" *Arch. Microbiol* 151:342-347, (1989). Krämer's A medium contained (per liter): 5 g $(NH_4)_2SO_4$, 5 g urea, 2 g $KH_2PO_4$, 1.53 g $K_2HPO_4$, 0.249 g $MgSO_4.7H_2O$, 50 g glucose, 0.01 g $FeSO_4.7H_2O$, 0.01 g $MnSO_4.H_2O$, 0.01 g $CaCl_2.2H_2O$, 0.03 mg $ZnSO_4.7H_2O$, 0.1 mg $H_3BO_3$, 0.07 mg $CaCl_2.6H_2O$, 0.01 mg $NiCl_2.2H_2O$, 0.03 mg $CuCl_2.2H_2O$, 0.1 mg as $Mo^{+6}$ from $(NH_4)_6Mo_7O_{24}.4H_2O$ and 1 μg or 200 μg biotin. The pH was adjusted to 7.0.

For treatments, inoculum was added to 0.100 absorbance (600 nm) in 100 mL medium volume in 500 mL baffled shake flasks. Conditions for treatments included 37° C. throughout the experiment and 250 rpm agitation. At 0.26-0.33 $OD_{600\,nm}$, induction of the monatin operon genes was initiated. IPTG at 0.5 mM was used for induction and 1.0 mM pyridoxine hydrochloride and 0.04 mM pyridoxal-5'-phosphate ("PLP") were also added at the time of induction. Additions of 1.0 g L-tryptophan and 5 g/L sodium pyruvate and ampicillin (either 0 or 10 μg/ml) were made 3 hours following induction. Samples for monatin and dry cell weight determination were taken at 24 and 48 hours.

TABLE 21.1

Addition of ampicillin and reduction of biotin resulted in increased monatin efflux per dry cell weight

| Treatment combination | Ampicillin (μg/mL) | Biotin (μg/L) | Monatin/dry cell weight (mg/g) | |
|---|---|---|---|---|
| | | | 24 hours | 48 hours |
| 1 | 0 | 200 | 0.9 | 1.7 |
| 2 | 0 | 1 | 1.9* | 4.5 |
| 3 | 10 | 200 | 12.1 | 9.3 |
| 4 | 10 | 1 | 16.2 | 13.5 | n = 2 or 3 depending on treatment combination
*n = 1

Addition of ampicillin at 3 hours following induction resulted in a 3 to 12 fold increase in monatin per dry cell weight. Reduction in biotin from 200 to 1 μg/L in the initial medium resulted in an increase in monatin per dry cell weight by 1.0 to 4.2 mg/g. The treatment combination of ampicillin and biotin (10 μg/mL and 1 μg/L, respectively) increased monatin per dry cell weight by 7.9 to 18 fold (13.5/1.7 and 16.2/0.9).

Thus we have demonstrated that through manipulation of the amount of biotin and ampicillin that the host organism is exposed to, monatin efflux can be increased. Presumably this increased efflux in monatin is accompanied by an increase in monatin production, but the direct impact of biotin and/or ampicillin on monatin efflux itself cannot be ruled out.

The continued use of statistical design of experiments, known in the art, to vary growth media composition and growth conditions, can be used to increase the amount of monatin produced and effluxed out of the cell. Further benefits in monatin efflux may be obtained through the use of ethambutol in combination with, but not limited to, one or more reagents that are known to affect the mycolic acid layer of *Corynebacterium,* including Tween®, biotin, and/or ampicillin. Eggeling, L. and Sahm, H., "The Cell Wall Barrier of *Corynebacterium glutamicum* and Amino Acid Efflux," *J. BioSci. and BioEng.* 92:201-213, (2001).

Example 22

Increase of Monatin Excretion in *Corynebacterium* Using Ethambutol

It was reported that the addition of ethambutol ("EMB") to growing cultures of *C. glutamicum* resulted in L-glutamate efflux whereas in the absence of EMB, no efflux occurred. Radmacher, E., et al., "Ethambutol, a cell wall inhibitor of *Mycobacterium tuberculosis,* elicits L-glutamate efflux of *Corynebacterium glutamicuin,*" *Microbiology* 151:1359-1368, (May 2005). EMB reportedly targets a series of arabinosyltransferases (EmbCAB) at the molecular level. A single arabinosyltransferase-encoding emb gene of *C. glutamicum* was placed under the control of a Tet repressor ("TetR"). Experiments with this strain, as well as with an emb-overexpressing strain, coupled with biochemical analyses showed that emb expression was correlated with L-glutamate efflux, and increased EMB resistance. In addition EMB caused less arabinan deposition in cell wall arabinogalactan, and a reduced content of cell-wall-bound mycolic acids. Thus, EMB addition resulted in a marked disordering of the cell envelope, which was also borne out through examination of the cellular morphology.

Because it is known that an altered lipid composition of the plasma membrane of *C. glutamicum* can result in L-glutamate efflux, it has been speculated that major structural alterations of the cell envelope are transmitted to the membrane, which in turn activates an export system, perhaps via increased membrane tension. Radmacher, E., et al., "Ethambutol, a cell wall inhibitor of *Mycobacterium tuberculosis,* elicits L-glutamate efflux of *Corynebacterium glutamicum,*" *Microbiology* 151: 1359-1368, (May 2005).

*C. glutamicum* ATCC 13032 strains transformed with aspCProApEKEX-2 were grown overnight in LB medium supplemented with 25 μg/mL kanamycin incubated at 30° C. and shaking at 250 rpm. For the experimental treatment flasks, 100 mL of Krämer's A medium was used in each shake flask. Hoischen, C. and Krämer, R., "Evidence for an efflux carrier system involved in the secretion of glutamate by *Corynebacterium glutamicum,*" *Arch. Microbiol* 151:342-347, (1989). Krämer's A medium contained (per liter): 5 g $(NH_4)_2SO_4$, 5 g urea, 2 g $KH_2PO_4$, 1.53 g $K_2HPO_4$, 0.249 g $MgSO_4.7H_2O$, 50 g glucose, 0.01 g $FeSO_4.7H_2O$, 0.01 g $MnSO_4.H_2O$, 0.01 g $CaCl_2.2H_2O$, 0.03 mg $ZnSO_4.7H_2O$, 0.1 mg $H_3BO_3$, 0.07 mg $CaCl_2.6H_2O$, 0.01 mg $NiCl_2.2H_2O$, 0.03 mg $CuCl_2.2H_2O$, 0.1 mg as $Mo^{+6}$ from $(NH_4)_6Mo_7O_{24}.4H_2O$ and 1 μg biotin. The pH was adjusted to 7.0.

For treatments, 3.5-5.0 v/v % of inoculum was added to 100 mL medium volume in 500 mL baffled shake flasks. Conditions for the treatments included 30° C. throughout the experiment and 250 rpm agitation. Ethambutol (10 mg/L) was added either prior to inoculation of shake flasks or at the first feeding time when tryptophan and pyruvate were added. At 0.40-0.51 $OD_{600\,nm}$, induction of the monatin operon genes was initiated. IPTG at 1.0 mM was used for induction, and additions at the time of induction included 0.2 mLs of Balch's vitamins and 0.5 mM pyridoxine hydrochloride. Additions of 1 g L-tryptophan, 10 g/L sodium pyruvate, 0.04 mM pyridoxal-5'-phosphate ("PLP"), were made 3 hours following induction. Samples for monatin and dry cell weight determination were taken at 24, 30/31 and 48 hours.

TABLE 22.1

Ethambutol addition increased monatin per dry cell weight

| | ethambutol | Monatin/dry cell weight (mg/g) | | |
|---|---|---|---|---|
| Strain | (mg/L) | 24 hours | 31 hours | 48 hours |
| C. glutamicum 13032::aspC/proA/ pEKEX2-2 | 0 | 0.43 | 0.47 | 0.51 |
| C. glutamicum 13032::aspC/proA/ pEKEX2-2 | 10 | 1.16 | 1.15 | 1.06 | n = 2 for all treatments

Monatin excretion (mg/g dry cell weight) increased with ethambutol addition. At 48 hours, the 10 mg/L ethambutol treatment resulted in an average of 1.06 mg of monatin per gram dry cell weight, while the control without ethambutol excreted 0.51 mg of monatin per gram dry cell weight on average.

TABLE 22.2

Ethambutol addition with additional sodium pyruvate increased monatin per dry cell weight

| | ethambutol | Monatin/dry cell weight (mg/g) | | |
|---|---|---|---|---|
| Strain | (mg/L) | 24 hours | 31 hours | 48 hours |
| C. glutamicum 13032::AspC/ProA/ pEKEX2-2 | 0 | 0.43 | 0.47 | 0.51 |
| C. glutamicum 13032::AspC/ProA/ pEKEX2-2 | 10 | 1.04 | 1.53 | 2.19 | n = 2 for all treatments

With another 10 g/L sodium pyruvate dosage at 24 hours following inoculation, a further increase in monatin production/excretion was observed. At 48 hours, the 10 mg/L ethambutol treatment with the additional sodium pyruvate supplementation, had 2.19 mg/g of monatin per dry cell weight on average versus 1.06 without additional pyruvate at 24 hours for the same ethambutol addition.

TABLE 22.3

Ethambutol addition combined with Tween ®/ampicillin treatment further increased monatin per dry cell weight

| | ethambutol | Monatin/dry cell weight (mg/g) | | |
|---|---|---|---|---|
| Strain | (mg/L) | 24 hours | 30 hours | 48 hours |
| C. glutamicum 13032::AP pEKEX2-2 | 0 | 0.30 | 0.33 | 0.74 |
| C. glutamicum 13032::AP pEKEX2-2 | 10 | 6.94 | 8.80 | 9.14 | n = 2 for all treatments

With addition of 0.2% Tween® 20 (polyoxyethylene 20-sorbitan monolaurate) and 10 µg/ml ampicillin at feeding time (3 hours following induction time) combined with ethambutol treatment, monatin excretion was observed to increase even more. There was a synergistic effect between Tween®, ampicillin and ethambutol treatment that was favorable for monatin efflux. The Tween®/ampicillin treatment with 10 mg/L ethambutol resulted in 12-fold greater monatin excreted per dry cell weight than the same treatment without ethambutol addition (9.14 mg monatin/g dry cell weight versus 0.74 monatin/g dry cell weight, respectively).

Thus we conclusively demonstrated that ethambutol addition has a positive impact on monatin efflux in *Corynebacterium*. These data also suggest that monatin may be excreted via the same transporter as glutamate because it is reported that ethambutol affects only glutamate excretion and not excretion of other amino acids. Radmacher E., et al., "Ethambutol, a cell wall inhibitor of *Mycobacterium tuberculosis*, elicits L-glutamate efflux of *Corynebacterium glutamicuin*," *Microbiology*, 151:1359-68, (May 2005). In addition, we also demonstrated that the positive effect of ethambutol treatment combined, with Tween® and ampicillin, results in an amplified monatin efflux response in *Corynebacterium* that is greater than that observed with ethambutol alone.

Example 23

Increase of Monatin Excretion in a Host Strain with a cysH Deletion

CysH (Phosphoadenylyl sulfate ("PAPS") reductase), icdA (isocitrate dehydrogenase), metE, or purB (adenylosuccinate lyase) mutations have been reported to cause an activation of the AcrAB transport system. The metabolites that accumulate upstream of the blocks caused by the mutations could increase the levels of the AcrAB-TolC pump. Helling R. B., et al., "Toxic waste disposal in *Escherichia coli*," *J Bacteriol.* 184:3699-3703, (2002). We tested the impact that a cysH deletion had on monatin efflux.

Primers were designed to create the desired knockout in *E. coli* BL21DE3 by PCR from template pKD4 as described. Datsenko, K. A., and Wanner, B. L., "One-step inactivation of chromosomal genes in *Escherichia coli* K-12 using PCR products," *Proceed. Natl. Acad. Sci. USA* 97:6640-6645, (2000).

cysH knockout primer sequences:

```
E. coli cysHKO-Forward
                                    (SEQ ID NO. 28)
5'CGCGTGAGCGTCGCATCAGGCAAGGCAAACAGTGAGGAATCTATGTCC

AAAGTGTAGGCTGGAGCTGCTTC 3'

E. coli cysHKO-reverse
                                    (SEQ ID NO. 29)
5'CGCCCCCATCATTTCTGACAGAGGCGTTTAATTTGTCCGGCAATATTT

ACCCTTCCATATGAATATCCTCCTTAG 3'.
```

The PCR products for deletion of cysH were amplified using the following PCR protocol. In a 100 µL reaction, 1 µL template (pKD4) (Datsenko, K. A., and Wanner, B. L., "One-step inactivation of chromosomal genes in *Escherichia coli* K-12 using PCR products," *Proceed. Natl. Acad. Sci. USA* 97:6640-6645, (2000)), 0.4 µM of each primer, 0.4 mM each dNTP, 1× PCR buffer, and 2 µL Pfu Turbo Polymerase (Stratagene, La Jolla, Calif.) were used. The thermocycler program used included a hot start at 94° C. for 30 seconds, 30 repetitions of the following steps: 94° C. for 1 minute, 55° C. for 1 minute, and 72° C. for 4 minutes. After the 30 repetitions the sample was maintained at 72° C. for 10 minutes and then stored at 4° C. This PCR protocol produced a product of 1.6 Kb.

The PCR product was purified using the Qiagen PCR Cleanup kit (Valencia, Calif.). The PCR product was quantified using a SmartSpec 3000™ spectrophotometer.

The purified PCR product was used to transform *E. coli* strain BW25113/pKD46. Datsenko, K. A., and Wanner, B. L., "One-step inactivation of chromosomal genes in *Escherichia* coli K-12 using PCR products, *Proceed. Natl. Acad. Sci. USA* 97:6640-6645 (2000). 1 µL of the PCR product was added to 40 µL of cells, which were transformed by electroporation using the BioRad Gene Pulsar II under the following conditions: 2.5 kV, 25 µF, 200 ohm in a 0.2 cm cuvette. The cells were allowed to recover in 500 µL of SOC for 3 hours at 37° C. with shaking at 225 rpm. Cells were plated on LB plates containing kanamycin (50 µg/mL). The plates were incubated at 37° C. overnight. Five kanamycin-resistant transformants were colony PCR-screened to confirm product.

Lysate production: P1 phage lysate was made for the BW25113ΔcysH strain, to allow transfer of the knockout into the *E. coli* BL21DE3 production host. The donor strain was grown overnight in LB medium containing 25 µg/mL kanamycin. The culture was used to inoculate fresh LB medium containing 5 mM $CaCl_2$ using a 1:10 dilution and were incubated for 70 minutes at 37° C. One mL of culture was incubated with 3 µL or 5 µL of a phage stock (ATCC 25404-B1) at 37° C. for 20 minutes. The phage/culture was then mixed with 4 mL of soft agar containing 5 mM $CaCl_2$ and overlaid on LB medium. Control experiments were set up using no phage. The plates were incubated at 37° C., right-side up, for 5 hours, after which confluent lysis was observed for all plates containing phage; the control plates had cell lawns as expected. The plates were incubated overnight at 37° C., after which phage-resistant colonies were observed on experimental plates as expected. The soft agar from each plate was scraped into a centrifuge tube using a sterile disposable loop. Two mL of LB was used to rinse the plate, and the rinse was combined with the soft agar in the centrifuge tube. Five drops of chloroform were added to the tubes, which were gently mixed and incubated at room temperature for 20 minutes. The mixtures were centrifuged at 10,000×g for 10 minutes and the supernatants were filtered with a 0.2 µm syringe filter to obtain phage lysates. The phage lysate was stored at 4° C.

Transduction into production host: The cysH knockout was transferred to strain *E. coli* BL21DE3 by P1 transduction to generate strain BL21DE3ΔcysH. *E. Coli* BL21DE3ΔcysH was grown overnight in LB medium containing 25 µg/mL chloramphenicol. The culture was used to inoculate 5 mL of fresh LB medium, supplemented with 5 mM $CaCl_2$ using a 1:10 dilution. The subculture was incubated for 60 minutes at 37° C. The culture was centrifuged, resuspended in 500 µL of MC buffer (0.1 M $MgSO_4$, 5 mM $CaCl_2$), and incubated at room temperature for 20 minutes. Various dilutions of the donor lysate (1:100 to 1× in MC buffer) were added in equal volume to 100 µL of culture. The mixtures were incubated for 20 minutes at 37° C., after which 200 µL of citrate buffer (0.1 M citric acid and 220 mM NaOH adjusted to pH 5.5) and one mL of LB were added to each tube. The cultures were incubated at 37° C. for one hour with agitation at 200 rpm, followed by centrifugation to obtain a cell pellet. The cell pellets were resuspended in 100 µL of citrate buffer and plated on LB medium containing 25 µg/mL kanamycin. Single kanamycin-resistant colonies were purified by restreaking on appropriate selective media.

Single kanamycin-resistant colonies were tested for cysteine and methionine auxotrophy (the phenotype which would confirm cysH deletion) by growth on M9 media supplemented with L-cysteine and/or L-methionine.

For inoculum, the *E. coli* strains BL21 DE3 aspC proA pET32 and BL21 DE3 ΔcysH: : aspCproA pET32 were grown overnight at 37° C. and 250 rpm in Luria-Bertani ("LB") medium with 100 µg/mL ampicillin.

For the experimental treatments, Trp-1+glucose medium, a minimal medium that has been used for increased production of tryptophan in *E. coli* cells (Zeman et al. *Folia Microbiol.* 35:200-204, (1990)), was prepared as follows. To 800 mL nanopure water the following reagents were added: 2 g $(NH_4)_2SO_4$ and 13.6 g $KH_2PO_4$. The pH was adjusted to 7.0, the volume was increased to 948 mL, and the medium was autoclaved. Following sterilization, 0.2 g $MgSO_4.7H_2O$, 0.01 g $CaCl_2.2H_2O$, and 0.5 mg $FeSO_4.7H_2O$ were ad to the medium in a 1.8 mL volume followed by addition of 0.2 mL of Neidhardt's micronutrient solution. Neidhardt, F. C., et al., "Culture medium for Enterobacteria," *J. Bacteriol.* 119:736-746 (1974). Neidhardt's medium includes (per liter): 0.18 g $(NH_4)_6(MO_7)_{24}.4H_2O$, 1.24 g $H_3BO_3$, 0.36 g $CoCl_2.6H_2O$, 0.12 g $CuSO_4$ (anhydrous), 0.8 g $MnCl_2.4H_2O$, and 0.14 g $ZnSO_4.7H_2O$. A 50% glucose solution was prepared separately and sterile-filtered. Forty mL of glucose solution and 10 mL of 1 M 3-Morpholinopropanesulfonic acid ("MOPS") buffer were added to the base medium (950 mL) for a 1 L final volume.

For treatments, 3.0-5.0 v/v % of inoculum was added to 100 mL medium volume in 500 mL baffled shake flasks with 100 µg/mL ampicillin. Conditions for the treatments included 250 rpm agitation throughout and 37° C. up to induction, then, 30° C. following induction. At an $OD_{600\ nm}$ between 0.44-0.52, induction of the plasmid genes was initiated. At induction, 1.0 mM IPTG, 0.5 mM pyridoxine hydrochloride, and 0.2 mL's of Balch's vitamins were added. Additions of 10 g/L L-tryptophan, 10 g/L sodium pyruvate, 0.04 mM pyridoxal-5'-phosphate ("PLP") and 0.2% Tween® 20 (polyoxyethylene 20-sorbitan monolaurate) were made 3.0 hours following induction. At 3 hours after the initial feeding of pyruvate, another 10 g/L of sodium pyruvate was added to each flask. Some treatments included 2.5 mM sodium decanoate (or sterile, distilled water for the 0 mM decanoate treatment) addition at 3.0 hours following induction. Samples for monatin and dry cell weight determination were taken at 24, 30 and 48 hours.

TABLE 23.1

Monatin per dry cell weight excreted by *E. coli* with no decanoate addition

| Strain | Sodium decanoate (mM) | Monatin/dry cell wt. (mg/g) | | |
|---|---|---|---|---|
| | | 24 hours | 30 hours | 48 hours |
| *E. coli* BL21 DE3 aspC proA pET32 | 0 | 4.6 | 5.2 | 4.2 |
| *E. coli* BL21 DE3 ☐cysH::aspC proA pET32 | 0 | 6.8 | 10.8 | 21.4 | n = 2

Without sodium decanoate addition, the ΔcysH mutant excreted greater than 5 fold more monatin per dry cell weight by 48 hours than the control strain (21.4 vs. 4.2 mg/g). These results demonstrated that the ΔcysH mutant strain excreted more monatin. This effect is most likely due to induction of the AcrAB and/or other transport systems.

TABLE 23.2

Monatin per dry cell weight excreted by E. coli with addition of sodium decanoate

| Strain | Sodium decanoate (mM) | Monatin/dry cell wt. (mg/g) | | |
|---|---|---|---|---|
| | | 24 hours | 30 hours | 48 hours |
| E. coli BL21 DE3 aspC proA pET32 | 2.5 | 70.9 | 75.0 | 44.0 |
| E. coli BL21 DE3 ΔcysH::aspC proA pET32 | 2.5 | 115.0 | 103.1 | 73.3 | n = 2

With the addition of sodium decanoate which is an inducer of the AcrAB transport system, even greater amounts of monatin were excreted in the ΔcysH mutant. The mutant strain excreted greater than 100 mg/g of monatin per dry cell weight by 24 hours. This is greater than 60% more than the control strain (115.0 vs. 70.9 mg monatin/g dry cell weight). These results confirmed that the ΔcysH mutant strain excreted more monatin. This effect is most likely due to induction of the AcrAB and/or other transport systems. The fact that maximum monatin efflux was observed with a combination of the ΔcysH mutant and sodium decanoate addition points to the involvement of the AcrAB transport system and/or other transport systems.

Because cysH, icdA (isocitrate dehydrogenase), metE, or purB (adenylosuccinate lyase) mutations have all been reported to cause an activation of the AcrAB transport system (Helling, R. B., et al., "Toxic waste disposal in *Escherichia coli*," *J. Bacteriol.* 184:3699-3703, (2002), we would expect an increased monatin efflux in strains with deletions in one or more of the following genes: cysH, iedA, metE, or purB Example 24

AcrEF Transporter System May Impact Monatin Efflux

*Escherichia coli* produces indole, a metabolite of tryptophan, under certain physiological conditions. Inactivation of the acrEF gene, the product of which is an energy-dependent multiple drug efflux pump, was shown to decrease indole excretion. Reintroduction of the acrEF gene restored indole excretion. A delta acrEF mutant reportedly accumulated more intracellular indole than the parent. This mutant was more susceptible to the growth-inhibitory effect of indole than the parent. These results were taken as evidence that the AcrEF system plays a significant role in indole efflux. Kawamura-Sato, K, et al., "Role of multiple efflux pumps in *Escherichia coli* in indole expulsion," *FEMS Microbiol Lett.* 179:345-352, (1999). Inactivation of the envR gene results in over-expression of the AcrEF transport system.

Primers were designed to create the ΔenvR knockout product by PCR from template pKD3. Datsenko, K. A. and Wanner, B. L., "One-step inactivation of chromosomal genes in *Escherichia coli* K-12 using PCR products," *Proceed. Natl. Acad. Sci. USA* 97:6640-6645, (2000).

The ΔenvR knockout product was constructed and amplified using Pfu Turbo DNA polymerase (Stratagene, La Jolla, Calif.) and pKD3 (Datsenko, K. A., and Wanner, B. L., "One-step inactivation of chromosomal genes in *Escherichia coli* K-12 using PCR products," *Proceed. Natl. Acad. Sci. USA* 97:6640-6645, (2000)) as a template and primers ENVR1 (5' CACTCTGTGTCGAATATATTTATTTCCT-GAATAATTAATCTGGTGTA GGCTGGAGCTGCTTC 3' (SEQ ID NO. 30)) and ENVR2 (5' ACTGTGACGAACT-GAATTTTCAGGACAGAATGTGAATTTACATATG AATATCCTCCTTA 3' (SEQ ID NO. 31)). The thermnocycler program used included a hot start at 95° C. for 2 minutes, 10 repetitions of 95° C. for 30 seconds, 50° C. for 30 seconds, and 72° C. for 2 minutes, followed by 25 cycles of incubations at 95° C. for 30 seconds, 58° C. for 30 seconds, and 72° C. for 2 minutes. The final step was incubation at 70° C. for 7 minutes. The PCR product from two PCR reactions (200 μL total volume) was purified using the QIAquick Gel Extraction Kit (Qiagen Hilden, Germany) using the manufacturer's instructions. The ΔenvR knockout PCR product was eluted with 10 μL of double distilled water.

Strain BW25113/pKD46 (Datsenko, K. A. and Wanner, B. L., "One-step inactivation of chromosomal genes in *Escherichia coli* K-12 using PCR products," Proceed. Natl. Acad. Sci., USA, 97:6640-6645, (2000)) was transformed with 1 μL of PCR product (250 ng) by electroporation using the Gene Pulsar II Electroporation system (Bio-Rad, Hercules, Calif.) as recommended by the manufacturer and plated on LB solid media with chloramphenicol 10 μg/mL after a 150 minutes of outgrowth in SOC medium (Molecular Cloning, A Laboratory Manual 3rd Edition 2001, Sambrook and Russell, Cold Spring Harbor Laboratory Press, NY USA). The plates were incubated at 37° C. overnight.

Chloramphenicol resistant colonies were screened by PCR to determine the status of the envR locus. Colony PCR with primers ENVR3 (5' CCTCTCGTATAAATACACATTAGGT-GATAGATTAACCTTCG 3' (SEQ ID. NO. 32)) and ENVR4 (5' GCAACAGAAACAGACAAATGCCGCAATATG 3' (SEQ ID NO. 33)) resulted in a 1.2 kb band or a 0.8 kb if envR was disrupted by the chloramphenicol resistant gene or if envR gene was not disrupted, respectively. ΔenvR deletion strains were identified and named BW25113 ΔEnvR.

To generate the lysate, P1 phage lysates were made from BW25113 ΔEnvR as described in Example 3 to allow transfer of the knockouts into the *E. coli* MG1655 monatin production strain.

For transduction into production hosts, the envR deletion was transferred to strain *E. coli* MG1655 containing the plasmid paspCproA ProNdedel as described in Example 3 for emrB and acrAB knockouts. Strains with the deleted envr gene were selected by plating on LB plates containing 25 μg/mL of chloramphenicol and 50 μg/mL of kanamycin. A ΔenvR deletion strain was identified and named MG1165 ΔEnvR pApProNdedel.

To allow the disruptions of other genes in MG1165 ΔEnvR pApProNdedel background, the chloramphenicol resistant marker was excised from the envR locus. MG1165 ΔEnvR pApProNdedel was transformed with 15 ng of pCP20 (Datsenko, K. A. and Wanner, B. L., "One-step inactivation of chromosomal genes in *Escherichia coli* K-12 using PCR products," *Proceed. Natl. Acad. Sci. USA* 97:6640-6645, (2000)) using the Transformation and Storage Solution protocol (TSS, Epicentre Biotechnologies, Madison, Wis.) as recommended by the manufacture. After an outgrowth of 30 minutes at 30° C., the cells were plated on LB plates containing 50 μg/mL of ampicillin and 25 μg/mL of kanamycin and incubated overnight at 30° C. Single colonies were obtain and replated for single colonies on LB plates containing 25 μg/mL of kanamycin and incubated at 42° C. overnight. Single colonies from the previous step, were replica plated on LB containing 25 μg/mL of kanamycin and on plates containing 25 μg/mL of chloramphenicol. Chloramphenicol-sensitive kanamycin-resistant strains were tested for loss of the chloramphenicol marker from the envR locus by colony PCR using primers ENV3 and ENVR4 as described above. Amplification of the envR locus that had lost the chloramphenicol resistant marker resulted in a 0.3 kb band in contrast to a 1.2 kb band produced from the amplification of the envR locus containing the chloramphenicol resistant marker. The resulting strain was named MG1165 ΔEnvR pApProNdedel CanS. The emrB and or acrAB genes can now be disrupted in the same manner as described in Example 3.

Because the AcrAB and EmrAB transport systems can also transport monatin, the impact of the envR deletion, and consequent activation of the AcrEF transport system, on monatin transport, will probably be most prominent in a host strain that has one, or both, of the AcrAB and EmrAB transport systems deleted.

Given the structural similarities between indole and monatin, it would be expected that the AcrEF transporter would function for indole-3-pyruvate efflux as well. Consequently, it may be possible that a deletion of the gene that encodes the AcrEF transporter might prevent monatin intermediates from leaking out of the cell; thus allowing more flux into monatin production. At the same time, the AcrEF transporter may function for monatin efflux. Example 25 shows that a transporter that effluxes indole-3-acetic acid also functions for monatin efflux. The decision to inactivate or overexpress the AcrEF transport system will depend on the relative rate of monatin transport to indole-3-pyruvate transport.

Example 25

Increase of Monatin Excretion with Overexpression of the *Arabidopsis* Auxin Transporter Auxin (primarily indole-3-acetic acid, IAA) is a plant hormone. The directional transport of auxin has been shown to be essential for normal plant growth and development and is mainly mediated by an efflux carrier complex that is characterized by the PIN-FORMED (PIN) family of proteins. Plant orthologs of mammalian multidrug-resistance/P-glycoproteins (MDR/PGPs) also function in auxin efflux. MDR/PGPs are reported to stabilize efflux complexes on the plasma membrane and to function as ATP-dependent auxin transporters. The specificity and directionality of transport is reportedly provided by interacting PIN proteins. Blakeslee J. J., et al., "Auxin transport," *Curr. Opin. Plant Biol.* 8:494-500, (October 2005). Other researchers have suggested an involvement of MDR/PGP-like ABC transporters in transport of the auxin and, AtPGP1 (NP_181228) has been directly implicated in the primary active export of auxin (MDR-like ABC transporter AtPGP4 is involved in auxin-mediated lateral root and root hair development. Santelia D., et al., *FEBS Lett.* 579: 5399-5406, (October 2005); Geisler M., et al., "Cellular efflux of auxin catalyzed by the *Arabidopsis* MDR/PGP transporter AtPGP1," *The Plant Journal* 44:179 (2005)). Because some aspects of monatin have structural similarities with auxin, the use of auxin transporters to efflux monatin was investigated.

*Arabidopsis thaliana* mRNA (Cat # M1634310) was obtained from Biochain (Hayward, Calif.). The mRNA was diluted 10 fold to a final concentration of 50 ng/μL with RNAse free water. cDNA was made from the mRNA using the Reverse Transcription System (Promega, Madison, Wis.) and Random Primers as described but using 100 ng of mRNA instead of 1 μg of total RNA as template.

The AtPGP1 gene was amplified in three parts by PCR using Pfu Turbo DNA polymerase (Stratagene, La Jolla, Calif.) and *Arabidopsis thaliana* cDNA as a template. From base 1 to 1453 of the open reading frame was amplified using primers PGP1 (5' CATATGATGGATAATGACGGTGGT-GCTCCTCCTCC 3' (SEQ ID NO. 34)) and PGP2 (5' CATTTGCGACTCGAGCAGCCTCCTCTATCTC 3' (SEQ ID NO. 35)). This introduced an Nde I restriction site at the 5' of the open reading frame. An annealing temperature of 63° C. and extension time of 2 minutes was used. The PCR fragment was purified by agarose gel electrophoresis and extracted using the QIAquick® Gel Extraction Kit (Qiagen Hilden, Germany) as recommended by the manufacture. The purified PCR product was cloned into pCR4.0 Blunt-TOPO (Invitrogen, Carlsbad, Calif.) as recommended the manufacture. The sequence was verified by direct sequencing (Agencourt, Beverly Mass.). The resulting plasmid was named pAtPGP1-5'. From base 1423 to 2829 of the open reading frame was amplified using primers PGP3 (5' GAGATAGAGGAG-GCTGCTCGAGTCGCAAATG 3' (SEQ ID NO. 36)) and PGP4 (5' GAGAGCATAAGATGCATAAAGACA-GAACTGAGCTACACC 3' (SEQ ID NO. 37)). An annealing temperature of 55° C. and extension time of 2 minutes was used. The PCR fragment was purified, cloned into pCR4.0 Blunt-TOPO and the sequence verified, as described above. The resulting plasmid was named pAtPGP1-C. From base 2791 to 3861 of the open reading frame was amplified using primers PGP5 (5' GCGGCCGCCTAAGCATCATCTTCCT-TAACCCTAGAACTTGAACCTG AC 3' (SEQ ID NO. 38)) and primers PGP6 (5' GGTGTAGCTCAGTTCTGTCTT-TATGCATCTTATGCTCTC 3' (SEQ ID NO. 39)). An annealing temperature of 55° C. and extension time of 2 minutes was used. This introduced a Not I restriction site at the end of the open reading frame. The PCR fragment was purified, cloned into pCR4.0 Blunt-TOPO and the sequence verified as described earlier. The resulting plasmid was named pAt-PGP1-3'.

Once the three pieces were individually cloned, the 3' and the center piece were ligated together. The resulting piece was then ligated with the 5' piece to reassemble the full open reading frame and placed in the final plasmid. pAtPGP1-C, pAtPGP1-3', and pBluescript SK-(Stratagene, La Jolla, Calif.) were digested with either Xho I and Nsi I, Nsi I and Not I, or Xho I and Not I, respectively. The 1.4 kb (pAtPGP1-C), 1.0 kb (pAtPGP1-3') and 3.0 kb (pBluescript® SK-) fragments were purified by agarose gel electrophoresis and extracted as described above. The purified fragments were ligated using Quick Ligation Ligase (New England Biolabs, Ipswich, Mass.) using the manufacturer's instructions. The resulting plasmid was named pAtPGP1-C3'. pAtPGP1-C3', pAtPGP1-5', and pProNdedel were digested with either Xho I and Not I, Nde I and Not I, or Nde I and Not I, respectively. The 2.4 kb (pAtPGP1-C3'), 1.4 kb (pAtPGP1-5') and 2.6 kb (pProNdedel—we have a procedure that describes the construction of pProNdedel, See Example 15) fragments were purified by agarose gel electrophoresis and extracted as described above. The purified fragments were ligated as described above. The resulting plasmid was named pPro-AtPGP1 and verified by restriction enzyme analysis.

Competent *E. coli* B121-DE3 ::aspCproApET32 were prepared using Transformation and Storage Solution (TSS, Epicentre Biotechnologies). pPro-AtPGP1 was transformed into competent *E. coli*, B121-DE3: :aspCproApET32 as recommended by manufacturer and plated in LB plates with 100 μg/mL of ampicillin and 50 μg/mL of kanamycin. The transformants *E. coli* B121-DE3 : : aspCproApET32 containing a second plasmid pPro-AtPGP1 were verified by PCR amplification of the 5' and 3' region of AtPGP1, using primers PGP1 and PGP2 or PGP5 and PGP6, respectively, as described above.

For inoculum preparation, the *E. coli* strains were grown overnight at 37° C. and 250 rpm in Luria-Bertani ("LB") medium with 100 µg/mL ampicillin and 50 µg/mL kanamycin. For the experimental treatments, Trp-1+glucose medium, a minimal medium that has been used for increased production of tryptophan in *E. coli* cells (Zeman, et al. *Folia Microbiol.* 35:200-204, (1990)), was prepared as follows. To 800 mL nanopure water the following reagents were added: 2 g $(NH_4)_2SO_4$ and 13.6 g $KH_2PO_4$. The pH was adjusted to 7.0, the volume was increased to 948 mL, and the medium was autoclaved. Following sterilization, 0.2 g $MgSO_4.7H_2O$, 0.01 g $CaCl_2.2H_2O$, and 0.5 mg $FeSO_4.7H_2O$ were added to the medium in a 1.8 mL volume followed by addition of 0.2 mL of Neidhardt's micronutrient solution. Neidhardt F. C., et al., "Culture medium for Enterobacteria," *J. Bacteriol.* 119: 736-746, (1974). Neidhardt's medium includes (per liter): 0.18 g $(NH_4)_6(MO_7)_{24}.4H_2O$, 1.24 g $H_3BO_3$, 0.36 g $CoCl_2.6H_2O$, 0.12 g $CuSO_4$ (anhydrous), 0.8 g $MnCl_2.4H_2O$, and 0.14 g $ZnSO_4.7H_2O$. A 50% glucose solution was prepared separately and sterile-filtered. Forty mL of glucose solution and 10 mL of 1 M 3-Morpholinopropanesulfonic acid ("MOPS") buffer were added to the base medium (950 mL) for a 1 L final volume.

For treatments, 3.5 v/v % of inoculum was added to 100 mL medium volume in 500 mL baffled shake flasks with 100 µg/mL ampicillin and 50 µg/mL kanamycin. Conditions for the treatments included 250 rpm agitation throughout and 37° C. up to induction, then, 30° C. following induction. At 0.54-0.62 $OD_{600\ nm}$, induction of the plasmid genes was initiated. At induction, 1.0 mM IPTG, 0.5% L-arabinose, 0.5 mM pyridoxine hydrochloride, and 0.2 mLs of Balch's vitamins were added. Additions of 10 g/L L-tryptophan, 10 g/L sodium pyruvate, 0.04 mM pyridoxal-5'-phosphate ("PLP") and 0 or 0.2% Tween® 20 (polyoxyethylene 20-sorbitan monolaurate) were made 3 hours following induction. Samples for monatin and dry cell weight determination were taken at 24, 30 and 48 hours.

TABLE 25.1

Increase in Monatin per dry cell weight excreted by *E. coli* due to auxin gene expression

| | Tween® | Monatin/dry cell wt. (mg/g) | | |
|---|---|---|---|---|
| | 20 (%) | 24 hours | 30 hours | 48 hours |
| *E. coli* BL21DE3 AP pET32/no auxin transporter gene on pProNde del | 0 | 1.5 | 1.6 | 1.5 |
| *E. coli* BL21DE3 AP pET32/no auxin transporter gene on pProNde del | 0.2 | 2.2 | 2.5 | 2.2 |
| *E. coli* BL21DE3 AP pET32/ *Arabidopsis* auxin transporter gene on pProNde del | 0 | 9.6 | 8.2 | 6.2 |
| *E. coli* BL21DE3 AP pET32/ *Arabidopsis* auxin transporter gene on pProNde del | 0.2 | 29.4 | 26.7* | 19.7 | n = 3 for all treatments except *n = 2

Induction of the *Arabidopsis* auxin transporter gene in strains with the monatin operon on a plasmid resulted in increased monatin per dry cell weight compared to the control treatments with a blank vector (no auxin gene). The 24 hour monatin per dry cell weight result was 9.6 mg/g on average versus 1.5 for the blank vector control without the auxin gene. Additionally, treatment with Tween® 20 at 3 hours following induction, resulted in an increased monatin per dry cell weight average of 29.4 mg/g at 24 hours versus 2.2 for the blank vector control. This represents a 13-fold increase in monatin excreted per dry cell weight for the strain expressing the AtPGP1 auxin transporter gene.

It has been reported that the auxin transporter AtPGP19 (Q9LJX0) has a similar function to AtPGP1 and would also be expected to transport monatin. In addition the literature reports three clusters/clades of p-glycoproteins (PGPs) based on phyogenetic analysis of the *Arabidopsis* PGPs. At PGP1 is a prototype of Class I, catalyzing auxin transport. In addition to AtPGP1 and AtPGP19, other members of class I PGPs that are expected to play a role in auxin transport include: AtPGP13, AtPGP14, AtPGP10, AtPGP2 from *Arabidopsis* and OsPGP9, OsPGP8, OsPGP7 and OsPGP6 from *Oryza sativa* (rice) ("Geisler, M. and A. S. Murphy, "The ABC of auxin transport: The role of p-glycoproteins in plant development," *FEBS Letters* 580:1094-1102, (2006)). The PGPs of Class I as mentioned above would all be expected to have some ability for monatin transport.

In addition a BLAST analysis of the NCBI database using the AtPGP1 protein sequence as a query, indicates that there are a number of homologs such as, but not limited to, BrABB97035, StAAD10836, SbAAR10387, OsXP_483819, OS_CAD59580, ZmPGP1_AAR00316, and AtPGP19, that could all play a role in monatin transport. The sequence alignment for all of the homologs are shown in FIG. 1.

Thus, we present strong evidence supporting the role of auxin transporters for monatin efflux.

Example 26

In vivo R,R Monatin Production and Transport by *E. coli*

Operons were constructed to demonstrate in vivo production of R,R monatin in *E. coli* using a D-aminotransferase ("DAT") and an R-specific aldolase. The R,R monatin was made from D-tryptophan using the pathway described in U.S. Patent Application Publication No. US 2005/0282260 A1 (FIGS. 1 and 2 and Example 11). Briefly, D-tryptophan is converted, in vivo, to indole-3-pyruvate by a transamination reaction in which an alpha-keto acid is also converted into a D-amino acid. Pyruvate is reacted with indole-3-pyruvate in vivo in an aldol condensation using an R-specific aldolase to produce predominantly R-MP. Lastly, the R-MP and the D-amino acid from the first reaction (or any D-amino acid in the cell) are converted in vivo to R,R monatin and the corresponding alpha-keto acid.

Construction of plasmid pCEC-Nde: Plasmid pCEC-Nde was constructed by replacing the p15A origin of replication of pPRO-Nde with the Col E1 origin of replication from pPRO-Tet.E133 (Clontech Laboratories, Inc., Mountain View, Calif.). Both plasmids were treated with restriction enzymes Avr II and Aat II (New England Biolabs, Beverly, Mass.) and the appropriate fragments (1731-bp fragment from pPRO-Tet.E133 carrying the Col E1 origin and chloramphenicol-resistance gene, and 760-bp from pPRO-Nde carrying the $P_{lac/ara}$ promoter region and multiple cloning site) were purified by agarose gel electrophoresis followed by extraction and recovery using the QIAquick® Gel Extraction Kit (Qiagen, Valencia, Calif.). The purified DNA fragments were ligated together using the Quick Ligation Kit (New England Biolabs, Beverly, Mass.) and the ligation mixture transformed into chemically-competent *E. coli* TOP10 cells (Invitrogen, Carlsbad, Calif.). Clones were isolated on LB agar containing 50 µg/mL chloramphenicol and confirmed by restriction digests of the plasmid.

Vector pCEC-Nde was digested with Nde I and BamH I in BamH I buffer (New England Biolabs, Ipswich, Mass.) and treated with shrimp alkaline-phosphatase (Roche) according to the manufacturer's instructions ATCC 4978 DAT (SEQ ID NO. 40) was digested from vector pET28 (Novagen, Madison, Wis.) with Nde I and BamH I in BamH I buffer. The Nde I and BamH I digested vector and insert were purified using the Qiagen QIAquick® Gel Extraction Kit. Ligations were done using the Roche Rapid DNA Ligation Kit (Roche) and purified using the Roche High-Pure PCR purification kit. The ligations were transformed into *Escherichia coli* DH10B cells (Invitrogen, Carlsbad, Calif.) using a 0.2 cm cuvette and a Bio-Rad Gene Pulser® II system as described in the Bio-Rad electroporation manual. The cells were allowed to recover in 1.0 mL SOC medium (Sambrook, J., et al. *Molecular Cloning: A Laboratory Manual* 2nd ed., Plainview, N.Y., (1989), 1.76-1.81 & A.2)) for 1 hour at 37° C. at 250 rpm. Cells were plated on LB-agar plates containing chloramphenicol (25 µg/mL). Plasmid DNA was purified using the Qiagen spin miniprep kit and screened for the correct inserts by PCR and restriction digestion with Nde I and BamH I. The amino acid sequence of ATCC 4978 DAT is shown as SEQ ID NO. 41.

PCR of the Aldolase Having the DNA Sequence of SEQ ID NO. 42

Primers were designed based on the DNA sequence of SEQ ID NO. 42, which encodes an enzyme having aldolase activity. The aldolase amino acid sequence of SEQ ID NO. 43 and the plasmid containing the nucleic acid sequence having SEQ ID NO. 42 and encoding that aldolase, were obtained from Diversa Corporation, San Diego, Calif. DNA having the sequence of SEQ ID NO. 42 was part of a library that was screened by Diversa Corporation for aldolase genes. However, an aldolase gene having the sequence of SEQ ID NO. 42 may be reconstructed by any method known to a person of ordinary skill in the art. For example, an aldolase gene having the sequence of SEQ ID NO. 42 may be reconstructed utilizing assembly PCR methods known to one skilled in the art. The primers were designed to contain restriction sites and a ribosomal binding site in front of the aldolase gene for cloning and expression. The oligonucleotide primer sequences that were used were:

```
AldolaseFpstIrbs
                                        (SEQ ID NO. 44)
5'-GGCCGGAACTGCAGAAGAAGGAGATATATAATGAAGCCGGTGGTGGT G-3'
and AldolaseRxbaI
                                        (SEQ ID NO. 45)
5'-GGCCAAGGTCTAGATTAGACATAGGTGAGCCC-3'.
```

PCR was done using the above primers, with template pET28/aldolase. PCR was carried out as follows: per 50 µL reaction 0.5 µL template, 0.8 µL of each primer, 2 µL dNTPs, 0.8 µL Expand High Fidelity Polymerase (Roche, Indianapolis, Ind.), 1× Expand™ buffer, and 0.2 µL Pfu polymerase (Stratagene, La Jolla, Calif.) were added. A 3 minute hot start was done at 94° C., followed by 8 cycles of 94° C. for 30 seconds, 50° C. for 30 seconds, and 72° C. for 90 seconds. Twenty-two more cycles were done with an increased annealing temperature of 55° C. Lastly, a chain extension step was done for seven minutes at 72° C. The PCR product was purified using the Qiagen QIAquick® PCR purification kit (Qiagen, Valencia, Calif.), and digested with Pst I and Xba I in Buffer 3 (New England Biolabs, Ipswich, Mass.). Pst I and Xba I digested vector pCECNde/4978 DAT and insert were ligated using the Roche Rapid DNA Ligation Kit (Roche, Indianapolis, Ind.) and purified using the QIAquick® PCR purification kit. The ligation was transformed into *Escherichia coli* DH10B cells using a 0.2 cm cuvette and a Bio-Rad Gene Pulser® II system as described in the Bio-Rad electroporation manual. The cells were allowed to recover in 1.0 mL SOC medium for 1 hour at 37° C. at 250 rpm. Cells were plated on LB-agar plates containing chloramphenicol (25 µg/mL).

Transformants were grown in LB broth containing chloramphenicol (25 µg/mL) at 37° C. with shaking at 250 rpm. Plasmid DNA was purified using the Qiagen spin miniprep kit and inserts were verified by restriction digestion with Pst I and Xba I. The sequences of plasmids appearing to have the correct dicistronic insert were verified by dideoxy chain termination DNA sequencing. The resulting plasmid, pCECNde/4978DAT/SEQ ID NO. 42, designated RR2 (vector RR2), was used to transform strain *Escherichia coli* MG1655 as described below.

*E. coli* MG1655 strain was grown in LB broth at 37° C. with shaking at 250 rpm. Electrocompetent *E. coli* MG1655 were prepared by subculturing a 1% inoculum of cells to an OD 600 of ~0.6. The bacteria were pelleted by centrifugation (10 minutes at 10,000×g) and washed in an equal volume of 10% glycerol. The wash was repeated twice in half volume of 10% glycerol. Finally, the cells were washed in one-fourth volume of 10% glycerol. Following centrifugation, the cells were resuspended in 500 µL of 10% glycerol. Thirty µL aliquots were frozen and kept at −80° C. until use.

Vector RR2 (i.e., plasmid pCECNde/4978DAT/SEQ ID NO. 42, prepared above), was transformed into electrocompetent *E. coli* MG1655 cells using a 0.2 cm cuvette and a Bio-Rad Gene Pulser® II system as described in the Bio-Rad electroporation manual. The cells were allowed to recover in 1 mL SOC medium for 1 hour at 37° C. with shaking at 250 rpm. Cells were plated on LB-agar plates containing chloramphenicol (25 µg/mL).

For inoculum preparation, the *E. coli* MG1655 : : pCECNde/4978 DAT/SEQ ID NO. 42 were grown overnight at 37° C. with shaking at 250 rpm in Luria-Bertani ("LB") medium with 25 µg/mL chloramphenicol. For the experimental treatments, Trp-1+glucose medium, a minimal medium that has been used for increased production of tryptophan in *E. coli* cells (Zeman et al. *Folia Microbiol.* 35:200-4, 1990), was prepared as follows. To 800 mL nanopure water the following reagents were added: 2 g $(NH_4)_2SO_4$, 13.6 g $KH_2PO_4$. The pH was adjusted to 7.0, the volume was increased to 948 mL, and the medium was autoclaved. Following sterilization, 0.2 g $MgSO_4.7H_2O$, 0.01 g $CaCl_2.2H_2O$, and 0.5 mg $FeSO_4.7H_2O$ were added to the medium in a 1.8 mL volume followed by addition of 0.2 mL of Neidhardt's micronutrient solution (Neidhardt F. C., Bloch P. L., and Smith D. F., 1974. Culture medium for Enterobacteria. J. Bacteriol. 119: 736-746). Neidhardt's medium includes (per liter): 0.18 g $(NH_4)_6(MO_7)_{24}.4H_2O$, 1.24 g $H_3BO_3$, 0.36 g $CoCl_2.6H_2O$, 0.12 g $CuSO_4$ (anhydrous), 0.8 g $MnCl_2.4H_2O$, and 0.14 g $ZnSO_4.7H_2O$. A 50% glucose solution was prepared separately and sterile-filtered. Forty mL of glucose solution and 10 mL of 1 M 3-morpholinopropanesulfonic acid ("MOPS") buffer were added to the base medium (950 mL) for a 1 L final volume.

For treatments, 3.1 v/v % of inoculum was added to 100 mL medium volume in 500 mL baffled shake flasks with 25 µg/mL chloramphenicol. Conditions for the treatments included 250 rpm agitation throughout and 37° C. up to induction, then, 30° C. following induction. At 0.50-0.526 $OD_{600\ nm}$, induction of the plasmid genes was initiated. At induction, 1.0 mM IPTG, 0.5% L-arabinose, 0.5 mM pyridoxine hydrochloride, and 0.2 mL's of Balch's vitamins (Balch, W. E., et al., 1979, Microbiol. Rev. 43:260-296) were added. Additions of 10 g/L D-tryptophan, 10 g/L sodium pyruvate, 0.04 mM pyridoxal-5'-phosphate ("PLP") were made at 3 hours following induction, while 0.2% Tween® 20 (polyoxyethylene 20-sorbitan monolaurate) and 10 µg/mL ampicillin were added 6 hours following induction. Either 5 mM D-glutamate or D-alanine was also added at 3 hours following induction. A second addition of 10 g/L sodium pyruvate was made at 24 hours following inoculation. Samples for monatin and dry cell weight determination were taken at 48 hours.

The monatin from the 48 hour samples was concentrated via a solid phase extraction ("SPE") column (see Example 27). Then, the R,R and S,S stereoisomers were analyzed by the method of Example 13.

TABLE 26.1

R,R Monatin excreted by E. coli

| Strain | D-amino acid treatment | 48 hour Monatin/ dry cell wt. (mg/g) Total Monatin | Portion as: R,R Monatin | S,S Monatin |
|---|---|---|---|---|
| E. coli MG1655:: pCECNde/4978 DAT/SEQ ID NO. 42 | D-glutamate | 0.47 | ~50% | ~50% |
| E. coli MG1655:: pCECNde/4978 DAT/SEQ ID NO. 42 | D-alanine | 0.33 | nd | nd |

R,R Monatin production and transport was conclusively demonstarted using the strain E. coli MG165 : : pCECNde/4978 DAT/SEQ ID NO. 42 and D-glutamate. Some S,S monatin was produced, probably as a result of using the E. coli MG1655 strain that normally expresses other aminotransferases that are capable of making intermediates that are precursors to S,S monatin. The total monatin produced with D-alanine was not enough to conduct an analysis to determine the stereoisomeric ratio of monatin produced. However, it is expected that the same ratio of R,R monatin would be formed, even though the amount produced was below the threshold of analysis. It is also expected that the same transporters capable of transporting S,S monatin should be capable of transporting R,R monatin as well.

Example 27

Concentration of Monatin Utilizing a Solid Phase Extraction Column

The 48 hour samples of Example 26 were concentrated prior to the analysis of the samples by the method of Example 13. An Oasis® HLB 3cc (60 mg) Extraction Cartridge (Waters Corp., Milford, Mass.) was used to concentrate the samples.

The fermentation samples were first centrifuged to remove cell material. Formic acid was added to the fermentation sample for a final concentration of about 1%.

The extraction cartridge was conditioned with at least 2 mL methanol, followed by 2 mL 1% formic acid prior to the addition of the fermentation sample. Each solution was drawn through the extraction cartridge separately.

Then, up to 5 mL of the undiluted, centrifuged fermentation sample containing 1% formic acid was added to the extraction cartridge. The fermentation solution was allowed to draw through the cartridge slowly.

The cartridge was rinsed with at least 2 mL of 1% formic acid. 1 mL of either acetonitrile or methanol was added to the cartridge and was allowed to draw through the cartridge slowly. This eluent was placed under a gentle stream of nitrogen until it was dry. The dry sample was reconstituted into 150-200 µL water or mobile phase. 150 µL was placed into a 300 µL HPLC plastic vial and was injected into the liquid chromatograph.

What is claimed is:

1. A method of producing R,R monatin by converting tryptophan to indole-3-pyruvate using a first aminotransferase, converting indole-3-pyruvate to R-2-hydroxy 2-(indole-3-yl-methyl)-4-keto glutaric acid ("R-monatin precursor") using an R-specific aldolase, and converting R-monatin precursor to R,R monatin using either the first aminotransferase or a second aminotransferase, the method comprising:
   a) genetically engineering a bacteria to express:
      i) a nucleic acid that encodes the first aminotransferase;
      ii) where a second aminotransferase is present, a nucleic acid that encodes the second aminotransferase;
      iii) a nucleic acid that encodes the R-specific aldolase; and
      iv) a nucleic acid that encodes one or more polypeptide components of a multi-drug transporter system, wherein said polypeptide components are selected from the group consisting of AcrA, AcrB, EmrA, and EmrB, and wherein said multi-drug transporter system is capable of secreting R,R monatin;
   b) culturing the microorganism, wherein the microorganism expresses nucleic acids sufficient for the intracellular synthesis of R,R monatin;
   c) secreting R,R monatin using the one or more polypeptide components of the multi-drug transporter system; and
   d) collecting at least a portion of the secreted R,R monatin.

2. The method of claim 1 where the microorganism is genetically engineered to express the nucleic acid that encodes one or more polypeptide components of the multi-drug transporter system.

3. The method of claim 1 wherein the microorganism is genetically engineered to express the nucleic acid that encodes the R-specific aldolase.

4. The method of claim 1 wherein the R-specific aldolase is chosen from 4-hydroxy-2-oxoglutarate glyoxylate-lyase (EC 4.1.3.16), 4-hydroxy-4-methyl-2-oxoglutarate pyruvate-lyase (EC 4.1.3.17), or a combination thereof.

5. The method of claim 1 wherein the microorganism is genetically engineered to express the nucleic acid that encodes the first aminotransferase.

6. The method of claim 5 wherein the first aminotransferase is chosen from tryptophan aminotransferase (EC 2.6.1.27), tyrosine (aromatic) aminotransferase (EC 2.6.1.5), tryptophan dehydrogenase (EC 1.4.1.19), tryptophan-phenylpyruvate transaminase (EC 2.6.1.28), aspartate aminotransferase (EC 2.6.1.1.), L-amino acid oxidase (EC 1.4.3.2), D-amino acid dehydrogenase (EC 1.4.99.1), D-amino acid oxidase (EC 1.4.3.3), D-amino acid (D-alanine) aminotransferase (EC 2.6.1.21), or a combination thereof.

7. The method of claim 1 wherein the microorganism is genetically engineered to express the nucleic acid that encodes the second aminotransferase.

8. The method of claim 1 wherein the second aminotransferase is chosen from tryptophan aminotransferase (EC 2.6.1.27), tyrosine (aromatic) aminotransferase (EC 2.6.1.5), tryptophan dehydrogenase (EC 1.4.1.19), aspartate aminotransferase (EC 2.6.1.1.), glutamate dehydrogenase (EC 1.4.1.2-4), phenylalanine dehydrogenase (EC 1.4.1.20), D-amino acid dehydrogenase (EC 1.4.99.1), D-amino acid (D-alanine) aminotransferase (EC 2.6.1.21), or a combination thereof.

9. The method of claim 1 wherein the second aminotransferase is the same as the first aminotransferase.

10. The method of claim 1 wherein the microorganism is *E. coli*.

11. The method of claim 1 wherein the microorganism is a member of the Pantoea family.

12. The method of claim 1 wherein the microorganism is a member of the Corynebacterium family.

* * * * *